(12) United States Patent
Alexander et al.

(10) Patent No.: US 9,868,749 B2
(45) Date of Patent: Jan. 16, 2018

(54) FUSED IMIDAZOLE AND PYRAZOLE DERIVATIVES AS MODULATORS OF TNF ACTIVITY

(71) Applicant: UCB BIOPHARMA SPRL, Brussels (BE)

(72) Inventors: Rikki Peter Alexander, Slough (GB); Jonathan Mark Bentley, Abingdon (GB); Gareth Neil Brace, Abingdon (GB); Daniel Christopher Brookings, Slough (GB); Prafulkumar Tulshibhai Chovatia, Abingdon (GB); Hervé Jean Claude Deboves, Abingdon (GB); Craig Johnstone, Abingdon (GB); Elizabeth Pearl Jones, Slough (GB); Boris Kroeplien, Slough (GB); Fabien Claude Lecomte, Slough (GB); James Madden, Abingdon (GB); Craig Miller, Abingdon (GB); John Robert Porter, Slough (GB); Matthew Duncan Selby, Slough (GB); Michael Alan Shaw, Slough (GB); Darshan Gunvant Vaidya, Abingdon (GB); Ian Andrew Yule, Abingdon (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/100,825

(22) PCT Filed: Dec. 8, 2014

(86) PCT No.: PCT/EP2014/076845
§ 371 (c)(1),
(2) Date: Jun. 1, 2016

(87) PCT Pub. No.: WO2015/086506
PCT Pub. Date: Jun. 18, 2015

(65) Prior Publication Data
US 2016/0297837 A1  Oct. 13, 2016

(30) Foreign Application Priority Data
Dec. 9, 2013 (GB) .................... 1321738.5

(51) Int. Cl.
*C07D 519/00* (2006.01)
*C07D 471/04* (2006.01)
*A61K 31/4355* (2006.01)
*A61K 31/4709* (2006.01)
*A61K 31/538* (2006.01)
*A61K 31/5383* (2006.01)

(52) U.S. Cl.
CPC ........ *C07D 519/00* (2013.01); *A61K 31/4355* (2013.01); *A61K 31/4709* (2013.01); *A61K 31/538* (2013.01); *A61K 31/5383* (2013.01); *C07D 471/04* (2013.01)

(58) Field of Classification Search
CPC C07D 519/00; C07D 471/04; A61K 31/4355; A61K 31/4709; A61K 31/538; A61K 31/5383
See application file for complete search history.

(56) References Cited

U.S. PATENT DOCUMENTS

| 8,178,533 B2 * | 5/2012 | Kenda | C07D 401/06 514/248 |
| 2014/0031547 A1 * | 1/2014 | Sheridan | A61K 31/437 544/284 |

FOREIGN PATENT DOCUMENTS

| CN | 102203101 | 9/2011 | |
| CN | 103145706 | 6/2012 | |
| CN | 103145706 | 6/2013 | |
| EP | 1 329 218 A1 | 7/2003 | |
| EP | 1 356 815 A1 | 10/2003 | |
| WO | 04/014900 A1 | 2/2004 | |
| WO | WO 2009/152072 | 12/2009 | |
| WO | WO 2011/055320 | 5/2011 | |
| WO | WO 2011/137587 | 11/2011 | |
| WO | WO 2012080729 A2 * | 6/2012 | ........... A61K 31/437 |
| WO | 13/186229 A1 | 12/2013 | |
| WO | 14/009295 A1 | 1/2014 | |
| WO | 14/009296 A1 | 1/2014 | |

OTHER PUBLICATIONS

Tansey et al., "The TNF superfamily in 2009: new pathways, new indications, and new drugs", Drug Discovery Today, 2009, 14(23/24), 1082-1088.
Carneiro et al., "Emerging Role for TNF-α in Erectile Dysfunction", J. Sexual Medicine, 2010, vol. 7, 3823-3834.
Wu et al., "Do TNF Inhibitors Reduce the Risk of Myocardial Infarction in Psoriasis Patients?", JAMA, 2013, 309(19), 2043-2044.
Hauwermeiren et al., "Safe TNF-based antitumor therapy following p55TNFR reduction in intestinal epithelium", The Journal of Clinical Investigation, 2013, 123(6), 2590-2603.
Chinese office action dated Dec. 1, 2016 for Chinese Application No. 201480067071.1.

* cited by examiner

Primary Examiner — Kahsay Habte

(57) ABSTRACT

A series of substituted benzimidazole, imidazo[1,2-a]pyridine and pyrazolo[1,5-a]pyridine derivatives, and analogues thereof, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

7 Claims, No Drawings

FUSED IMIDAZOLE AND PYRAZOLE DERIVATIVES AS MODULATORS OF TNF ACTIVITY

This application is the U.S. national phase under 35 U.S.C. §371 of international application PCT/EP2014/076845, filed Dec. 8, 2014, which claims priority to GB application 1321738.5, filed Dec. 9, 2013.

The present invention relates to a class of fused imidazole and pyrazole derivatives, and to their use in therapy. More particularly, this invention is concerned with pharmacologically active substituted benzimidazole, imidazo[1,2-a]pyridine and pyrazolo[1,5-a]pyridine derivatives, and analogues thereof. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

Co-pending international patent applications WO 2013/186229 (published 19 Dec. 2013), WO 2014/009295 (published 16 Jan. 2014) and WO 2014/009296 (also published 16 Jan. 2014) describe fused imidazole derivatives which are modulators of human TNFα activity.

None of the prior art available to date, however, discloses or suggests the precise structural class of fused imidazole and pyrazole derivatives as provided by the present invention.

The compounds in accordance with the present invention potently inhibit the binding of a fluorescence conjugate to TNFα when tested in the fluorescence polarisation assay described herein. Indeed, when tested in that assay, the compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound).

Certain compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, certain compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 20 nM or less (as before, the skilled person will appreciate that a lower $IC_{50}$ figure denotes a more active compound).

The present invention provides a compound of formula (IA), (IB) or (IC) or an N-oxide thereof, or a pharmaceutically acceptable salt or solvate thereof, or a glucuronide derivative thereof, or a co-crystal thereof:

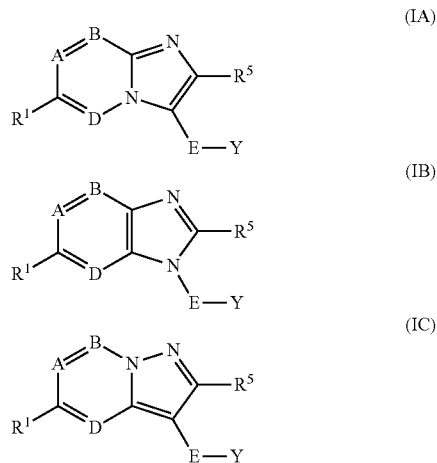

wherein
A represents C—$R^2$ or N;
B represents C—$R^3$ or N;
D represents C—$R^4$ or N;

E represents a covalent bond; or E represents —O—, —S—, —S(O)—, —S(O)$_2$—, —S(O)(NR$^6$)— or —N(R$^6$)—; or E represents an optionally substituted straight or branched C$_{1-4}$ alkylene chain;

Y represents a group of formula (Ya), (Yb), (Yc), (Yd), (Ye) or (Yf):

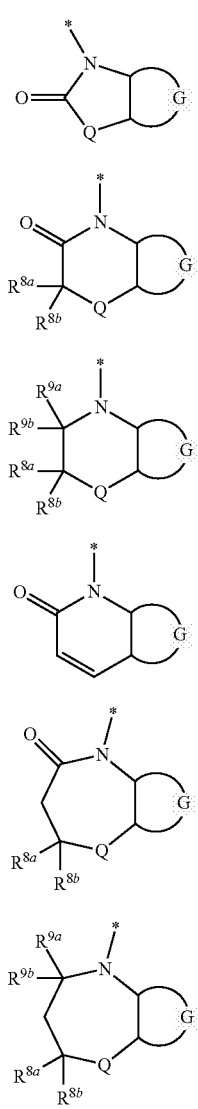

(Ya)

(Yb)

(Yc)

(Yd)

(Ye)

(Yf)

the asterisk (*) represents the point of attachment to the remainder of the molecule;

Q represents —O—, —S—, —S(O)—, —S(O)$_2$—, —S(O)(NR$^6$)—, —N(R$^6$)—, —C(O)— or —C(R$^{7a}$)(R$^{7b}$)—;

G represents the residue of an optionally substituted benzene ring; or an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl and triazolyl; or an optionally substituted six-membered heteroaromatic ring selected from pyridinyl, pyridazinyl, pyrimidinyl, pyrazinyl and triazinyl;

R$^1$, R$^2$, R$^3$ and R$^4$ independently represent hydrogen, halogen, cyano, nitro, hydroxy, trifluoromethyl, trifluoromethoxy, —OR$^a$, —SR$^a$, —SOR$^a$, —SO$_2$R$^a$, —SF$_5$, —NR$^b$R$^c$, —NR$^c$COR$^d$, —NR$^c$CO$_2$R$^d$, —NHCONR$^b$R$^c$, —NR$^c$SO$_2$R$^e$, —N(SO$_2$R$^e$)$_2$, —NHSO$_2$NR$^b$R$^c$, —COR$^d$, —CO$_2$R$^d$, —CONR$^b$R$^c$, —CON(OR$^a$)R$^b$, —SO$_2$NR$^b$R$^c$ or —SO(NR$^b$)R$^d$; or C$_{1-6}$ alkyl, C$_{2-6}$ alkenyl, C$_{2-6}$ alkynyl, C$_{3-7}$ cycloalkyl, C$_{4-7}$ cycloalkenyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, C$_{3-7}$ heterocycloalkenyl, C$_{4-9}$ heterobicycloalkyl, heteroaryl, heteroaryl(C$_{1-6}$)alkyl, (C$_{3-7}$)heterocycloalkyl(C$_{1-6}$)alkyl-aryl-, heteroaryl(C$_{3-7}$)heterocycloalkyl-, (C$_{3-7}$)cycloalkyl-heteroaryl-, (C$_{3-7}$)cycloalkyl(C$_{1-6}$)alkyl-heteroaryl-, (C$_{4-7}$)cycloalkenyl-heteroaryl-, (C$_{4-9}$)bicycloalkyl-heteroaryl-, (C$_{3-7}$)heterocycloalkyl-heteroaryl-, (C$_{3-7}$)hetero cyclo alkyl(C$_{1-6}$) alkyl-hetero aryl-, (C$_{3-7}$)hetero cyclo alkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one or more substituents;

R$^5$ represents C$_{1-6}$ alkyl, optionally substituted by halogen, hydroxy or C$_{1-6}$ alkoxy;

R$^6$ represents hydrogen or C$_{1-6}$ alkyl;

R$^{7a}$ and R$^{7b}$ independently represent hydrogen or C$_{1-6}$ alkyl;

R$^{8a}$ and R$^{8b}$ independently represent hydrogen, halogen or C$_{1-6}$ alkyl; or R$^{8a}$ and R$^{8b}$, when taken together with the carbon atom to which they are both attached, represent C$_{3-7}$ cycloalkyl or C$_{3-7}$ heterocycloalkyl, either of which groups may be optionally substituted by one or more substituents; or R$^{7a}$ and R$^{8a}$, when taken together with the two intervening carbon atoms, represent C$_{3-7}$ cycloalkyl or C$_{3-7}$ heterocycloalkyl, either of which groups may be optionally substituted by one or more substituents;

R$^{9a}$ and R$^{9b}$ independently represent hydrogen or C$_{1-6}$ alkyl; or

R$^{9a}$ and R$^{9b}$, when taken together with the carbon atom to which they are both attached, represent C$_{3-7}$ cycloalkyl or C$_{3-7}$ heterocycloalkyl, either of which groups may be optionally substituted by one or more substituents;

R$^a$ represents C$_{1-6}$ alkyl, aryl, aryl(C$_{1-6}$)alkyl, heteroaryl or heteroaryl(C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

R$^d$ represents hydrogen; or C$_{1-6}$ alkyl, C$_{3-7}$ cycloalkyl, aryl, C$_{3-7}$ heterocycloalkyl or heteroaryl, any of which groups may be optionally substituted by one or more substituents; and R$^e$ represents C$_{1-6}$ alkyl, aryl or heteroaryl, any of which groups may be optionally substituted by one or more substituents.

The present invention also provides a compound of formula (IA), (IB) or (IC) as defined above or an N-oxide thereof, or a pharmaceutically acceptable salt or solvate thereof, or a glucuronide derivative thereof, or a co-crystal thereof, for use in therapy.

The present invention also provides a compound of formula (IA), (IB) or (IC) as defined above or an N-oxide thereof, or a pharmaceutically acceptable salt or solvate thereof, or a glucuronide derivative thereof, or a co-crystal thereof, for use in the treatment and/or prevention of disorders for which the administration of a modulator of TNFα function is indicated.

In another aspect, the present invention provides a compound of formula (IA), (IB) or (IC) as defined above or an N-oxide thereof, or a pharmaceutically acceptable salt or solvate thereof, or a glucuronide derivative thereof, or a co-crystal thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (IA), (IB) or (IC) as defined above or an N-oxide thereof, or a pharmaceutically acceptable salt or solvate thereof, or a glucuronide derivative thereof, or a co-crystal thereof.

In another aspect, the present invention provides a method for the treatment and/or prevention of an inflammatory or autoimmune disorder, a neurological or neuro-degenerative disorder, pain or a nociceptive disorder, a cardiovascular disorder, a metabolic disorder, an ocular disorder, or an oncological disorder, which comprises administering to a patient in need of such treatment an effective amount of a compound of formula (IA), (IB) or (IC) as defined above or an N-oxide thereof, or a pharmaceutically acceptable salt or solvate thereof, or a glucuronide derivative thereof, or a co-crystal thereof.

Where any of the groups in the compounds of formula (IA), (IB) or (IC) above is stated to be optionally substituted, this group may be unsubstituted, or substituted by one or more substituents. Typically, such groups will be unsubstituted, or substituted by one or two substituents.

For use in medicine, the salts of the compounds of formula (IA), (IB) or (IC) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of use in the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; ammonium salts; and salts formed with suitable organic ligands, e.g. quaternary ammonium salts, and meglumine salts.

The present invention includes within its scope solvates of the compounds of formula (IA), (IB) or (IC) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (IA), (IB) or (IC) may be formed with water, in which case they will be hydrates.

The present invention also includes co-crystals within its scope. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012). Typical examples of co-crystal formers, which may be present in the co-crystal alongside the active pharmaceutical ingredient, include L-ascorbic acid, citric acid, glutaric acid, urea and nicotinamide.

The present invention includes within its scope prodrugs of the compounds of formula (IA), (IB) or (IC) above. In general, such prodrugs will be functional derivatives of the compounds of formula (IA), (IB) or (IC) which are readily convertible in vivo into the required compound of formula (IA), (IB) or (IC). Conventional procedures for the selection and preparation of suitable prodrug derivatives are described, for example, in *Design of Prodrugs*, ed. H. Bundgaard, Elsevier, 1985.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-4}$ alkylene chain" refers to a divalent straight or branched alkylene chain containing 1 to 4 carbon atoms. Typical examples include methylene, ethylene, methylmethylene, ethylmethylene and dimethylmethylene.

Suitable $C_{2-6}$ alkenyl groups include vinyl and allyl.

Suitable $C_{2-6}$ alkynyl groups include ethynyl, propargyl and butynyl.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[3.1.0]hexanyl, bicyclo[4.1.0]heptanyl and bicyclo[2.2.2]octanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, isothiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 6-oxa-3-azabicyclo[3.1.1]heptanyl, 3-azabicyclo[4.1.0]-heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo-[3.3.1]nonanyl, 3,7-dioxa-9-azabicyclo[3.3.1]nonanyl and 3,9-diazabicyclo[4.2.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Suitable spiroheterocycloalkyl groups include 5-azaspiro[2.3]hexanyl, 5-azaspiro[2.4]heptanyl, 2-azaspiro[3.3]heptanyl, 2-oxa-6-azaspiro[3.3]heptanyl, 3-oxa-6-azaspiro[3.3]-heptanyl, 6-thia-2-azaspiro[3.3]heptanyl, 2-oxa-6-azaspiro[3.4]octanyl, 2-oxa-6-azaspiro[3.5]nonanyl, 7-oxa-2-azaspiro[3.5]nonanyl, 2-oxa-7-azaspiro[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]-pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (IA), (IB) or (IC) have one or more asymmetric centres, they may accordingly exist as enantiomers. Where the compounds of use in the invention possess two or more asymmetric centres, they may additionally exist as diastereomers. The invention is to be understood to extend to the use of all such enantiomers and diastereomers, and to mixtures thereof in any proportion, including racemates. Formula (IA), (IB) or (IC) and the formulae depicted hereinafter are intended to represent all individual stereoisomers and all possible mixtures thereof, unless stated or shown otherwise. In addition, compounds of formula (IA), (IB) or (IC) may exist as tautomers, for example keto ($CH_2C=O$)⇌enol ($CH=CHOH$) tautomers or amide ($NHC=O$)⇌hydroxyimine ($N=COH$) tautomers. Formula (IA), (IB) or (IC) and the formulae depicted hereinafter are intended to represent all individual tautomers and all possible mixtures thereof, unless stated or shown otherwise.

It is to be understood that each individual atom present in formula (IA), (IB) or (IC), or in the formulae depicted hereinafter, may in fact be present in the form of any of its naturally occurring isotopes, with the most abundant isotope(s) being preferred. Thus, by way of example, each individual hydrogen atom present in formula (IA), (IB) or (IC), or in the formulae depicted hereinafter, may be present as a $^{1}H$, $^{2}H$ (deuterium) or $^{3}H$ (tritium) atom, preferably $^{1}H$. Similarly, by way of example, each individual carbon atom present in formula (IA), (IB) or (IC), or in the formulae depicted hereinafter, may be present as a $^{12}C$, $^{13}C$ or $^{14}C$ atom, preferably $^{12}C$.

In one aspect, the present invention provides a compound of formula (IA), (IB) or (IC) as depicted above or an N-oxide thereof, or a pharmaceutically acceptable salt or solvate thereof, or a glucuronide derivative thereof, or a co-crystal thereof, wherein $R^1$ represents halogen or cyano; or $C_{1-6}$ alkyl, $C_{2-6}$ alkenyl, $C_{2-6}$ alkynyl, $C_{3-7}$ cycloalkyl, $C_{4-7}$ cycloalkenyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl, heteroaryl($C_{1-6}$)alkyl, ($C_{3-7}$)heterocycloalkyl($C_{1-6}$)alkyl-aryl-, heteroaryl($C_{3-7}$)heterocycloalkyl-, ($C_{3-7}$)cycloalkyl-heteroaryl-, ($C_{3-7}$)cycloalkyl-($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)hetero cyclo alkyl ($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$) spiroheterocycloalkyl-heteroaryl-, any of which groups may be optionally substituted by one or more substituents; and A, B, D, E, Y and $R^5$ are as defined above.

In one embodiment, A represents C—$R^2$. In another embodiment, A represents N.

In one embodiment, B represents C—$R^3$. In another embodiment, B represents N.

In one embodiment, D represents C—$R^4$. In another embodiment, D represents N.

In a first embodiment, A represents C—R², B represents C—R³ and D represents C—R⁴.

In a second embodiment, A represents C—R², B represents C—R³ and D represents N.

In a third embodiment, A represents C—R², B represents N and D represents C—R⁴.

In a fourth embodiment, A represents C—R², B represents N and D represents N.

In a fifth embodiment, A represents N, B represents C—R³ and D represents C—R⁴.

In a sixth embodiment, A represents N, B represents C—R³ and D represents N.

In a seventh embodiment, A represents N, B represents N and D represents C—R⁴.

In an eighth embodiment, A represents N, B represents N and D represents N.

Suitably, A represents C—R², and B and D are as defined above; or A represents N, B represents C—R³, and D is as defined above.

Suitably, A represents C—R², B represents C—R³ and D is as defined above; or A represents N, B represents C—R³ and D represents C—R⁴.

Particular sub-classes of compounds in accordance with the present invention include the compounds of formula (IA-A), (IA-B) and (IA-C):

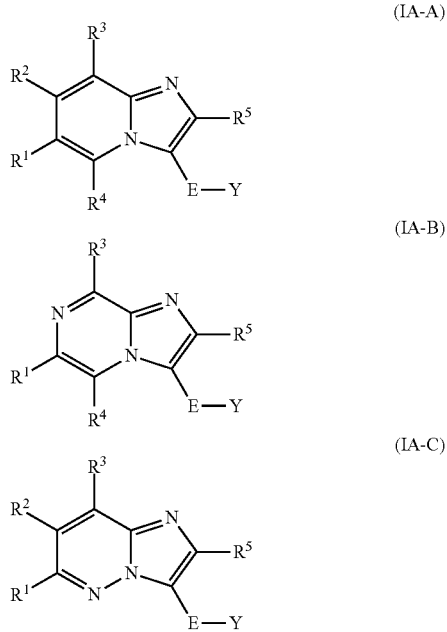

wherein E, Y, R¹, R², R³, R⁴ and R⁵ are as defined above.

Where the compounds in accordance with the invention comprise an optionally substituted straight or branched alkylene chain, typical values thereof include methylene (—CH₂—), (methyl)methylene, ethylene (—CH₂CH₂—), (ethyl)methylene, (dimethyl)-methylene, (methyl)ethylene, propylene (—CH₂CH₂CH₂—), (propyl)methylene and (dimethyl)ethylene, any of which chains may be optionally substituted by one or more substituents. Suitably, such chains are unsubstituted, monosubstituted or disubstituted. Typically, such chains are unsubstituted or monosubstituted. In one embodiment, such chains are unsubstituted. In another embodiment, such chains are monosubstituted. In a further embodiment, such chains are disubstituted.

Examples of typical substituents on the alkylene chain which may be present in a compound in accordance with the invention include halogen, cyano, trifluoromethyl, oxo, hydroxy, $C_{1-6}$ alkoxy, carboxy($C_{1-6}$)alkoxy, trifluoromethoxy, amino, $C_{1-6}$ alkylamino, di($C_{1-6}$)alkylamino, $C_{2-6}$ alkylcarbonylamino, carboxy, benzyloxycarbonyl, tetrazolyl, aminocarbonyl, $C_{1-6}$ alkylaminocarbonyl and di($C_{1-6}$)alkylaminocarbonyl.

Specific examples of suitable substituents on the alkylene chain which may be present in a compound in accordance with the invention include fluoro, cyano, trifluoromethyl, oxo, hydroxy, methoxy, carboxymethoxy, amino, acetylamino, carboxy, benzyloxycarbonyl and tetrazolyl.

In a first embodiment, E represents a covalent bond, whereby the integer Y is attached directly to the five-membered ring.

In a second embodiment, E represents —O—, —S—, —S(O)—, —S(O)₂—, —S(O)(NR⁶)— or —N(R⁶)—. In a first aspect of that embodiment, E represents —O—. In a second aspect of that embodiment, E represents —S—. In a third aspect of that embodiment, E represents —S(O)—. In a fourth aspect of that embodiment, E represents —S(O)₂—. In a fifth aspect of that embodiment, E represents —S(O)(NR⁶)—. In a sixth aspect of that embodiment, E represents —N(R⁶)—.

In a third embodiment, E represents an optionally substituted straight or branched $C_{1-4}$ alkylene chain. In a first aspect of that embodiment, E represents an optionally substituted methylene (—CH₂—) linkage. In a second aspect of that embodiment, E represents an optionally substituted (methyl)methylene linkage. In a third aspect of that embodiment, E represents an optionally substituted (ethyl)methylene linkage.

Generally, E represents a covalent bond; or E represents —N(R⁶)—; or E represents an optionally substituted straight or branched $C_{1-4}$ alkylene chain.

Typically, E represents —N(R⁶)—; or E represents an optionally substituted straight or branched $C_{1-4}$ alkylene chain.

Suitably, E represents a covalent bond; or E represents —N(R⁶)—; or E represents methylene (—CH₂—), (methyl)methylene or (ethyl)methylene, any of which groups may be optionally substituted by one or more substituents.

Generally, E represents —N(R⁶)—; or E represents methylene (—CH₂—) or (methyl)methylene, either of which groups may be optionally substituted by one or more substituents.

Appositely, E represents methylene (—CH₂—) or (methyl)methylene, either of which groups may be optionally substituted by one or more substituents.

Selected examples of typical substituents on the linkage represented by E include halogen, trifluoromethyl, oxo, hydroxy, $C_{1-6}$ alkoxy, carboxy($C_{1-6}$)alkoxy, trifluoromethoxy, amino, $C_{1-6}$ alkylamino, di($C_{1-6}$)alkylamino, $C_{2-6}$ alkylcarbonylamino, carboxy, benzyloxycarbonyl and tetrazolyl.

Specific examples of typical substituents on the linkage represented by E include fluoro, trifluoromethyl, oxo, hydroxy, methoxy, carboxymethoxy, trifluoromethoxy, amino, methylamino, dimethylamino, acetylamino, carboxy, benzyloxycarbonyl and tetrazolyl.

Typical values of E include —N(R⁶)—, —CH₂—, —C(O)—, —CH(OH)—, —CH(OCH₃)—, —CH(OCH₂CO₂H)—, —CH(NH₂)—, —CH(NHCOCH₃)—, —CH(CO₂H)—, —CH(CO₂benzyl)-, —CH(CH₃)—, —C(CH$_3$)(OH)— and —CH(CH$_2$CH$_3$)—; or E may represent a covalent bond.

Suitable values of E include —CH$_2$— and —CH(CH$_3$)—.

In one embodiment, E represents —CH$_2$—.

In another embodiment, E represents —CH(CH$_3$)—. In a particular aspect of that embodiment, the —CH(CH$_3$)— linkage represented by E is in the (S) stereochemical configuration.

Typically, Q represents —O—, —S—, —S(O)— or —C(R$^{7a}$)(R$^{7b}$)—.

Suitably, Q represents —O— or —C(R$^{7a}$)(R$^{7b}$)—.

In a first embodiment, Q represents —O—. In a second embodiment, Q represents —S—. In a third embodiment, Q represents —S(O)—. In a fourth embodiment, Q represents —S(O)$_2$—. In a fifth embodiment, Q represents —S(O)(NR$^6$)—. In a sixth embodiment, Q represents —N(R$^6$)—. In a seventh embodiment, Q represents —C(O)—. In an eighth embodiment, Q represents —C(R$^{7a}$)(R$^{7b}$)—.

In the compounds of the invention, the moiety G is defined as representing the residue of an optionally substituted benzene ring, or an optionally substituted five-membered or six-membered heteroaromatic ring as specified above. From this it is to be understood that the variable G, when taken together with the two carbon atoms of the ring to which the G-containing ring is fused, represents an optionally substituted benzene ring, or an optionally substituted five-membered or six-membered heteroaromatic ring as specified above.

In a first embodiment, the moiety G in the compounds of the invention represents the residue of an optionally substituted benzene ring.

In a second embodiment, the moiety G in the compounds of the invention represents the residue of an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl, triazolyl and tetrazolyl.

In a third embodiment, the moiety G in the compounds of the invention represents the residue of an optionally substituted six-membered heteroaromatic ring selected from pyridinyl, pyridazinyl, pyrimidinyl, pyrazinyl and triazinyl.

Generally, G represents the residue of an optionally substituted benzene ring, or an optionally substituted six-membered heteroaromatic ring as specified above.

Suitably, G represents the residue of an optionally substituted benzene ring; or an optionally substituted six-membered heteroaromatic ring selected from pyridinyl and pyrimidinyl.

The aromatic or heteroaromatic ring of which the moiety G is the residue may be unsubstituted, or may be substituted, where possible, by one or more substituents, generally by one, two or three substituents, typically by one or two substituents. In one embodiment, this ring is unsubstituted. In another embodiment, this ring is monosubstituted. In a further embodiment, this ring is disubstituted. In a still further embodiment, this ring is trisubstituted.

Typical examples of optional substituents on the aromatic or heteroaromatic ring of which the moiety G is the residue include halogen, cyano, C$_{1-6}$ alkyl, fluoromethyl, difluoromethyl, trifluoromethyl, hydroxy, hydroxy(C$_{1-6}$)alkyl, C$_{1-6}$ alkoxy, difluoro-methoxy, trifluoromethoxy, pentafluorothio, C$_{1-6}$ alkylthio, C$_{1-6}$ alkylsulphinyl, C$_{1-6}$ alkylsulphonyl, amino, amino(C$_{1-6}$)alkyl, C$_{1-6}$ alkylamino, di(C$_{1-6}$)alkylamino, formyl, C$_{2-6}$ alkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulphonyl, C$_{1-6}$ alkylaminosulphonyl, di(C$_{1-6}$)alkyl-aminosulphonyl, (C$_{1-6}$)alkylsulphoximinyl and [(C$_{1-6}$)alkyl][N—(C$_{1-6}$)alkyl]sulphoximinyl. Additional examples include hydroxy(C$_{1-6}$)alkylaminocarbonyl, (C$_{1-6}$)alkoxy(C$_{1-6}$)alkyl-aminocarbonyl, (C$_{3-7}$)cycloalkylaminocarbonyl, heteroaryl(C$_{1-6}$)alkylaminocarbonyl, hydroxy(C$_{3-7}$)heterocycloalkyl, (C$_{1-6}$)alkoxy(C$_{3-7}$)heterocycloalkyl, (C$_{3-7}$)heterocycloalkylcarbonyl, hydroxy(C$_{3-7}$)heterocycloalkylcarbonyl, oxo(C$_{3-7}$)heterocycloalkylcarbonyl, (C$_{1-6}$)alkylsulphonyl(C$_{3-7}$)heterocycloalkylcarbonyl and (C$_{2-6}$)alkoxycarbonyl-(C$_{3-7}$)heterocycloalkylcarbonyl.

Selected examples of optional substituents on the aromatic or heteroaromatic ring of which the moiety G is the residue include halogen, cyano, trifluoromethyl, hydroxy (C$_{1-6}$)alkyl, C$_{1-6}$ alkylthio, C$_{1-6}$ alkylsulphinyl, C$_{1-6}$ alkylsulphonyl, carboxy, C$_{2-6}$ alkoxycarbonyl, aminocarbonyl, C$_{1-6}$ alkylaminocarbonyl, di(C$_{1-6}$)alkylaminocarbonyl, hydroxy(C$_{1-6}$)alkylamino carbonyl, (C$_{1-6}$)alkoxy(C$_{1-6}$)alkylamino carbonyl, (C$_{3-7}$)cyclo alkyl-aminocarbonyl, heteroaryl(C$_{1-6}$)alkylaminocarbonyl, hydroxy(C$_{3-7}$)heterocycloalkyl, (C$_{1-6}$)alkoxy(C$_{3-7}$)heterocycloalkyl, (C$_{3-7}$)heterocycloalkylcarbonyl, hydroxy(C$_{3-7}$)-heterocycloalkylcarbonyl, oxo(C$_{3-7}$)heterocycloalkylcarbonyl, (C$_{1-6}$)alkylsulphonyl-(C$_{3-7}$)heterocycloalkylcarbonyl and (C$_{2-6}$)alkoxycarbonyl(C$_{3-7}$)heterocycloalkylcarbonyl.

Illustrative examples of optional substituents on the aromatic or heteroaromatic ring of which the moiety G is the residue include halogen, cyano, trifluoromethyl, hydroxy (C$_{1-6}$)alkyl, carboxy, C$_{2-6}$ alkoxycarbonyl and C$_{1-6}$ alkylaminocarbonyl.

Typical examples of particular substituents on the aromatic or heteroaromatic ring of which the moiety G is the residue include fluoro, chloro, bromo, cyano, methyl, fluoromethyl, difluoromethyl, trifluoromethyl, hydroxy, hydroxymethyl, hydroxyethyl, hydroxyisopropyl, methoxy, difluoromethoxy, trifluoromethoxy, pentafluorothio, methylthio, methylsulphinyl, methylsulphonyl, amino, aminomethyl, methylamino, dimethylamino, formyl, acetyl, carboxy, methoxycarbonyl, ethoxycarbonyl, tert-butoxycarbonyl, aminocarbonyl, methylaminocarbonyl, dimethylaminocarbonyl, aminosulphonyl, methylaminosulphonyl, dimethylaminosulphonyl, methylsulphoximinyl and (methyl)(N-methyl)sulphoximinyl. Additional examples include ethylaminocarbonyl, isopropylaminocarbonyl, hydroxyethylaminocarbonyl, hydroxyisopropylaminocarbonyl, 1-hydroxy-2-methylprop-2-ylaminocarbonyl, methoxyethylaminocarbonyl, cyclopropyl-aminocarbonyl, oxazolylmethylaminocarbonyl, hydroxyoxetanyl, methoxyoxetanyl, piperazinylcarbonyl, hydroxypyrrolidinylcarbonyl, oxopiperazinylcarbonyl, methylsulphonylazetidinylcarbonyl and tert-butoxycarbonylpiperazinylcarbonyl.

Selected examples of particular substituents on the aromatic or heteroaromatic ring of which the moiety G is the residue include fluoro, chloro, bromo, cyano, trifluoromethyl, hydroxyisopropyl, methylthio, methylsulphinyl, methylsulphonyl, carboxy, methoxy-carbonyl, aminocarbonyl, methylaminocarbonyl, ethylaminocarbonyl, isopropylamino-carbonyl, dimethylaminocarbonyl, hydroxyethylaminocarbonyl, hydroxyisopropylamino-carbonyl, 1-hydroxy-2-methylprop-2-ylaminocarbonyl, methoxyethylaminocarbonyl, cyclopropylaminocarbonyl, oxazolylmethylaminocarbonyl, hydroxyoxetanyl, methoxyoxetanyl, piperazinylcarbonyl, hydroxypyrrolidinylcarbonyl, oxopiperazinylcarbonyl, methylsulphonylazetidinylcarbonyl and tert-butoxycarbonylpiperazinylcarbonyl.

Illustrative examples of particular substituents on the aromatic or heteroaromatic ring of which the moiety G is the residue include fluoro, chloro, bromo, cyano, trifluoromethyl, hydroxyisopropyl, carboxy, methoxycarbonyl and methylaminocarbonyl.

Particular values of Y include the groups of formula (Ya-1), (Ya-2), (Ya-3), (Yb-1), (Yb-2), (Yb-3), (Yb-4), (Yb-5), (Yb-6), (Yb-7), (Yc-1) and (Yd-1):

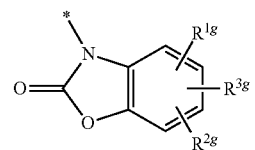
(Ya-1)

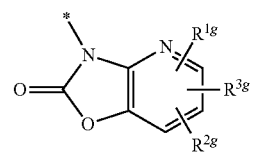
(Ya-2)

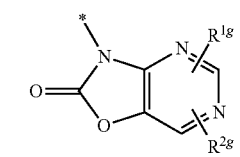
(Ya-3)

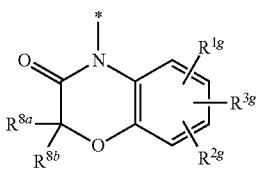
(Yb-1)

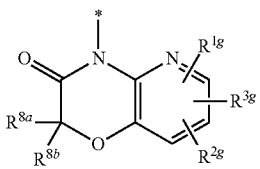
(Yb-2)

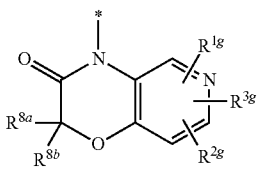
(Yb-3)

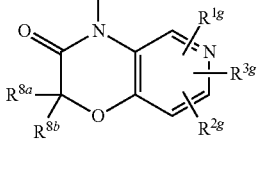
(Yb-4)

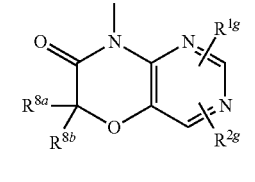
(Yb-5)

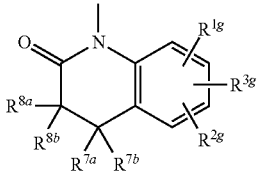
(Yb-5...

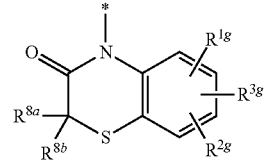
(Yb-6)

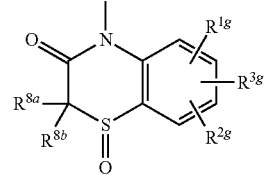
(Yb-7)

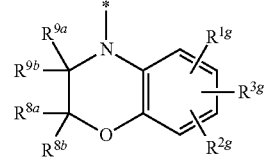
(Yc-1)

(Yd-1)

wherein the asterisk (*) represents the point of attachment to the remainder of the molecule;

$R^{1g}$ represents hydrogen, halogen, cyano, $C_{1-6}$ alkyl, fluoromethyl, difluoromethyl, trifluoromethyl, hydroxy, hydroxy($C_{1-6}$)alkyl, $C_{1-6}$ alkoxy, difluoromethoxy, trifluoromethoxy, pentafluorothio, $C_{1-6}$ alkylthio, $C_{1-6}$ alkylsulphinyl, $C_{1-6}$ alkylsulphonyl, amino, amino($C_{1-6}$)alkyl, $C_{1-6}$ alkylamino, di($C_{1-6}$)alkylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkyl-aminocarbonyl, hydroxy($C_{1-6}$) alkylamino carbonyl, ($C_{1-6}$)alkoxy($C_{1-6}$)alkylaminocarbonyl, ($C_{3-7}$)cycloalkylaminocarbonyl, heteroaryl($C_{1-6}$) alkylaminocarbonyl, aminosulphonyl, $C_{1-6}$ alkylaminosulphonyl, di($C_{1-6}$)alkylaminosulphonyl, ($C_{1-6}$) alkylsulphoximinyl, [($C_{1-6}$)alkyl][N—($C_{1-6}$)alkyl]sulphoximinyl, hydroxy($C_{3-7}$)hetero cyclo alkyl, ($C_{1-6}$)alkoxy-($C_{3-7}$) heterocycloalkyl, ($C_{3-7}$)heterocycloalkylcarbonyl, hydroxy ($C_{3-7}$)heterocycloalkyl-carbonyl, oxo($C_{3-7}$) heterocycloalkylcarbonyl, ($C_{1-6}$)alkylsulphonyl($C_{3-7}$) heterocycloalkyl-carbonyl or ($C_{2-6}$)alkoxycarbonyl($C_{3-7}$) heterocycloalkylcarbonyl;

$R^{2g}$ and $R^{3g}$ independently represent hydrogen or halogen; and $R^{7a}$, $R^{7b}$, $R^{8a}$, $R^{8b}$, $R^{9a}$ and $R^{9b}$ are as defined above.

Suitable values of Y include the groups of formula (Ya-1), (Ya-2), (Ya-3), (Yb-1), (Yb-2), (Yb-3), (Yb-4), (Yb-5), (Yc-1) and (Yd-1) as depicted above.

Appositely, $R^{1g}$ represents hydrogen, halogen, cyano, $C_{1-6}$ alkyl, fluoromethyl, difluoromethyl, trifluoromethyl, hydroxy, hydroxy($C_{1-6}$)alkyl, $C_{1-6}$ alkoxy, difluoromethoxy, trifluoromethoxy, pentafluorothio, $C_{1-6}$ alkylthio, $C_{1-6}$ alkylsulphinyl, $C_{1-6}$ alkylsulphonyl, amino, amino($C_{1-6}$)alkyl, $C_{1-6}$ alkylamino, di($C_{1-6}$)alkylamino, formyl, $C_{2-6}$ alkylcarbonyl, carboxy, $C_{2-6}$ alkoxycarbonyl, aminocarbonyl, $C_{1-6}$ alkylamino-carbonyl, di($C_{1-6}$)alkylaminocarbonyl, aminosulphonyl, $C_{1-6}$ alkylaminosulphonyl, di($C_{1-6}$)alkylaminosulphonyl, ($C_{1-6}$)alkylsulphoximinyl or [($C_{1-6}$)alkyl][N—($C_{1-6}$)alkyl]-sulphoximinyl.

Typically, $R^{1g}$ represents hydrogen, halogen, cyano, trifluoromethyl, hydroxy($C_{1-6}$)alkyl, $C_{1-6}$ alkylthio, $C_{1-6}$ alkylsulphinyl, $C_{1-6}$ alkylsulphonyl, carboxy, $C_{2-6}$ alkoxycarbonyl, aminocarbonyl, $C_{1-6}$ alkylaminocarbonyl, di($C_{1-6}$)alkylaminocarbonyl, hydroxy($C_{1-6}$)alkylaminocarbonyl, ($C_{1-6}$)alkoxy($C_{1-6}$)alkylaminocarbonyl, ($C_{3-7}$)cycloalkylaminocarbonyl, heteroaryl($C_{1-6}$)alkylaminocarbonyl, hydroxy($C_{3-7}$)heterocycloalkyl, ($C_{1-6}$)alkoxy($C_{3-7}$)heterocycloalkyl, ($C_{3-7}$)heterocycloalkylcarbonyl, hydroxy($C_{3-7}$)-heterocycloalkylcarbonyl, oxo($C_{3-7}$)heterocycloalkylcarbonyl, ($C_{1-6}$)alkylsulphonyl($C_{3-7}$)-heterocycloalkylcarbonyl or ($C_{2-6}$)alkoxycarbonyl($C_{3-7}$)heterocycloalkylcarbonyl.

Suitably, $R^{1g}$ represents hydrogen, halogen, cyano, trifluoromethyl, hydroxy($C_{1-6}$)-alkyl, carboxy, $C_{2-6}$ alkoxycarbonyl or $C_{1-6}$ alkylaminocarbonyl.

Typical values of $R^{1g}$ include hydrogen, fluoro, chloro, bromo, cyano, methyl, fluoromethyl, difluoromethyl, trifluoromethyl, hydroxy, hydroxymethyl, hydroxyethyl, hydroxyisopropyl, methoxy, difluoromethoxy, trifluoromethoxy, pentafluorothio, methylthio, methylsulphinyl, methylsulphonyl, amino, aminomethyl, methylamino, dimethylamino, formyl, acetyl, carboxy, methoxycarbonyl, ethoxycarbonyl, tert-butoxycarbonyl, aminocarbonyl, methylaminocarbonyl, dimethylaminocarbonyl, aminosulphonyl, methylaminosulphonyl, dimethylaminosulphonyl, methylsulphoximinyl and (methyl)(N-methyl)sulphoximinyl.

Selected values of $R^{1g}$ include hydrogen, fluoro, chloro, bromo, cyano, trifluoro-methyl, hydroxyisopropyl, methylthio, methylsulphinyl, methylsulphonyl, carboxy, methoxycarbonyl, aminocarbonyl, methylaminocarbonyl, ethylaminocarbonyl, isopropyl-aminocarbonyl, dimethylaminocarbonyl, hydroxyethylaminocarbonyl, hydroxyisopropyl-aminocarbonyl, 1-hydroxy-2-methyl-prop-2-ylaminocarbonyl, methoxyethylamino-carbonyl, cyclopropylaminocarbonyl, oxazolylmethylaminocarbonyl, hydroxyoxetanyl, methoxyoxetanyl, piperazinylcarbonyl, hydroxypyrrolidinylcarbonyl, oxopiperazinyl-carbonyl, methylsulphonylazetidinylcarbonyl and tert-butoxycarbonylpiperazinylcarbonyl.

Illustrative values of $R^{1g}$ include hydrogen, fluoro, chloro, bromo, cyano, trifluoro-methyl, hydroxyisopropyl, carboxy, methoxycarbonyl and methylaminocarbonyl.

In a first embodiment, $R^{2g}$ represents hydrogen. In a second embodiment, $R^{2g}$ represents halogen. In one aspect of that embodiment, $R^{2g}$ especially represents fluoro. In another aspect of that embodiment, $R^{2g}$ represents chloro.

In a first embodiment, $R^{3g}$ represents hydrogen. In a second embodiment, $R^{3g}$ represents halogen, especially fluoro.

Suitably, $R^1$, $R^2$, $R^3$ and $R^4$ independently represent hydrogen, halogen, cyano, trifluoromethyl or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, ($C_{3-7}$)heterocycloalkyl($C_{1-6}$)alkyl-aryl-, heteroaryl-($C_{3-7}$)heterocycloalkyl-, ($C_{3-7}$)cycloalkyl-heteroaryl-, ($C_{3-7}$)cycloalkyl($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)hetero cyclo alkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Examples of optional substituents which may be present on $R^1$, $R^2$, $R^3$ or $R^4$ include one, two or three substituents independently selected from halogen, halo-($C_{1-6}$)alkyl, cyano, cyano($C_{1-6}$)alkyl, nitro, nitro($C_{1-6}$)alkyl, $C_{1-6}$ alkyl, difluoromethyl, trifluoromethyl, difluoroethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, carboxy($C_{3-7}$)cycloalkyl-oxy, $C_{1-3}$ alkylenedioxy, $C_{1-6}$ alkoxy($C_{1-6}$)alkyl, pentafluorothio, $C_{1-6}$ alkylthio, $C_{1-6}$ alkylsulphinyl, $C_{1-6}$ alkylsulphonyl, ($C_{1-6}$)alkylsulphonyl($C_{1-6}$)alkyl, oxo, amino, amino-($C_{1-6}$)alkyl, $C_{1-6}$ alkylamino, di($C_{1-6}$)alkylamino, hydroxy($C_{1-6}$)alkylamino, $C_{1-6}$ alkoxyamino, ($C_{1-6}$)alkoxy($C_{1-6}$)alkylamino, [($C_{1-6}$)alkyl](hydroxy)($C_{1-6}$)alkylamino, [($C_{1-6}$)alkylthio](hydroxy)($C_{1-6}$)alkylamino, N—[($C_{1-6}$)alkyl]-N-[hydroxy($C_{1-6}$)alkyl]amino, di($C_{1-6}$)alkylamino($C_{1-6}$)alkylamino, N-[di($C_{1-6}$)alkylamino($C_{1-6}$)alkyl]-N-[hydroxy($C_{1-6}$)-alkyl]amino, hydroxy($C_{1-6}$)alkyl($C_{3-7}$)cycloalkylamino, (hydroxy)[($C_{3-7}$)cycloalkyl($C_{1-6}$)-alkyl]amino, ($C_{3-7}$)heterocycloalkyl($C_{1-6}$)alkylamino, oxo($C_{3-7}$)hetero cyclo alkyl($C_{1-6}$)alkylamino, ($C_{1-6}$)alkylheteroarylamino, heteroaryl($C_{1-6}$)alkylamino, ($C_{1-6}$)alkylheteroaryl($C_{1-6}$)-alkylamino, $C_{2-6}$ alkylcarbonylamino, N—[($C_{1-6}$)alkyl]-N—[($C_{2-6}$)alkylcarbonyl]amino, ($C_{2-6}$)-alkylcarbonylamino($C_{1-6}$)alkyl, $C_{3-6}$ alkenylcarbonylamino, bis[($C_{3-6}$)alkenylcarbonyl]-amino, N—[($C_{1-6}$)alkyl]-N—[($C_{3-7}$)cycloalkylcarbonyl]amino, $C_{2-6}$ alkoxycarbonylamino, $C_{2-6}$ alkoxycarbonyl($C_{1-6}$)alkylamino, $C_{1-6}$ alkylaminocarbonylamino, $C_{1-6}$ alkylsulphonyl-amino, N—[($C_{1-6}$)alkyl]-N—[($C_{1-6}$)alkylsulphonyl]amino, bis[($C_{1-6}$)alkylsulphonyl]amino, N—[($C_{1-6}$)alkyl]-N-[carboxy($C_{1-6}$)alkyl]amino, carboxy($C_{3-7}$)cycloalkylamino, carboxy-($C_{3-7}$)cycloalkyl($C_{1-6}$)alkylamino, formyl, $C_{2-6}$ alkylcarbonyl, ($C_{3-7}$)cycloalkylcarbonyl, phenylcarbonyl, ($C_{2-6}$)alkylcarbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, a carboxylic acid isostere or prodrug moiety $\Omega$, —($C_{1-6}$)alkyl-$\Omega$, aminocarbonyl, $C_{1-6}$ alkylaminocarbonyl, hydroxy($C_{1-6}$)alkylamino-carbonyl, di($C_{1-6}$)alkylaminocarbonyl, aminocarbonyl($C_{1-6}$)alkyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl. Additional examples include trifluoromethylsulphoximinyl, [($C_{1-6}$)alkyl]-[N-carboxy($C_{1-6}$)alkyl]sulphoximinyl, [N—($C_{2-6}$)alkoxycarbonyl ($C_{1-6}$)alkyl][($C_{1-6}$)alkyl]-sulphoximinyl, ($C_{3-7}$)cycloalkylsulphoximinyl and N-[di($C_{1-6}$)alkylsulfoxo]iminyl.

By the expression "carboxylic acid isostere or prodrug moiety" is meant any functional group, structurally distinct from a carboxylic acid moiety, that will be recognised by a biological system as being similar to, and thus capable of mimicking, a carboxylic acid moiety, or will be readily convertible by a biological system in vivo into a carboxylic acid moiety. A synopsis of some common carboxylic acid isosteres is presented by N. A. Meanwell in *J. Med. Chem.*, 2011, 54, 2529-2591 (cf. in particular FIGS. 25 and 26). An alternative carboxylic acid isostere is described by N Pemberton et al. in *ACS Med. Chem. Lett.*, 2012, 3, 574-578. Typical examples of suitable carboxylic acid isostere or prodrug moieties represented by $\Omega$ include the functional groups of formula (i) to (xliii):

(i)

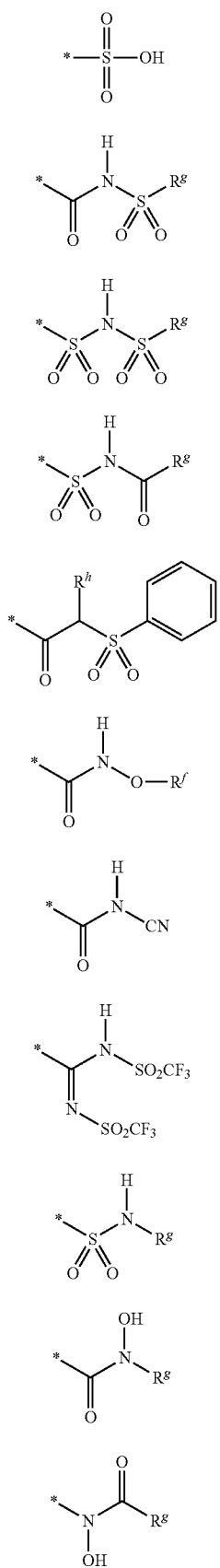
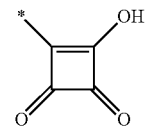
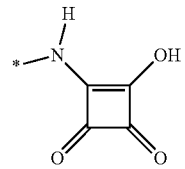
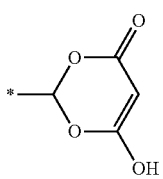
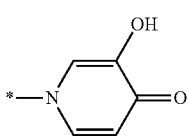
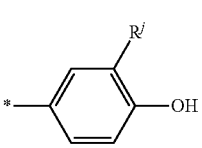
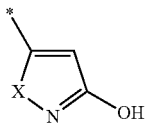
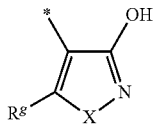
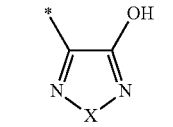
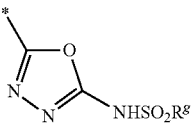
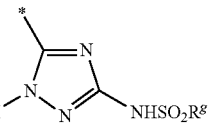
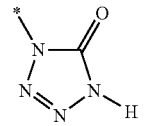

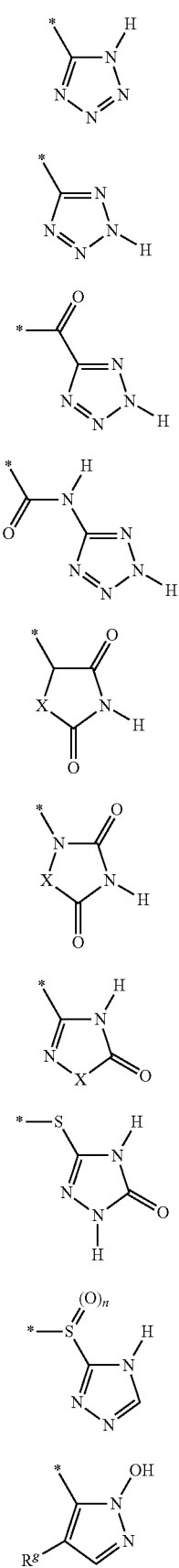
(xxiv)
(xxv)
(xxvi)
(xxvii)
(xxviii)
(xxix)
(xxx)
(xxxi)
(xxxii)
(xxxiii)
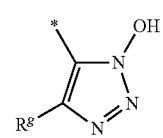
(xxxiv)
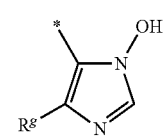
(xxxv)
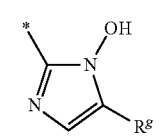
(xxxvi)
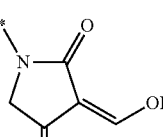
(xxxvii)
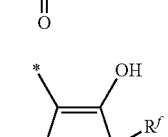
(xxxviii)
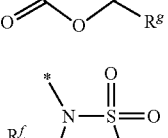
(xxxix)
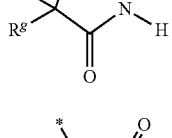
(xl)
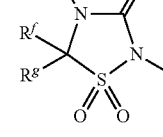
(xli)
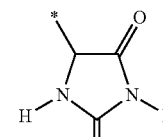
(xlii)
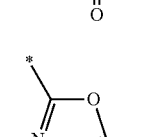
(xliii)
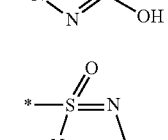

wherein the asterisk (*) represents the site of attachment to the remainder of the molecule;

n is zero, 1 or 2;

X represents oxygen or sulphur;

$R^f$ represents hydrogen, $C_{1-6}$ alkyl or —CH$_2$CH(OH)CH$_2$OH;

$R^g$ represents $C_{1-6}$ alkyl, trifluoromethyl, —CH$_2$CH$_2$F, —CH$_2$CHF$_2$, —CH$_2$CF$_3$ or —CF$_2$CF$_3$;

$R^h$ represents hydrogen, cyano or —CO$_2$R$^d$, in which $R^d$ is as defined above; and $R^j$ represents hydrogen or halogen.

In one embodiment, n is zero. In another embodiment, n is 1. In a further embodiment, n is 2.

In one embodiment, X represents oxygen. In another embodiment, X represents sulphur.

In one embodiment, $R^f$ represents hydrogen. In another embodiment, $R^f$ represents $C_{1-6}$ alkyl, especially methyl. In a further embodiment, $R^f$ is —CH$_2$CH(OH)CH$_2$OH.

In one embodiment, $R^g$ represents $C_{1-6}$ alkyl, especially methyl. In another embodiment, $R^g$ represents trifluoromethyl, —CH$_2$CH$_2$F, —CH$_2$CHF$_2$, —CH$_2$CF$_3$ or —CF$_2$CF$_3$. In a first aspect of that embodiment, $R^g$ represents trifluoromethyl. In a second aspect of that embodiment, $R^g$ represents —CH$_2$CH$_2$F. In a third aspect of that embodiment, $R^g$ represents —CH$_2$CHF$_2$. In a fourth aspect of that embodiment, $R^g$ represents —CH$_2$CF$_3$. In a fifth aspect of that embodiment, $R^g$ represents —CF$_2$CF$_3$.

In one embodiment, $R^h$ is hydrogen. In another embodiment, $R^h$ represents cyano. In a further embodiment, $R^h$ represents —CO$_2$R$^d$, especially methoxycarbonyl.

In one embodiment, $R^j$ represents hydrogen. In another embodiment, $R^j$ represents halogen, especially chloro.

In a selected embodiment, Ω represents tetrazolyl, especially a C-linked tetrazolyl moiety of formula (xxiv) or (xxv) as depicted above, in particular a group of formula (xxiv) as depicted above.

In another embodiment, Ω represents $C_{1-6}$ alkylsulphonylaminocarbonyl, i.e. a moiety of formula (iii) as depicted above wherein $R^g$ represents $C_{1-6}$ alkyl.

In another embodiment, Ω represents $C_{1-6}$ alkylaminosulphonyl, i.e. a moiety of formula (x) as depicted above wherein $R^g$ represents $C_{1-6}$ alkyl.

In a further embodiment, Ω represents (C$_{1-6}$)alkylcarbonylaminosulphonyl, i.e. a moiety of formula (v) as depicted above wherein $R^g$ represents $C_{1-6}$ alkyl.

Selected examples of optional substituents which may be present on $R^1$, $R^2$, $R^3$ or $R^4$ include one, two or three substituents independently selected from halogen, $C_{1-6}$ alkyl, trifluoromethyl, difluoroethyl, hydroxy, hydroxy(C$_{1-6}$)alkyl, pentafluorothio, $C_{1-6}$ alkyl-sulphonyl, oxo, amino, carboxy, $C_{2-6}$ alkoxycarbonyl, (C$_{1-6}$)alkylsulphoximinyl, trifluoromethylsulphoximinyl, [(C$_{1-6}$)alkyl][N—(C$_{1-6}$)alkyl]sulphoximinyl, [(C$_{1-6}$)alkyl]-[N-carboxy (C$_{1-6}$)alkyl]sulphoximinyl, [N—(C$_{2-6}$)alkoxycarbonyl(C$_{1-6}$)alkyl][(C$_{1-6}$)alkyl]-sulphoximinyl, (C$_{3-7}$)cycloalkylsulphoximinyl and N-[di(C$_{1-6}$)alkylsulfoxo]iminyl.

Typical examples of optional substituents which may be present on $R^1$, $R^2$, $R^3$ or $R^4$ include one, two or three substituents independently selected from halogen, $C_{1-6}$ alkyl, trifluoromethyl, difluoroethyl, hydroxy, hydroxy (C$_{1-6}$)alkyl, pentafluorothio, $C_{1-6}$ alkyl-sulphonyl, oxo, carboxy and $C_{2-6}$ alkoxycarbonyl.

Examples of particular substituents on $R^1$, $R^2$, $R^3$ or $R^4$ include fluoro, chloro, bromo, fluoromethyl, fluoroisopropyl, cyano, cyanoethyl, nitro, nitromethyl, methyl, ethyl, isopropyl, isobutyl, tert-butyl, difluoromethyl, trifluoromethyl, difluoroethyl, trifluoro-ethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylene-dioxy, ethylenedioxy, methoxymethyl, methoxyethyl, pentafluorothio, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethyl-amino, (hydroxy)(methoxy)(methyl)propylamino, (hydroxy)(methylthio)butylamino, N-(hydroxyethyl)-N-(methyl)amino, dimethylaminoethylamino, (dimethylamino)(methyl)-propylamino, N-(dimethylaminoethyl)-N-(hydroxyethyl)amino, hydroxymethyl-cyclopentylamino, hydroxycyclobutylmethylamino, (cyclopropyl)(hydroxy)propylamino, morpholinylethylamino, oxopyrrolidinylmethylamino, ethyloxadiazolylamino, methyl-thiadiazolylamino, thiazolylmethylamino, thiazolylethylamino, pyrimidinylmethylamino, methylpyrazolylmethylamino, acetylamino, N-acetyl-N-methylamino, N-isopropyl-carbonyl-N-methylamino, acetylaminomethyl, ethenylcarbonylamino, bis(ethenyl-carbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis(methylsulphonyl)amino, N-(carboxymethyl)-N-methyl-amino, N-(carboxyethyl)-N-methylamino, carboxycyclopentylamino, carboxycyclopropyl-methylamino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonyl-methylidenyl, methylsulphonylaminocarbonyl, acetylaminosulphonyl, methoxyamino-carbonyl, tetrazolyl, tetrazolylmethyl, hydroxyoxadiazolyl, aminocarbonyl, methylamino-carbonyl, hydroxyethylaminocarbonyl, dimethylaminocarbonyl, aminocarbonylmethyl, aminosulphonyl, methylaminosulphonyl, dimethylaminosulphonyl, methylsulphoximinyl and (methyl)(N-methyl)sulphoximinyl. Additional examples include ethylsulphoximinyl, trifluoromethylsulphoximinyl, (N-carboxymethyl)(methyl)sulphoximinyl, (N-tert-butoxycarbonylmethyl)(methyl)sulphoximinyl, cyclopropylsulphoximinyl and N-(dimethyl-sulfoxo)iminyl.

Selected examples of particular substituents on $R^1$, $R^2$, $R^3$ or $R^4$ include fluoro, methyl, ethyl, trifluoromethyl, difluoroethyl, hydroxy, hydroxyisopropyl, pentafluorothio, methylsulphonyl, oxo, amino, carboxy, methoxycarbonyl, ethoxycarbonyl, tert-butoxy-carbonyl, methylsulphoximinyl, ethylsulphoximinyl, trifluoromethylsulphoximinyl, (methyl)(N-methyl)sulphoximinyl, (N-carboxymethyl)(methyl)sulphoximinyl, (N-tert-butoxycarbonylmethyl)(methyl)sulphoximinyl, cyclopropylsulphoximinyl and N-(dimethylsulfoxo)iminyl.

Typical examples of particular substituents on $R^1$, $R^2$, $R^3$ or $R^4$ include fluoro, methyl, trifluoromethyl, difluoroethyl, hydroxy, hydroxyisopropyl, pentafluorothio, methylsulphonyl, oxo, carboxy, methoxycarbonyl, ethoxycarbonyl and tert-butoxy-carbonyl.

Typically, $R^1$ represents hydrogen, halogen, cyano or —CO$_2$R$^d$; or $C_{1-6}$ alkyl, $C_{2-6}$ alkynyl, aryl, $C_{3-7}$ heterocycloalkyl, $C_{3-7}$ heterocycloalkenyl, heteroaryl, (C$_{3-7}$)heterocycloalkyl(C$_{1-6}$)alkyl-aryl-, heteroaryl(C$_{3-7}$)heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$hetero cyclo alkyl$(C_{1-6})$alkyl-hetero aryl-, $(C_{3-7})$hetero cyclo alkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Suitably, $R^1$ represents halogen, cyano or —$CO_2R^d$; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$hetero cyclo alkyl-hetero aryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

Generally, $R^1$ represents halogen or cyano; or $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl$(C_{3-7})$heterocycloalkyl-, $(C_{3-7})$cycloalkyl-heteroaryl-, $(C_{3-7})$cycloalkyl-$(C_{1-6})$alkyl-hetero aryl-, $(C_{4-7})$ cyclo alkenyl-hetero aryl-, $(C_{4-9})$bicycloalkyl-heteroaryl-, $(C_{3-7})$heterocycloalkyl-heteroaryl-, $(C_{3-7})$hetero cyclo alkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

More generally, $R^1$ represents halogen; or $R^1$ represents aryl, $C_{3-7}$ heterocycloalkyl, heteroaryl, $(C_{3-7})$cycloalkyl-heteroaryl-, $(C_{3-7})$heterocycloalkyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents.

In a first embodiment, $R^1$ represents hydrogen.

In a second embodiment, $R^1$ represents halogen. In one aspect of that embodiment, $R^1$ represents bromo.

In a third embodiment, $R^1$ represents cyano.

In a fourth embodiment, $R^1$ represents —$CO_2R^d$.

In a fifth embodiment, $R^1$ represents optionally substituted $C_{1-6}$ alkyl. In one aspect of that embodiment, $R^1$ represents optionally substituted ethyl.

In a sixth embodiment, $R^1$ represents optionally substituted $C_{2-6}$ alkynyl. In one aspect of that embodiment, $R^1$ represents optionally substituted butyryl.

In a seventh embodiment, $R^1$ represents optionally substituted aryl. In one aspect of that embodiment, $R^1$ represents optionally substituted phenyl.

In an eighth embodiment, $R^1$ represents optionally substituted $C_{3-7}$ heterocycloalkyl.

In a ninth embodiment, $R^1$ represents optionally substituted $C_{3-7}$ heterocycloalkenyl.

In a tenth embodiment, $R^1$ represents optionally substituted heteroaryl. In selected aspects of that embodiment, $R^1$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In an eleventh embodiment, $R^1$ represents optionally substituted $(C_{3-7})$-heterocycloalkyl$(C_{1-6})$alkyl-aryl-. In a first aspect of that embodiment, $R^1$ represents optionally substituted pyrrolidinylmethylphenyl-. In a second aspect of that embodiment, $R^1$ represents optionally substituted piperazinylmethylphenyl-.

In a twelfth embodiment, $R^1$ represents optionally substituted heteroaryl$(C_{3-7})$-heterocycloalkyl-. In one aspect of that embodiment, $R^1$ represents optionally substituted pyridinylpiperazinyl-.

In a thirteenth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclobutylpyridinyl-. In a third aspect of that embodiment, $R^1$ represents optionally substituted cyclohexylpyridinyl-. In a fourth aspect of that embodiment, $R^1$ represents optionally substituted cyclopropylpyrimidinyl-. In a fifth aspect of that embodiment, $R^1$ represents optionally substituted cyclobutylpyrimidinyl-. In a sixth aspect of that embodiment, $R^1$ represents optionally substituted cyclopentylpyrimidinyl-. In a seventh aspect of that embodiment, $R^1$ represents optionally substituted cyclohexyl-pyrimidinyl-. In an eighth aspect of that embodiment, $R^1$ represents optionally substituted cyclohexylpyrazinyl-.

In a fourteenth embodiment, $R^1$ represents optionally substituted $(C_{4-7})$-cycloalkenyl-heteroaryl-.

In a fifteenth embodiment, $R^1$ represents optionally substituted $(C_{3-7})$-heterocycloalkyl-heteroaryl-. In a first aspect of that embodiment, $R^1$ represents optionally substituted pyrrolidinylpyridinyl-. In a second aspect of that embodiment, $R^1$ represents optionally substituted tetrahydropyranylpyridinyl-. In a third aspect of that embodiment, $R^1$ represents optionally substituted piperidinylpyridinyl-. In a fourth aspect of that embodiment, $R^1$ represents optionally substituted piperazinylpyridinyl-. In a fifth aspect of that embodiment, $R^1$ represents optionally substituted morpholinylpyridinyl-. In a sixth aspect of that embodiment, $R^1$ represents optionally substituted thiomorpholinyl-pyridinyl-. In a seventh aspect of that embodiment, $R^1$ represents optionally substituted diazepanylpyridinyl-. In an eighth aspect of that embodiment, $R^1$ represents optionally substituted oxetanylpyrimidinyl-. In a ninth aspect of that embodiment, $R^1$ represents optionally substituted azetidinylpyrimidinyl-. In a tenth aspect of that embodiment, $R^1$ represents optionally substituted tetrahydrofuranylpyrimidinyl-. In an eleventh aspect of that embodiment, $R^1$ represents optionally substituted pyrrolidinylpyrimidinyl-. In a twelfth aspect of that embodiment, $R^1$ represents optionally substituted tetrahydropyranyl-pyrimidinyl-. In a thirteenth aspect of that embodiment, $R^1$ represents optionally substituted piperidinylpyrimidinyl-. In a fourteenth aspect of that embodiment, $R^1$ represents optionally substituted piperazinylpyrimidinyl-. In a fifteenth aspect of that embodiment, $R^1$ represents optionally substituted morpholinylpyrimidinyl-. In a sixteenth aspect of that embodiment, $R^1$ represents optionally substituted thiomorpholinyl-pyrimidinyl-. In a seventeenth aspect of that embodiment, $R^1$ represents optionally substituted azepanylpyrimidinyl-. In an eighteenth aspect of that embodiment, $R^1$ represents optionally substituted oxazepanylpyrimidinyl-. In a nineteenth aspect of that embodiment, $R^1$ represents optionally substituted diazepanylpyrimidinyl-. In a twentieth aspect of that embodiment, $R^1$ represents optionally substituted thiadiazepanyl-pyrimidinyl-. In a twenty-first aspect of that embodiment, $R^1$ represents optionally substituted oxetanylpyrazinyl-. In a twenty-second aspect of that embodiment, $R^1$ represents optionally substituted piperidinylpyrazinyl-.

In a sixteenth embodiment, $R^1$ represents optionally substituted $(C_{3-7})$-heterocycloalkyl$(C_{1-6})$alkyl-heteroaryl-. In a first aspect of that embodiment, $R^1$ represents optionally substituted morpholinylmethylthienyl-. In a second aspect of that embodiment, $R^1$ represents optionally substituted morpholinylethylpyrazolyl-.

In a seventeenth embodiment, $R^1$ represents optionally substituted $(C_{3-7})$-heterocycloalkenyl-heteroaryl-.

In an eighteenth embodiment, $R^1$ represents optionally substituted $(C_{4-9})$-heterobicycloalkyl-heteroaryl-.

In a nineteenth embodiment, $R^1$ represents optionally substituted $(C_{4-9})$-spiroheterocycloalkyl-heteroaryl-.

In a twentieth embodiment, $R^1$ represents optionally substituted $(C_{3-7})$cycloalkyl-$(C_{1-6})$alkyl-heteroaryl-. In one aspect of that embodiment, $R^1$ represents optionally substituted cyclohexylmethylpyrimidinyl-.

In a twenty-first embodiment, $R^1$ represents optionally substituted $(C_{4-9})$-bicycloalkyl-heteroaryl-.

Appositely, $R^1$ represents hydrogen, bromo, iodo or —$CO_2R^d$; or ethyl, butynyl, phenyl, pyrrolidinyl, piperidinyl, piperazinyl, morpholinyl, 1,2,3,6-tetrahydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexyl-pyrimidinyl, cyclohexylpyrazinyl, cyclohexyl-methylpyrimidinyl, cyclohexenylpyridinyl, cyclohexenylpyrimidinyl, bicyclo[3.1.0]hexanylpyridinyl, bicyclo[3.1.0]hexanyl-pyrimidinyl, bicyclo[4.1.0]heptanylpyrimidinyl, bicyclo[2.2.2]octanylpyrimidinyl, pyrrolidinylpyridinyl, tetrahydropyranylpyridinyl, piperidinylpyridinyl, piperazinyl-pyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinyl-pyrimidinyl, tetrahydropyranylpyrimidinyl, piperidinylpyrimidinyl, piperazinyl-pyrimidinyl, hexahydro-[1,2,5]thiadiazolo[2,3-a]pyrazinylpyrimidinyl, morpholinyl-pyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinyl-pyrazinyl, morpholinylmethylthienyl, morpholinylethylpyrazolyl, 3-azabicyclo[3.1.0]hexanylpyridinyl, 3-azabicyclo[3.1.0]hexanylpyridazinyl, 3-azabicyclo[3.1.0]hexanyl-pyrimidinyl, 2-oxa-5-azabicyclo[2.2.1]heptanylpyrimidinyl, 3-azabicyclo[3.1.1]heptanyl-pyrimidinyl, 6-oxa-3-azabicyclo[3.1.1]heptanylpyrimidinyl, 3-azabicyclo[4.1.0]heptanyl-pyrimidinyl, 3-azabicyclo[4.1.0]heptanylpyrimidinyl, 2-oxabicyclo[2.2.2]octanyl-pyrimidinyl, 3-azabicyclo[3.2.1]octanylpyrimidinyl, 8-azabicyclo[3.2.1]octanylpyrimidinyl, 3-oxa-8-azabicyclo[3.2.1]octanylpyrimidinyl, 3,6-diazabicyclo[3.2.2]-nonanylpyrimidinyl, 3-oxa-7-azabicyclo[3.3.1]nonanylpyrimidinyl, 3,7-dioxa-9-azabicyclo[3.3.1]nonanylpyrimidinyl, 5-azaspiro[2.3]hexanylpyrimidinyl, 5-azaspiro-[2.4]heptanylpyrimidinyl, 2-azaspiro[3.3]heptanylpyrimidinyl, 2-oxa-6-azaspiro[3.3]-heptanylpyrimidinyl, 3-oxa-6-azaspiro[3.3]heptanylpyrimidinyl, 6-thia-2-azaspiro[3.3]-heptanylpyrimidinyl, 2-oxa-6-azaspiro[3.4]octanylpyrimidinyl, 2-oxa-6-azaspiro[3.5]-nonanylpyrimidinyl, 2-oxa-7-azaspiro[3.5]nonanylpyrimidinyl or 2,4,8-triazaspiro[4.5]-decanylpyrimidinyl, any of which groups may be optionally substituted by one or more substituents. Additionally, $R^1$ may represent cyclobutylpyridinyl, which group may be optionally substituted by one or more substituents.

Selectively, $R^1$ represents bromo; or $R^1$ represents phenyl, morpholinyl, pyrazolyl, pyridinyl, pyrimidinyl, cyclobutylpyridinyl, cyclopropylpyrimidinyl, cyclobutyl-pyrimidinyl, cyclohexylpyrimidinyl, tetrahydropyranylpyridinyl, piperazinylpyridinyl, oxetanylpyrimidinyl, azetidinylpyrimidinyl, tetrahydropyranylpyrimidinyl, piperidinyl-pyrimidinyl, piperazinylpyrimidinyl, morpholinylpyrimidinyl, diazepanylpyrimidinyl, 6-oxa-3-azabicyclo[3.1.1]heptanylpyrimidinyl, 3-azabicyclo[3.2.1]octanylpyrimidinyl, 3,7-dioxa-9-azabicyclo[3.3.1]nonanylpyrimidinyl, 3-oxa-6-azaspiro[3.3]heptanylpyrimidinyl or 6-thia-2-azaspiro[3.3]heptanylpyrimidinyl, any of which groups may be optionally substituted by one or more substituents.

Illustratively, $R^1$ represents bromo or iodo; or $R^1$ represents phenyl, morpholinyl, pyrazolyl, pyridinyl, pyrimidinyl, cyclopropylpyrimidinyl, cyclobutylpyrimidinyl, cyclohexylpyrimidinyl, piperazinylpyrimidinyl, oxetanylpyrimidinyl, azetidinylpyrimidinyl, tetrahydropyranylpyrimidinyl, piperidinylpyrimidinyl, piperazinylpyrimidinyl, morpholinylpyrimidinyl, diazepanylpyrimidinyl, 6-oxa-3-azabicyclo[3.1.1]heptanyl-pyrimidinyl, 3-azabicyclo[3.2.1]octanylpyrimidinyl, 3,7-dioxa-9-azabicyclo[3.3.1]-nonanylpyrimidinyl, 3-oxa-6-azaspiro[3.3]heptanylpyrimidinyl or 6-thia-2-azaspiro[3.3]-heptanylpyrimidinyl, any of which groups may be optionally substituted by one or more substituents.

Typical examples of optional substituents on $R^1$ include one, two or three substituents independently selected from halogen, halo$(C_{1-6})$alkyl, cyano, cyano$(C_{1-6})$alkyl, nitro$(C_{1-6})$alkyl, $C_{1-6}$ alkyl, trifluoromethyl, difluoroethyl, trifluoroethyl, $C_{2-6}$ alkenyl, hydroxy, hydroxy$(C_{1-6})$alkyl, $C_{1-6}$ alkoxy, trifluoroethoxy, carboxy$(C_{3-7})$cycloalkyloxy, pentafluorothio, $C_{1-6}$ alkylthio, $C_{1-6}$ alkylsulphonyl, $(C_{1-6})$alkylsulphonyl$(C_{1-6})$alkyl, oxo, amino, amino$(C_{1-6})$alkyl, $C_{1-6}$ alkylamino, di$(C_{1-6})$alkylamino, $(C_{1-6})$alkoxy$(C_{1-6})$alkyl-amino, N—[$(C_{1-6})$alkyl]-N-[hydroxy$(C_{1-6})$alkyl]amino, $(C_{2-6})$alkylcarbonylamino$(C_{1-6})$alkyl, $C_{1-6}$ alkylsulphonylamino, N—[$(C_{1-6})$alkyl]-N—[$(C_{1-6})$alkylsulphonyl]amino, bis[$(C_{1-6})$alkyl-sulphonyl]amino, N—[$(C_{1-6})$alkyl]-N-[carboxy$(C_{1-6})$alkyl]amino, carboxy$(C_{3-7})$cycloalkyl-amino, carboxy$(C_{3-7})$cycloalkyl$(C_{1-6})$alkylamino, formyl, $C_{2-6}$ alkylcarbonyl, $(C_{2-6})$alkyl-carbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonyl-methylidenyl, a carboxylic acid isostere or prodrug moiety Ω as defined herein, —$(C_{1-6})$alkyl-Ω, aminocarbonyl, aminosulphonyl, $(C_{1-6})$alkylsulphoximinyl and [$(C_{1-6})$alkyl][N—$(C_{1-6})$alkyl]sulphoximinyl. Additional examples include trifluoromethyl-sulphoximinyl, [$(C_{1-6})$alkyl][N-carboxy$(C_{1-6})$alkyl]sulphoximinyl, [N—$(C_{2-6})$alkoxy-carbonyl$(C_{1-6})$alkyl][$(C_{1-6})$alkyl]sulphoximinyl, $(C_{3-7})$cycloalkylsulphoximinyl and N-[di$(C_{1-6})$alkylsulfoxo]iminyl.

Selected examples of optional substituents on $R^1$ include one, two or three substituents independently selected from halogen, $C_{1-6}$ alkyl, trifluoromethyl, difluoro-ethyl, hydroxy, hydroxy$(C_{1-6})$alkyl, pentafluorothio, $C_{1-6}$ alkylsulphonyl, oxo, amino, carboxy, $C_{2-6}$ alkoxycarbonyl, $(C_{1-6})$alkylsulphoximinyl, trifluoromethylsulphoximinyl, [$(C_{1-6})$alkyl][N—$(C_{1-6})$alkyl]sulphoximinyl, [$(C_{1-6})$alkyl][N-carboxy$(C_{1-6})$alkyl]-sulphoximinyl, [N—$(C_{2-6})$alkoxycarbonyl$(C_{1-6})$alkyl][$(C_{1-6})$alkyl]sulphoximinyl, $(C_{3-7})$cycloalkylsulphoximinyl and N-[di$(C_{1-6})$alkylsulfoxo]iminyl.

Suitable examples of optional substituents on $R^1$ include one, two or three substituents independently selected from halogen, $C_{1-6}$ alkyl, trifluoromethyl, difluoro-ethyl, hydroxy, hydroxy$(C_{1-6})$alkyl, pentafluorothio, $C_{1-6}$ alkylsulphonyl, oxo, carboxy and $C_{2-6}$ alkoxycarbonyl.

Typical examples of particular substituents on $R^1$ include one, two or three substituents independently selected from fluoro, chloro, fluoromethyl, fluoroisopropyl, cyano, cyanoethyl, nitromethyl, methyl, ethyl, isopropyl, trifluoromethyl, difluoroethyl, ethenyl, hydroxy, hydroxymethyl, hydroxyisopropyl, methoxy, isopropoxy, trifluoro-ethoxy, carboxycyclobutyloxy, pentafluorothio, methylthio, methylsulphonyl, methyl-sulphonylethyl, oxo, amino, aminomethyl, aminoisopropyl, methylamino, dimethylamino, methoxyethylamino, N-(hydroxyethyl)-N-(methyl)amino, acetylaminomethyl, methyl-sulphonylamino, N-methyl-N-(methylsulphonyl)amino, bis(methylsulphonyl)amino, N-(carboxyethyl)-N-(methyl)amino, carboxycyclopentylamino, carboxycyclopropylmethyl-amino, formyl, acetyl, acetoxyisopropyl, carboxy, carboxymethyl, carboxyethyl, methoxy-carbonyl, ethoxycarbonyl, n-butoxycarbonyl, tert-butoxycarbonyl, methoxycarbonyl-methyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, aminosulphonyl, methylsulphoximinyl and (methyl)(N-methyl)sulphoximinyl. Additional examples include ethylsulphoximinyl, trifluoromethylsulphoximinyl, (N-carboxymethyl)-(methyl)sulphoximinyl, (N-tert-butoxycarbonylmethyl)(methyl)sulphoximinyl, cyclopropylsulphoximinyl and N-(dimethylsulfoxo)iminyl.

Selected examples of particular substituents on $R^1$ include fluoro, methyl, ethyl, trifluoromethyl, difluoroethyl, hydroxy, hydroxyisopropyl, pentafluorothio, methyl-sulphonyl, oxo, amino, carboxy, methoxycarbonyl, ethoxycarbonyl, tert-butoxycarbonyl, methylsulphoximinyl, ethylsulphoximinyl, trifluoromethylsulphoximinyl, (methyl)(N-methyl)sulphoximinyl, (N-carboxymethyl)(methyl)sulphoximinyl, (N-tert-butoxycarbonyl-methyl)(methyl)sulphoximinyl, cyclopropylsulphoximinyl and N-(dimethylsulfoxo)iminyl.

Suitable examples of particular substituents on $R^1$ include one, two or three substituents independently selected from fluoro, methyl, trifluoromethyl, difluoroethyl, hydroxy, hydroxyisopropyl, pentafluorothio, methylsulphonyl, oxo, carboxy, methoxy-carbonyl, ethoxycarbonyl and tert-butoxycarbonyl.

In a particular embodiment, $R^1$ is substituted by hydroxy $(C_{1-6})$alkyl. In one aspect of that embodiment, $R^1$ is substituted by hydroxyisopropyl, especially 2-hydroxyprop-2-yl.

Selected values of $R^1$ include hydrogen, bromo, iodo, —$CO_2R^d$, methoxycarbonyl-ethyl, ethoxycarbonylethyl, hydroxybutynyl, chlorophenyl, hydroxyphenyl, pentafluoro-thiophenyl, methylsulphonylphenyl, aminomethylphenyl, aminoisopropylphenyl, acetyl-aminomethylphenyl, acetylphenyl, methoxycarbonylphenyl, aminocarbonylphenyl, aminosulphonylphenyl, acetylaminosulphonylphenyl, (methoxycarbonyl)(methyl)-pyrrolidinyl, oxopiperidinyl, ethoxycarbonylpiperidinyl, methylsulphonylpiperazinyl, morpholinyl, methylsulphonyl-1,2,3,6-tetrahydropyridinyl, acetyl-1,2,3,6tetrahydropyridinyl, -tert-butoxycarbonyl-1,2,3,6-tetrahydropyridinyl, methoxycarbonyl-methyl-1,2,3,6-tetrahydropyridinyl, benzofuryl, thienyl, indolyl, pyrazolyl, methyl-pyrazolyl, dimethylpyrazolyl, (methyl)[N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, fluoropyridinyl, cyanopyridinyl, methylpyridinyl, (cyano)-(methyl)pyridinyl, dimethylpyridinyl, trifluoromethylpyridinyl, ethenylpyridinyl, hydroxyisopropylpyridinyl, methoxypyridinyl, (methoxy)(methyl)pyridinyl, isopropoxy-pyridinyl, trifluoroethoxypyridinyl, (methyl)(trifluoroethoxy)pyridinyl, methylsulphonyl-pyridinyl, oxopyridinyl, (methyl)(oxo)pyridinyl, (dimethyl)(oxo)pyridinyl, amino-pyridinyl, methylaminopyridinyl, dimethylaminopyridinyl, methoxyethylaminopyridinyl, N-(hydroxyethyl)-N-(methyl)aminopyridinyl, methylsulphonylaminopyridinyl, [bis(methylsulphonyl)amino]pyridinyl, carboxypyridinyl, quinolinyl, hydroxypyridazinyl, pyrimidinyl, fluoroisopropylpyrimidinyl, difluoroethylpyrimidinyl, hydroxyisopropyl-pyrimidinyl, methoxypyrimidinyl, carboxycyclobutyloxypyrimidinyl, methylthio-pyrimidinyl, methylsulphonylpyrimidinyl, oxopyrimidinyl, aminopyrimidinyl, dimethyl-aminopyrimidinyl, methoxyethylaminopyrimidinyl, N-(carboxyethyl)-N-(methyl)amino-pyrimidinyl, carboxycyclopentylaminopyrimidinyl, carboxycyclopropylmethylaminopyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinyl-methylphenyl, pyridinylpiperazinyl, carboxycyclohexylpyrazolyl, carboxycyclohexyl-pyridinyl, fluoromethylcyclopropylpyrimidinyl, hydroxycyclopropylpyrimidinyl, acetyl-aminomethylcyclopropylpyrimidinyl, hydroxycyclobutylpyrimidinyl, (difluoro)-(hydroxy)cyclobutylpyrimidinyl, carboxycyclopentylpyrimidinyl, carboxycyclohexylpyrimidinyl, (carboxy)(methyl)cyclohexylpyrimidinyl, (carboxy)(hydroxy)cyclohexyl-pyrimidinyl, carboxymethylcyclohexylpyrimidinyl, ethoxycarbonylcyclohexyl-pyrimidinyl, (methoxycarbonyl)(methyl)cyclohexylpyrimidinyl, (ethoxycarbonyl)-(methyl)cyclohexylpyrimidinyl, carboxycyclohexylpyrazinyl, carboxycyclohexylmethyl-pyrimidinyl, carboxycyclohexenylpyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexanylpyrimidinyl, ethoxycarbonylbicyclo[3.1.0]hexanyl-pyrimidinyl, carboxybicyclo[4.1.0]heptanylpyrimidinyl, carboxybicyclo[2.2.2]octanyl-pyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)piperidinyl](fluoro)pyridinyl, [(carboxy)(methyl)piperidinyl](chloro)pyridinyl, piperazinylpyridinyl, (methyl)-(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)-(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, fluorooxetanylpyrimidinyl, hydroxyoxetanylpyrimidinyl, difluoroazetidinylpyrimidinyl, hydroxyazetidinyl-pyrimidinyl, (hydroxy)(methyl)azetidinylpyrimidinyl, (hydroxy)(trifluoromethyl)-azetidinylpyrimidinyl, carboxyazetidinylpyrimidinyl, (tert-butoxycarbonyl)(hydroxy)-azetidinylpyrimidinyl, tetrazolylazetidinylpyrimidinyl, hydroxytetrahydrofuranyl-pyrimidinyl, hydroxypyrrolidinylpyrimidinyl, carboxypyrrolidinylpyrimidinyl, (carboxy)-(methyl)pyrrolidinylpyrimidinyl, carboxymethylpyrrolidinylpyrimidinyl, ethoxycarbonyl-pyrrolidinylpyrimidinyl, fluorotetrahydropyranylpyrimidinyl, hydroxytetrahydropyranyl-pyrimidinyl, difluoropiperidinylpyrimidinyl, (cyano)(methyl)piperidinylpyrimidinyl, (hydroxy)(nitromethyl)piperidinylpyrimidinyl, (hydroxy)(methyl)

piperidinylpyrimidinyl, (hydroxy)(trifluoromethyl) piperidinylpyrimidinyl, (hydroxymethyl)(methyl) piperidinyl-pyrimidinyl, methylsulphonylpiperidinylpyrimidinyl, oxopiperidinylpyrimidinyl, (formyl)(methyl)piperidinylpyrimidinyl, carboxypiperidinylpyrimidinyl, (carboxy)-(fluoro)piperidinylpyrimidinyl, (carboxy)(methyl)piperidinylpyrimidinyl, (carboxy)-(ethyl)piperidinylpyrimidinyl, (carboxy)(trifluoromethyl)piperidinylpyrimidinyl, (carboxy)(hydroxy)piperidinylpyrimidinyl, (carboxy)(hydroxymethyl)piperidinylpyrimidinyl, (carboxy)(methoxy)piperidinylpyrimidinyl, (amino)(carboxy)piperidinyl-pyrimidinyl, carboxymethylpiperidinylpyrimidinyl, methoxycarbonylpiperidinyl-pyrimidinyl, ethoxycarbonylpiperidinylpyrimidinyl, (ethoxycarbonyl)(fluoro)piperidinyl-pyrimidinyl, (methoxycarbonyl)(methyl)piperidinylpyrimidinyl, (ethyl)(methoxy-carbonyl) piperidinylpyrimidinyl, (isopropyl)(methoxycarbonyl) piperidinylpyrimidinyl, (ethoxycarbonyl)(methyl) piperidinylpyrimidinyl, (n-butoxycarbonyl)(methyl) piperidinyl-pyrimidinyl, (ethoxycarbonyl)(trifluoromethyl) piperidinylpyrimidinyl, (ethoxycarbonyl)-(hydroxymethyl) piperidinylpyrimidinyl, (methoxy)(methoxycarbonyl) piperidinyl-pyrimidinyl, (carboxy)(methoxycarbonyl) piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylaminosulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethylpiperazinylpyrimidinyl, tert-butoxycarbonylpiperazinylpyrimidinyl, tetrazolylmethyl-piperazinylpyrimidinyl, trioxohexahydro-[1,2,5]thiadiazolo[2,3-a]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, dioxothiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinylpyrazinyl, (ethoxycarbonyl)(methyl)piperidinylpyrazinyl, morpholinylmethylthienyl, morpholinylethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanyl-pyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, 6-oxa-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]-heptanylpyrimidinyl, ethoxycarbonyl-3-azabicyclo[4.1.0]heptanylpyrimidinyl, (hydroxy)-(methyl)(oxo)-2-oxabicyclo[2.2.2]octanylpyrimidinyl, carboxy-3-azabicyclo[3.2.1]-octanylpyrimidinyl, methoxycarbonyl-3-azabicyclo[3.2.1]octanylpyrimidinyl, oxo-8-azabicyclo[3.2.1] octanylpyrimidinyl, ethoxycarbonylmethylidenyl-8-azabicyclo[3.2.1]-octanylpyrimidinyl, 3-oxa-8-azabicyclo[3.2.1]octanylpyrimidinyl, oxo-3,6-diazabicyclo-[3.2.2]nonanylpyrimidinyl, carboxy-3-oxa-7-azabicyclo[3.3.1]nonanylpyrimidinyl, 3,7-dioxa-9-azabicyclo[3.3.1] nonanylpyrimidinyl, carboxy-5-azaspiro[2.3]hexanylpyrimidinyl, (carboxy)(methyl)-5-azaspiro[2.3] hexanylpyrimidinyl, carboxy-5-azaspiro-[2.4] heptanylpyrimidinyl, carboxy-2-azaspiro[3.3] heptanylpyrimidinyl, 2-oxa-6-azaspiro-[3.3] heptanylpyrimidinyl, 3-oxa-6-azaspiro[3.3] heptanylpyrimidinyl, dioxo-6-thia-2-azaspiro[3.3] heptanylpyrimidinyl, 2-oxa-6-azaspiro[3.4] octanylpyrimidinyl, 2-oxa-6-azaspiro[3.5] nonanylpyrimidinyl, 2-oxa-7-azaspiro[3.5] nonanylpyrimidinyl and (dioxo)(methyl)-2,4,8-triazaspiro [4.5]decanylpyrimidinyl. Additional values include methylsulphoximinylphenyl, trifluoromethylsulphoximinylphenyl, (N-carboxymethyl)-(methyl)sulphoximinylphenyl, (N-tert-butoxycarbonylmethyl)(methyl)sulphoximinyl-phenyl, methylsulphoximinylpyridinyl, ethylsulphoximinylpyridinyl, (methyl)-(methylsulphoximinyl)pyridinyl, (methyl)(N-methyl)sulphoximinylpyridinyl, cyclopropylsulphoximinylpyridinyl, N-(dimethylsulfoxo)iminylpyridinyl, (hydroxyisopropyl)(methyl)pyrimidinyl, (dihydroxy)(methyl)cyclobutylpyridinyl, dihydroxycyclobutylpyrimidinyl, (dihydroxy)(methyl)cyclobutylpyrimidinyl, (dihydroxy)(ethyl)cyclobutylpyrimidinyl, (amino)(hydroxy)cyclobutylpyrimidinyl and (amino)(hydroxy)(methyl)cyclobutylpyrimidinyl.

Definitive values of $R^1$ include bromo, pentafluorothiophenyl, methylsulphonyl-phenyl, methylsulphoximinylphenyl, trifluoromethylsulphoximinylphenyl, (N-carboxymethyl)(methyl)sulphoximinylphenyl, (N-tert-butoxycarbonylmethyl)(methyl)-sulphoximinylphenyl, morpholinyl, methylpyrazolyl, hydroxyisopropylpyridinyl, methylsulphonylpyridinyl, methylsulphoximinylpyridinyl, ethylsulphoximinylpyridinyl, (methyl)(methylsulphoximinyl)pyridinyl, (methyl)(N-methyl)sulphoximinylpyridinyl, cyclopropylsulphoximinylpyridinyl, N-(dimethylsulfoxo) iminylpyridinyl, difluoroethyl-pyrimidinyl, hydroxyisopropylpyrimidinyl, (hydroxyisopropyl)(methyl)pyrimidinyl, (dihydroxy)(methyl)cyclobutylpyridinyl, hydroxycyclopropylpyrimidinyl, hydroxycyclobutylpyrimidinyl, (difluoro)(hydroxy)cyclobutylpyrimidinyl, dihydroxycyclobutylpyrimidinyl, (dihydroxy)(methyl)cyclobutylpyrimidinyl, (dihydroxy)(ethyl)cyclobutylpyrimidinyl, (amino)(hydroxy) cyclobutylpyrimidinyl, (amino)(hydroxy)(methyl)cyclobutylpyrimidinyl, carboxycyclohexylpyrimidinyl, hydroxytetrahydropyranylpyridinyl, piperazinylpyridinyl, fluorooxetanylpyrimidinyl, hydroxyoxetanylpyrimidinyl, difluoroazetidinylpyrimidinyl, hydroxyazetidinyl-pyrimidinyl, (hydroxy)(methyl)azetidinylpyrimidinyl, (hydroxy)(trifluoromethyl)-azetidinylpyrimidinyl, hydroxytetrahydropyranylpyrimidinyl, (carboxy)(methyl)-piperidinylpyrimidinyl, (ethoxycarbonyl)(methyl) piperidinylpyrimidinyl, piperazinyl-pyrimidinyl, oxopiperazinylpyrimidinyl, tert-butoxycarbonylpiperazinylpyrimidinyl, morpholinylpyrimidinyl, oxodiazepanylpyrimidinyl, (methyl)(oxo)diazepanylpyrimidinyl, 6-oxa-3-azabicyclo[3.1.1]heptanylpyrimidinyl, carboxy-3-azabicyclo[3.2.1]octanyl-pyrimidinyl, methoxycarbonyl-3-azabicyclo[3.2.1]octanylpyrimidinyl, 3,7-dioxa-9-azabicyclo[3.3.1]nonanylpyrimidinyl, 3-oxa-6-azaspiro[3.3]heptanylpyrimidinyl and dioxo-6-thia-2-azaspiro[3.3] heptanylpyrimidinyl.

Illustrative values of $R^1$ include bromo, pentafluorothiophenyl, methylsulphonyl-phenyl, morpholinyl, methylpyrazolyl, hydroxyisopropylpyridinyl, methylsulphonyl-pyridinyl, difluoroethylpyrimidinyl, hydroxyisopropylpyrimidinyl, hydroxycyclopropyl-pyrimidinyl, hydroxycyclobutylpyrimidinyl, (difluoro)(hydroxy)cyclobutylpyrimidinyl, carboxycyclohexylpyrimidinyl, piperazinylpyridinyl, fluorooxetanylpyrimidinyl, hydroxyoxetanylpyrimidinyl, difluoroazetidinylpyrimidinyl, hydroxyazetidinyl-pyrimidinyl, (hydroxy)(methyl)azetidinylpyrimidinyl, (hydroxy)(trifluoromethyl)-azetidinylpyrimidinyl, hydroxytetrahydropyranylpyrimidinyl, (carboxy)(methyl)-piperidinylpyrimidinyl, (ethoxycarbonyl)(methyl)piperidinylpyrimidinyl, piperazinyl-pyrimidinyl, oxopiperazinylpyrimidinyl, tert-butoxycarbonylpiperazinylpyrimidinyl, morpholinylpyrimidinyl, oxodiazepanylpyrimidinyl, 6-oxa-3-azabicyclo[3.1.1]heptanyl-pyrimidinyl, methoxycarbonyl-3-azabicyclo[3.2.1]octanylpyrimidinyl, 3,7-dioxa-9-azabicyclo[3.3.1]nonanylpyrimidinyl, 3-oxa-6-azaspiro[3.3]heptanylpyrimidinyl and dioxo-6-thia-2-azaspiro[3.3]heptanylpyrimidinyl.

Typically, $R^2$ represents hydrogen, halogen, trifluoromethyl or —$OR^a$; or $R^2$ represents optionally substituted $C_{1-6}$ alkyl.

Suitably, $R^2$ represents hydrogen or halogen.

Typical examples of optional substituents on $R^2$ include $C_{2-6}$ alkoxycarbonyl.

Typical examples of particular substituents on $R^2$ include ethoxycarbonyl.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents trifluoromethyl. In a fourth embodiment, $R^2$ represents —$OR^a$. In a fifth embodiment, $R^2$ represents optionally substituted $C_{1-6}$ alkyl. In one aspect of that embodiment, $R^2$ represents unsubstituted methyl. In another aspect of that embodiment, $R^2$ represents unsubstituted ethyl. In a further aspect of that embodiment, $R^2$ represents monosubstituted methyl or monosubstituted ethyl.

Typical values of $R^2$ include hydrogen, fluoro, chloro, trifluoromethyl, —$OR^a$, methyl and ethoxycarbonylethyl.

Suitable values of $R^2$ include hydrogen and fluoro.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents $C_{1-6}$ alkyl. In one aspect of that embodiment, $R^3$ represents methyl. In another aspect of that embodiment, $R^3$ represents ethyl.

In a particular embodiment, $R^4$ represents hydrogen.

Typically, $R^5$ is methyl, which may be unsubstituted, or substituted by fluoro, chloro, hydroxy or methoxy.

Suitably, $R^5$ is methyl, which may be unsubstituted, or substituted by hydroxy.

In a first embodiment, $R^5$ represents unsubstituted $C_{1-6}$ alkyl. In one aspect of that embodiment, $R^5$ represents unsubstituted methyl.

In a second embodiment, $R^5$ represents $C_{1-6}$ alkyl substituted by halogen. In a first aspect of that embodiment, $R^5$ represents $C_{1-6}$ alkyl substituted by fluoro, especially fluoromethyl. In a second aspect of that embodiment, $R^5$ represents $C_{1-6}$ alkyl substituted by chloro, especially chloromethyl.

In a third embodiment, $R^5$ represents $C_{1-6}$ alkyl substituted by hydroxy. In one aspect of that embodiment, $R^5$ represents hydroxymethyl.

In a fourth embodiment, $R^5$ represents $C_{1-6}$ alkyl substituted by $C_{1-6}$ alkoxy. In one aspect of that embodiment, $R^5$ represents $C_{1-6}$ alkyl substituted by methoxy. In another aspect of that embodiment, $R^5$ represents methyl substituted by $C_{1-6}$ alkoxy. In a particular aspect of that embodiment, $R^5$ represents methoxymethyl.

Appositely, $R^5$ represents methyl or hydroxymethyl.

Suitably, $R^6$ represents hydrogen or methyl.

In a first embodiment, $R^6$ represents hydrogen. In a second embodiment, $R^6$ represents $C_{1-6}$ alkyl, especially methyl.

Suitably, $R^{7a}$ represents hydrogen or methyl.

In a first embodiment, $R^{7a}$ represents hydrogen. In a second embodiment, $R^{7a}$ represents $C_{1-6}$ alkyl, especially methyl.

Suitably, $R^{7b}$ represents hydrogen or methyl.

In a first embodiment, $R^{7b}$ represents hydrogen. In a second embodiment, $R^{7b}$ represents $C_{1-6}$ alkyl, especially methyl.

Suitably, $R^{8a}$ represents hydrogen, fluoro or methyl.

In a first embodiment, $R^{8a}$ represents hydrogen. In a second embodiment, $R^{8a}$ represents halogen. In one aspect of that embodiment, $R^{8a}$ represents fluoro. In a third embodiment, $R^{8a}$ represents $C_{1-6}$ alkyl. In one aspect of that embodiment, $R^{8a}$ represents methyl.

Suitably, $R^{8b}$ represents hydrogen, fluoro or methyl.

In a first embodiment, $R^{8b}$ represents hydrogen. In a second embodiment, $R^{8b}$ represents halogen. In one aspect of that embodiment, $R^{8b}$ represents fluoro. In a third embodiment, $R^{8b}$ represents $C_{1-6}$ alkyl. In one aspect of that embodiment, $R^{8b}$ represents methyl.

Alternatively, $R^{8a}$ and $R^{8b}$ may together form an optionally substituted spiro linkage. Thus, $R^{8a}$ and $R^{8b}$, when taken together with the carbon atom to which they are both attached, may represent $C_{3-7}$ cycloalkyl or $C_{3-7}$ heterocycloalkyl, either of which groups may be unsubstituted, or substituted by one or more substituents, typically by one or two substituents. In one embodiment, $R^{8a}$ and $R^{8b}$, when taken together with the carbon atom to which they are both attached, may suitably represent an optionally substituted cyclopropyl ring. In another embodiment, $R^{8a}$ and $R^{8b}$, when taken together with the carbon atom to which they are both attached, may suitably represent an optionally substituted oxetanyl ring.

Typical examples of optional substituents on the spirocycle formed by $R^{8a}$ and $R^{8b}$ include $C_{1-6}$ alkyl, halogen, cyano, trifluoromethyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino and di($C_{1-6}$)alkylamino.

Typical examples of particular substituents on the spirocycle formed by $R^{8a}$ and $R^{8b}$ include methyl, fluoro, chloro, bromo, cyano, trifluoromethyl, hydroxy, methoxy, methylthio, methylsulphinyl, methylsulphonyl, acetyl, amino, methylamino and dimethylamino.

Alternatively, $R^{7a}$ and $R^{8a}$ may together form an optionally substituted fused bicyclic ring system. Thus, $R^{7a}$ and $R^{8a}$, when taken together with the two intervening carbon atoms, may represent $C_{3-7}$ cycloalkyl or $C_{3-7}$ heterocycloalkyl, either of which groups may be unsubstituted, or substituted by one or more substituents, typically by one or two substituents. In one embodiment, $R^{7a}$ and $R^{8a}$, when taken together with the two intervening carbon atoms, may suitably represent an optionally substituted cyclopropyl ring. In another embodiment, $R^{7a}$ and $R^{8a}$, when taken together with the two intervening carbon atoms, may suitably represent an optionally substituted oxetanyl ring.

Typical examples of optional substituents on the fused bicyclic ring system formed by $R^{7a}$ and $R^{8a}$ include $C_{1-6}$ alkyl, halogen, cyano, trifluoromethyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino and di($C_{1-6}$)alkylamino.

Typical examples of particular substituents on the fused bicyclic ring system formed by $R^{7a}$ and $R^{8a}$ include methyl, fluoro, chloro, bromo, cyano, trifluoromethyl, hydroxy, methoxy, methylthio, methylsulphinyl, methylsulphonyl, acetyl, amino, methylamino and dimethylamino.

Suitably, $R^{9a}$ represents hydrogen or methyl.

In a first embodiment, $R^{9a}$ represents hydrogen. In a second embodiment, $R^{9a}$ represents $C_{1-6}$ alkyl, especially methyl.

Suitably, $R^{9b}$ represents hydrogen or methyl.

In a first embodiment, $R^{9b}$ represents hydrogen. In a second embodiment, $R^{9b}$ represents $C_{1-6}$ alkyl, especially methyl.

Alternatively, $R^{9a}$ and $R^{9b}$ may together form an optionally substituted spiro linkage. Thus, $R^{9a}$ and $R^{9b}$, when taken together with the carbon atom to which they are both attached, may represent $C_{3-7}$ cycloalkyl or $C_{3-7}$ heterocycloalkyl, either of which groups may be unsubstituted, or substituted by one or more substituents, typically by one or two substituents. In one embodiment, $R^{9a}$ and $R^{9b}$, when taken together with the carbon atom to which they are both attached, may suitably represent an optionally substituted cyclopropyl ring. In another embodiment, $R^{9a}$ and $R^{9b}$, when taken together with the carbon atom to which they are both attached, may suitably represent an optionally substituted oxetanyl ring.

Typical examples of optional substituents on the spirocycle formed by $R^{9a}$ and $R^{9b}$ include $C_{1-6}$ alkyl, halogen, cyano, trifluoromethyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino and di($C_{1-6}$)alkylamino.

Typical examples of particular substituents on the spirocycle formed by $R^{9a}$ and $R^{9b}$ include methyl, fluoro, chloro, bromo, cyano, trifluoromethyl, hydroxy, methoxy, methylthio, methylsulphinyl, methylsulphonyl, acetyl, amino, methylamino and dimethylamino.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$) alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolyl-propyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$) alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonyl-amino, $C_{2-6}$ alkylcarbonylamino($C_{1-6}$)alkyl, $C_{2-6}$ alkoxycarbonylamino, $C_{1-6}$ alkyl-sulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxy-carbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxo-thiazolidinyl.

Selected examples of specific values for $R^d$ include hydrogen, methyl, acetoxy-methyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

Illustrative sub-classes of compounds according to the invention are represented by the compounds of formula (IIA-A), (IIA-B) and (IIA-C) and N-oxides thereof, and pharmaceutically acceptable salts and solvates thereof, and glucuronide derivatives thereof, and co-crystals thereof:

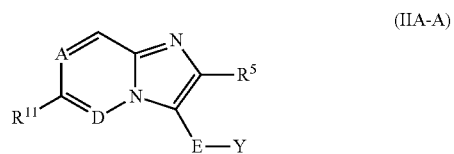

(IIA-A)

-continued (IIA-B)

[Chemical structure showing a bicyclic imidazole-type ring system with substituents A, D, R¹¹, N, R⁵, E—Y]

(IIA-C)

[Chemical structure showing a bicyclic pyrazolo-type ring system with substituents A, D, R¹¹, N, R⁵, E—Y]

wherein $R^{11}$ represents halogen or cyano; or $R^{11}$ represents $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl-$(C_{1-6})$alkyl-aryl-, heteroaryl$(C_{3-7})$heterocycloalkyl-, $(C_{3-7})$cycloalkyl-heteroaryl-, $(C_{3-7})$cyclo alkyl$(C_{1-6})$alkyl-heteroaryl-, $(C_{4-7})$cycloalkenyl-heteroaryl-, $(C_{4-9})$bicycloalkyl-heteroaryl-, $(C_{3-7})$heterocycloalkyl-heteroaryl-, $(C_{3-7})$heterocycloalkyl$(C_{1-6})$alkyl-heteroaryl-, $(C_{3-7})$heterocycloalkenyl-heteroaryl-, $(C_{4-9})$heterobicycloalkyl-heteroaryl- or $(C_{4-9})$spiroheterocycloalkyl-heteroaryl-, any of which groups may be optionally substituted by one or more substituents; and A, D, E, Y and $R^5$ are as defined above.

Examples of optional substituents which may be present on $R^{11}$ include one, two or three substituents independently selected from halogen, halo$(C_{1-6})$alkyl, cyano, cyano$(C_{1-6})$alkyl, nitro, nitro$(C_{1-6})$alkyl, $C_{1-6}$ alkyl, difluoromethyl, trifluoromethyl, difluoroethyl, trifluoroethyl, $C_{2-6}$ alkenyl, hydroxy, hydroxy$(C_{1-6})$alkyl, $C_{1-6}$ alkoxy, difluoromethoxy, trifluoromethoxy, trifluoroethoxy, carboxy$(C_{3-7})$cycloalkyloxy, $C_{1-3}$ alkylenedioxy, $C_{1-6}$ alkoxy$(C_{1-6})$alkyl, pentafluorothio, $C_{1-6}$ alkylthio, $C_{1-6}$ alkylsulphinyl, $C_{1-6}$ alkylsulphonyl, $(C_{1-6})$alkylsulphonyl$(C_{1-6})$alkyl, oxo, amino, amino$(C_{1-6})$alkyl, $C_{1-6}$ alkylamino, di$(C_{1-6})$alkylamino, hydroxy$(C_{1-6})$alkylamino, $C_{1-6}$ alkoxyamino, $(C_{1-6})$alkoxy-$(C_{1-6})$alkylamino, $[(C_{1-6})$alkoxy](hydroxy)$(C_{1-6})$alkylamino, $[(C_{1-6})$alkylthio](hydroxy)-$(C_{1-6})$alkylamino, N—$[(C_{1-6})$alkyl]-N-[hydroxy$(C_{1-6})$alkyl]amino, di$(C_{1-6})$alkylamino$(C_{1-6})$-alkylamino, N-[di$(C_{1-6})$alkylamino$(C_{1-6})$alkyl]-N-[hydroxy$(C_{1-6})$alkyl]amino, hydroxy-$(C_{1-6})$alkyl $(C_{3-7})$cycloalkylamino, (hydroxy)[$(C_{3-7})$cyclo alkyl$(C_{1-6})$alkyl]amino, $(C_{3-7})$heterocycloalkyl$(C_{1-6})$alkylamino, oxo $(C_{3-7})$heterocycloalkyl$(C_{1-6})$alkylamino, $(C_{1-6})$alkylheteroarylamino, heteroaryl$(C_{1-6})$alkylamino, $(C_{1-6})$alkylheteroaryl$(C_{1-6})$alkyl-amino, $C_{2-6}$ alkylcarbonylamino, N—$[(C_{1-6})$alkyl]-N—$[(C_{2-6})$alkylcarbonyl]amino, $(C_{2-6})$alkyl-carbonylamino$(C_{1-6})$alkyl, $C_{3-6}$ alkenylcarbonylamino, bis[$(C_{3-6})$alkenylcarbonyl]amino, N—$[(C_{1-6})$alkyl]-N—$[(C_{3-7})$cycloalkylcarbonyl]amino, $C_{2-6}$ alkoxycarbonylamino, $C_{2-6}$ alkoxycarbonyl$(C_{1-6})$alkylamino, $C_{1-6}$ alkylaminocarbonylamino, $C_{1-6}$ alkylsulphonyl-amino, N—$[(C_{1-6})$alkyl]-N—$[(C_{1-6})$alkylsulphonyl]amino, bis[$(C_{1-6})$alkylsulphonyl]amino, N—$[(C_{1-6})$alkyl]-N-[carboxy$(C_{1-6})$alkyl]amino, carboxy$(C_{3-7})$cycloalkylamino, carboxy-$(C_{3-7})$cycloalkyl$(C_{1-6})$alkylamino, formyl, $C_{2-6}$ alkylcarbonyl, $(C_{3-7})$cycloalkylcarbonyl, phenylcarbonyl, $(C_{2-6})$alkylcarbonyloxy$(C_{1-6})$alkyl, carboxy, carboxy$(C_{1-6})$alkyl, $C_{2-6}$ alkoxycarbonyl, $C_{2-6}$ alkoxycarbonyl$(C_{1-6})$alkyl, morpholinyl$(C_{1-6})$alkoxycarbonyl, $C_{2-6}$ alkoxycarbonylmethylidenyl, a carboxylic acid isostere or prodrug moiety Ω as defined herein, —$(C_{1-6})$alkyl-Ω, aminocarbonyl, $C_{1-6}$ alkylaminocarbonyl, hydroxy$(C_{1-6})$alkylamino-carbonyl, di$(C_{1-6})$alkylaminocarbonyl, aminocarbonyl$(C_{1-6})$alkyl, aminosulphonyl, di$(C_{1-6})$alkylaminosulphonyl, $(C_{1-6})$alkylsulphoximinyl and $[(C_{1-6})$alkyl][N—$(C_{1-6})$alkyl]-sulphoximinyl. Additional examples include trifluoromethylsulphoximinyl, $[(C_{1-6})$alkyl]-[N-carboxy$(C_{1-6})$alkyl] sulphoximinyl, [N—$(C_{2-6})$alkoxycarbonyl$(C_{1-6})$alkyl] $[(C_{1-6})$alkyl]-sulphoximinyl, $(C_{3-7})$cycloalkylsulphoximinyl and N-[di$(C_{1-6})$alkylsulfoxo]iminyl.

Examples of particular substituents on $R^{11}$ include fluoro, chloro, bromo, fluoromethyl, fluoroisopropyl, cyano, cyanoethyl, nitro, nitromethyl, methyl, ethyl, isopropyl, isobutyl, tert-butyl, difluoromethyl, trifluoromethyl, difluoroethyl, trifluoro-ethyl, ethenyl, hydroxy, hydroxymethyl, hydroxyisopropyl, methoxy, isopropoxy, difluoromethoxy, trifluoromethoxy, trifluoroethoxy, carboxycyclobutyloxy, methylene-dioxy, ethylenedioxy, methoxymethyl, methoxyethyl, pentafluorothio, methylthio, methylsulphinyl, methylsulphonyl, methylsulphonylethyl, oxo, amino, aminomethyl, aminoisopropyl, methylamino, ethylamino, dimethylamino, hydroxyethylamino, hydroxypropylamino, (hydroxy)(methyl)propylamino, methoxyamino, methoxyethyl-amino, (hydroxy)(methoxy)(methyl)propylamino, (hydroxy)(methylthio)butylamino, N-(hydroxyethyl)-N-(methyl)amino, dimethylaminoethylamino, (dimethylamino)(methyl)-propylamino, N-(dimethylaminoethyl)-N-(hydroxyethyl) amino, hydroxymethyl-cyclopentylamino, hydroxycyclobutylmethylamino, (cyclopropyl)(hydroxy)propylamino, morpholinylethylamino, oxopyrrolidinylmethylamino, ethyloxadiazolylamino, methyl-thiadiazolylamino, thiazolylmethylamino, thiazolylethylamino, pyrimidinylmethylamino, methylpyrazolylmethylamino, acetylamino, N-acetyl-N-methylamino, N-isopropyl-carbonyl-N-methyl-amino, acetylaminomethyl, ethenylcarbonylamino, bis(ethenyl-carbonyl)amino, N-cyclopropylcarbonyl-N-methylamino, methoxycarbonylamino, ethoxycarbonylamino, tert-butoxycarbonylamino, methoxycarbonylethylamino, ethylaminocarbonylamino, butylaminocarbonylamino, methylsulphonylamino, N-methyl-N-(methylsulphonyl)amino, bis (methylsulphonyl)amino, N-(carboxymethyl)-N-methyl-amino, N-(carboxyethyl)-N-methylamino, carboxycyclopentylamino, carboxycyclopropyl-methyl-amino, formyl, acetyl, isopropylcarbonyl, cyclobutylcarbonyl, phenylcarbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonyl-methylidenyl, methylsulphonylaminocarbonyl, acetylaminosulphonyl, methoxyamino-carbonyl, tetrazolyl, tetrazolylmethyl, hydroxyoxadiazolyl, aminocarbonyl, methylamino-carbonyl, hydroxyethylaminocarbonyl, dimethylaminocarbonyl, aminocarbonylmethyl, aminosulphonyl, methylaminosulphonyl, dimethylaminosulphonyl, methylsulphoximinyl and (methyl)(N-methyl)sulphoximinyl. Additional examples include ethylsulphoximinyl, trifluoromethylsulphoximinyl, (N-carboxymethyl)(methyl)sulphoximinyl, (N-tert-butoxycarbonylmethyl)(methyl)sulphoximinyl, cyclopropylsulphoximinyl and N-(dimethyl-sulfoxo)iminyl.

Generally, $R^{11}$ represents $C_{1-6}$ alkyl, $C_{2-6}$ alkynyl, aryl, $C_{3-7}$ heterocycloalkyl, $C_{3-7}$ heterocycloalkenyl, heteroaryl, $(C_{3-7})$heterocycloalkyl$(C_{1-6})$alkyl-aryl-, heteroaryl-$(C_{3-7})$ heterocycloalkyl-, $(C_{3-7})$cycloalkyl-heteroaryl-, $(C_{3-7})$cycloalkyl$(C_{1-6})$alkyl-heteroaryl-, $(C_{4-7})$cycloalkenyl-heteroaryl-, $(C_{4-9})$ bicycloalkyl-heteroaryl-, $(C_{3-7})$ heterocycloalkyl-heteroaryl-, $(C_{3-7})$hetero cyclo alkyl$(C_{1-6})$ alkyl-hetero aryl-, $(C_{3-7})$heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

More generally, $R^{11}$ represents halogen; or $R^{11}$ represents aryl, $C_{3-7}$ heterocycloalkyl, heteroaryl, ($C_{3-7}$)cycloalkyl-heteroaryl-, ($C_{3-7}$)heterocycloalkyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

In a first embodiment, $R^{11}$ represents halogen. In one aspect of that embodiment, $R^{11}$ represents bromo. In one aspect of that embodiment, $R^{11}$ represents iodo.

In a second embodiment, $R^{11}$ represents cyano.

In a third embodiment, $R^{11}$ represents optionally substituted $C_{1-6}$ alkyl. In one aspect of that embodiment, $R^{11}$ represents optionally substituted ethyl.

In a fourth embodiment, $R^{11}$ represents optionally substituted $C_{2-6}$ alkynyl. In one aspect of that embodiment, $R^{11}$ represents optionally substituted butynyl.

In a fifth embodiment, $R^{11}$ represents optionally substituted aryl. In one aspect of that embodiment, $R^{11}$ represents optionally substituted phenyl.

In a sixth embodiment, $R^{11}$ represents optionally substituted $C_{3-7}$ heterocycloalkyl.

In a seventh embodiment, $R^{11}$ represents optionally substituted $C_{3-7}$ heterocycloalkenyl.

In an eighth embodiment, $R^{11}$ represents optionally substituted heteroaryl. In selected aspects of that embodiment, $R^{11}$ represents benzofuryl, thienyl, indolyl, pyrazolyl, indazolyl, isoxazolyl, thiazolyl, imidazolyl, pyridinyl, quinolinyl, pyridazinyl, pyrimidinyl or pyrazinyl, any of which groups may be optionally substituted by one or more substituents.

In a ninth embodiment, $R^{11}$ represents optionally substituted ($C_{3-7}$)-heterocycloalkyl($C_{1-6}$)alkyl-aryl-. In a first aspect of that embodiment, $R^{11}$ represents optionally substituted pyrrolidinylmethylphenyl-. In a second aspect of that embodiment, $R^{11}$ represents optionally substituted piperazinylmethylphenyl-.

In a tenth embodiment, $R^{11}$ represents optionally substituted heteroaryl($C_{3-7}$)-heterocycloalkyl-. In one aspect of that embodiment, $R^{11}$ represents optionally substituted pyridinylpiperazinyl-.

In an eleventh embodiment, $R^{11}$ represents optionally substituted ($C_{3-7}$)cycloalkyl-heteroaryl-. In a first aspect of that embodiment, $R^{11}$ represents optionally substituted cyclohexylpyrazolyl-. In a second aspect of that embodiment, $R^{11}$ represents optionally substituted cyclobutylpyridinyl-. In a third aspect of that embodiment, $R^{11}$ represents optionally substituted cyclohexylpyridinyl-. In a fourth aspect of that embodiment, $R^{11}$ represents optionally substituted cyclopropylpyrimidinyl-. In a fifth aspect of that embodiment, $R^{11}$ represents optionally substituted cyclobutylpyrimidinyl-. In a sixth aspect of that embodiment, $R^{11}$ represents optionally substituted cyclopentylpyrimidinyl-. In a seventh aspect of that embodiment, $R^{11}$ represents optionally substituted cyclohexyl-pyrimidinyl-. In an eighth aspect of that embodiment, $R^{11}$ represents optionally substituted cyclohexyl-pyrazinyl-.

In a twelfth embodiment, $R^{11}$ represents optionally substituted ($C_{4-7}$)cycloalkenyl-heteroaryl-.

In a thirteenth embodiment, $R^{11}$ represents optionally substituted ($C_{3-7}$)-heterocycloalkyl-heteroaryl-. In a first aspect of that embodiment, $R^{11}$ represents optionally substituted pyrrolidinylpyridinyl-. In a second aspect of that embodiment, $R^{11}$ represents optionally substituted tetrahydropyranylpyridinyl-. In a third aspect of that embodiment, $R^{11}$ represents optionally substituted piperidinylpyridinyl-. In a fourth aspect of that embodiment, $R^{11}$ represents optionally substituted piperazinylpyridinyl-. In a fifth aspect of that embodiment, $R^{11}$ represents optionally substituted morpholinyl-pyridinyl-. In a sixth aspect of that embodiment, $R^{11}$ represents optionally substituted thiomorpholinylpyridinyl-. In a seventh aspect of that embodiment, $R^{11}$ represents optionally substituted diazepanylpyridinyl-. In an eighth aspect of that embodiment, $R^{11}$ represents optionally substituted oxetanylpyrimidinyl-. In a ninth aspect of that embodiment, $R^{11}$ represents optionally substituted azetidinylpyrimidinyl-. In a tenth aspect of that embodiment, $R^{11}$ represents optionally substituted tetrahydrofuranyl-pyrimidinyl-. In an eleventh aspect of that embodiment, $R^{11}$ represents optionally substituted pyrrolidinylpyrimidinyl-. In a twelfth aspect of that embodiment, $R^{11}$ represents optionally substituted tetrahydropyranylpyrimidinyl-. In a thirteenth aspect of that embodiment, $R^{11}$ represents optionally substituted piperidinylpyrimidinyl-. In a fourteenth aspect of that embodiment, $R^{11}$ represents optionally substituted piperazinyl-pyrimidinyl-. In a fifteenth aspect of that embodiment, $R^{11}$ represents optionally substituted morpholinylpyrimidinyl-. In a sixteenth aspect of that embodiment, $R^{11}$ represents optionally substituted thiomorpholinylpyrimidinyl-. In a seventeenth aspect of that embodiment, $R^{11}$ represents optionally substituted azepanylpyrimidinyl-. In an eighteenth aspect of that embodiment, $R^{11}$ represents optionally substituted oxazepanyl-pyrimidinyl-. In a nineteenth aspect of that embodiment, $R^{11}$ represents optionally substituted diazepanylpyrimidinyl-. In a twentieth aspect of that embodiment, $R^{11}$ represents optionally substituted thiadiazepanylpyrimidinyl-. In a twenty-first aspect of that embodiment, $R^{11}$ represents optionally substituted oxetanylpyrazinyl-. In a twenty-second aspect of that embodiment, $R^{11}$ represents optionally substituted piperidinyl-pyrazinyl-.

In a fourteenth embodiment, $R^{11}$ represents optionally substituted ($C_{3-7}$)-heterocycloalkyl($C_{1-6}$)alkyl-heteroaryl-. In a first aspect of that embodiment, $R^{11}$ represents optionally substituted morpholinylmethylthienyl-. In a second aspect of that embodiment, $R^{11}$ represents optionally substituted morpholinylethylpyrazolyl-.

In a fifteenth embodiment, $R^{11}$ represents optionally substituted ($C_{3-7}$)-heterocycloalkenyl-heteroaryl-.

In a sixteenth embodiment, $R^{11}$ represents optionally substituted ($C_{4-9}$)-heterobicycloalkyl-heteroaryl-.

In a seventeenth embodiment, $R^{11}$ represents optionally substituted ($C_{4-9}$)-spiroheterocycloalkyl-heteroaryl-.

In an eighteenth embodiment, $R^{11}$ represents optionally substituted ($C_{3-7}$)-cycloalkyl($C_{1-6}$)alkyl-heteroaryl-. In one aspect of that embodiment, $R^{11}$ represents optionally substituted cyclohexylmethylpyrimidinyl-.

In a nineteenth embodiment, $R^{11}$ represents optionally substituted ($C_{4-9}$)-bicycloalkyl-heteroaryl-.

Appositely, $R^{11}$ represents bromo or iodo; or $R^{11}$ represents ethyl, butynyl, phenyl, pyrrolidinyl, piperidinyl, piperazinyl, morpholinyl, 1,2,3,6-tetrahydropyridinyl, benzofuryl, thienyl, indolyl, pyrazolyl, indazolyl, isoxazolyl, thiazolyl, imidazolyl, pyridinyl, quinolinyl, pyridazinyl, pyrimidinyl, pyrazinyl, pyrrolidinylmethylphenyl, piperazinylmethylphenyl, pyridinylpiperazinyl, cyclohexylpyrazolyl, cyclohexylpyridinyl, cyclopropylpyrimidinyl, cyclobutylpyrimidinyl, cyclopentylpyrimidinyl, cyclohexylpyrimidinyl, cyclohexylpyrazinyl, cyclohexylmethylpyrimidinyl, cyclohexenylpyridinyl, cyclohexenylpyrimidinyl, bicyclo[3.1.0]hexanylpyridinyl, bicyclo[3.1.0]hexanyl-pyrimidinyl, bicyclo[4.1.0]heptanylpyrimidinyl, bicyclo

[2.2.2]octanylpyrimidinyl, pyrrolidinylpyridinyl, tetrahydropyranylpyridinyl, piperidinylpyridinyl, piperazinylpyridinyl, morpholinylpyridinyl, thiomorpholinylpyridinyl, diazepanylpyridinyl, oxetanylpyrimidinyl, azetidinylpyrimidinyl, tetrahydrofuranylpyrimidinyl, pyrrolidinyl-pyrimidinyl, tetrahydropyranylpyrimidinyl, piperidinylpyrimidinyl, piperazinyl-pyrimidinyl, hexahydro-[1,2,5]thiadiazolo[2,3-a]pyrazinylpyrimidinyl, morpholinyl-pyrimidinyl, thiomorpholinylpyrimidinyl, azepanylpyrimidinyl, oxazepanylpyrimidinyl, diazepanylpyrimidinyl, thiadiazepanylpyrimidinyl, oxetanylpyrazinyl, piperidinylpyrazinyl, morpholinylmethylthienyl, morpholinylethylpyrazolyl, 3-azabicyclo[3.1.0]-hexanylpyridinyl, 3-azabicyclo[3.1.0]hexanylpyridazinyl, 3-azabicyclo[3.1.0]hexanylpyrimidinyl, 2-oxa-5-azabicyclo[2.2.1]heptanylpyrimidinyl, 3-azabicyclo[3.1.1]heptanyl-pyrimidinyl, 6-oxa-3-azabicyclo[3.1.1]heptanylpyrimidinyl, 3-azabicyclo[4.1.0]heptanyl-pyridinyl, 3-azabicyclo[4.1.0]heptanylpyrimidinyl, 2-oxabicyclo[2.2.2]octanyl-pyrimidinyl, 3-azabicyclo[3.2.1]octanylpyrimidinyl, 8-azabicyclo[3.2.1]octanyl-pyrimidinyl, 3-oxa-8-azabicyclo[3.2.1]octanylpyrimidinyl, 3,6-diazabicyclo[3.2.2]-nonanylpyrimidinyl, 3-oxa-7-azabicyclo[3.3.1]nonanylpyrimidinyl, 3,7-dioxa-9-azabicyclo[3.3.1]nonanylpyrimidinyl, 5-azaspiro[2.3]hexanylpyrimidinyl, 5-azaspiro-[2.4]heptanylpyrimidinyl, 2-azaspiro[3.3]heptanylpyrimidinyl, 2-oxa-6-azaspiro[3.3]heptanylpyrimidinyl, 3-oxa-6-azaspiro[3.3]heptanylpyrimidinyl, 6-thia-2-azaspiro[3.3]heptanylpyrimidinyl, 2-oxa-6-azaspiro[3.4]octanylpyrimidinyl, 2-oxa-6-azaspiro[3.5]nonanylpyrimidinyl, 2-oxa-7-azaspiro[3.5]nonanylpyrimidinyl or 2,4,8-triazaspiro[4.5]decanylpyrimidinyl, any of which groups may be optionally substituted by one or more substituents. Additionally, $R^{11}$ may represent cyclobutylpyridinyl, which group may be optionally substituted by one or more substituents.

Selectively, $R^{11}$ represents bromo; or $R^{11}$ represents phenyl, morpholinyl, pyrazolyl, pyridinyl, pyrimidinyl, cyclobutylpyridinyl, cyclopropylpyrimidinyl, cyclobutylpyrimidinyl, cyclohexylpyrimidinyl, tetrahydropyranylpyridinyl, piperazinyl-pyridinyl, oxetanylpyrimidinyl, azetidinylpyrimidinyl, tetrahydropyranylpyrimidinyl, piperidinylpyrimidinyl, piperazinylpyrimidinyl, morpholinylpyrimidinyl, diazepanyl-pyrimidinyl, 6-oxa-3-azabicyclo[3.1.1]heptanylpyrimidinyl, 3-azabicyclo[3.2.1]octanyl-pyrimidinyl, 3,7-dioxa-9-azabicyclo[3.3.1]nonanylpyrimidinyl, 3-oxa-6-azaspiro[3.3]heptanylpyrimidinyl or 6-thia-2-azaspiro[3.3]heptanylpyrimidinyl, any of which groups may be optionally substituted by one or more substituents.

Illustratively, $R^{11}$ represents bromo or iodo; or $R^{11}$ represents phenyl, morpholinyl, pyrazolyl, pyridinyl, pyrimidinyl, cyclopropylpyrimidinyl, cyclobutylpyrimidinyl, cyclohexylpyrimidinyl, piperazinylpyridinyl, oxetanylpyrimidinyl, azetidinylpyrimidinyl, tetrahydropyranylpyrimidinyl, piperidinylpyrimidinyl, pip erazinylpyrimidinyl, morpholinylpyrimidinyl, diazepanylpyrimidinyl, 6-oxa-3-azabicyclo[3.1.1]heptanyl-pyrimidinyl, 3-azabicyclo[3.2.1]octanylpyrimidinyl, 3,7-dioxa-9-azabicyclo[3.3.1]-nonanylpyrimidinyl, 3-oxa-6-azaspiro[3.3]heptanylpyrimidinyl or 6-thia-2-azaspiro[3.3]-heptanylpyrimidinyl, any of which groups may be optionally substituted by one or more substituents.

Typical examples of optional substituents on $R^{11}$ include one, two or three substituents independently selected from halogen, halo($C_{1-6}$)alkyl, cyano, cyano($C_{1-6}$)alkyl, nitro($C_{1-6}$)alkyl, $C_{1-6}$ alkyl, trifluoromethyl, difluoroethyl, trifluoroethyl, $C_{2-6}$ alkenyl, hydroxy, hydroxy($C_{1-6}$)alkyl, $C_{1-6}$ alkoxy, trifluoroethoxy, carboxy($C_{3-7}$)cycloalkyloxy, pentafluorothio, $C_{1-6}$ alkylthio, $C_{1-6}$ alkylsulphonyl, ($C_{1-6}$)alkylsulphonyl($C_{1-6}$)alkyl, oxo, amino, amino($C_{1-6}$)alkyl, $C_{1-6}$ alkylamino, di($C_{1-6}$)alkylamino, ($C_{1-6}$)alkoxy($C_{1-6}$)alkyl-amino, N—[($C_{1-6}$)alkyl]-N-[hydroxy($C_{1-6}$)alkyl]amino, ($C_{2-6}$)alkylcarbonylamino($C_{1-6}$)alkyl, $C_{1-6}$ alkylsulphonylamino, N—[($C_{1-6}$)alkyl]-N—[($C_{1-6}$)alkylsulphonyl]amino, bis[($C_{1-6}$)alkyl-sulphonyl]amino, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonyl-methylidenyl, a carboxylic acid isostere or prodrug moiety Ω as defined herein, —($C_{1-6}$)alkyl-Ω, aminocarbonyl, aminosulphonyl, ($C_{1-6}$)alkylsulphoximinyl and [($C_{1-6}$)alkyl][N—($C_{1-6}$)alkyl]sulphoximinyl. Additional examples include trifluoromethyl-sulphoximinyl, [($C_{1-6}$)alkyl][N-carboxy($C_{1-6}$)alkyl]sulphoximinyl, [N—($C_{2-6}$)alkoxy-carbonyl($C_{1-6}$)alkyl][($C_{1-6}$)alkyl]sulphoximinyl, ($C_{3-7}$)cycloalkylsulphoximinyl and N-[di($C_{1-6}$)alkylsulfoxo]iminyl.

Selected examples of optional substituents on $R^{11}$ include one, two or three substituents independently selected from halogen, $C_{1-6}$ alkyl, trifluoromethyl, difluoro-ethyl, hydroxy, hydroxy($C_{1-6}$)alkyl, pentafluorothio, $C_{1-6}$ alkylsulphonyl, oxo, amino, carboxy, $C_{2-6}$ alkoxycarbonyl, ($C_{1-6}$)alkylsulphoximinyl, trifluoromethylsulphoximinyl, [($C_{1-6}$)alkyl][N—($C_{1-6}$)alkyl]sulphoximinyl, [($C_{1-6}$)alkyl][N-carboxy($C_{1-6}$)alkyl]-sulphoximinyl, [N—($C_{2-6}$)alkoxycarbonyl($C_{1-6}$)alkyl][($C_{1-6}$)alkyl]sulphoximinyl, ($C_{3-7}$)cycloalkylsulphoximinyl and N-[di($C_{1-6}$)alkylsulfoxo]iminyl.

Suitable examples of optional substituents on $R^{11}$ include one, two or three substituents independently selected from halogen, $C_{1-6}$ alkyl, trifluoromethyl, difluoro-ethyl, hydroxy, hydroxy($C_{1-6}$)alkyl, pentafluorothio, $C_{1-6}$ alkylsulphonyl, oxo, carboxy and $C_{2-6}$ alkoxycarbonyl.

Typical examples of particular substituents on $R^{11}$ include one, two or three substituents independently selected from fluoro, chloro, fluoromethyl, fluoroisopropyl, cyano, cyanoethyl, nitromethyl, methyl, ethyl, isopropyl, trifluoromethyl, difluoroethyl, ethenyl, hydroxy, hydroxymethyl, hydroxyisopropyl, methoxy, isopropoxy, trifluoro-ethoxy, carboxycyclobutyloxy, pentafluorothio, methylthio, methylsulphonyl, methyl-sulphonylethyl, oxo, amino, aminomethyl, aminoisopropyl, methylamino, dimethylamino, methoxyethylamino, N-(hydroxyethyl)-N-(methyl)amino, acetylaminomethyl, methyl-sulphonylamino, N-methyl-N-(methylsulphonyl)amino, bis(methylsulphonyl)amino, N-(carboxyethyl)-N-(methyl)amino, carboxycyclopentylamino, carboxycyclopropylmethyl-amino, formyl, acetyl, acetoxyisopropyl, carboxy, carboxymethyl, carboxyethyl, methoxy-carbonyl, ethoxycarbonyl, n-butoxycarbonyl, tert-butoxycarbonyl, methoxycarbonyl-methyl, ethoxycarbonylmethyl, ethoxycarbonylethyl, morpholinylethoxycarbonyl, ethoxycarbonylmethylidenyl, methylsulphonylaminocarbonyl, acetylaminosulphonyl, methoxyaminocarbonyl, tetrazolyl, tetrazolylmethyl, hydroxyoxadiazolyl, aminocarbonyl, aminosulphonyl, methylsulphoximinyl and (methyl)(N-methyl)sulphoximinyl. Additional examples include ethylsulphoximinyl, trifluoromethylsulphoximinyl, (N-carboxymethyl)-(methyl)sulphoximinyl, (N-tert-butoxycarbonylmethyl)(methyl)sulphoximinyl, cyclopropylsulphoximinyl and N-(dimethylsulfoxo)iminyl.

Selected examples of particular substituents on $R^{11}$ include fluoro, methyl, ethyl, trifluoromethyl, difluoroethyl, hydroxy, hydroxyisopropyl, pentafluorothio, methyl-sulphonyl, oxo, amino, carboxy, methoxycarbonyl, ethoxycarbonyl, tert-butoxycarbonyl, methylsulphoximinyl, ethylsulphoximinyl, trifluoromethylsulphoximinyl, (methyl)(N-methyl)sulphoximinyl, (N-carboxymethyl)(methyl)sulphoximinyl, (N-tert-butoxycarbonyl-methyl)(methyl)sulphoximinyl, cyclopropylsulphoximinyl and N-(dimethylsulfoxo)iminyl.

Suitable examples of particular substituents on $R^{11}$ include one, two or three substituents independently selected from fluoro, methyl, trifluoromethyl, difluoroethyl, hydroxy, hydroxyisopropyl, pentafluorothio, methylsulphonyl, oxo, carboxy, methoxy-carbonyl, ethoxycarbonyl and tert-butoxycarbonyl.

In a particular embodiment, $R^{11}$ is substituted by hydroxy $(C_{1-6})$alkyl. In one aspect of that embodiment, $R^{11}$ is substituted by hydroxyisopropyl, especially 2-hydroxyprop-2-yl.

Selected values of $R^{11}$ include bromo, iodo, methoxycarbonylethyl, ethoxycarbonylethyl, hydroxybutynyl, chlorophenyl, hydroxyphenyl, pentafluoro-thiophenyl, methylsulphonylphenyl, aminomethylphenyl, aminoisopropylphenyl, acetyl-aminomethylphenyl, acetylphenyl, methoxycarbonylphenyl, aminocarbonylphenyl, aminosulphonylphenyl, acetylaminosulphonylphenyl, (methoxycarbonyl)(methyl)-pyrrolidinyl, oxopiperidinyl, ethoxycarbonylpiperidinyl, methylsulphonylpiperazinyl, morpholinyl, methylsulphonyl-1,2,3,6-tetrahydropyridinyl, acetyl-1,2,3,6-tetrahydropyridinyl, tert-butoxycarbonyl-1,2,3,6-tetrahydropyridinyl, methoxycarbonyl-methyl-1,2,3,6-tetrahydropyridinyl, benzofuryl, thienyl, indolyl, pyrazolyl, methyl-pyrazolyl, dimethylpyrazolyl, (methyl)[N-methyl-N-(methylsulfonyl)amino]pyrazolyl, methylindazolyl, dimethylisoxazolyl, hydroxyisopropylthiazolyl, methylimidazolyl, dimethylimidazolyl, pyridinyl, fluoropyridinyl, cyanopyridinyl, methylpyridinyl, (cyano)-(methyl)pyridinyl, dimethylpyridinyl, trifluoromethylpyridinyl, ethenylpyridinyl, hydroxyisopropylpyridinyl, methoxypyridinyl, (methoxy)(methyl)pyridinyl, isopropoxy-pyridinyl, trifluoroethoxypyridinyl, (methyl)(trifluoroethoxy)pyridinyl, methylsulphonyl-pyridinyl, oxopyridinyl, (methyl)(oxo)pyridinyl, (dimethyl)(oxo)pyridinyl, amino-pyridinyl, methylaminopyridinyl, dimethylaminopyridinyl, methoxyethylaminopyridinyl, N-(hydroxyethyl)-N-(methyl)aminopyridinyl, methylsulphonylaminopyridinyl, [bis(methylsulphonyl)amino]pyridinyl, carboxypyridinyl, quinolinyl, hydroxypyridazinyl, pyrimidinyl, fluoroisopropylpyrimidinyl, difluoroethylpyrimidinyl, hydroxyisopropyl-pyrimidinyl, methoxypyrimidinyl, carboxycyclobutyloxypyrimidinyl, methylthio-pyrimidinyl, methylsulphonylpyrimidinyl, oxopyrimidinyl, aminopyrimidinyl, dimethyl-aminopyrimidinyl, methoxyethylaminopyrimidinyl, N-(carboxyethyl)-N-(methyl)amino-pyrimidinyl, carboxycyclopentylaminopyrimidinyl, carboxycyclopropylmethylamino-pyrimidinyl, acetoxyisopropylpyrimidinyl, ethoxycarbonylethylpyrimidinyl, hydroxypyrazinyl, hydroxyisopropylpyrazinyl, pyrrolidinylmethylphenyl, piperazinyl-methylphenyl, pyridinylpiperazinyl, carboxycyclohexylpyrazolyl, carboxycyclohexyl-pyridinyl, fluoromethylcyclopropylpyrimidinyl, hydroxycyclopropylpyrimidinyl, acetyl-aminomethylcyclopropylpyrimidinyl, hydroxycyclobutylpyrimidinyl, (difluoro)-(hydroxy)cyclobutylpyrimidinyl, carboxycyclopentylpyrimidinyl, carboxycyclohexyl-pyrimidinyl, (carboxy)(methyl)cyclohexylpyrimidinyl, (carboxy)(hydroxy)cyclohexyl-pyrimidinyl, carboxymethylcyclohexylpyrimidinyl, ethoxycarbonylcyclohexyl-pyrimidinyl, (methoxycarbonyl)(methyl)cyclohexylpyrimidinyl, (ethoxycarbonyl)-(methyl)cyclohexylpyrimidinyl, carboxycyclohexylpyrazinyl, carboxycyclohexylmethyl-pyrimidinyl, carboxycyclohexenylpyridinyl, carboxycyclohexenylpyrimidinyl, ethoxycarbonylcyclohexenylpyrimidinyl, carboxybicyclo[3.1.0]hexanylpyridinyl, carboxybicyclo[3.1.0]hexanylpyrimidinyl, ethoxycarbonylbicyclo[3.1.0]hexanyl-pyrimidinyl, carboxybicyclo[4.1.0]heptanylpyrimidinyl, carboxybicyclo[2.2.2]octanyl-pyrimidinyl, pyrrolidinylpyridinyl, hydroxypyrrolidinylpyridinyl, hydroxytetrahydropyranylpyridinyl, piperidinylpyridinyl, acetylpiperidinylpyridinyl, (carboxy)(methyl)piperidinylpyridinyl, [(carboxy)(methyl)piperidinyl](fluoro)pyridinyl, [(carboxy)(methyl)piperidinyl](chloro)pyridinyl, piperazinylpyridinyl, (methyl)-(piperazinyl)pyridinyl, cyanoethylpiperazinylpyridinyl, trifluoroethylpiperazinylpyridinyl, methylsulphonylpiperazinylpyridinyl, methylsulphonylethylpiperazinylpyridinyl, oxopiperazinylpyridinyl, acetylpiperazinylpyridinyl, (tert-butoxycarbonylpiperazinyl)-(methyl)pyridinyl, carboxymethylpiperazinylpyridinyl, carboxyethylpiperazinylpyridinyl, ethoxycarbonylmethylpiperazinylpyridinyl, ethoxycarbonylethylpiperazinylpyridinyl, morpholinylpyridinyl, thiomorpholinylpyridinyl, oxothiomorpholinylpyridinyl, dioxothiomorpholinylpyridinyl, oxodiazepanylpyridinyl, fluorooxetanylpyrimidinyl, hydroxyoxetanylpyrimidinyl, difluoroazetidinylpyrimidinyl, hydroxyazetidinyl-pyrimidinyl, (hydroxy)(methyl)azetidinylpyrimidinyl, (hydroxy)(trifluoromethyl)-azetidinylpyrimidinyl, carboxyazetidinylpyrimidinyl, (tert-butoxycarbonyl)(hydroxy)-azetidinylpyrimidinyl, tetrazolylazetidinylpyrimidinyl, hydroxytetrahydrofuranylpyrimidinyl, hydroxypyrrolidinylpyrimidinyl, carboxypyrrolidinylpyrimidinyl, (carboxy)-(methyl)pyrrolidinylpyrimidinyl, carboxymethylpyrrolidinylpyrimidinyl, ethoxycarbonyl-pyrrolidinylpyrimidinyl, fluorotetrahydropyranylpyrimidinyl, hydroxytetrahydropyranyl-pyrimidinyl, difluoropiperidinylpyrimidinyl, (cyano)(methyl)piperidinylpyrimidinyl, (hydroxy)(nitromethyl)piperidinylpyrimidinyl, (hydroxy)(methyl)piperidinylpyrimidinyl, (hydroxy)(trifluoromethyl)piperidinylpyrimidinyl, (hydroxymethyl)(methyl)piperidinyl-pyrimidinyl, methylsulphonylpiperidinylpyrimidinyl, oxopiperidinylpyrimidinyl, (formyl)(methyl)piperidinylpyrimidinyl, carboxypiperidinylpyrimidinyl, (carboxy)-(fluoro)piperidinylpyrimidinyl, (carboxy)(methyl)piperidinylpyrimidinyl, (carboxy)-(ethyl)piperidinylpyrimidinyl, (carboxy)(trifluoromethyl)piperidinylpyrimidinyl, (carboxy)(hydroxy)piperidinylpyrimidinyl, (carboxy)(hydroxymethyl)piperidinyl-pyrimidinyl, (carboxy)(methoxy)piperidinylpyrimidinyl, (amino)(carboxy)piperidinyl-pyrimidinyl, carboxymethyl-piperidinylpyrimidinyl, methoxycarbonylpiperidinyl-pyrimidinyl, ethoxycarbonylpiperidinylpyrimidinyl, (ethoxycarbonyl)(fluoro)piperidinyl-pyrimidinyl, (methoxycarbonyl)(methyl)piperidinylpyrimidinyl, (ethyl)(methoxy-carbonyl)piperidinylpyrimidinyl, (isopropyl)(methoxycarbonyl)piperidinylpyrimidinyl, (ethoxycarbonyl)(methyl)piperidinylpyrimidinyl, (n-butoxycarbonyl)(methyl)piperidinyl-pyrimidinyl, (ethoxycarbonyl)(trifluoromethyl)piperidinylpyrimidinyl, (ethoxycarbonyl)-(hydroxymethyl)piperidinylpyrimidinyl, (methoxy)(methoxycarbonyl)piperidinyl-pyrimidinyl, (carboxy)(methoxycarbonyl)piperidinylpyrimidinyl, (methyl)-(morpholinylethoxycarbonyl)piperidinylpyrimidinyl, ethoxycarbonylmethylpiperidinyl-pyrimidinyl, methylsulphonylaminocarbonylpiperidinylpyrimidinyl, acetylaminosulphonylpiperidinylpyrimidinyl, methoxyaminocarbonylpiperidinylpyrimidinyl, tetrazolylpiperidinylpyrimidinyl, hydroxyoxadiazolylpiperidinylpyrimidinyl, amino-sulphonylpiperidinylpyrimidinyl, piperazinylpyrimidinyl, methylsulphonylpiperazinyl-pyrimidinyl, oxopiperazinylpyrimidinyl, carboxypiperazinylpyrimidinyl, carboxyethylpiperazinylpyrimidinyl, tert-butoxycarbonylpiperazinylpyrimidinyl, tetrazolylmethylpiperazinylpyrimidinyl, trioxohexahydro-[1,2,5]thiadiazolo[2,3-a]pyrazinylpyrimidinyl, morpholinylpyrimidinyl, dimethylmorpholinylpyrimidinyl, hydroxymethylmorpholinyl-pyrimidinyl, carboxymorpholinylpyrimidinyl, (carboxy)(methyl)morpholinylpyrimidinyl, carboxymethylmorpholinylpyrimidinyl, thiomorpholinylpyrimidinyl, dioxothiomorpholinylpyrimidinyl, carboxyazepanylpyrimidinyl, carboxyoxazepanyl-pyrimidinyl, oxodiazepanylpyrimidinyl, (oxodiazepanyl)(trifluoromethyl)pyrimidinyl, (oxodiazepanyl)(methoxy)pyrimidinyl, (methyl)(oxo)diazepanylpyrimidinyl, dioxo-thiadiazepanylpyrimidinyl, hydroxyoxetanylpyrazinyl, (carboxy)(methyl)piperidinylpyrazinyl, (ethoxycarbonyl)(methyl)piperidinylpyrazinyl, morpholinylmethylthienyl, morpholinylethylpyrazolyl, carboxy-3-azabicyclo[3.1.0]hexanylpyridinyl, carboxy-3-azabicyclo[3.1.0]hexanylpyridazinyl, carboxy-3-azabicyclo[3.1.0]hexanylpyrimidinyl, (carboxy)(methyl)-3-azabicyclo[3.1.0]hexanylpyrimidinyl, methoxycarbonyl-3-azabicyclo[3.1.0]hexanylpyrimidinyl, ethoxycarbonyl-3-azabicyclo[3.1.0]hexanyl-pyrimidinyl, 2-oxa-5-azabicyclo[2.2.1]heptanylpyrimidinyl, carboxy-2-oxa-5-azabicyclo-[2.2.1]heptanylpyrimidinyl, carboxy-3-azabicyclo[3.1.1]heptanylpyrimidinyl, 6-oxa-3-azabicyclo[3.1.1]heptanylpyrimidinyl, carboxy-3-azabicyclo[4.1.0]heptanylpyridinyl, carboxy-3-azabicyclo[4.1.0]heptanylpyrimidinyl, methoxycarbonyl-3-azabicyclo[4.1.0]-heptanylpyrimidinyl, ethoxycarbonyl-3-azabicyclo[4.1.0]heptanylpyrimidinyl, (hydroxy)-(methyl)(oxo)-2-oxabicyclo[2.2.2]octanylpyrimidinyl, carboxy-3-azabicyclo[3.2.1]-octanylpyrimidinyl, methoxycarbonyl-3-azabicyclo[3.2.1]octanylpyrimidinyl, oxo-8-azabicyclo[3.2.1]octanylpyrimidinyl, ethoxycarbonylmethylidenyl-8-azabicyclo[3.2.1]-octanylpyrimidinyl, 3-oxa-8-azabicyclo[3.2.1]octanylpyrimidinyl, oxo-3,6-diazabicyclo-[3.2.2]nonanylpyrimidinyl, carboxy-3-oxa-7-azabicyclo[3.3.1]nonanylpyrimidinyl, 3,7-dioxa-9-azabicyclo[3.3.1]nonanylpyrimidinyl, carboxy-5-azaspiro[2.3]hexanylpyrimidinyl, (carboxy)(methyl)-5-azaspiro[2.3]hexanylpyrimidinyl, carboxy-5-azaspiro-[2.4]heptanylpyrimidinyl, carboxy-2-azaspiro[3.3]heptanylpyrimidinyl, 2-oxa-6-azaspiro-[3.3]heptanylpyrimidinyl, 3-oxa-6-azaspiro[3.3]heptanylpyrimidinyl, dioxo-6-thia-2-azaspiro[3.3]heptanylpyrimidinyl, 2-oxa-6-azaspiro[3.4]octanylpyrimidinyl, 2-oxa-6-azaspiro[3.5]nonanylpyrimidinyl, 2-oxa-7-azaspiro[3.5]nonanylpyrimidinyl and (dioxo)(methyl)-2,4,8-triazaspiro[4.5]decanylpyrimidinyl. Additional values include methylsulphoximinylphenyl, trifluoromethylsulphoximinylphenyl, (N-carboxymethyl)-(methyl)sulphoximinylphenyl, (N-tert-butoxycarbonylmethyl)(methyl)sulphoximinyl-phenyl, methylsulphoximinylpyridinyl, ethylsulphoximinylpyridinyl, (methyl)-(methylsulphoximinyl)pyridinyl, (methyl)(N-methyl)sulphoximinylpyridinyl, cyclopropylsulphoximinylpyridinyl, N-(dimethylsulfoxo)iminylpyridinyl, (hydroxyisopropyl)(methyl)pyrimidinyl, (dihydroxy)(methyl)cyclobutylpyridinyl, dihydroxycyclobutylpyrimidinyl, (dihydroxy)(methyl)cyclobutylpyrimidinyl, (dihydroxy)(ethyl)cyclobutylpyrimidinyl, (amino)(hydroxy)cyclobutylpyrimidinyl and (amino)(hydroxy)(methyl)cyclobutylpyrimidinyl.

Definitive values of $R^{11}$ include bromo, pentafluorothiophenyl, methylsulphonyl-phenyl, methylsulphoximinylphenyl, trifluoromethylsulphoximinylphenyl, (N-carboxymethyl)(methyl)sulphoximinylphenyl, (N-tert-butoxycarbonylmethyl)(methyl)-sulphoximinylphenyl, morpholinyl, methylpyrazolyl, hydroxyisopropylpyridinyl, methylsulphonylpyridinyl, methylsulphoximinylpyridinyl, ethylsulphoximinylpyridinyl, (methyl)(methylsulphoximinyl)pyridinyl, (methyl)(N-methyl)sulphoximinylpyridinyl, cyclopropylsulphoximinylpyridinyl, N-(dimethylsulfoxo)iminylpyridinyl, difluoroethyl-pyrimidinyl, hydroxyisopropylpyrimidinyl, (hydroxyisopropyl)(methyl)pyrimidinyl, (dihydroxy)(methyl)cyclobutylpyridinyl, hydroxycyclopropylpyrimidinyl, hydroxycyclobutylpyrimidinyl, (difluoro)(hydroxy)cyclobutylpyrimidinyl, dihydroxycyclobutylpyrimidinyl, (dihydroxy)(methyl)cyclobutylpyrimidinyl, (dihydroxy)(ethyl)cyclobutylpyrimidinyl, (amino)(hydroxy)cyclobutylpyrimidinyl, (amino)(hydroxy)(methyl)cyclobutylpyrimidinyl, carboxycyclohexylpyrimidinyl, hydroxytetrahydropyranylpyridinyl, piperazinylpyridinyl, fluorooxetanylpyrimidinyl, hydroxyoxetanylpyrimidinyl, difluoroazetidinylpyrimidinyl, hydroxyazetidinyl-pyrimidinyl, (hydroxy)(methyl)azetidinylpyrimidinyl, (hydroxy)(trifluoromethyl)-azetidinylpyrimidinyl, hydroxytetrahydropyranylpyrimidinyl, (carboxy)(methyl)-piperidinylpyrimidinyl, (ethoxycarbonyl)(methyl)piperidinylpyrimidinyl, piperazinyl-pyrimidinyl, oxopiperazinylpyrimidinyl, tert-butoxycarbonylpiperazinylpyrimidinyl, morpholinylpyrimidinyl, oxodiazepanylpyrimidinyl, (methyl)(oxo)diazepanylpyrimidinyl, 6-oxa-3-azabicyclo[3.1.1]heptanylpyrimidinyl, carboxy-3-azabicyclo[3.2.1]octanyl-pyrimidinyl, methoxycarbonyl-3-azabicyclo[3.2.1]octanylpyrimidinyl, 3,7-dioxa-9-azabicyclo[3.3.1]nonanylpyrimidinyl, 3-oxa-6-azaspiro[3.3]heptanylpyrimidinyl and dioxo-6-thia-2-azaspiro[3.3]heptanylpyrimidinyl.

Illustrative values of $R^{11}$ include bromo, pentafluorothiophenyl, methylsulphonyl-phenyl, morpholinyl, methylpyrazolyl, hydroxyisopropylpyridinyl, methylsulphonyl-pyridinyl, difluoroethylpyrimidinyl, hydroxyisopropylpyrimidinyl, hydroxycyclopropyl-pyrimidinyl, hydroxycyclobutylpyrimidinyl, (difluoro)(hydroxy)cyclobutylpyrimidinyl, carboxycyclohexylpyrimidinyl, piperazinylpyridinyl, fluorooxetanylpyrimidinyl, hydroxyoxetanylpyrimidinyl, difluoroazetidinylpyrimidinyl, hydroxyazetidinyl-pyrimidinyl, (hydroxy)(methyl)azetidinylpyrimidinyl, (hydroxy)(trifluoromethyl)-azetidinylpyrimidinyl, hydroxytetrahydropyranylpyrimidinyl, (carboxy)(methyl)-piperidinylpyrimidinyl, (ethoxycarbonyl)(methyl)piperidinylpyrimidinyl, piperazinyl-pyrimidinyl, oxopiperazinylpyrimidinyl, tert-butoxycarbonylpiperazinylpyrimidinyl, morpholinylpyrimidinyl, oxodiazepanylpyrimidinyl, 6-oxa-3-azabicyclo[3.1.1]heptanyl-pyrimidinyl, methoxycarbonyl-3-azabicyclo[3.2.1]octanylpyrimidinyl, 3,7-dioxa-9-azabicyclo[3.3.1]nonanylpyrimidinyl, 3-oxa-6-azaspiro[3.3]heptanylpyrimidinyl and dioxo-6-thia-2-azaspiro[3.3]heptanylpyrimidinyl.

A particular sub-group of the compounds of formula (IIA-A) above is represented by the compounds of formula (IIB-A) and N-oxides thereof, and pharmaceutically acceptable salts and solvates thereof, and glucuronide derivatives thereof, and co-crystals thereof:

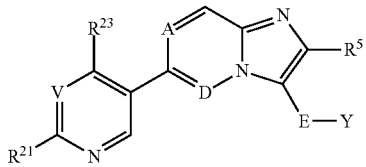

(IIB-A)

wherein

V represents C—R$^{22}$ or N;

R$^{21}$ represents hydrogen, halogen, halo(C$_{1-6}$)alkyl, cyano, C$_{1-6}$ alkyl, trifluoro-methyl, C$_{2-6}$ alkenyl, C$_{2-6}$ alkynyl, hydroxy, hydroxy(C$_{1-6}$)alkyl, C$_{1-6}$ alkoxy, (C$_{1-6}$)alkoxy-(C$_{1-6}$)alkyl, difluoromethoxy, trifluoromethoxy, trifluoroethoxy, carboxy(C$_{3-7}$)cycloalkyl-oxy, C$_{1-6}$ alkylthio, C$_{1-6}$ alkylsulphonyl, (C$_{1-6}$)alkylsulphonyl(C$_{1-6}$)alkyl, amino, amino-(C$_{1-6}$)alkyl, C$_{1-6}$ alkylamino, di(C$_{1-6}$)alkylamino, (C$_{1-6}$) alkoxy(C$_{1-6}$)alkylamino, N—[(C$_{1-6}$)-alkyl]-N-[hydroxy (C$_{1-6}$)alkyl]amino, C$_{2-6}$ alkylcarbonylamino, (C$_{2-6}$)alkylcarbonylamino-(C$_{1-6}$)alkyl, C$_{2-6}$ alkoxycarbonylamino, N—[(C$_{1-6}$)alkyl]-N-[carboxy(C$_{1-6}$)alkyl]amino, carboxy (C$_{3-7}$)cycloalkylamino, carboxy(C$_{3-7}$)cycloalkyl(C$_{1-6}$)alkylamino, C$_{1-6}$ alkyl-sulphonylamino, C$_{1-6}$ alkylsulphonylamino(C$_{1-6}$)alkyl, formyl, C$_{2-6}$ alkylcarbonyl, (C$_{2-6}$) alkylcarbonyloxy(C$_{1-6}$)alkyl, carboxy, carboxy(C$_{1-6}$)alkyl, C$_{2-6}$ alkoxycarbonyl, morpholinyl(C$_{1-6}$)alkoxycarbonyl, C$_{2-6}$ alkoxycarbonyl(C$_{1-6}$)alkyl, C$_{2-6}$ alkoxycarbonyl-methylidenyl, aminocarbonyl, C$_{1-6}$ alkylaminocarbonyl, di(C$_{1-6}$) alkylaminocarbonyl, aminosulphonyl, C$_{1-6}$ alkylaminosulphonyl, di(C$_{1-6}$)alkylaminosulphonyl, (C$_{1-6}$)alkylsulphoximinyl or [(C$_{1-6}$)alkyl][N—(C$_{1-6}$)alkyl] sulphoximinyl; or R$^{21}$ represents (C$_{3-7}$)cycloalkyl, (C$_{3-7}$) cycloalkyl(C$_{1-6}$)alkyl, (C$_{4-7}$)cycloalkenyl, (C$_{4-9}$) bicycloalkyl, (C$_{3-7}$)heterocycloalkyl, (C$_{3-7}$) heterocycloalkenyl, (C$_{4-9}$)heterobicycloalkyl or (C$_{4-9}$) spiroheterocycloalkyl, any of which groups may be optionally substituted by one or more substituents;

R$^{22}$ represents hydrogen, halogen or C$_{1-6}$ alkyl;

R$^{23}$ represents hydrogen, C$_{1-6}$ alkyl, trifluoromethyl or C$_{1-6}$ alkoxy; and A, D, E, Y and R$^{5}$ are as defined above.

In one embodiment, V represents C—R$^{22}$. In another embodiment, V represents N.

Typically, R$^{21}$ represents hydrogen, halogen, halo(C$_{1-6}$) alkyl, cyano, C$_{1-6}$ alkyl, trifluoromethyl, C$_{2-6}$ alkenyl, hydroxy, hydroxy(C$_{1-6}$)alkyl, C$_{1-6}$ alkoxy, trifluoroethoxy, carboxy(C$_{3-7}$)cycloalkyloxy, C$_{1-6}$ alkylthio, C$_{1-6}$ alkylsulphonyl, amino, C$_{1-6}$ alkylamino, di(C$_{1-6}$)alkylamino, (C$_{1-6}$) alkoxy(C$_{1-6}$)alkylamino, N—[(C$_{1-6}$)alkyl]-N-[hydroxy (C$_{1-6}$)alkyl]-amino, N—[(C$_{1-6}$)alkyl]-N-[carboxy(C$_{1-6}$) alkyl]amino, carboxy(C$_{3-7}$)cycloalkylamino, carboxy(C$_{3-7}$) cycloalkyl(C$_{1-6}$)alkylamino, C$_{1-6}$ alkylsulphonylamino, (C$_{2-6}$)alkylcarbonyl-oxy(C$_{1-6}$)alkyl, carboxy, morpholinyl (C$_{1-6}$)alkoxycarbonyl, C$_{2-6}$ alkoxycarbonyl(C$_{1-6}$)alkyl or C$_{2-6}$ alkoxycarbonylmethylidenyl; or R$^{21}$ represents (C$_{3-7}$) cycloalkyl, (C$_{3-7}$)cycloalkyl-(C$_{1-6}$)alkyl, (C$_{4-7}$)cycloalkenyl, (C$_{4-9}$)bicycloalkyl, (C$_{3-7}$)heterocycloalkyl, (C$_{4-9}$)heterobicycloalkyl or (C$_{4-9}$)spiroheterocycloalkyl, any of which groups may be optionally substituted by one or more substituents. Additionally, R$^{21}$ may represent (C$_{1-6}$)alkylsulphoximinyl or [(C$_{1-6}$)alkyl][N—(C$_{1-6}$)alkyl]sulphoximinyl.

More typically, R$^{21}$ represents hydroxy(C$_{1-6}$)alkyl C$_{1-6}$ alkylsulphonyl, (C$_{1-6}$)alkyl-sulphoximinyl or [(C$_{1-6}$)alkyl] [N—(C$_{1-6}$)alkyl]sulphoximinyl; or R$^{21}$ represents (C$_{3-7}$)-cycloalkyl, (C$_{3-7}$)heterocycloalkyl, (C$_{4-9}$)heterobicycloalkyl or (C$_{4-9}$)spiroheterocycloalkyl, any of which groups may be optionally substituted by one or more substituents.

Suitably, R$^{21}$ represents hydroxy(C$_{1-6}$)alkyl or C$_{1-6}$ alkyl-sulphonyl; or R$^{21}$ represents (C$_{3-7}$)cycloalkyl, (C$_{3-7}$)heterocycloalkyl, (C$_{4-9}$)heterobicycloalkyl or (C$_{4-9}$)spiroheterocycloalkyl, any of which groups may be optionally substituted by one or more substituents.

Where R$^{21}$ represents an optionally substituted (C$_{3-7}$) cycloalkyl group, typical values include cyclopropyl, cyclobutyl, cyclopentyl, cyclohexyl and cycloheptyl, any of which groups may be optionally substituted by one or more substituents.

Where R$^{21}$ represents an optionally substituted (C$_{3-7}$) cycloalkyl(C$_{1-6}$)alkyl group, a typical value is cyclohexyl-methyl, which group may be optionally substituted by one or more substituents.

Where R$^{21}$ represents an optionally substituted (C$_{4-7}$) cycloalkenyl group, typical values include cyclobutenyl, cyclopentenyl, cyclohexenyl and cycloheptenyl, any of which groups may be optionally substituted by one or more substituents.

Where R$^{21}$ represents an optionally substituted (C$_{4-9}$) bicycloalkyl group, typical values include bicyclo[3.1.0] hexanyl, bicyclo[4.1.0]heptanyl and bicyclo[2.2.2]octanyl, any of which groups may be optionally substituted by one or more substituents.

Where R$^{21}$ represents an optionally substituted (C$_{3-7}$) heterocycloalkyl group, typical values include oxetanyl, azetidinyl, tetrahydrofuranyl, pyrrolidinyl, tetrahydro-pyranyl, piperidinyl, piperazinyl, hexahydro-[1,2,5]thiadiazolo [2,3-a]pyrazinyl, morpholinyl, thiomorpholinyl, azepanyl, oxazepanyl, diazepanyl and thiadiazepanyl, any of which groups may be optionally substituted by one or more substituents.

Where R$^{21}$ represents an optionally substituted (C$_{3-7}$) heterocycloalkenyl group, a typical value is optionally substituted 1,2,3,6-tetrahydropyridinyl.

Where R$^{21}$ represents an optionally substituted (C$_{4-9}$) heterobicycloalkyl group, typical values include 3-azabicyclo[3.1.0]hexanyl, 2-oxa-5-azabicyclo[2.2.1]heptanyl, 3-azabicyclo[3.1.1]heptanyl, 6-oxa-3-azabicyclo[3.1.1]heptanyl, 3-azabicyclo[4.1.0]-heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo[3.2.1]octanyl, 3-oxa-8-azabicyclo[3.2.1]octanyl, 3,8-diazabicyclo[3.2.1] octanyl, 3,6-diazabicyclo[3.2.2]nonanyl, 3-oxa-7-azabicyclo-[3.3.1]nonanyl, 3,7-dioxa-9-azabicyclo[3.3.1]nonanyl and 3,9-diazabicyclo[4.2.1]nonanyl, any of which groups may be optionally substituted by one or more substituents.

Where R$^{21}$ represents an optionally substituted (C$_{4-9}$) spiroheterocycloalkyl group, typical values include 5-azaspiro[2.3]hexanyl, 5-azaspiro[2.4]heptanyl, 2-azaspiro [3.3]-heptanyl, 2-oxa-6-azaspiro[3.3]heptanyl, 3-oxa-6-azaspiro[3.3]heptanyl, 6-thia-2-azaspiro[3.3]heptanyl, 2-oxa-6-azaspiro[3.4]octanyl, 2-oxa-6-azaspiro[3.5] nonanyl, 2-oxa-7-azaspiro[3.5]nonanyl and 2,4,8-triazaspiro [4.5]decanyl, any of which groups may be optionally substituted by one or more substituents.

Illustratively, R$^{21}$ represents hydroxy, hydroxy(C$_{1-6}$) alkyl, methoxy, carboxy-cyclobutyloxy, methylthio, methylsulphonyl, methylamino, N-[carboxyethyl]-N-methylamino, carboxycyclopentylamino, carboxycyclopropylmethylamino or ethoxycarbonyl-ethyl; or R$^{21}$ represents cyclopropyl, cyclobutyl, cyclopentyl, cyclohexyl, cyclohexenyl, methylcyclohexenyl, bicyclo [3.1.0]hexanyl, bicyclo[4.1.0]heptanyl, bicyclo[2.2.2]-octanyl, oxetanyl, azetidinyl, tetrahydrofuranyl, pyrrolidinyl, tetrahydropyranyl, piperidinyl, piperazinyl, hexahydro-[1,2,5]thiadiazolo[2,3-a]pyrazinyl, morpholinyl, thiomorpholinyl, azepanyl, oxazepanyl, diazepanyl, thiadiazepanyl, 3-azabicyclo[3.1.0]-hexanyl, 2-oxa-5-azabicyclo[2.2.1]heptanyl, 3-azabicyclo[3.1.1]heptanyl, 6-oxa-3-azabicyclo[3.1.1]heptanyl, 3-azabicyclo[4.1.0]heptanyl, 2-oxabicyclo[2.2.2]octanyl, 3-azabicyclo[3.2.1]octanyl, 8-azabicyclo[3.2.1]octanyl, 3-oxa-8-azabicyclo[3.2.1]octanyl, 3,6-diazabicyclo[3.2.2]nonanyl, 3-oxa-7-azabicyclo[3.3.1]nonanyl, 3,7-dioxa-9-azabicyclo[3.3.1]nonanyl, 5-azaspiro[2.3]hexanyl, 5-azaspiro[2.4]heptanyl, 2-azaspiro-[3.3]heptanyl, 3-oxa-6-azaspiro[3.3]heptanyl or 6-thia-2-azaspiro[3.3]heptanyl, any of which groups may be optionally substituted by one or more substituents. Additionally, $R^{21}$ may represent methylsulphoximinyl, ethylsulphoximinyl or (methyl)(N-methyl)-sulphoximinyl.

More particularly, $R^{21}$ represents hydroxy($C_{1-6}$)alkyl, methylsulphonyl, methyl-sulphoximinyl, ethylsulphoximinyl or (methyl)(N-methyl)sulphoximinyl; or $R^{21}$ represents cyclopropyl, cyclobutyl, cyclohexyl, oxetanyl, azetidinyl, tetrahydropyranyl, piperidinyl, piperazinyl, morpholinyl, diazepanyl, 6-oxa-3-azabicyclo[3.1.1]heptanyl, 3-azabicyclo-[3.2.1]octanyl, 3,7-dioxa-9-azabicyclo[3.3.1]nonanyl, 3-oxa-6-azaspiro[3.3]heptanyl or 6-thia-2-azaspiro[3.3]heptanyl, any of which groups may be optionally substituted by one or more substituents.

Appositely, $R^{21}$ represents hydroxy($C_{1-6}$)alkyl or methylsulphonyl; or $R^{21}$ represents cyclopropyl, cyclobutyl, cyclohexyl, oxetanyl, azetidinyl, tetrahydropyranyl, piperidinyl, piperazinyl, morpholinyl, diazepanyl, 6-oxa-3-azabicyclo[3.1.1]heptanyl, 3-azabicyclo[3.2.1]octanyl, 3,7-dioxa-9-azabicyclo[3.3.1]nonanyl, 3-oxa-6-azaspiro[3.3]-heptanyl or 6-thia-2-azaspiro[3.3]heptanyl, any of which groups may be optionally substituted by one or more substituents.

Examples of optional substituents which may be present on $R^{21}$ include one, two or three substituents independently selected from halogen, halo($C_{1-6}$)alkyl, cyano, cyano-($C_{1-6}$)alkyl, nitro, nitro($C_{1-6}$)alkyl, $C_{1-6}$ alkyl, trifluoromethyl, trifluoroethyl, $C_{2-6}$ alkenyl, hydroxy, hydroxy($C_{1-6}$)alkyl, $C_{1-6}$ alkoxy, difluoromethoxy, trifluoromethoxy, trifluoroethoxy, $C_{1-6}$ alkylthio, $C_{1-6}$ alkylsulphonyl, ($C_{1-6}$)alkylsulphonyl($C_{1-6}$)alkyl, oxo, amino, $C_{1-6}$ alkylamino, di($C_{1-6}$)alkylamino, $C_{2-6}$ alkylcarbonylamino, ($C_{2-6}$)alkylcarbonylamino-($C_{1-6}$)alkyl, $C_{2-6}$ alkoxycarbonylamino, $C_{1-6}$ alkylsulphonylamino, formyl, $C_{2-6}$ alkylcarbonyl, carboxy, carboxy($C_{1-6}$)alkyl, $C_{2-6}$ alkoxycarbonyl, morpholinyl-($C_{1-6}$)alkoxycarbonyl, $C_{2-6}$ alkoxycarbonyl($C_{1-6}$)alkyl, $C_{2-6}$ alkoxycarbonylmethylidenyl, a carboxylic acid isostere or prodrug moiety Ω as defined herein, —($C_{1-6}$)alkyl-Ω, amino-carbonyl, $C_{1-6}$ alkylaminocarbonyl, di($C_{1-6}$)alkylaminocarbonyl, aminosulphonyl, di($C_{1-6}$)alkylaminosulphonyl, ($C_{1-6}$)alkylsulphoximinyl and [($C_{1-6}$)alkyl][N—($C_{1-6}$)alkyl]-sulphoximinyl.

Typical examples of optional substituents on $R^{21}$ include one, two or three substituents independently selected from halogen, $C_{1-6}$ alkyl, trifluoromethyl, hydroxy, oxo, amino, carboxy and $C_{2-6}$ alkoxycarbonyl.

Selected examples of optional substituents on $R^{21}$ include one, two or three substituents independently selected from halogen, $C_{1-6}$ alkyl, trifluoromethyl, hydroxy, oxo, carboxy and $C_{2-6}$ alkoxycarbonyl.

Suitable examples of particular substituents on $R^{21}$ include one, two or three substituents independently selected from fluoro, fluoromethyl, chloro, bromo, cyano, cyanomethyl, cyanoethyl, nitro, nitromethyl, methyl, ethyl, isopropyl, trifluoromethyl, trifluoroethyl, ethenyl, hydroxy, hydroxymethyl, methoxy, ethoxy, difluoromethoxy, trifluoromethoxy, trifluoroethoxy, methylthio, methylsulphonyl, methylsulphonylmethyl, methylsulphonylethyl, oxo, amino, methylamino, dimethylamino, acetylamino, acetyl-aminomethyl, methoxycarbonylamino, ethoxycarbonylamino, tert-butoxycarbonylamino, methylsulphonylamino, formyl, acetyl, carboxy, carboxymethyl, carboxyethyl, methoxycarbonyl, ethoxycarbonyl, n-butoxycarbonyl, tert-butoxycarbonyl, morpholinyl-ethoxycarbonyl, methoxycarbonylmethyl, ethoxycarbonylmethyl, ethoxycarbonylethyl, ethoxycarbonylmethylidenyl, acetylaminosulphonyl, methoxyaminocarbonyl, tetrazolyl, tetrazolylmethyl, hydroxyoxadiazolyl, aminocarbonyl, methylaminocarbonyl, dimethyl-aminocarbonyl, methylsulphonylaminocarbonyl, aminosulphonyl, methylaminosulphonyl, dimethylaminosulphonyl, methylsulphoximinyl and (methyl)(N-methyl)sulphoximinyl. Typical examples of particular substituents on $R^{21}$ include one, two or three substituents independently selected from fluoro, methyl, ethyl, trifluoromethyl, hydroxy, oxo, carboxy, methoxycarbonyl and ethoxycarbonyl.

Selected examples of particular substituents on $R^{21}$ include one, two or three substituents independently selected from fluoro, methyl, trifluoromethyl, hydroxy, oxo, amino, carboxy, methoxycarbonyl, ethoxycarbonyl and tert-butoxycarbonyl.

Typically, $R^{21}$ represents hydrogen, fluoro, fluoroisopropyl, cyano, methyl, trifluoromethyl, ethenyl, hydroxy, hydroxyisopropyl, methoxy, isopropoxy, trifluoro-ethoxy, carboxycyclobutyloxy, methylthio, methylsulphonyl, amino, methylamino, dimethylamino, methoxyethylamino, N-(hydroxyethyl)-N-(methyl)amino, N-[carboxy-ethyl]-N-methylamino, carboxycyclopentylamino, carboxycyclopropylmethylamino, methylsulphonylamino, acetoxyisopropyl, carboxy, ethoxycarbonylethyl, fluoromethyl-cyclopropyl, hydroxycyclopropyl, (difluoro)(hydroxy)cyclopropyl, acetylaminomethyl-cyclopropyl, hydroxycyclobutyl, carboxycyclopentyl, carboxycyclohexyl, (carboxy)-(methyl)cyclohexyl, (carboxy)(hydroxy)cyclohexyl, carboxymethylcyclohexyl, ethoxycarbonylcyclohexyl, (methoxycarbonyl)(methyl)cyclohexyl, (ethoxycarbonyl)-(methyl)cyclohexyl, carboxycyclohexylmethyl, carboxycyclohexenyl, ethoxycarbonyl-cyclohexenyl, carboxybicyclo[3.1.0]hexanyl, ethoxycarbonylbicyclo[3.1.0]hexanyl, carboxybicyclo[4.1.0]heptanyl, carboxybicyclo[2.2.2]octanyl, fluorooxetanyl, hydroxyoxetanyl, difluoroazetidinyl, hydroxyazetidinyl, (hydroxy)(methyl)azetidinyl, (hydroxy)(trifluoromethyl)azetidinyl, carboxyazetidinyl, (tert-butoxycarbonyl)(hydroxy)-azetidinyl, tetrazolylazetidinyl, hydroxytetrahydrofuranyl, pyrrolidinyl, hydroxy-pyrrolidinyl, carboxypyrrolidinyl, (carboxy)(methyl)pyrrolidinyl, carboxymethyl-pyrrolidinyl, ethoxycarbonylpyrrolidinyl, fluorotetrahydropyranyl, hydroxytetrahydro-pyranyl, piperidinyl, difluoropiperidinyl, (cyano)(methyl)piperidinyl, (hydroxy)-(nitromethyl)piperidinyl, (hydroxy)(methyl)piperidinyl, (hydroxy)(trifluoromethyl)-piperidinyl, (hydroxymethyl)(methyl)piperidinyl, methylsulphonylpiperidinyl, oxopiperidinyl, (formyl)(methyl)piperidinyl, acetylpiperidinyl, carboxypiperidinyl, (carboxy)(fluoro)piperidinyl, (carboxy)(methyl)piperidinyl, (carboxy)(ethyl)piperidinyl, (carboxy)(trifluoromethyl)piperidinyl, (carboxy)(hydroxy)piperidinyl, (carboxy)-(hydroxymethyl)piperidinyl, (carboxy)(methoxy)piperidinyl, (amino)(carboxy)piperidinyl, carboxymethylpiperidinyl, methoxycarbonylpiperidinyl, (methoxycarbonyl)(methyl)-piperidinyl, (ethyl)(methoxycarbonyl)piperidinyl, (isopropyl)(methoxycarbonyl)-piperidinyl, (methoxy)(methoxycarbonyl)piperidinyl, (carboxy)(methoxycarbonyl)-piperidinyl, ethoxycarbonylpiperidinyl, (ethoxycarbonyl)(fluoro)piperidinyl, (ethoxycarbonyl)(methyl)piperidinyl, (ethoxycarbonyl)(trifluoromethyl)piperidinyl, (ethoxycarbonyl)(hydroxymethyl)piperidinyl, (n-butoxycarbonyl)(methyl)piperidinyl, (methyl)(morpholinylethoxycarbonyl)piperidinyl, ethoxycarbonylmethylpiperidinyl, methylsulphonylaminocarbonylpiperidinyl, acetylaminosulphonylpiperidinyl, methoxyaminocarbonylpiperidinyl, tetrazolylpiperidinyl, hydroxyoxadiazolylpiperidinyl, aminosulphonylpiperidinyl, piperazinyl, cyanoethylpiperazinyl, trifluoroethylpiperazinyl, methylsulphonylpiperazinyl, methylsulphonylethylpiperazinyl, oxopiperazinyl, acetylpiperazinyl, carboxypiperazinyl, tert-butoxycarbonylpiperazinyl, carboxymethyl-piperazinyl, carboxyethylpiperazinyl, ethoxycarbonylmethylpiperazinyl, ethoxycarbonylethylpiperazinyl, tetrazolylmethylpiperazinyl, trioxohexahydro-[1,2,5]thiadiazolo[2,3-a]-pyrazinyl, morpholinyl, dimethylmorpholinyl, hydroxymethylmorpholinyl, carboxy-morpholinyl, (carboxy)(methyl)morpholinyl, carboxymethylmorpholinyl, thiomorpholinyl, oxothiomorpholinyl, dioxothiomorpholinyl, carboxyazepanyl, carboxyoxazepanyl, oxodiazepanyl, (methyl)(oxo)diazepanyl, dioxothiadiazepanyl, carboxy-3-azabicyclo-[3.1.0]hexanyl, (carboxy)(methyl)-3-azabicyclo[3.1.0]hexanyl, methoxycarbonyl-3-azabicyclo[3.1.0]hexanyl, ethoxycarbonyl-3-azabicyclo[3.1.0]hexanyl, 2-oxa-5-azabicyclo[2.2.1]heptanyl, carboxy-2-oxa-5-azabicyclo[2.2.1]heptanyl, carboxy-3-azabicyclo[3.1.1]heptanyl, 6-oxa-3-azabicyclo[3.1.1]heptanyl, carboxy-3-azabicyclo-[4.1.0]heptanyl, methoxycarbonyl-3-azabicyclo[4.1.0]heptanyl, ethoxycarbonyl-3-azabicyclo[4.1.0]heptanyl, (hydroxy)(methyl)(oxo)-2-oxabicyclo[2.2.2]octanyl, carboxy-3-azabicyclo[3.2.1]octanyl, methoxycarbonyl-3-azabicyclo[3.2.1]octanyl, oxo-8-azabicyclo[3.2.1]octanyl, ethoxycarbonylmethylidenyl-8-azabicyclo[3.2.1]octanyl, 3-oxa-8-azabicyclo[3.2.1]octanyl, oxo-3,6-diazabicyclo[3.2.2]nonanyl, carboxy-3-oxa-7-azabicyclo[3.3.1]nonanyl, 3,7-dioxa-9-azabicyclo[3.3.1]nonanyl, carboxy-5-azaspiro[2.3]hexanyl, (carboxy)(methyl)-5-azaspiro[2.3]hexanyl, carboxy-5-azaspiro[2.4]heptanyl, carboxy-2-azaspiro[3.3]heptanyl, 2-oxa-6-azaspiro[3.3]heptanyl, 3-oxa-6-azaspiro[3.3]-heptanyl, dioxo-6-thia-2-azaspiro[3.3]heptanyl, 2-oxa-6-azaspiro[3.4]octanyl, 2-oxa-6-azaspiro[3.5]nonanyl, 2-oxa-7-azaspiro[3.5]nonanyl or (dioxo)(methyl)-2,4,8-triazaspiro-[4.5]decanyl. Additionally, $R^{21}$ may represent methylsulphoximinyl, ethylsulphoximinyl, (methyl)(N-methyl)sulphoximinyl, (difluoro)(hydroxy)cyclobutyl, (dihydroxy)cyclobutyl, (dihydroxy)(methyl)cyclobutyl, (dihydroxy)(ethyl)cyclobutyl, (amino)(hydroxy)-cyclobutyl or (amino)(hydroxy)(methyl)cyclobutyl.

Selected values of $R^{21}$ include hydroxyisopropyl, methylsulphonyl, methylsulphoximinyl, ethylsulphoximinyl, (methyl)(N-methyl)sulphoximinyl, hydroxycyclopropyl, hydroxycyclobutyl, (difluoro)(hydroxy)cyclobutyl, (dihydroxy)-cyclobutyl, (dihydroxy)(methyl)cyclobutyl, (dihydroxy)(ethyl)cyclobutyl, (amino)-(hydroxy)cyclobutyl, (amino)(hydroxy)(methyl)cyclobutyl, carboxycyclohexyl, fluoro-oxetanyl, hydroxyoxetanyl, difluoroazetidinyl, hydroxyazetidinyl, (hydroxy)(methyl)-azetidinyl, (hydroxy)(trifluoromethyl)azetidinyl, hydroxytetrahydropyranyl, (carboxy)-(methyl)piperidinyl, (ethoxycarbonyl)(methyl)piperidinyl, piperazinyl, oxopiperazinyl, tert-butoxycarbonylpiperazinyl, morpholinyl, oxodiazepanyl, (methyl)(oxo)diazepanyl, 6-oxa-3-azabicyclo[3.1.1]heptanyl, carboxy-3-azabicyclo[3.2.1]octanyl, methoxycarbonyl-3-azabicyclo[3.2.1]octanyl, 3,7-dioxa-9-azabicyclo[3.3.1]nonanyl, 3-oxa-6-azaspiro[3.3]-heptanyl and dioxo-6-thia-2-azaspiro[3.3]heptanyl.

Illustrative values of $R^{21}$ include hydroxyisopropyl, methylsulphonyl, hydroxycyclopropyl, (difluoro)(hydroxy)cyclopropyl, hydroxycyclobutyl, carboxy-cyclohexyl, fluorooxetanyl, hydroxyoxetanyl, difluoroazetidinyl, hydroxyazetidinyl, (hydroxy)(methyl)azetidinyl, (hydroxy)(trifluoromethyl)azetidinyl, hydroxytetrahydro-pyranyl, (carboxy)(methyl)piperidinyl, (ethoxycarbonyl)(methyl)piperidinyl, piperazinyl, oxopiperazinyl, tert-butoxycarbonylpiperazinyl, morpholinyl, oxodiazepanyl, 6-oxa-3-azabicyclo[3.1.1]heptanyl, methoxycarbonyl-3-azabicyclo[3.2.1]octanyl, 3,7-dioxa-9-azabicyclo[3.3.1]nonanyl, 3-oxa-6-azaspiro[3.3]heptanyl and dioxo-6-thia-2-azaspiro-[3.3]heptanyl.

In a particular embodiment, $R^{21}$ represents hydroxy $(C_{1-6})$alkyl. In one aspect of that embodiment, $R^{21}$ represents hydroxyisopropyl, especially 2-hydroxyprop-2-yl.

Generally, $R^{22}$ represents hydrogen or $C_{1-6}$ alkyl.

Suitably, $R^{22}$ represents hydrogen, chloro or methyl.

Typically, $R^{22}$ represents hydrogen or methyl.

In one embodiment, $R^{22}$ represents hydrogen. In another embodiment, $R^{22}$ represents $C_{1-6}$ alkyl, especially methyl. In a further embodiment, $R^{22}$ represents halogen.

In one aspect of that embodiment, $R^{22}$ represents fluoro. In another aspect of that embodiment, $R^{22}$ represents chloro.

Generally, $R^{23}$ represents hydrogen or $C_{1-6}$ alkyl.

Suitably, $R^{23}$ represents hydrogen, methyl, trifluoromethyl or methoxy.

Typically, $R^{23}$ represents hydrogen or methyl.

In one embodiment, $R^{23}$ represents hydrogen. In another embodiment, $R^{23}$ represents $C_{1-6}$ alkyl, especially methyl. In a further embodiment, $R^{23}$ represents trifluoromethyl. In an additional embodiment, $R^{23}$ represents $C_{1-6}$ alkoxy, especially methoxy.

A particular sub-group of the compounds of formula (IIA-B) above is represented by the compounds of formula (IIB-B) and N-oxides thereof, and pharmaceutically acceptable salts and solvates thereof, and glucuronide derivatives thereof, and co-crystals thereof:

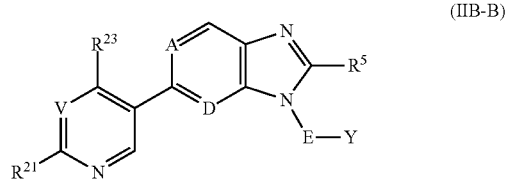

(IIB-B)

wherein A, D, E, Y, V, $R^5$, $R^{21}$ and $R^{23}$ are as defined above.

A particular sub-group of the compounds of formula (IIA-C) above is represented by the compounds of formula (IIB-C) and N-oxides thereof, and pharmaceutically acceptable salts and solvates thereof, and glucuronide derivatives thereof, and co-crystals thereof:

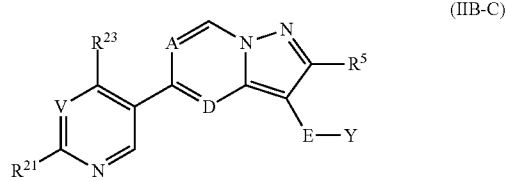

(IIB-C)

wherein A, D, E, Y, V, $R^5$, $R^{21}$ and $R^{23}$ are as defined above.

Particular sub-groups of the compounds of formula (IIB-A) above are represented by the compounds of formula (IIC-A), (IID-A), (IIE-A), (IIF-A), (IIG-A), (IIH-A), (IIJ-A), (IIK-A) and (IIL-A), and N-oxides thereof, and pharmaceutically acceptable salts and solvates thereof, and glucuronide derivatives thereof, and co-crystals thereof:

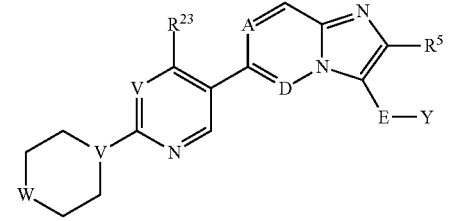
(IIC-A)

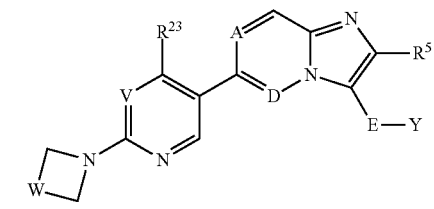
(IID-A)

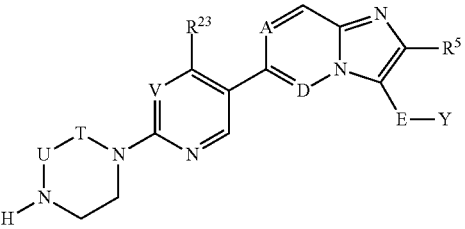
(IIE-A)

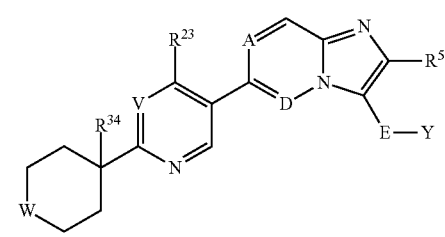
(IIF-A)

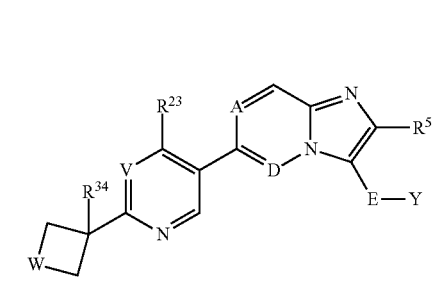
(IIG-A)

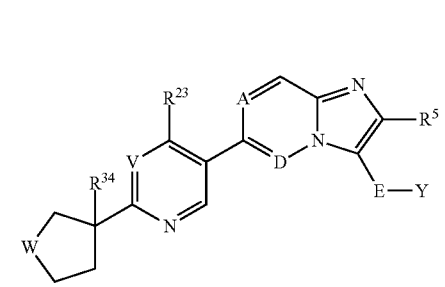
(IIH-A)

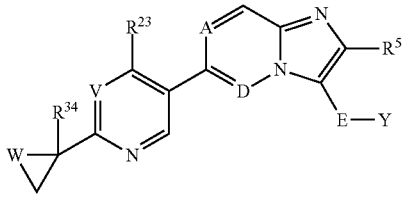
(IIJ-A)

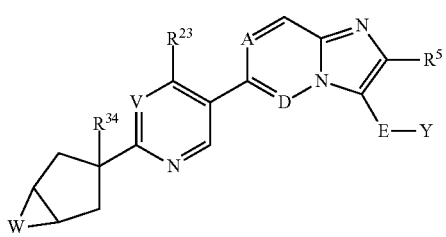
(IIK-A)

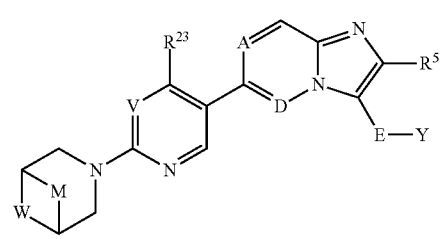
(IIL-A)

wherein

T represents —CH$_2$— or —CH$_2$CH$_2$—;

U represents C(O) or S(O)$_2$;

W represents O, S, S(O), S(O)$_2$, S(O)(NR$^6$), N(R$^{31}$) or C(R$^{32}$)(R$^{33}$);

-M- represents —CH$_2$— or —CH$_2$CH$_2$—;

R$^{31}$ represents hydrogen, cyano(C$_{1-6}$)alkyl, C$_{1-6}$ alkyl, trifluoromethyl, trifluoro-ethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, a carboxylic acid isostere or prodrug moiety Ω, —(C$_{1-6}$)alkyl-Ω, aminocarbonyl, C$_{1-6}$ alkylaminocarbonyl, di(C$_{1-6}$)alkylaminocarbonyl, aminosulphonyl or di(C$_{1-6}$)alkylamino-sulphonyl;

R$^{32}$ represents hydrogen, halogen, cyano, hydroxy, hydroxy(C$_{1-6}$)alkyl, C$_{1-6}$ alkylsulphonyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkyl-sulphoximinyl, [(C$_{1-6}$)alkyl][N—(C$_{1-6}$)alkyl]sulphoximinyl, a carboxylic acid isostere or prodrug moiety Ω, or —(C$_{1-6}$)alkyl-Ω;

R$^{33}$ represents hydrogen, halogen, C$_{1-6}$ alkyl, trifluoromethyl, hydroxy, hydroxy-(C$_{1-6}$)alkyl, C$_{1-6}$ alkoxy, amino or carboxy;

R$^{34}$ represents hydrogen, halogen, halo(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, (C$_{2-6}$)alkylcarbonylamino, (C$_{2-6}$)alkylcarbonylamino(C$_{1-6}$)alkyl, (C$_{1-6}$)alkyl-sulphonylamino or (C$_{1-6}$)alkylsulphonylamino(C$_{1-6}$)alkyl; and A, D, E, Y, R$^5$, R$^6$, V, R$^{23}$ and Ω are as defined above.

In a first embodiment, T represents —CH$_2$—. In a second embodiment, T represents —CH$_2$CH$_2$—.

In a first embodiment, U represents C(O). In a second embodiment, U represents S(O)$_2$.

Generally, W represents O, S(O)$_2$, N(R$^{31}$) or C(R$^{32}$)(R$^{33}$).

Typically, W represents O, N(R$^{31}$) or C(R$^{32}$)(R$^{33}$).

In a first embodiment, W represents O. In a second embodiment, W represents S. In a third embodiment, W represents S(O). In a fourth embodiment, W represents S(O)$_2$. In a fifth embodiment, W represents S(O)(NR$^6$). In a sixth embodiment, W represents N(R$^{31}$). In a seventh embodiment, W represents C(R$^{32}$)(R$^{33}$).

In one embodiment, -M- represents —CH$_2$—. In another embodiment, -M- represents —CH$_2$CH$_2$—.

Typically, R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$)alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl-(C$_{1-6}$)alkyl, tetrazolyl(C$_{1-6}$)alkyl, aminocarbonyl, C$_{1-6}$ alkylaminocarbonyl, di(C$_{1-6}$)alkylaminocarbonyl, aminosulphonyl, C$_{1-6}$ alkylaminosulphonyl or di(C$_{1-6}$)alkylamino-sulphonyl.

Suitably, R$^{31}$ represents hydrogen, C$_{1-6}$ alkyl or C$_{2-6}$ alkoxycarbonyl.

Typical values of R$^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxy-carbonyl, ethoxycarbonylmethyl, ethoxycarbonylethyl, tetrazolylmethyl, aminocarbonyl, methylaminocarbonyl, dimethylaminocarbonyl, aminosulphonyl, methylaminosulphonyl and dimethylaminosulphonyl.

Suitable values of R$^{31}$ include hydrogen, methyl and tert-butoxycarbonyl.

A particular value of R$^{31}$ is hydrogen.

Generally, R$^{32}$ represents hydrogen, halogen, hydroxy, carboxy, carboxy(C$_{1-6}$)-alkyl, C$_{2-6}$ alkoxycarbonyl, C$_{2-6}$ alkoxycarbonyl(C$_{1-6}$)alkyl, a carboxylic acid isostere or prodrug moiety Ω, or —(C$_{1-6}$)alkyl-Ω.

Typically, R$^{32}$ represents hydrogen, halogen, cyano, hydroxy, hydroxy(C$_{1-6}$)alkyl, C$_{1-6}$ alkylsulphonyl, formyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_{1-6}$)alkyl][N—(C$_{1-6}$)alkyl]sulphoximinyl, (C$_{1-6}$)alkylsulphonylamino carbonyl, (C$_{2-6}$)alkylcarbonylamino-sulphonyl, (C$_{1-6}$)alkoxyaminocarbonyl, tetrazolyl or hydroxyoxadiazolyl.

Suitably, R$^{32}$ represents hydrogen, halogen, hydroxy, carboxy or C$_{2-6}$ alkoxy-carbonyl.

Typical values of R$^{32}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, acetylaminosulphonyl, methoxyaminocarbonyl, tetrazolyl and hydroxyoxadiazolyl.

Suitable values of R$^{32}$ include hydrogen, fluoro, hydroxy, carboxy, methoxy-carbonyl and ethoxycarbonyl.

In a selected embodiment, R$^{32}$ represents carboxy.

Suitably, R$^{33}$ represents hydrogen, halogen, C$_{1-6}$ alkyl, trifluoromethyl or amino.

Generally, R$^{33}$ represents hydrogen, halogen, C$_{1-6}$ alkyl or trifluoromethyl.

Selected values of R$^{33}$ include hydrogen, fluoro, methyl, ethyl, isopropyl, trifluoromethyl, hydroxy, hydroxymethyl, methoxy, amino and carboxy.

Specific values of R$^{33}$ include hydrogen, fluoro, methyl, ethyl, trifluoromethyl and amino.

Particular values of R$^{33}$ include hydrogen, fluoro, methyl and trifluoromethyl.

In a first embodiment, R$^{33}$ represents hydrogen. In a second embodiment, R$^{33}$ represents halogen. In one aspect of that embodiment, R$^{33}$ represents fluoro. In a third embodiment, R$^{33}$ represents C$_{1-6}$ alkyl. In a first aspect of that embodiment, R$^{33}$ represents methyl. In a second aspect of that embodiment, R$^{33}$ represents ethyl. In a third aspect of that embodiment, R$^{33}$ represents isopropyl. In a fourth embodiment, R$^{33}$ represents trifluoromethyl. In a fifth embodiment, R$^{33}$ represents hydroxy. In a sixth embodiment, R$^{33}$ represents hydroxy(C$_{1-6}$)alkyl. In one aspect of that embodiment, R$^{33}$ represents hydroxymethyl. In a seventh embodiment, R$^{33}$ represents C$_{1-6}$ alkoxy. In one aspect of that embodiment, R$^{33}$ represents methoxy. In an eighth embodiment, R$^{33}$ represents amino. In a ninth embodiment, R$^{33}$ represents carboxy.

In a first embodiment, R$^{34}$ represents hydrogen. In a second embodiment, R$^{34}$ represents halogen. In one aspect of that embodiment, R$^{34}$ represents fluoro. In a third embodiment, R$^{34}$ represents halo(C$_{1-6}$)alkyl. In one aspect of that embodiment, R$^{34}$ represents fluoromethyl. In a fourth embodiment, R$^{34}$ represents hydroxy. In a fifth embodiment, R$^{34}$ represents C$_{1-6}$ alkoxy, especially methoxy. In a sixth embodiment, R$^{34}$ represents C$_{1-6}$ alkylthio, especially methylthio. In a seventh embodiment, R$^{34}$ represents C$_{1-6}$ alkylsulphinyl, especially methylsulphinyl. In an eighth embodiment, R$^{34}$ represents C$_{1-6}$ alkylsulphonyl, especially methylsulphonyl. In a ninth embodiment, R$^{34}$ represents amino. In a tenth embodiment, R$^{34}$ represents C$_{1-6}$ alkylamino, especially methylamino. In an eleventh embodiment, R$^{34}$ represents di(C$_{1-6}$)alkylamino, especially dimethylamino. In a twelfth embodiment, R$^{34}$ represents (C$_{2-6}$) alkylcarbonylamino, especially acetylamino. In a thirteenth embodiment, R$^{34}$ represents (C$_{2-6}$)alkylcarbonylamino(C$_{1-6}$)alkyl, especially acetylaminomethyl. In a fourteenth embodiment, R$^{34}$ represents (C$_{1-6}$)alkylsulphonyl-amino, especially methylsulphonylamino. In a fifteenth embodiment, R$^{34}$ represents (C$_{1-6}$)alkylsulphonylamino(C$_{1-6}$)alkyl, especially methylsulphonylaminomethyl.

Typically, R$^{34}$ represents hydrogen, halogen, halo(C$_{1-6}$) alkyl, hydroxy or (C$_{2-6}$)alkylcarbonylamino(C$_{1-6}$)alkyl.

Appositely, R$^{34}$ represents hydrogen, halogen, hydroxy or amino.

Suitably, R$^{34}$ represents hydrogen, halogen or hydroxy.

Selected values of R$^{34}$ include hydrogen, fluoro, fluoromethyl, hydroxy, methoxy, methylthio, methylsulphinyl, methylsulphonyl, amino, methylamino, dimethylamino and acetylaminomethyl.

Particular values of R$^{34}$ include hydrogen, fluoro, fluoromethyl, hydroxy and acetylaminomethyl.

Specific values of R$^{34}$ include hydrogen, fluoro, hydroxy and amino.

Suitably, R$^{34}$ represents hydrogen, fluoro or hydroxy.

Particular sub-groups of the compounds of formula (IIB-B) above are represented by the compounds of formula (IIC-B), (IID-B), (IIE-B), (IIF-B), (IIG-B), (IIH-B), (IIJ-B), (IIK-B) and (IIL-B), and N-oxides thereof, and pharmaceutically acceptable salts and solvates thereof, and glucuronide derivatives thereof, and co-crystals thereof:

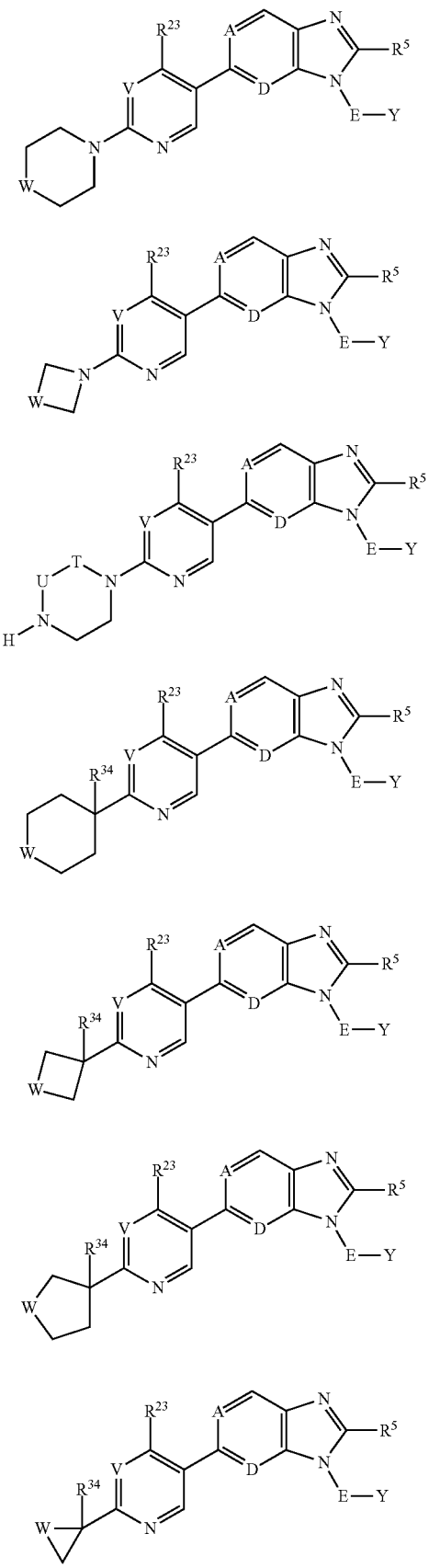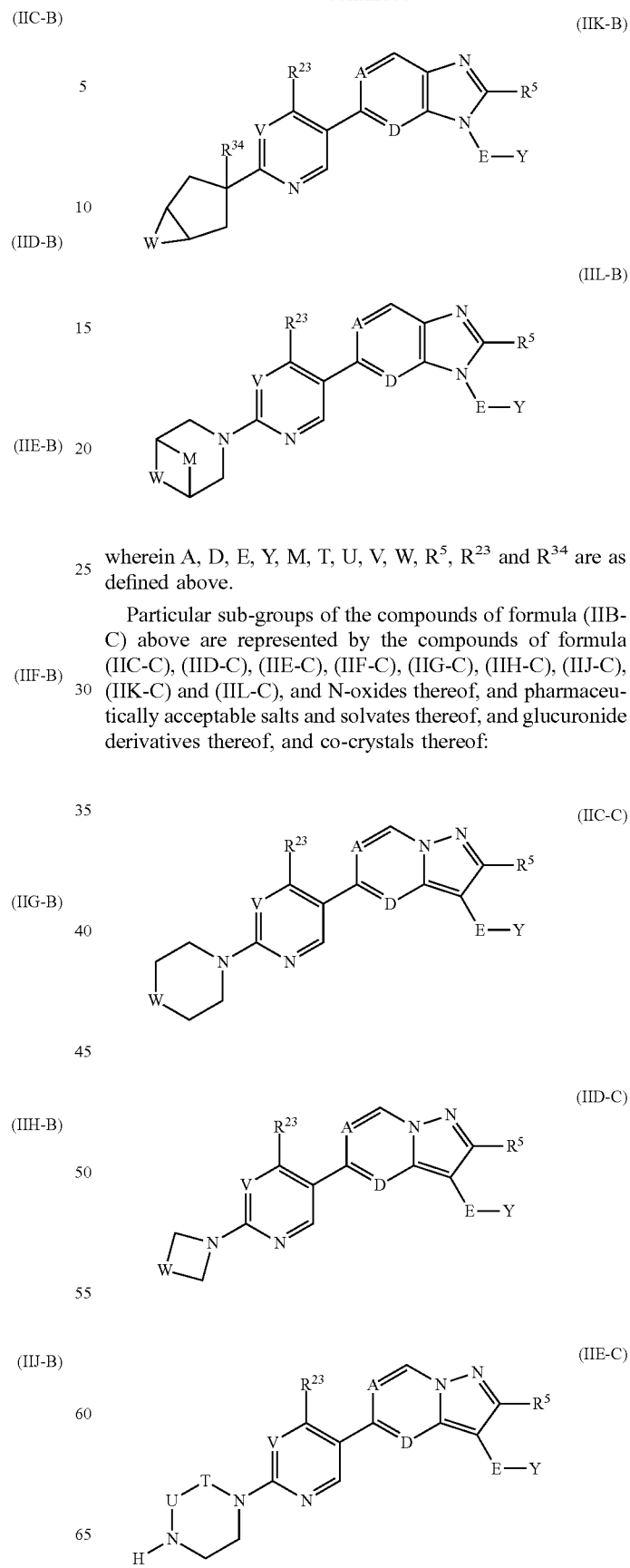
wherein A, D, E, Y, M, T, U, V, W, $R^5$, $R^{23}$ and $R^{34}$ are as defined above.
Particular sub-groups of the compounds of formula (IIB-C) above are represented by the compounds of formula (IIC-C), (IID-C), (IIE-C), (IIF-C), (IIG-C), (IIH-C), (IIJ-C), (IIK-C) and (IIL-C), and N-oxides thereof, and pharmaceutically acceptable salts and solvates thereof, and glucuronide derivatives thereof, and co-crystals thereof:

-continued

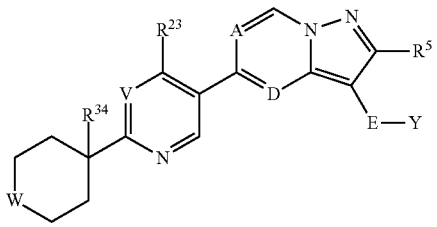
(IIF-C)

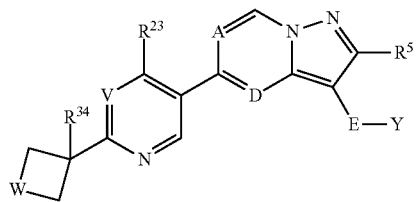
(IIG-C)

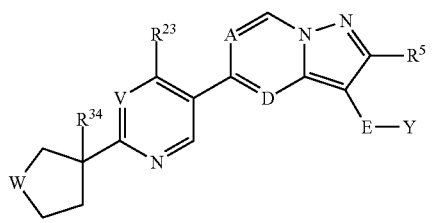
(IIH-C)

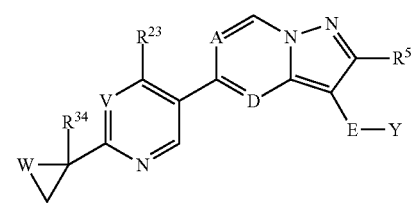
(IIJ-C)

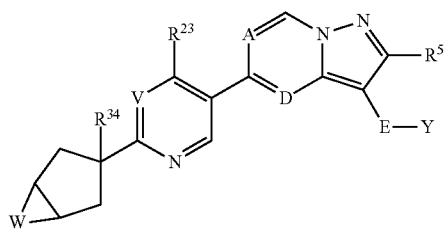
(IIK-C)

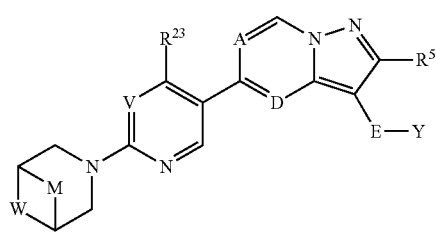
(IIL-C)

wherein A, D, E, Y, M, T, U, V, W, $R^5$, $R^{23}$ and $R^{34}$ are as defined above.

An alternative sub-class of compounds of formula (IIA-A) above is represented by the compounds of formula (IIM-A) and N-oxides thereof, and pharmaceutically acceptable salts and solvates thereof, and glucuronide derivatives thereof, and co-crystals thereof:

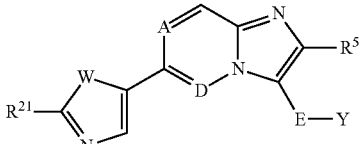
(IIM-A)

wherein
A, D, E, Y, W, $R^5$ and $R^{21}$ are as defined above.

An alternative sub-class of compounds of formula (IIA-B) above is represented by the compounds of formula (IIM-B) and N-oxides thereof, and pharmaceutically acceptable salts and solvates thereof, and glucuronide derivatives thereof, and co-crystals thereof:

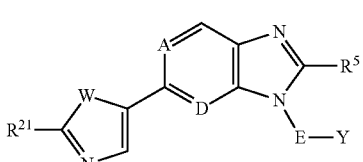
(IIM-B)

wherein
A, D, E, Y, W, $R^5$ and $R^{21}$ are as defined above.

An alternative sub-class of compounds of formula (IIA-C) above is represented by the compounds of formula (IIM-C) and N-oxides thereof, and pharmaceutically acceptable salts and solvates thereof, and glucuronide derivatives thereof, and co-crystals thereof:

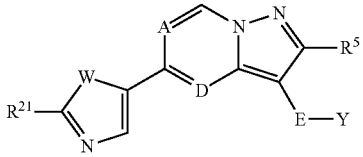
(IIM-C)

wherein
A, D, E, Y, W, $R^5$ and $R^{21}$ are as defined above.

With specific reference to formula (IIM-A), (IIM-B) and (IIM-C), the integer W is suitably O, S or N—$R^{31}$, especially S or N—$R^{31}$.

Specific novel compounds in accordance with the present invention include each of the compounds whose preparation is described in the accompanying Examples, and pharmaceutically acceptable salts and solvates thereof, and co-crystals thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (IA), (IB) or (IC) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (IA), (IB) or (IC) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule such as methotrexate or prednisolone.

The compounds of formula (IA), (IB) and (IC) above may be prepared by a process which comprises reacting a compound of formula Y—H with a compound of formula (IIIA), (IIIB) or (IIIC):

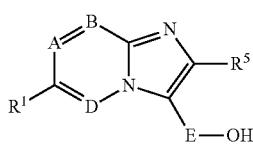

(IIIA)

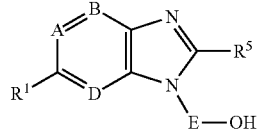

(IIIB)

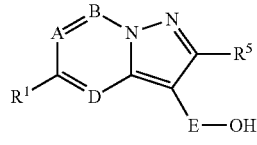

(IIIC)

wherein A, B, D, E, Y, $R^1$ and $R^5$ are as defined above.

The procedure is suitably effected in the presence of triphenylphosphine and a $C_{1-6}$ alkyl ester of azodicarboxylic acid, e.g. diisopropyl azodicarboxylate. Alternatively, the procedure may be effected in the presence of (cyanomethylene)tributylphosphorane or (tributyl-$\lambda^5$-phosphanylidene)acetonitrile. The reaction is conveniently carried out in a suitable solvent, e.g. a cyclic ether such as tetrahydrofuran, or a chlorinated solvent such as dichloromethane, or an organic nitrile such as acetonitrile, or an aromatic hydrocarbon such as toluene.

Alternatively, the procedure may be effected in the presence of a sulphonic acid derivative, e.g. a $C_{1-6}$ alkylsulphonic acid such as methanesulphonic acid. The reaction is conveniently carried out at an elevated temperature in a suitable solvent, e.g. a cyclic ether such as 1,4-dioxane.

In an alternative procedure, the compounds of formula (IA), (IB) and (IC) above may be prepared by a process which comprises reacting a compound of formula Y—H with a compound of formula (IVA), (IVB) or (IVC):

(IVA)

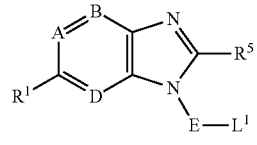

(IVB)

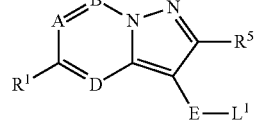

(IVC)

wherein A, B, D, E, Y, $R^1$ and $R^5$ are as defined above, and $L^1$ represents a suitable leaving group.

The leaving group $L^1$ is suitably a halogen atom, e.g. chloro; or a sulphonate derivative, e.g. a $C_{1-6}$ alkylsulphonate such as methylsulphonate.

Where $L^1$ is halo, the procedure is suitably effected in the presence of a base, e.g. an alkali metal carbonate such as cesium carbonate or potassium carbonate. The reaction is conveniently carried out at ambient or elevated temperature in a suitable solvent, e.g. a dipolar aprotic solvent such as N,N-dimethylformamide or N,N-dimethylacetamide.

Where $L^1$ is a sulphonate derivative, e.g. methylsulphonate, the procedure is suitably effected in the presence of a base, e.g. an alkali metal hydride such as sodium hydride. The reaction is conveniently carried out at an elevated temperature in a suitable solvent, e.g. a dipolar aprotic solvent such as N,N-dimethylformamide.

The intermediates of formula (IVA), (IVB) and (IVC) wherein $L^1$ is chloro may be prepared from the corresponding compound of formula (IIIA), (IIIB) or (IIIC) by treatment with a chlorinating agent such as thionyl chloride. The reaction is conveniently carried out in a suitable solvent, e.g. a cyclic ether such as tetrahydrofuran, or a chlorinated solvent such as dichloromethane.

The intermediates of formula (IVA), (IVB) and (IVC) wherein $L^1$ is methyl-sulphonate may be prepared from the corresponding compound of formula (IIIA), (IIIB) or (IIIC) by treatment with methanesulphonic anhydride, typically in the presence of a base, e.g. an alkali metal hydride such as sodium hydride. The reaction is conveniently carried out at an elevated temperature in a suitable solvent, e.g. a dipolar aprotic solvent such as N,N-dimethylformamide.

The intermediates of formula (IIIA) and (IIIC) above wherein E is methylene may be prepared by reducing a compound of formula (VA) or (VC):

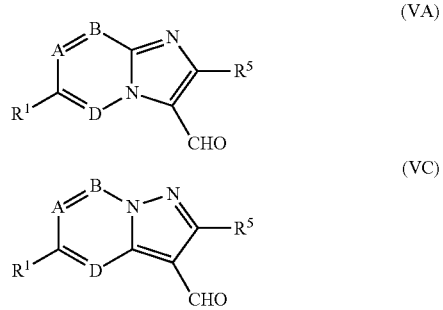

wherein A, B, D, $R^1$ and $R^5$ are as defined above.

The procedure is suitably effected by contacting compound (VA) or (VC) with a reducing agent, e.g. sodium borohydride. The reaction is conveniently carried out in a suitable solvent, e.g. a $C_{1-4}$ alkanol such as methanol.

The intermediates of formula (VA) and (VC) may be prepared by reacting a compound of formula (VIA) or (VIC):

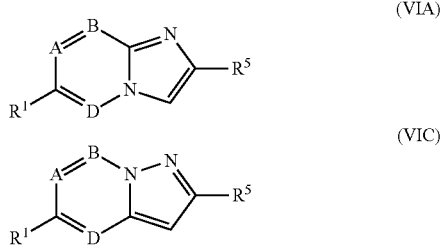

wherein A, B, D, $R^1$ and $R^5$ are as defined above; with phosphorus oxychloride and N,N-dimethylformamide.

The intermediates of formula (VIA) may be prepared by reacting a compound of formula (VII) with a compound of formula (VIII) or an acetal derivative thereof, e.g. the dimethyl acetal derivative:

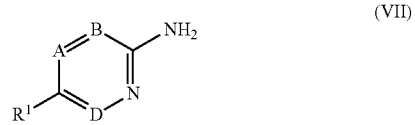

wherein A, B, D, $R^1$ and $R^5$ are as defined above, and $L^3$ represents a suitable leaving group.

The leaving group $L^3$ is typically a halogen atom, e.g. chloro or bromo.

The reaction is conveniently effected at an elevated temperature in a suitable solvent, e.g. a $C_{1-4}$ alkanol such as ethanol or isopropanol.

In an alternative procedure, the intermediates of formula (IIIA) above wherein E is methylene or (methyl)methylene may be prepared by reacting a compound of formula (VIA) as defined above with formaldehyde or acetaldehyde respectively.

The reaction is conveniently effected at an elevated temperature in a suitable solvent, e.g. water, optionally in the presence of acetic acid and sodium acetate.

The intermediates of formula (IIIB) above may be prepared by reacting a compound of formula $L^2$-E-OH with a compound of formula (IX):

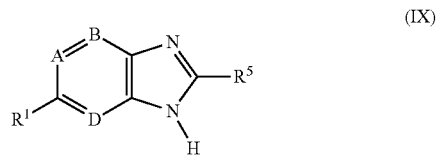

wherein A, B, D, E, $R^1$ and $R^5$ are as defined above, and $L^2$ represents a suitable leaving group.

The leaving group $L^2$ is suitably a halogen atom, e.g. chloro or bromo.

The reaction is conveniently effected at ambient or elevated temperature in a suitable solvent, e.g. a dipolar aprotic solvent such as N,N-dimethylformamide or a chlorinated solvent such as dichloromethane. The reaction may be performed in the presence of a suitable base, e.g. an inorganic base such as potassium carbonate, cesium carbonate or sodium hydride.

The intermediates of formula (IX) above may be prepared by reacting a compound of formula $R^5$—$CO_2H$ or a carboxylate salt thereof (e.g. a carboxylate salt with an alkali metal such as lithium, sodium or potassium) with a compound of formula (X):

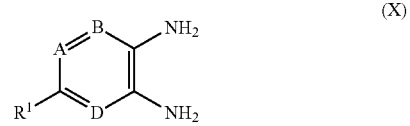

wherein A, B, D, $R^1$ and $R^5$ are as defined above.

The reaction may advantageously be performed in the presence of a coupling reagent such as 1-[bis(dimethylamino)methylene]-1H-1,2,3-triazolo[4,5-b]pyridinium 3-oxid hexafluorophosphate (HATU), optionally in the presence of a suitable base, e.g. an organic base such as N,N-diisopropylethylamine. The reaction is conveniently effected at ambient or elevated temperature in a suitable solvent, e.g. N,N-dimethylformamide or a chlorinated solvent such as dichloromethane. The product thereby obtained is suitably treated with an acid, ideally an organic acid such as acetic acid, or a mineral acid such as hydrochloric acid, typically at an elevated temperature.

Alternatively, the reaction may conveniently be effected in the presence of a coupling reagent such as 1-(3-dimethylaminopropyl)-3-ethylcarbodiimide hydrochloride (EDC), typically at ambient temperature in a suitable solvent, e.g. a chlorinated solvent such as dichloromethane, in the presence of a suitable base, e.g. an organic base such as triethylamine.

Alternatively, the reaction may conveniently be effected at an elevated temperature in the presence of a mineral acid, e.g. hydrochloric acid.

Alternatively, the reaction may conveniently be effected at an elevated temperature in the presence of a lower alkanol, e.g. a $C_{1-4}$ alkanol such as methanol.

The compounds of formula (VIC) above may be prepared by a two-step procedure which comprises (i) reacting a compound of formula $H_2N-L^3$ with a compound of formula (XI):

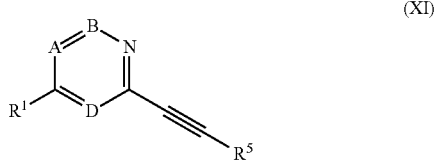

wherein A, B, D, $R^1$ and $R^5$ are as defined above, and $L^3$ represents a suitable leaving group; and (ii) treatment with a base.

The leaving group $L^3$ is typically an arylsulphonate moiety, e.g. 2,4,6-trimethyl-benzenesulphonate.

Step (i) is conveniently effected at ambient temperature in a suitable solvent, e.g. a $C_{1-4}$ alkanol such as ethanol.

Step (ii) is conveniently effected at elevated temperature in a suitable solvent, e.g. a $C_{1-4}$ alkanol such as ethanol. The base employed in the reaction will suitably be an inorganic base, e.g. an alkaline earth metal carbonate such as potassium carbonate.

The intermediates of formula (XI) above may be prepared by reacting a compound of formula H—C≡C—$R^5$ with a compound of formula (XII):

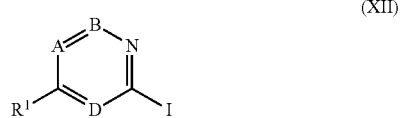

wherein A, B, D, $R^1$ and $R^5$ are as defined above; in the presence of a transition metal catalyst.

The transition metal catalyst of use in the foregoing reaction is suitably a palladium complex such as [1,1'-bis(diphenylphosphino)ferrocene]dichloropalladium(II). The reaction is conveniently effected at ambient temperature in the presence of a copper(I) salt, e.g. copper(I) iodide, and a base, suitably an organic base such as triethylamine.

Where they are not commercially available, the starting materials of formula (VII), (VIII), (X) and (XII), as well as the compounds of formula Y—H, may be prepared by methods analogous to those described in the accompanying Examples, or by standard methods well known from the art.

It will be understood that any compound of formula (IA), (IB) or (IC) initially obtained from any of the above processes may, where appropriate, subsequently be elaborated into a further compound of formula (IA), (IB) or (IC) by techniques known from the art. By way of example, a compound wherein E represents —C(O)— may be converted into the corresponding compound wherein E represents —CH(OH)— by treatment with a reducing agent such as sodium borohydride.

A compound wherein E represents —CH(OH)— may be converted into the corresponding compound wherein E represents —CH$_2$— by heating with elemental iodine and phosphinic acid in acetic acid; or by treating with triethylsilane and an acid, e.g. an organic acid such as trifluoroacetic acid, or a Lewis acid such as boron trifluoride diethyl etherate; or by treating with chlorotrimethylsilane and sodium iodide; or by a two-step procedure which comprises: (i) treatment with thionyl bromide; and (ii) treatment of the product thereby obtained with a transition metal catalyst, e.g. (2,2'-bipyridine)dichloro-ruthenium(II) hydrate, in the presence of diethyl 1,4-dihydro-2,6-dimethyl-3,5-pyridine-dicarboxylate (Hantzsch ester) and a base, e.g. an organic base such as N,N-diisopropyl-ethylamine.

A compound wherein E represents —CH$_2$— may be converted into the corresponding compound wherein E represents —CH(CH$_3$)— by treatment with a methyl halide, e.g. methyl iodide, in the presence of a base such as lithium hexamethyldisilazide.

A compound containing a benzene ring may be nitrated by treatment with nitric acid, typically in admixture with acetic acid.

A compound substituted by nitro (—NO$_2$) may be converted into the corresponding compound substituted by amino (—NH$_2$) by treatment with a reducing agent, e.g. iron powder in acetic acid.

A compound which contains a hydroxy group may be alkylated by treatment with the appropriate alkyl halide in the presence of a base, e.g. sodium hydride, or silver oxide. A compound which contains hydroxy may be converted into the corresponding fluoro-substituted compound by treatment with diethylaminosulfur trifluoride (DAST) or bis(2-methoxyethyl)aminosulfur trifluoride (BAST). A compound which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound which contains an N—H moiety may be alkylated by treatment with the appropriate alkyl halide, typically at an elevated temperature in an organic solvent such as acetonitrile; or at ambient temperature in the presence of a base, e.g. an alkali metal carbonate such as potassium carbonate or cesium carbonate, in a suitable solvent, e.g. a dipolar aprotic solvent such as N,N-dimethylformamide. Alternatively, a compound which contains an N—H moiety may be alkylated by treatment with the appropriate alkyl tosylate in the presence of a base, e.g. an inorganic base such as sodium hydride, or an organic base such as 1,8-diazabicyclo[5.4.0]undec-7-ene (DBU).

A compound which contains an N—H moiety may be methylated by treatment with formaldehyde in the presence of a reducing agent, e.g. sodium triacetoxyborohydride.

A compound which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine or N,N-diisopropylethylamine. A compound which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound substituted by amino (—NH$_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride. Similarly, a compound substituted by hydroxy (—OH) may be converted into the corresponding compound substituted by $C_{1-6}$ alkylsulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride. A compound containing the moiety —S— may be converted into the corresponding compound containing the moiety —S(O)— by treatment with 3-chloroperoxybenzoic acid.

Likewise, a compound containing the moiety —S(O)— may be converted into the corresponding compound containing the moiety —S(O)$_2$— by treatment with 3-chloroperoxy-benzoic acid. Alternatively, a compound containing the moiety —S— may be converted into the corresponding compound containing the moiety —S(O)$_2$— by treatment with Oxone® (potassium peroxymonosulfate).

A compound containing the moiety —S(O)CH$_3$ may be converted into the corresponding compound containing the moiety —S(O)(NH)CH$_3$ via a two-step procedure which comprises: (i) reaction with 2,2,2-trifluoroacetamide and a transition metal catalyst such as tetrakis(acetato-κO)dirhodium(Rh—Rh), typically in the presence of bis(acetyloxy)-(phenyl)-λ$^3$-iodane and magnesium oxide; and (ii) reaction of the compound thereby obtained with a base, e.g. an inorganic base such as potassium carbonate.

A compound containing an aromatic nitrogen atom may be converted into the corresponding N-oxide derivative by treatment with 3-chloroperoxybenzoic acid.

A bromophenyl derivative may be converted into the corresponding optionally substituted 2-oxopyrrolidin-1-ylphenyl or 2-oxooxazolidin-3-ylphenyl derivative by treatment with pyrrolidin-2-one or oxazolidin-2-one, or an appropriately substituted analogue thereof. The reaction is conveniently effected at an elevated temperature in the presence of copper(I) iodide, trans-N,N'-dimethylcyclohexane-1,2-diamine and an inorganic base such as potassium carbonate.

A compound wherein R$^1$ represents halogen, e.g. bromo or iodo, may be converted into the corresponding compound wherein R$^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected in the presence of a transition metal catalyst, e.g. [1,1'-bis(diphenylphosphino)ferrocene]dichloropalladium (II), tetrakis(triphenylphosphine)palladium(0), or bis[3-(diphenylphosphanyl)cyclopenta-2,4-dien-1-yl]iron-dichloropalladium-dichloromethane complex, or dichlorobis(triphenyl-phosphine)palladium(II), and a base, e.g. an inorganic base such as sodium carbonate or potassium carbonate, or potassium phosphate.

A compound wherein R$^1$ represents halogen, e.g. bromo, may be converted into the corresponding compound wherein R$^1$ represents an optionally substituted aryl, heteroaryl or heterocycloalkenyl moiety via a two-step procedure which comprises: (i) reaction with bis(pinacolato)diboron or bis(neopentyl glycolato)diboron; and (ii) reaction of the compound thereby obtained with an appropriately functionalised halo- or tosyloxy-substituted aryl, heteroaryl or heterocycloalkenyl derivative. Step (i) is conveniently effected in the presence of a transition metal catalyst such as [1,1'-bis(diphenylphosphino)-ferrocene]dichloropalladium(II), or bis[3-(diphenylphosphanyl)cyclopenta-2,4-dien-1-yl]iron-dichloropalladium-dichloromethane complex. Step (ii) is conveniently effected in the presence of a transition metal catalyst such as tetrakis(triphenylphosphine)-palladium(0), or bis[3-(diphenylphosphanyl)cyclopenta-2,4-dien-1-yl] iron-dichloropalladium-dichloromethane complex, and a base, e.g. an inorganic base such as sodium carbonate or potassium carbonate.

A compound wherein R$^1$ represents halogen, e.g. bromo, may be converted into the corresponding compound wherein R$^1$ represents an optionally substituted $C_{2-6}$ alkynyl moiety by treatment with an appropriately substituted alkyne derivative, e.g. 2-hydroxybut-3-yne. The reaction is conveniently accomplished with the assistance of a transition metal catalyst, e.g. tetrakis(triphenylphosphine)palladium (0), typically in the presence of copper(I) iodide and a base, e.g. an organic base such as triethylamine.

A compound wherein R$^1$ represents halogen, e.g. bromo, may be converted into the corresponding compound wherein R$^1$ represents an optionally substituted imidazol-1-yl moiety by treatment with the appropriately substituted imidazole derivative, typically in the presence of copper(II) acetate and an organic base such as N,N,N',N'-tetramethyl-ethylenediamine (TMEDA).

A compound wherein R$^1$ represents halogen, e.g. bromo, may be converted into the corresponding compound wherein R$^1$ represents 2-(methoxycarbonyl)ethyl via a two-step procedure which comprises: (i) reaction with methyl acrylate; and (ii) catalytic hydrogenation of the alkenyl derivative thereby obtained, typically by treatment with a hydrogenation catalyst, e.g. palladium on charcoal, under an atmosphere of hydrogen gas. Step (i) is typically effected in the presence of a transition metal catalyst, e.g. palladium(II) acetate or bis(dibenzylideneacetone)palladium(0), and a reagent such as tri(ortho-tolyl)-phosphine.

In general, a compound containing a —C═C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide, or an organic base such as triethylamine.

A compound wherein R$^1$ represents 6-methoxypyridin-3-yl may be converted into the corresponding compound wherein R$^1$ represents 2-oxo-1,2-dihydropyridin-5-yl by treatment with pyridine hydrochloride; or by heating with a mineral acid such as hydrochloric acid. By utilising similar methodology, a compound wherein $R^1$ represents 6-methoxy-4-methylpyridin-3-yl may be converted into the corresponding compound wherein $R^1$ represents 4-methyl-2-oxo-1,2-dihydropyridin-5-yl; and a compound wherein $R^1$ represents 6-methoxy-5-methylpyridin-3-yl may be converted into the corresponding compound wherein $R^1$ represents 3-methyl-2-oxo-1,2-dihydropyridin-5-yl.

A compound wherein $R^1$ represents 2-oxo-1,2-dihydropyridin-5-yl may be converted into the corresponding compound wherein $R^1$ represents 2-oxopiperidin-5-yl by catalytic hydrogenation, typically by treatment with gaseous hydrogen in the presence of a hydrogenation catalyst such as platinum(IV) oxide.

A compound containing an ester moiety, e.g. a $C_{2-6}$ alkoxycarbonyl group such as methoxycarbonyl or ethoxycarbonyl, may be converted into the corresponding compound containing a carboxy (—$CO_2H$) moiety by treatment with an acid, e.g. a mineral acid such as hydrochloric acid.

A compound containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound containing an ester moiety, e.g. a $C_{2-6}$ alkoxycarbonyl group such as methoxycarbonyl or ethoxycarbonyl, may alternatively be converted into the corresponding compound containing a carboxy (—$CO_2H$) moiety by treatment with a base, e.g. an alkali metal hydroxide selected from lithium hydroxide, sodium hydroxide and potassium hydroxide; or an organic base such as sodium methoxide or sodium ethoxide.

A compound containing a carboxy (—$CO_2H$) moiety may be converted into the corresponding compound containing an amide moiety by treatment with the appropriate amine in the presence of a condensing agent such as 1-ethyl-3-(3-dimethylaminopropyl)-carbodiimide, or a coupling agent such as 1-[bis(dimethylamino)methylene]-1H-1,2,3-triazolo[4,5-b]pyridinium 3-oxid hexafluorophosphate (HATU).

A compound containing a carbonyl (C=O) moiety may be converted into the corresponding compound containing a —$C(CH_3)(OH)$— moiety by treatment with methylmagnesium bromide. Similarly, a compound containing a carbonyl (C=O) moiety may be converted into the corresponding compound containing a —$C(CF_3)(OH)$— moiety by treatment with (trifluoromethyl)trimethylsilane and cesium fluoride. A compound containing a carbonyl (C=O) moiety may be converted into the corresponding compound containing a —$C(CH_2NO_2)(OH)$— moiety by treatment with nitromethane.

A compound containing a hydroxymethyl moiety may be converted into the corresponding compound containing a formyl (—CHO) moiety by treatment with an oxidising agent such as Dess-Martin periodinane. A compound containing a hydroxymethyl moiety may be converted into the corresponding compound containing a carboxy moiety by treatment with an oxidising agent such as tetrapropylammonium perruthenate. Similarly, a compound containing a —CH(OH)— moiety may be converted into the corresponding compound containing a —C(O)— moiety by treatment with an oxidising agent such as tetrapropylammonium perruthenate.

A compound wherein $R^1$ represents a substituent containing at least one nitrogen atom, which substituent is linked to the remainder of the molecule via a nitrogen atom, may be prepared by reacting a compound wherein $R^1$ represents halogen, e.g. bromo, with the appropriate compound of formula $R^1$—H [e.g. 1-(pyridin-3-yl)piperazine or morpholine]. The reaction is conveniently effected with the assistance of a transition metal catalyst, e.g. tris(dibenzylideneacetone)dipalladium(0), in the presence of an amination ligand such as 2-dicyclohexylphosphino-2',4',6'-triisopropylbiphenyl (XPhos) or 2,2'-bis(diphenylphosphino)-1,1'-binaphthalene (BINAP) and a base, e.g. an inorganic base such as sodium tert-butoxide. Alternatively, the reaction may be effected using palladium diacetate, in the presence of a reagent such as [2',6'-bis(propan-2-yloxy)-biphenyl-2-yl](dicyclohexyl)phosphane and a base, e.g. an inorganic base such as cesium carbonate.

A compound containing an oxo moiety can be converted into the corresponding compound containing an ethoxycarbonylmethylidene moiety by treatment with triethyl phosphonoacetate in the presence of a base such as sodium hydride.

A compound wherein $R^{21}$ represents ethenyl may be prepared by reacting a compound wherein $R^{21}$ represents halogen, e.g. chloro, with potassium vinyl trifluoro-borate. The reaction is typically effected in the presence of a transition metal catalyst, e.g. [1,1'-bis(diphenylphosphino)ferrocene]dichloropalladium(II), and a base, e.g. an organic base such as triethylamine.

A compound wherein $R^{21}$ represents halogen, e.g. chloro, may be converted into the corresponding compound wherein $R^{21}$ represents an optionally substituted $C_{4-7}$ cycloalkenyl moiety by treatment with the appropriately substituted cycloalkenyl boronic acid or a cyclic ester thereof formed with an organic diol, e.g. pinacol, 1,3-propanediol or neopentyl glycol. The reaction is typically effected in the presence of a transition metal catalyst, e.g. bis[3-(diphenylphosphanyl)cyclopenta-2,4-dien-1-yl]iron-dichloropalladium-dichloromethane complex, and a base, e.g. an inorganic base such as potassium carbonate.

A compound wherein $R^{21}$ represents a substituent containing at least one nitrogen atom, which substituent is linked to the remainder of the molecule via a nitrogen atom, may be prepared by reacting a compound wherein $R^{21}$ represents halogen, e.g. chloro, with the appropriate compound of formula $R^{21}$—H [e.g. 2-methoxyethylamine, N-methyl-L-alanine, 2-aminocyclopentanecarboxylic acid, 3-aminocyclopentanecarboxylic acid, 1-(aminomethyl)cyclopropanecarboxylic acid, methyl azetidine-3-carboxylate, pyrrolidin-3-ol, pyrrolidine-3-carboxylic acid, piperidine-2-carboxylic acid, piperidine-3-carboxylic acid, 4-(1H-tetrazol-5-yl)piperidine, piperazine, 1-(methylsulfonyl)piperazine, piperazin-2-one, 2-(piperazin-1-yl)propanoic acid, morpholine, morpholine-2-carboxylic acid, thiomorpholine, thiomorpholine 1,1-dioxide, 1,4-diazepan-5-one, 2-oxa-5-azabicyclo-[2.2.1]heptane or an appropriately substituted azaspiroalkane], optionally in the presence of a base, e.g. an organic base such as triethylamine or N,N-diisopropylethylamine and/or 1-methyl-2-pyrrolidinone, or pyridine, or an inorganic base such as potassium carbonate.

A compound wherein $R^5$ represents methyl may be converted into the corresponding compound wherein $R^5$ represents hydroxymethyl by treatment with Selectfluor™.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (IA), (IB) or (IC), this may be produced from a corresponding mixture of enantiomers using any suitable conventional procedure for resolving enantiomers. Thus, for example, diastereomeric derivatives, e.g. salts, may be produced by reaction of a mixture of enantiomers of formula (IA), (IB) or (IC), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (IA), (IB) or (IC) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the binding of a fluorescence conjugate to TNFα when tested in the fluorescence polarisation assay described below. Moreover, certain compounds in accordance with this invention potently inhibit TNFα-induced NF-κB activation in the reporter gene assay described below.

Fluorescence Polarisation Assay

Preparation of Compound (A)

1-(2,5-Dimethylbenzyl)-6-[4-(piperazin-1-ylmethyl)phenyl]-2-(pyridin-4-yl-methyl)-1H-benzimidazole hereinafter referred to as "Compound (A)" can be prepared by the procedure described in Example 499 of WO 2013/186229 (published 19 Dec. 2013); or by a procedure analogous thereto.

Preparation of Fluorescence Conjugate

Compound (A) (27.02 mg, 0.0538 mmol) was dissolved in DMSO (2 mL). 5 (-6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Compound (A). No peak was observed for unreacted 5(-6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An IC$_{50}$ value was calculated using XLfit™ (4 parameter logistic model) in ActivityBase.

When tested in the fluorescence polarisation assay, the compounds of the accompanying Examples were all found to exhibit IC$_{50}$ values of 50 μM or better.

Reporter Gene Assay

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound) and an IC$_{50}$ value calculated using XLfit™ (4 parameter logistic model) in ActivityBase.

When tested in the reporter gene assay, certain compounds of the accompanying Examples were found to exhibit IC$_{50}$ values of 50 μM or better.

EXAMPLES

| Abbreviations | |
|---|---|
| DCM: dichloromethane | EtOAc: ethyl acetate |
| MeOH: methanol | DMSO: dimethylsulfoxide |
| EtOH: ethanol | DIPEA: N,N-diisopropylethyl-amine |
| DMF: N,N-dimethylformamide | DMA: N,N-dimethylacetamide |
| TBAF: tetrabutylammonium fluoride | THF: tetrahydrofuran |
| m-CPBA: 3-chloroperoxybenzoic acid | DABCO: 1,4-diazabi-cyclo[2.2.2]octane |
| DBU: 1,8-diazabicyclo[5.4.0]undec-7-ene | |
| BAST: bis(2-methoxyethyl)aminosulfur trifluoride | |
| Pd(dppf)Cl$_2$: [1,1'-bis(diphenylphosphino)ferrocene]dichloropalladium(II) | |
| Herrmann's catalyst: trans-bis(acetato)bis[o-(di-o-tolylphosphino)benzyl]dipalladium(II) | |
| Selectfluor™: 1-chloromethyl-4-fluoro-1,4-diazoniabicyclo[2.2.2]octane bis(tetrafluoroborate) | |
| HATU: 1-[bis(dimethylamino)methylene]-1H-1,2,3-triazolo[4,5-b]pyridinium 3-oxid hexafluorophosphate | |
| h: hour | M: mass |
| HPLC: High Performance Liquid Chromatography | |
| LCMS: Liquid Chromatography Mass Spectrometry | |
| RT: retention time | |

Nomenclature

Compounds were named with the aid of ACD/Name Batch (Network) version 12.0, and/or Accelrys Draw 4.0, and/or MarvinDraw.

Analytical Conditions

NMR

NMR spectra were obtained using a Bruker DPX 250 MHz NMR spectrometer; a Bruker Fourier 300 MHz NMR spectrometer; a Bruker AVIII 400 MHz NMR spectrometer; a Bruker DRX 500 MHz NMR spectrometer; or an AV 600 MHz NMR spectrometer. Chemical shift values are reported in ppm (δ) with zero corresponding to the corrected residual deuterated solvent shift as an internal reference, or with zero corresponding to tetramethylsilane as an internal standard. The NMR spectra were recorded at a temperature ranging from 5 to 110° C. When more than one conformer was detected the chemical shifts for the most abundant conformer are reported.

LCMS

LCMS data were obtained using the method described below, or an analogous method. Mass spectra were generated by using ESI ionisation.

Column: Waters, X-Bridge, 20×2.1 mm, 2.5 μm
pH: high (approximately pH 9.5)
Mobile Phase A: 10 mM ammonium formate in water+0.1% ammonia
Mobile Phase B: acetonitrile+5% solvent A+0.1% ammonia
Injection Volume: 5.0 μL
Flow Rate: 1.00 mL/minute
Column temperature: 40° C.
Gradient program:

| Time | A % | B % |
|---|---|---|
| 0.00 | 95.0 | 5.0 |
| 1.50 | 5.0 | 95.0 |
| 2.25 | 5.0 | 95.0 |
| 2.30 | 95.0 | 5.0 |

Chiral

Chiral compounds were separated by HPLC using supercritical CO$_2$ with methanol or isopropanol (with diethylamine added as a modifier) and a stationary phase such as ChiralPak IA, ChiralPak AS, Chiralcel OJ-H or Cellulose-3; or using methanol (with diethylamine added as a modifier) and a stationary phase such as Lux C4.

Intermediate 1

6-Bromo-2-methylimidazo[1,2-a]pyridine

5-Bromopyridin-2-amine (6.2 g) was dissolved in ethanol (60 mL) and chloro-acetone (5.7 mL) was added. The mixture was heated under reflux at 90° C. for 16 h with stirring. The reaction mixture was cooled and concentrated in vacuo. The resulting crude yellow solid was purified on silica gel, eluting with a gradient of 2-15% methanol in dichloromethane, to afford the title compound (6.1 g, 80.6%) as a yellow solid. δ$_H$ (500 MHz, CD$_3$OD) 9.03 (s, 1H), 8.02 (m, 1H), 7.93 (s, 1H), 7.79 (d, J 9.4 Hz, 1H), 2.56 (d, J 1.0 Hz, 3H).

Intermediate 2

6-Bromo-2-methylimidazo[1,2-a]pyridine-3-carbaldehyde

N,N-Dimethylformamide (15 mL) was cooled to 0° C. and phosphoric trichloride (3.7 g, 24.31 mmol) was added dropwise with stirring. After 5 minutes, Intermediate 1 (2.7 g, 12.15 mmol) was added. The reaction mixture warmed to room temperature, then heated with stirring at 50° C. for 6 h. The reaction mixture was cooled and allowed to stir at room temperature overnight. The reaction mixture was quenched with a mixture of ice and saturated aqueous sodium hydrogencarbonate solution, then extracted with ethyl acetate (3×100 mL). The combined organic layer was washed with water (50 mL) and brine (50 mL), then dried over magnesium sulfate. The crude residue was purified on silica gel, eluting with a gradient of 0-10% methanol in dichloromethane, to afford the title compound (2.6 g, 53.7%) at 60% purity. δ$_H$ (500 MHz, CD$_3$OD) 10.03 (s, 1H), 9.67 (d, J 1.2 Hz, 1H), 7.82-7.74 (m, 1H), 7.65-7.57 (m, 1H), 2.70 (s, 3H).

Intermediate 3

6-[4-(Methanesulfonyl)phenyl]-2-methylimidazo[1,2-a]pyridine-3-carbaldehyde

Intermediate 2 (1 g, 2.51 mmol) and 4-(methanesulfonyl)phenylboronic acid (903 mg, 4.52 mmol) were stirred in 1,4-dioxane (20 mL), then 2M aqueous sodium carbonate solution (3.7 mL) was added. The mixture was degassed with nitrogen for 10 minutes before addition of bis[3-(diphenylphosphanyl)cyclopenta-2,4-dien-1-yl]iron-dichloro-palladium-dichloromethane complex (93 mg, 0.21 mmol), and the resulting mixture was heated at 100° C. with continuous stirring for 3 h. The reaction mixture was cooled to room temperature and diluted with ethyl acetate. The suspension was filtered through a pad of Celite and washed with ethyl acetate. The filtrate was concentrated in vacuo. The resulting crude material was purified on silica gel, eluting with 0-6% methanol in dichloromethane, to afford the title compound (660 mg, 71.1%) as a colourless solid at 85% purity. δ$_H$ (500 MHz, CD$_3$OD) 10.08 (s, 1H), 9.86 (s, 1H), 8.11 (d, J 8.5 Hz, 2H), 8.05 (dd, J 9.2, 1.9 Hz, 1H), 7.98 (d, J 8.5 Hz, 2H), 7.81 (d, J 9.2 Hz, 1H), 3.19 (s, 3H), 2.74 (s, 3H).

Intermediate 4

{6-[4-(Methanesulfonyl)phenyl]-2-methylimidazo[1,2-a]pyridin-3-yl}methanol

Intermediate 3 (720 mg, 2.29 mmol) was dissolved in methanol (10 mL) and cooled to 0° C. in an ice-water bath. Sodium borohydride (130 mg, 3.43 mmol) was added and the mixture was stirred at 0° C. for 30 minutes. Further sodium borohydride (130 mg, 3.43 mmol) was added, then the reaction mixture was allowed to warm to room temperature and stirred for 16 h. The solvent was removed under vacuum and the residue was purified on silica gel, eluting with 0-10% methanol in dichloromethane with 1% triethylamine, to afford the title compound (620 mg, 72.7%) at 85% purity. $\delta_H$ (250 MHz, CD$_3$OD) 8.69 (s, 1H), 8.12-7.93 (m, 4H), 7.75-7.53 (m, 2H), 4.99 (s, 2H), 3.17 (s, 3H), 2.47 (s, 3H).

Intermediate 5

(6-Bromo-2-methylimidazo[1,2-a]pyridin-3-yl)methanol

Intermediate 2 (1.60 g, 4.01 mmol) was suspended in methanol (20 mL) and cooled to 0° C. in an ice-water bath. Sodium borohydride (228 mg, 6.02 mmol) was added and the mixture was stirred at 0° C. for 30 minutes, then warmed to room temperature and stirred for 1 h. The solvent was removed in vacuo. The residue was diluted with water (50 mL) and extracted with dichloromethane (2×100 mL), then further extracted using ethyl acetate (2×100 mL). The combined organic layers were dried and concentrated in vacuo, then purified on silica gel, eluting with 0-10% methanol in dichloromethane, to afford the title compound (620 mg, 63.4%) as a white solid. $\delta_H$ (500 MHz, CD$_3$OD) 8.60 (s, 1H), 7.43 (s, 2H), 4.94 (s, 2H), 2.44 (s, 3H).

Intermediate 6

6-Bromo-3-(chloromethyl)-2-methylimidazo[1,2-a]pyridine

Intermediate 5 (100 mg, 0.41 mmol) was stirred in dry dichloromethane (3 mL) before the dropwise addition of thionyl chloride (0.27 mL, 3.72 mmol) over 5 minutes. The reaction mixture was heated with stirring at 55° C. under an atmosphere of nitrogen for 1 h. The reaction mixture was cooled to room temperature and the solvent was removed in vacuo. The residue was re-dissolved in dichloromethane (50 mL) and concentrated under vacuum. This process was repeated twice more to afford the title compound (108 mg, 99%) as the crude chloride. LCMS m/z 242.

Intermediate 7

4-[(6-Bromo-2-methylimidazo[1,2-a]pyridin-3-yl)methyl]-2H,3H,4H-pyrido[3,2-b][1,4]-oxazin-3-one To a stirred solution of 2H,3H,4H-pyrido[3,2-b][1,4]oxazin-3-one (316 mg, 2.10 mmol) in dry DMA (10.5 mL) was added caesium carbonate (2.74 g, 8.40 mmol). To the mixture was added Intermediate 6 (551 mg, 2.10 mmol) in dry DMF (10.5 mL) dropwise. The reaction mixture was stirred at room temperature for 16 h. The residue was dissolved in ethyl acetate (15 mL) and water (15 mL). The aqueous layer was further extracted with ethyl acetate (3×50 mL). The combined organic layers were washed with brine (15 mL) and dried over sodium sulphate, then the solvents were removed in vacuo. The crude residue was purified on silica (Biotage, 25 g), eluting with 0-80% ethyl acetate in heptane followed by 20% methanol in dichloromethane. A further purification using preparative HPLC afforded the title compound (150 mg, 18%). $\delta_H$ (250 MHz, DMSO-d$_6$) 9.00-8.89 (br s, 1H), 8.03 (dd, J 4.8, 1.4 Hz, 1H), 7.44-7.35 (m, 2H), 7.30 (dd, J 9.5, 1.8 Hz, 1H), 7.07 (dd, J 7.9, 4.8 Hz, 1H), 5.53 (s, 2H), 4.82 (s, 2H), 2.43 (s, 3H). LCMS m/z 373/375.

Intermediate 8

3-[(6-Bromo-2-methylimidazo[1,2-a]pyridin-3-yl)methyl]-2H,3H-[1,3]oxazolo[4,5-b]-pyridin-2-one Intermediate 5 (200 mg, 0.83 mmol), [1,3]oxazolo[4,5-b]pyridin-2(3H)-one (124 mg, 0.91 mmol) and 1,4-dioxane (4 mL) were charged into a 10 mL microwave tube. Methanesulfonic acid (0.27 mL, 4.15 mmol) was added and the reaction mixture was heated under microwave irradiation at 150° C., with stirring, for 1 h. The reaction mixture was allowed to cool to ambient temperature. The solvent was removed in vacuo and the residue was dissolved in dichloromethane (30 mL). The organic layer was washed sequentially with saturated aqueous sodium hydrogencarbonate solution (20 mL) and brine (20 mL), then dried over sodium sulphate. The solvent was removed in vacuo. The residue was purified on silica gel, eluting with 0-10% methanol in dichloromethane, to afford the title compound (190 mg, 63%) as a pale yellow solid. $\delta_H$ (500 MHz, DMSO-d$_6$) 9.00-8.96 (m, 1H), 8.16 (dd, J 5.3, 1.2 Hz, 1H), 7.71 (dd, J 7.9, 1.2 Hz, 1H), 7.45 (d, J 9.4 Hz, 1H), 7.35 (dd, J 9.4, 1.9 Hz, 1H), 7.19 (dd, J 7.9, 5.3 Hz, 1H), 5.37 (s, 2H), 2.54 (s, 3H). LCMS m/z 359/361.

Intermediate 9

2-Chloro-5-methoxypyrimidin-4-amine 2,4-Dichloro-5-methoxypyrimidine (10 g, 55.86 mmol) was dissolved in 1,4-dioxane (20 mL) in a pressure tube and 15M aqueous ammonium hydroxide solution (26 mL) was added. The tube was sealed and heated at 100° C., with stirring, for 18 h. The reaction mixture was cooled and the solid which formed was filtered. The reaction mixture was diluted using ethyl acetate, then washed with water (2×20 mL) and brine (20 mL). The organic phases were recombined, dried over sodium sulfate and concentrated in vacuo. Trituration in diethyl ether afforded the title compound (7.77 g, 87%) as a fluffy solid. $\delta_H$ (500 MHz, DMSO-d$_6$) 3.81 (3H, s), 7.10 (1H, br s), 7.42 (1H, br s), 7.68 (1H, s). LCMS m/z 160.

Intermediate 10

4-Amino-2-chloropyrimidin-5-ol

Intermediate 9 (7.7 g, 48.25 mmol) was dissolved in dichloromethane (400 mL) under an atmosphere of nitrogen, and the reaction mixture was cooled to 0° C. Tribromoborane (1M, 193 mL) was added slowly. The reaction mixture was allowed to warm to room temperature and stirred continuously for 5 days. The reaction mixture was quenched slowly with methanol until the solution became clear, then the solvent was removed in vacuo. The crude residue was azeotroped with methanol (4×), then purified on silica gel, eluting with 10% methanol in dichloromethane, to afford the title compound (8.2 g, 92%) as a cream solid at 80% UV purity. $\delta_H$ (500 MHz, DMSO-$d_6$) 7.49 (s, 1H), 7.46 (s, 1H).

Intermediate 11

2-Chloro-6H,7H,8H-pyrimido[5,4-b][1,4]oxazin-7-one

Intermediate 10 (2 g, 12.5 mmol) was dissolved in anhydrous DMF (20 mL) at room temperature. Potassium carbonate (3.46 g, 25.01 mmol) was added to the mixture, followed by chloroacetyl chloride (1.2 mL, 15.01 mmol). The reaction mixture was stirred at 70° C. for 1 h. Chloroacetyl chloride (1.2 mL, 15.01 mmol) was added and the reaction mixture was stirred for a further 1 h. The reaction mixture was diluted with dichloromethane (50 mL) and washed with water (50 mL). The aqueous phase was extracted with dichloromethane (2×100 mL) and the combined organic layers were washed with brine (2×100 mL), then dried over magnesium sulfate and concentrated in vacuo. The crude residue was purified on silica gel, eluting with 0-80% ethyl acetate in heptane, to afford the title compound (800 mg, 33%) as a white solid. $\delta_H$ (250 MHz, DMSO-$d_6$) 12.01 (s, 1H), 8.20 (d, J 11.9 Hz, 1H), 4.76 (d, J 1.5 Hz, 2H).

Intermediate 12

6H,7H,8H-Pyrimido[5,4-b][1,4]oxazin-7-one

Intermediate 11 (800 mg, 4.31 mmol), ammonium formate (2.67 g, 0.04 mol) and Pd(OH)$_2$ on charcoal (10% w/w) were suspended in ethanol (43 mL) and degassed with nitrogen. The mixture was stirred for 1 h at 75° C. The reaction mixture was cooled to room temperature, then extracted with ethyl acetate (30 mL) and washed with water (30 mL). The filtrate was concentrated in vacuo to afford the title compound (150 mg, 20.7%) as a white solid. $\delta_H$ (250 MHz, DMSO-$d_6$) 11.71 (s, 1H), 8.45 (s, 1H), 8.28 (s, 1H), 4.74 (s, 2H).

Intermediate 13

8-[(6-Bromo-2-methylimidazo[1,2-a]pyridin-3-yl) methyl]-6H,7H,8H-pyrimido[5,4-b]-[1,4]oxazin-7-one Intermediate 12 (50 mg, 0.21 mmol), Intermediate 5 (79.76 mg, 0.33 mmol) and 1,4-dioxane (4 mL) were charged into a 10 mL microwave tube. Methanesulfonic acid (0.1 mL, 1.5 mmol) was added and the reaction mixture was heated under microwave irradiation, with stirring, at 150° C. for 1 h. The reaction mixture was allowed to cool to room temperature and the solvent was removed in vacuo. The residue was dissolved in dichloromethane (30 mL) and washed with saturated aqueous sodium hydrogencarbonate solution (20 mL) and brine (20 mL), then dried over sodium sulphate and filtered. The solvent was removed in vacuo. The residue was purified on silica gel, eluting with 0-100% methanol in dichloromethane, to afford the title compound (65 mg, 53%) as a white solid. $\delta_H$ (500 MHz, DMSO-$d_6$) 8.92 (s, 1H), 8.63 (s, 1H), 8.35 (s, 1H), 7.42 (br d, J 9.4 Hz, 1H), 7.32 (dd, J 9.4, 1.9 Hz, 1H), 5.49 (s, 2H), 4.92 (s, 2H), 2.46 (s, 3H).

Intermediate 14

Ethyl (2R)-2-[(2-nitropyridin-3-yl)oxy]propanoate

A solution of 2-nitropyridin-3-ol (5 g, 35.7 mmoL), ethyl (S)-lactate (4.13 mL, 35.7 mmoL) and triphenylphosphine (10.4 g, 39.3 mmoL) in dichloromethane (300 mL) was stirred at room temperature for 10 minutes. The solution was cooled to 0° C. in an ice-water bath and a solution of diisopropyl azodicarboxylate (8.22 mL, 39.3 mmoL) in dichloromethane (50 mL) was added dropwise. The mixture was warmed to room temperature and stirred for 16 h, then diluted with water (100 mL). The layers were separated and the aqueous phase was extracted with dichloromethane (100 mL). The combined organic layers were washed with water (80 mL) and brine (80 mL), then dried over magnesium sulfate. The crude material was purified on silica (Biotage, 340 g) with an eluent of 0-100% ethyl acetate in heptanes. This was followed by a second purification on silica (Biotage, 100 g), eluting with 100% dichloromethane, to afford the title compound (7.84 g, 92%) as a yellow oil. $\delta_H$ (500 MHz, CDCl$_3$) 8.15 (dd, J 4.5, 1.2 Hz, 1H), 7.51 (dd, J 8.4, 4.5 Hz, 1H), 7.43 (dd, J 8.4, 1.1 Hz, 1H), 4.86 (q, J 6.8 Hz, 1H), 4.33-4.13 (m, 2H), 1.71 (d, J 6.8 Hz, 3H), 1.27 (t, J 7.1 Hz, 3H). LCMS m/z 241.

Intermediate 15

(2R)-2-Methyl-2H,3H,4H-pyrido[3,2-b][1,4]oxazin-3-one

Intermediate 14 (7.84 g, 32.64 mmol) was dissolved in acetic acid (200 mL) and iron powder (18.23 g, 326.4 mmol) was added. The mixture was stirred at 50° C. under an atmosphere of nitrogen for 6 h, before cooling to room temperature and stirring for 16 h. The mixture was filtered through a Celite pad and washed with ethyl acetate. The solvent was concentrated in vacuo, then the residue was dissolved in ethyl acetate (300 mL) and washed with saturated aqueous sodium hydrogencarbonate solution (2×80 mL). The aqueous phase was extracted with ethyl acetate (2×50 mL). The combined organic layers were washed with aqueous sodium hydrogencarbonate solution (20 mL), water (50 mL) and brine (50 mL), then dried over magnesium sulfate. The crude material was purified on silica gel, with a gradient of 0-100% ethyl acetate in heptanes, to afford the title compound (4.82 g, 90%) as a white crystalline solid. $\delta_H$ (500 MHz, CDCl$_3$) 9.58 (s, 1H), 8.03 (dd, J 5.0, 1.2 Hz, 1H), 7.30 (dd, J 8.0, 1.3 Hz, 1H), 6.98 (dd, J 7.9, 5.0 Hz, 1H), 4.75 (q, J 6.9 Hz, 1H), 1.64 (d, J 6.9 Hz, 3H).

Intermediate 16

(2R)-4-[(6-Bromo-2-methylimidazo[1,2-a]pyridin-3-yl)methyl]-2-methyl-2H,3H,4H-pyrido[3,2-b][1,4] oxazin-3-one Prepared from Intermediate 5 and Intermediate 15 by a method analogous to that used to prepare Intermediate 13. $\delta_H$ (500 MHz, DMSO-$d_6$) 8.99-8.95 (m, 1H), 8.06 (dd, J 4.8, 1.2 Hz, 1H), 7.45-7.39 (m, 2H), 7.31 (dd, J 9.4, 1.8 Hz, 1H), 7.10 (dd, J 7.9, 4.9 Hz, 1H), 5.57 (d, J 15.6 Hz, 1H), 5.53 (d, J 15.6 Hz, 1H), 4.95 (q, J 6.7 Hz, 1H), 2.43 (s, 3H), 1.49 (d, J 6.7 Hz, 3H).

Intermediate 17

1-[(6-Bromo-2-methylimidazo[1,2-a]pyridin-3-yl)methyl]-1,2-dihydroquinolin-2-one Prepared from Intermediate 5 and quinolin-2(1H)-one by a method analogous to that used to prepare Intermediate 13. $\delta_H$ (500 MHz, DMSO-$d_6$) 9.34 (s, 1H), 8.12-8.05 (m, 2H), 7.90 (d, J 9.5 Hz, 1H), 7.83 (d, J 7.7 Hz, 1H), 7.64 (d, J 3.9 Hz, 2H), 7.37-7.31 (m, 1H), 6.76 (d, J 9.5 Hz, 1H), 5.93 (s, 2H), 2.08 (s, 3H).

Intermediate 18

1-[(6-Bromo-2-methylimidazo[1,2-a]pyridin-3-yl)methyl]-1,2,3,4-tetrahydroquinolin-2-one Prepared from Intermediate 5 and 3,4-dihydroquinolin-2(1H)-one by a method analogous to that used to prepare Intermediate 13. $\delta_H$ (250 MHz, CD$_3$OD) 8.52 (s, 1H), 7.35 (s, 2H), 7.26-7.15 (m, 3H), 7.04-6.95 (m, 1H), 5.56 (s, 2H), 2.87-2.77 (m, 2H), 2.70 (dd, J 9.2, 5.4 Hz, 2H), 2.42 (s, 3H).

Intermediate 19

Ethyl 2-(2-fluoro-6-nitrophenoxy)acetate

2-Fluoro-6-nitrophenol (10 g, 63.65 mmol) was dissolved in acetonitrile (120 mL). Ethyl bromoacetate (7.76 mL, 70.02 mmol) and potassium carbonate (17.59 g, 127.31 mmol) were added. The reaction mixture was stirred for 2 h at 90° C., then allowed to cool to room temperature. The solvent was removed in vacuo and the residue was dissolved in dichloromethane (70 mL). The organic layer was washed sequentially with saturated aqueous sodium hydrogencarbonate solution (50 mL), then the aqueous layer was further extracted with dichloromethane (50 mL). The organic layers were combined, dried over sodium sulfate and concentrated in vacuo, to afford the title compound (11.57 g, 74.7%) as a dark yellow oil. $\delta_H$ (250 MHz, CDCl$_3$) 7.62 (dt, J 8.2, 1.6 Hz, 1H), 7.35 (ddd, J 10.9, 8.4, 1.7 Hz, 1H), 7.17 (td, J 8.3, 4.9 Hz, 1H), 4.81 (d, J 0.7 Hz, 2H), 4.24 (q, J 7.1 Hz, 2H), 1.27 (t, J 7.1 Hz, 3H).

Intermediate 20

8-Fluoro-3,4-dihydro-2H-1,4-benzoxazin-3-one

Prepared from Intermediate 19 by a method analogous to that used to prepare Intermediate 15, to give the title compound (5.2 g, 95%) as a beige crystalline solid. $\delta_H$ (500 MHz, DMSO-$d_6$) 10.88 (s, 1H), 6.93 (td, J 8.1, 5.6 Hz, 1H), 6.87 (ddd, J 10.0, 8.4, 1.5 Hz, 1H), 6.72 (dt, J 7.8, 1.3 Hz, 1H), 4.65 (s, 2H).

Intermediate 21

4-[(6-Bromo-2-methylimidazo[1,2-a]pyridin-3-yl)methyl]-8-fluoro-3,4-dihydro-2H-1,4-benzoxazin-3-one Intermediate 20 (1 g, 5.98 mmol), Intermediate 5 (2.16 g, 8.97 mmol) and triphenylphosphine (2.35 g, 8.97 mmol) were suspended in anhydrous tetrahydrofuran (80 mL) under an atmosphere of nitrogen and the reaction mixture was cooled to 0° C. Diisopropyl azadicarboxylate (1.78 mL, 8.97 mmol) was added as a solution in tetrahydrofuran (20 mL) dropwise over 10 minutes. The reaction mixture was stirred at 0° C. for 10 minutes, then warmed to room temperature and stirred for 4 h. The solvent was removed in vacuo without heating and the crude residue was purified on silica (Biotage, 100 g), eluting with 0-100% ethyl acetate in heptane, to afford the title compound (765 mg, 32.1%) as a white solid. $\delta_H$ (250 MHz, CDCl$_3$) 8.40 (s, 1H), 7.40 (d, J 9.6 Hz, 1H), 7.28-7.20 (d, 1H), 7.00-6.76 (m, 3H), 5.43 (s, 2H), 4.76 (s, 2H), 2.57 (s, 3H).

Intermediate 22

7-Fluoro-2,3-dihydro-1,3-benzoxazol-2-one

To a solution of 2-amino-6-fluorophenol (500 mg, 3.93 mmol) in tetrahydrofuran (5 mL) was added 1,1'-carbonyldiimidazole (765 mg, 4.72 mmol). The reaction mixture was heated with stirring at 60° C. for 1 h. The reaction mixture was cooled to ambient temperature, then 2M hydrochloric acid (5 mL) added and the material was extracted with ethyl acetate (2×20 mL). The organic extracts were combined and dried over sodium sulphate, then the solvent was removed in vacuo, to afford the title compound (541 mg, 87%) as a brown solid. $\delta_H$ (500 MHz, DMSO-$d_6$) 11.95 (s, 1H), 7.18-7.12 (m, 1H), 7.02 (ddd, J 10.4, 8.6, 0.8 Hz, 1H), 6.94 (dd, J 7.8, 0.8 Hz, 1H).

Intermediate 23

3-[(6-Bromo-2-methylimidazo[1,2-a]pyridin-3-yl)methyl]-7-fluoro-2,3-dihydro-1,3-benzoxazol-2-one Prepared from Intermediate 5 and Intermediate 23 by a method analogous to that used to prepare Intermediate 13. The title compound (80.2 mg, 41%) was isolated as a pale orange solid. $\delta_H$ (500 MHz, DMSO-$d_6$) 8.70 (d, J 1.2 Hz, 1H), 7.47 (d, J 9.4 Hz, 1H), 7.38 (dd, J 9.5, 1.8 Hz, 1H), 7.24 (td, J 8.4, 5.0 Hz, 1H), 7.13-7.06 (m, 1H), 7.02 (d, J 7.9 Hz, 1H), 5.47 (s, 2H), 2.50 (s, 3H). LCMS m/z 376/378.

Intermediate 24

5-Chloro-2H,3H-[1,3]oxazolo[4,5-d]pyrimidin-2-one

Intermediate 10 (1.5 g, 10.31 mmol) was dissolved in tetrahydrofuran (30 mL). 1,1'-Carbonyldiimidazole (2.0 g, 12.37 mmol) was added to this mixture. The reaction mixture was heated with stirring at 60° C. for 2 h, then cooled to room temperature. Hydrochloric acid (2M, 5 mL) was added and the material was extracted with ethyl acetate (2×20 mL). The organic extracts were combined and dried over sodium sulphate, then the solvent was removed in vacuo, to give the title compound (609 mg, 34%) as a white solid. LCMS m/z 171.

Intermediate 25

2H,3H-[1,3]Oxazolo[4,5-d]pyrimidin-2-one

Intermediate 24 (509 mg, 2.97 mmol), ammonium formate (1.84 g, 0.03 mol) and palladium dihydroxide (10%, 417 mg, 0.3 mmol) were suspended in ethanol (29 mL). The mixture was heated under reflux for 1 h at 75° C., then cooled to room temperature. The reaction mixture was diluted with ethyl acetate (30 mL) and washed with water (30 mL). The organic phase was concentrated in vacuo to give a white solid (60 mg). The aqueous phase was extracted with isopropanol:chloroform (1:1). The organic phase was dried over magnesium sulfate and concentrated in vacuo to afford a white solid (60 mg). The aqueous phase was concentrated in vacuo. The crude solid was purified on silica gel, eluting with 0-60% methanol in dichloromethane, to afford a white solid (208 mg), giving a total yield over three batches of the title compound formate salt (328 mg, 80%) as a white solid. $\delta_H$ (250 MHz, DMSO-$d_6$) 8.28 (s, 1H), 8.13 (s, 1H), 7.93 (s, 1H), 7.90 (s, 1H), 7.62 (s, 1H).

Intermediate 26

3-[(6-Bromo-2-methylimidazo[1,2-a]pyridin-3-yl)methyl]-2H,3H-[1,3]oxazolo[4,5-d]-pyrimidin-2-one Prepared from Intermediate 5 and Intermediate 25 by a method analogous to that used to prepare Intermediate 13. $\delta_H$ (250 MHz, DMSO-$d_6$) 8.85 (s, 1H), 8.77 (s, 1H), 8.58 (s, 1H), 7.47-7.41 (m, 1H), 7.40-7.24 (m, 1H), 5.36 (s, 2H), 2.53 (s, 3H).

Intermediate 27

Ethyl (2R)-2-(2-fluoro-6-nitrophenoxy)propanoate

Prepared from 2-fluoro-6-nitrophenol and ethyl (2S)-2-hydroxypropanoate by a method analogous to that used to prepare Intermediate 14. $\delta_H$ (500 MHz, CDCl$_3$) 7.62 (dt, J 8.2, 1.5 Hz, 1H), 7.34 (ddd, J 11.0, 8.4, 1.5 Hz, 1H), 7.16 (td, J 8.3, 4.9 Hz, 1H), 4.93 (q, J 6.8 Hz, 1H), 4.25-4.17 (m, 2H), 1.70 (d, J 6.8 Hz, 3H), 1.26 (t, J 7.1 Hz, 3H).

Intermediate 28

(2R)-8-Fluoro-2-methyl-3,4-dihydro-2H-1,4-benzoxazin-3-one

Prepared from Intermediate 27 by a method analogous to that used to prepare Intermediate 15. $\delta_H$ (500 MHz, CDCl$_3$) 8.14 (s, 1H), 6.92 (td, J 8.2, 5.2 Hz, 1H), 6.84 (ddd, J 9.9, 8.4, 1.3 Hz, 1H), 6.63-6.59 (m, 1H), 4.75 (q, J 6.8 Hz, 1H), 1.66 (d, J 6.8 Hz, 3H).

Intermediate 29

(2R)-4-[(6-Bromo-2-methylimidazo[1,2-a]pyridin-3-yl)methyl]-8-fluoro-2-methyl-3,4-dihydro-2H-1,4-benzoxazin-3-one Prepared from Intermediate 5 and Intermediate 28 by a method analogous to that used to prepare Intermediate 21. $\delta_H$ (250 MHz, DMSO-$d_6$) 8.61-8.57 (m, 1H), 7.43 (d, J 9.4 Hz, 1H), 7.33 (dd, J 9.5, 1.7 Hz, 1H), 7.11 (d, J 8.2 Hz, 1H), 7.04 (td, J 8.3, 5.7 Hz, 1H), 7.01-6.96 (m, 1H), 5.66 (d, J 16.5 Hz, 1H), 5.46 (d, J 16.5 Hz, 1H), 4.93 (q, J 6.7 Hz, 1H), 2.31 (s, 3H), 1.52 (d, J 6.7 Hz, 3H).

Intermediate 30 tert-Butyl 4-(5-{3-[(8-fluoro-3-oxo-3,4-dihydro-2H-1,4-benzoxazin-4-yl)methyl]-2-methylimidazo[1,2-a]pyridin-6-yl}pyridin-2-yl)piperazine-1-carboxylate Prepared from Intermediate 21 and tert-butyl 4-[5-(4,4,5,5-tetramethyl-1,3,2-dioxaborolan-2-yl)pyridin-2-yl]piperazine-1-carboxylate by a method analogous to that used to prepare Intermediate 3. $\delta_H$ (250 MHz, CDCl$_3$) 8.43-8.32 (m, 2H), 7.66 (dd, J 8.8, 2.5 Hz, 1H), 7.56 (d, J 9.3 Hz, 1H), 7.40 (dd, J 9.3, 1.6 Hz, 1H), 6.99-6.69 (m, 4H), 5.50 (s, 2H), 4.74 (s, 2H), 3.58 (s, 8H), 2.61 (s, 3H), 1.49 (s, 9H).

Intermediate 31

Ethyl 4-(5-{3-[(8-fluoro-3-oxo-3,4-dihydro-2H-1,4-benzoxazin-4-yl)methyl]-2-methyl-imidazo[1,2-a]pyridin-6-yl}pyrimidin-2-yl)cyclohex-3-ene-1-carboxylate Prepared from Intermediate 21 and Intermediate 157 by a method analogous to that used to prepare Intermediate 3. $\delta_H$ (500 MHz, DMSO-$d_6$) 9.10 (s, 2H), 8.86 (s, 1H), 7.69 (dd, J 9.3, 1.6 Hz, 1H), 7.59 (d, J 9.3 Hz, 1H), 7.31 (s, 1H), 7.15 (d, J 8.2 Hz, 1H), 7.09-6.91 (m, 2H), 5.63 (s, 2H), 4.87 (s, 2H), 4.11 (2×dq, J 7.0, 3.7 Hz, 2H), 2.76 (d, J 18.0 Hz, 1H), 2.72-2.61 (m, 1H), 2.59-2.51 (m, 2H), 2.36 (s, 3H), 2.12 (dd, J 8.7, 3.8 Hz, 1H), 1.73 (ddt, J 15.6, 10.4, 5.5 Hz, 1H), 1.21 (t, J 7.1 Hz, 3H).

Intermediate 32

Ethyl 4-(5-{3-[8-fluoro-3-oxo-3,4-dihydro-2H-1,4-benzoxazin-4-yl)methyl]-2-methyl-imidazo[1,2-a]pyridin-6-yl}pyrimidin-2-yl)cyclohexane-1-carboxylate Intermediate 31 (216 mg, 0.4 mmol) was dissolved in ethanol (7 mL) and ethyl acetate (7 mL). Palladium on charcoal (10%, 84.89 mg, 0.08 mmol) was added. The reaction mixture was flushed three times with nitrogen gas, followed by hydrogen gas three times. The reaction mixture was stirred under an atmosphere of hydrogen at room temperature for 2 days. The reaction mixture was filtered through Celite and concentrated in vacuo. The residue was purified on silica gel, eluting with 0-3% methanol in dichloromethane, to afford the title compound (140 mg, 64%). LCMS m/z 542.

Intermediate 33

6-Bromo-7-fluoro-2-methylimidazo[1,2-a]pyridine

5-Bromo-4-fluoropyridin-2-amine (5 g, 26.18 mmol) was dissolved in ethanol (50 mL) and chloroacetone (4.25 mL, 52.82 mmol) was added. The reaction mixture was stirred at 90° C. for 16 h, then further chloroacetone (2.5 mL) was added and the reaction mixture was stirred for a further 4 h at 90° C. The reaction mixture was concentrated in vacuo and redissolved in ethyl acetate (15 mL), then washed with saturated aqueous sodium hydrogencarbonate solution (10 mL) and brine (10 mL). The aqueous layer was re-extracted with ethyl acetate (2×10 mL), then the combined organic phase was washed with brine (10 mL), dried over sodium sulfate and concentrated to in vacuo. The crude residue was purified on silica gel, eluting with 0-100% ethyl acetate in heptanes, to afford the title compound (1.18 g, 20%) as a white solid. $\delta_H$ (500 MHz, DMSO-$d_6$) 8.97 (d, J 7.0 Hz, 1H), 7.62 (s, 1H), 7.51 (d, J 9.8 Hz, 1H), 2.30 (s, 3H).

Alternative Preparation

A suspension of 5-bromo-4-fluoropyridin-2-amine (1 g, 5.24 mmol) in isopropanol (10 mL) was treated with 1-bromo-2,2-dimethoxypropane (1.16 g, 6.28 mmol). The resulting mixture was heated at 80° C. for 21 h, then cooled to room temperature and concentrated under vacuum at 40° C. The residue was treated with ethyl acetate (15 mL) and water (15 mL) and the phases were separated. The aqueous phase was basified with aqueous NaOH solution (32% w/w) to pH 8, then extracted with ethyl acetate (10 mL, then 15 mL). The organic phases were pooled and concentrated under vacuum at 40° C. to give the title compound (0.93 g, 78%) as a beige solid.

Intermediate 34

(6-Bromo-7-fluoro-2-methylimidazo[1,2-a]pyridin-3-yl)methanol

Intermediate 33 (500 mg, 2.07 mmol) was suspended in water (10 mL) and heated at 40° C. for 10 minutes. Formaldehyde in water (37%, 3.1 mL, 41.48 mmol) was added and the reaction mixture was heated at 80° C. for 1 h, then cooled. The solid which had formed was filtered under suction. The filter cake was washed with water (20 mL) and dried under suction to afford the title compound (486.7 mg, 90%) as a white solid. $\delta_H$ (500 MHz, DMSO-$d_6$) 8.70 (d, J 6.9 Hz, 1H), 7.55 (d, J 9.7 Hz, 1H), 5.14 (t, J 5.5 Hz, 1H), 4.75 (d, J 5.4 Hz, 2H), 2.31 (s, 3H).

Intermediate 35

(2R)-4[(6-Bromo-7-fluoro-2-methylimidazo[1,2-a]pyridin-3-yl)methyl]-8-fluoro-2-methyl-3,4-dihydro-2H-1,4-benzoxazin-3-one Intermediate 28 (150 mg, 0.83 mmol), Intermediate 34 (257.41 mg, 0.99 mmol) and triphenylphosphine (260.6 mg, 0.99 mmol) were suspended in anhydrous tetrahydrofuran (3.5 mL), and the external reaction temperature was cooled to −25° C. A solution of diisopropyl azadicarboxylate (0.20 mL, 0.99 mmol) in anhydrous tetrahydrofuran was added dropwise. Stirring of the resulting clear yellow solution was continued at −25° C. for 10 minutes, then the temperature was gradually increased to 0° C. over 45 minutes. The solvent was removed in vacuo. The residue was purified on silica (Biotage, 10 g), eluting with 0-10% methanol in tert-butyl methyl ether, to afford the title compound (278 mg, 60%) as a yellow powder. $\delta_H$ (500 MHz, DMSO-$d_6$) 8.75 (d, J 6.7 Hz, 1H), 7.66-7.51 (m, 1H), 7.13 (d, J 8.2 Hz, 1H), 7.04 (td, J 8.3, 5.8 Hz, 1H), 7.02-6.97 (m, 1H), 5.63 (d, J 16.6 Hz, 1H), 5.46 (d, J 16.5 Hz, 1H), 4.93 (q, J 6.7 Hz, 1H), 2.28 (s, 3H), 1.51 (d, J 6.7 Hz, 3H).

Intermediate 36

Ethyl (2R)-2-(2,4-difluoro-6-nitrophenoxy)propanoate

Prepared from 2,4-difluoro-6-nitrophenol and ethyl (2S)-2-hydroxypropanoate by a method analogous to that used to prepare Intermediate 14. $\delta_H$ (500 MHz, DMSO-$d_6$) 7.89-7.80 (m, 2H), 4.93 (q, J 6.8 Hz, 1H), 4.10 (qq, J 7.2, 3.7 Hz, 2H), 1.50 (d, J 6.8 Hz, 3H), 1.15 (t, J 7.1 Hz, 3H).

Intermediate 37

(2R)-6,8-Difluoro-2-methyl-3,4-dihydro-2H-1,4-benzoxazin-3-one

Prepared from Intermediate 36 by a method analogous to that used to prepare Intermediate 15. $\delta_H$ (500 MHz, DMSO-$d_6$) 10.94 (s, 1H), 6.94 (ddd, J 11.4, 9.4, 2.9 Hz, 1H), 6.56 (dt, J 9.1, 2.2 Hz, 1H), 4.76 (q, J 6.8 Hz, 1H), 1.44 (d, J 6.8 Hz, 3H).

Intermediate 38

(2R)-4-[(6-Bromo-7-fluoro-2-methylimidazo[1,2-a]pyridin-3-yl)methyl]-6,8-difluoro-2-methyl-3,4-dihydro-2H-1,4-benzoxazin-3-one Prepared from Intermediate 34 and Intermediate 37 by a method analogous to that used to prepare Intermediate 21. $\delta_H$ (500 MHz, DMSO-$d_6$) 8.77 (d, J 6.7 Hz, 1H), 7.56 (d, J 9.6 Hz, 1H), 7.21 (dt, J 10.5, 1.9 Hz, 1H), 7.11 (td, J 11.4, 10.3, 2.7 Hz, 1H), 5.63 (d, J 16.6 Hz, 1H), 5.45 (d, J 16.6 Hz, 1H), 4.92 (q, J 6.7 Hz, 1H), 2.28 (s, 3H), 1.50 (d, J 6.7 Hz, 3H).

Intermediate 39

Ethyl 4-[5-(3-{[(2R)-8-fluoro-2-methyl-3-oxo-3,4-dihydro-2H-1,4-benzoxazin-4-yl]-methyl}-2-methyl-imidazo[1,2-a]pyridin-6-yl)pyrimidin-2-yl]cyclohex-3-ene-1-carboxylate Prepared from Intermediate 29 and Intermediate 157 by a method analogous to that used to prepare Intermediate 3. $\delta_H$ (500 MHz, DMSO-$d_6$) 9.10 (s, 2H), 8.83 (s, 1H), 7.69 (dd, J 9.3, 1.6 Hz, 1H), 7.59 (d, J 9.3 Hz, 1H), 7.31 (s, 1H), 7.15 (d, J 8.2 Hz, 1H), 7.04 (td, J 8.3, 5.7 Hz, 1H), 7.01-6.96 (m, 1H), 5.71 (d, J 16.5 Hz, 1H), 5.57 (d, J 16.5 Hz, 1H), 4.95 (q, J 6.7 Hz, 1H), 4.11 (qq, J 7.0, 3.7 Hz, 2H), 2.77 (d, J 16.7 Hz, 1H), 2.71-2.64 (m, 1H), 2.54 (s, 2H), 2.34 (s, 3H), 2.16-2.08 (m, 1H), 1.79-1.68 (m, 1H), 1.51 (d, J 6.7 Hz, 3H), 1.21 (t, J 7.1 Hz, 3H).

Intermediate 40

Ethyl 4-[5-(3-{[(2R)-8-fluoro-2-methyl-3-oxo-3,4-dihydro-2H-1,4-benzoxazin-4-yl]-methyl}-2-methyl-imidazo[1,2-a]pyridin-6-yl)pyrimidin-2-yl]cyclohexane-1-carboxylate Intermediate 39 (476 mg, 0.86 mmol) was dissolved in ethanol (15.4 mL) and ethyl acetate (15.4 mL). Triethylamine (0.13 mL, 0.94 mmol) was added, followed by palladium on charcoal (10%, 182 mg, 0.17 mmol). The reaction mixture was flushed three times with nitrogen gas and three times with hydrogen gas. The reaction mixture was stirred under an atmosphere of hydrogen gas at room temperature for 2 h. The reaction mixture was retreated with palladium on charcoal (10%, 182 mg, 0.17 mmol), then flushed three times with nitrogen gas and three times with hydrogen gas. The reaction mixture was stirred for 6 h under an atmosphere of hydrogen gas, then filtered through a pad of Celite and washed with ethyl acetate. The filtrate was concentrated in vacuo and purified on silica gel, eluting with 0-10% methanol in dichloromethane, to afford the title compound (222.8 mg, 46%). $\delta_H$ (500 MHz, DMSO-$d_6$) 9.08 (d, J 3.4 Hz, 2H), 8.82 (s, 1H), 7.68 (dd, J 9.3, 1.6 Hz, 1H), 7.60 (d, J 9.3 Hz, 1H), 7.15 (d, J 8.1 Hz, 1H), 7.08-7.02 (m, 1H), 7.00 (t, J 9.3 Hz, 1H), 5.71 (d, J 16.5 Hz, 1H), 5.57 (d, J 16.5 Hz, 1H), 4.96 (q, J 6.7 Hz, 1H), 4.10 (q, J 7.1 Hz, 2H), 3.08-2.98 (m, 1H), 2.88 (d, J 11.8 Hz, 0H), 2.68 (t, J 4.7 Hz, 1H), 2.34 (d, J 3.5 Hz, 3H), 2.11-1.90 (m, 4H), 1.86 (d, J 4.3 Hz, 2H), 1.75-1.61 (m, 2H), 1.52 (dd, J 6.7, 2.4 Hz, 4H), 1.21 (td, J 7.1, 3.1 Hz, 3H).

Intermediate 41

3-(5-Bromopyrimidin-2-yl)oxetan-3-ol

5-Bromo-2-iodopyrimidine (5 g, 17.55 mmol) was dissolved in anhydrous toluene (75 mL) and cooled to −78° C. under an atmosphere of nitrogen. n-Butyllithium in hexanes (2.5M, 7.37 mL) was added dropwise, then the reaction mixture was aged for 30 minutes prior to dropwise addition of oxetan-3-one (1.13 mL, 19.31 mmol). The reaction mixture was stirred at −78° C. for 30 minutes, then allowed to warm to room temperature for 1 h. The reaction mixture was diluted with water (200 mL) and extracted with ethyl acetate (3×200 mL). The combined organic extracts were successively washed with water (50 mL) and brine (50 mL), then dried over magnesium sulphate. The solvent was removed in vacuo. The resulting crude brown solid was purified on silica (Biotage, 100 g), eluting with 0-100% ethyl acetate in heptane, to afford the title compound (1.51 g, 36.5%) as a yellow solid. $\delta_H$ (500 MHz, DMSO-$d_6$) 9.07 (s, 2H), 6.44 (s, 1H), 4.94 (d, J 6.8 Hz, 2H), 4.67 (d, J 6.8 Hz, 2H).

Intermediate 42

5-Bromo-2-{3-[(trimethylsilyl)oxy]oxetan-3-yl}pyrimidine

Intermediate 41 (1.81 g, 7.83 mmol) and 1H-imidazole (0.78 mL, 11.75 mmol) were dissolved in dichloromethane (40 mL) and chloro(trimethyl)silane (1.29 mL, 10.18 mmol) was added. The reaction mixture was stirred at room temperature for 1 h, then washed with water (2×50 mL). The aqueous phase was re-extracted with dichloro-methane (20 mL). The combined organic extracts were dried over magnesium sulfate and concentrated in vacuo. The resulting yellow oil was purified on silica (Biotage, 50 g), eluting with 0-25% ethyl acetate in heptanes, to afford the title compound (1.83 g, 77%) as a colourless oil. $\delta_H$ (500 MHz, DMSO-$d_6$) 9.12 (s, 2H), 4.98 (d, J 7.0 Hz, 2H), 4.76 (d, J 7.0 Hz, 2H), −0.03 (s, 9H).

Intermediate 43

5-(4,4,5,5-Tetramethyl-1,3,2-dioxaborolan-2-yl)-2-{3-[(trimethylsilyl)oxy]oxetan-3-yl}-pyrimidine Intermediate 42 (4.88 g, 16.09 mmol) was dissolved in anhydrous 1,4-dioxane (50 mL), then treated with bis(pinacolato)diboron (4.90 g, 19.31 mmol) and potassium acetate (4.74 g, 48.28 mmol). The mixture was degassed with nitrogen for 10 minutes prior to addition of bis[3-(diphenylphosphanyl)cyclopenta-2,4-dien-1-yl]iron-dichloropalladium-dichloromethane complex (657 mg, 0.80 mmol). The reaction mixture was stirred at 80° C. for 1 h. The reaction mixture was concentrated in vacuo and redissolved in ethyl acetate (100 mL), then washed with water (50 mL) and brine (50 mL). The organic phase was dried over magnesium sulfate and the solvent was concentrated in vacuo. The resulting brown solid was slurried with heptanes and filtered through a pad of Celite. The filtrate was concentrated in vacuo and the residue was dissolved in dichloromethane (50 mL), then washed using water (2×50 mL) and brine (50 mL). The organic layers were dried over sodium sulfate and concentrated in vacuo, to afford the title compound (7.65 g, 68% yield, 50% purity) as an orange solid. $\delta_H$ (500 MHz, DMSO-$d_6$) 9.00 (d, J 10.6 Hz, 2H), 5.00 (d, J 6.8 Hz, 2H), 4.75 (d, J 6.8 Hz, 2H), 1.33 (s, 12H), −0.06 (s, 9H).

Intermediate 44 tert-Butyl 3-(5-bromopyrimidin-2-yl)-3-hydroxyazetidine-1-carboxylate

A solution of 5-bromo-2-iodopyrimidine (5 g, 17.55 mmol) in a mixture of anhydrous toluene (50 mL) and m-xylene (15 mL) was cooled to −70° C. with stirring under an atmosphere of nitrogen gas. A 2.5M solution of n-butyllithium in hexanes (7.2 mL) was added dropwise over 10 minutes. The resulting brown slurry was stirred at −70° C. for 50 minutes, then a solution of tert-butyl 3-oxoazetidine-1-carboxylate (3.3 g, 19.28 mmol) in anhydrous toluene (5 mL) was added dropwise. The reaction mixture was allowed to warm to ambient temperature and stirred for 1 h, then quenched with saturated aqueous ammonium chloride solution (50 mL) and diluted with water (50 mL). The crude residue was extracted using ethyl acetate (2×80 mL). The combined organic phases were dried over sodium sulfate and concentrated in vacuo. The resulting dark brown oil was purified on silica (Biotage, 100 g), eluting with 0-90% ethyl acetate in heptanes, to afford the title compound (3.48 g, 60.1%) as a yellow solid. $\delta_H$ (500 MHz, CDCl$_3$) 8.84 (s, 2H), 4.91 (s, 1H), 4.35 (d, J 9.0 Hz, 2H), 4.22 (d, J 9.1 Hz, 2H), 1.47 (s, 9H).

Intermediate 45 tert-Butyl 3-(5-bromopyrimidin-2-yl)-3-[(trimethylsilyl)oxy]azetidine-1-carboxylate Prepared from Intermediate 44 by a method analogous to that used to prepare Intermediate 42. $\delta_H$ (500 MHz, CDCl$_3$) 8.81 (s, 2H), 4.47 (d, J 9.6 Hz, 2H), 4.16 (d, J 9.5 Hz, 2H), 1.44 (s, 9H), 0.03 (s, 9H).

Intermediate 46 tert-Butyl 3-[5-(4,4,5,5-tetramethyl-1,3,2-dioxaborolan-2-yl)pyrimidin-2-yl]-3-[(trimethylsilyl)oxy]azetidine-1-carboxylate Prepared from Intermediate 45 by a method analogous to that used to prepare Intermediate 43. $\delta_H$ (500 MHz, CDCl$_3$) 9.04 (s, 2H), 4.52 (d, J 9.0 Hz, 2H), 4.17 (d, J 8.9 Hz, 2H), 1.45 (s, 9H), 1.36 (s, 12H), 0.02 (s, 9H).

Intermediate 47 tert-Butyl 3-[5-(3-{[(2R)-6,8-difluoro-2-methyl-3-oxo-3,4-dihydro-2H-1,4-benzoxazin-4-yl]methyl}-7-fluoro-2-methylimidazo[1,2-a]pyridin-6-yl)pyrimidin-2-yl]-3-hydroxy-azetidine-1-carboxylate Prepared from Intermediate 38 and Intermediate 46 by a method analogous to that used to prepare Intermediate 3, followed by treatment with TBAF at room temperature. $\delta_H$ (500 MHz, DMSO-$d_6$) 9.10 (d, J 1.3 Hz, 2H), 8.80 (d, J 7.3 Hz, 1H), 7.58 (d, J 11.2 Hz, 1H), 7.24 (dt, J 10.6, 1.8 Hz, 1H), 7.11 (ddd, J 11.6, 9.1, 2.8 Hz, 1H), 6.51 (s, 1H), 5.65 (d, J 16.6 Hz, 1H), 5.52 (d, J 16.6 Hz, 1H), 4.93 (q, J 6.6 Hz, 1H), 4.39 (s, 2H), 4.01 (d, J 6.6 Hz, 2H), 2.31 (s, 3H), 1.48 (d, J 6.7 Hz, 3H), 1.41 (s, 9H).

Intermediate 48

4-(5-Bromopyrimidin-2-yl)tetrahydropyran-4-ol

Prepared from 5-bromo-2-iodopyrimidine and tetrahydro-4H-pyran-4-one by a method analogous to that used to prepare Intermediate 41. $\delta_H$ (500 MHz, CDCl$_3$) 8.80 (s, 2H), 4.02-3.86 (m, 4H), 2.37 (ddd, J 13.1, 11.4, 6.3 Hz, 2H), 1.54 (dd, J 13.6, 2.0 Hz, 2H).

Intermediate 49

[4-(5-Bromopyrimidin-2-yl)tetrahydropyran-4-yl]oxy(trimethyl)silane

Prepared from Intermediate 48 by a method analogous to that used to prepare Intermediate 42. $\delta_H$ (500 MHz, CDCl$_3$) 8.80 (s, 2H), 3.90 (td, J 11.1, 2.5 Hz, 2H), 3.73 (dt, J 11.4, 4.1 Hz, 2H), 2.26 (ddd, J 14.1, 10.4, 4.4 Hz, 2H), 2.08-1.90 (m, 2H), −0.05 (s, 9H).

Intermediate 50

(Trimethyl){4-[5-(4,4,5,5-tetramethyl-1,3,2-dioxaborolan-2-yl)pyrimidin-2-yl]-tetrahydropyran-4-yl}oxysilane Prepared from Intermediate 49 by a method analogous to that used to prepare Intermediate 43. $\delta_H$ (250 MHz, CDCl$_3$) 9.02 (s, 2H), 3.92 (td, J 10.9, 2.6 Hz, 2H), 3.75 (dt, J 11.4, 4.1 Hz, 2H), 2.31 (ddd, J 14.3, 10.4, 4.4 Hz, 2H), 1.99 (d, J 13.3 Hz, 2H), 1.37 (s, 12H), −0.06 (s, 9H).

Intermediate 51

1-(5-Bromopyrimidin-2-yl)cyclobutan-1-ol

Prepared from 5-bromo-2-iodopyrimidine and cyclobutanone by a method analogous to that used to prepare Intermediate 41. $\delta_H$ (500 MHz, CD$_3$OD) 8.80 (s, 2H), 2.57 (dddd, J 11.2, 5.2, 4.4, 2.5 Hz, 2H), 2.32-2.23 (m, 2H), 1.93-1.76 (m, 2H).

Intermediate 52

[1-(5-Bromopyrimidin-2-yl)cyclobutoxy](trimethyl)silane

Prepared from Intermediate 51 by a method analogous to that used to prepare Intermediate 42. $\delta_H$ (500 MHz, CD$_3$OD) 8.91 (s, 2H), 2.76 (tt, J 8.6, 3.1 Hz, 2H), 2.43 (qd, J 9.6, 2.7 Hz, 2H), 1.85 (tdd, J 13.1, 6.7, 3.3 Hz, 1H), 1.69-1.55 (m, 1H), −0.02 (s, 9H).

Intermediate 53

(Trimethyl){1-[5-(4,4,5,5-tetramethyl-1,3,2-dioxaborolan-2-yl)pyrimidin-2-yl]-cyclobutoxy}silane Prepared from Intermediate 52 by a method analogous to that used to prepare Intermediate 43. $\delta_H$ (500 MHz, CDCl$_3$) 9.03 (s, 2H), 2.79 (tt, J 8.6, 3.2 Hz, 2H), 2.53-2.41 (m, 2H), 1.86 (dddd, J 13.2, 9.9, 6.7, 3.4 Hz, 1H), 1.70-1.60 (m, 1H), 1.36 (s, 12H), −0.03 (s, 9H).

Intermediate 54

1-(6-Bromo-7-fluoro-2-methylimidazo[1,2-a]pyridin-3-yl)ethan-1-ol

Intermediate 33 (1 g, 4.37 mmol) was suspended in water (20 mL) in a 100 mL stainless steel pressure vessel and acetaldehyde (20 mL, 356.4 mmol) was added. The vessel was sealed and the reaction mixture was heated at 80° C. for 10 h. The reaction mixture was allowed to cool to room temperature and the solid that had formed was collected by filtration. The filtrate was extracted with ethyl acetate (20 mL) and a precipitate formed in the organic layer which was collected by filtration. Heptane was added to the residual organic layer (20 mL) and a solid formed, which was combined with the first solid which had formed and triturated with dichloromethane (5 mL). This solid was combined with the initial solid from the organic layer to afford the title compound (620 mg, 52%) as an off-white solid. $\delta_H$ (500 MHz, DMSO-d$_6$) 8.80 (d, J 7.0 Hz, 1H), 7.54 (d, J 9.8 Hz, 1H), 5.49 (d, J 3.8 Hz, 1H), 5.24 (qd, J 6.8, 4.0 Hz, 1H), 2.32 (s, 3H), 1.49 (d, J 6.9 Hz, 3H).

Intermediate 55

(2R)-4-[1-(6-Bromo-7-fluoro-2-methylimidazo[1,2-a]pyridin-3-yl)ethyl]-8-fluoro-2-methyl-3,4-dihydro-2H-1,4-benzoxazin-3-one Intermediate 28 (150 mg, 0.83 mmol), Intermediate 54 (275 mg, 1.01 mmol) and triphenylphosphine (265 mg, 1.01 mmol) were dissolved in tetrahydrofuran (4 mL) and cooled to −30° C. under an atmosphere of nitrogen gas. A solution of diisopropyl azadicarboxylate (0.2 mL, 1.01 mmol) in tetrahydrofuran (1 mL) was added dropwise, maintaining the internal temperature between −30° C. and −25° C. The resulting mixture was stirred at −25° C. under nitrogen for 10 minutes, then allowed to warm to 0° C. over 45 minutes. The reaction mixture was concentrated in vacuo. The residue was purified on silica gel, eluting with 0-100% ethyl acetate in heptane, to yield the title compound (227 mg, 32.1%). LCMS: MH+m/z 436.

Intermediate 56

Ethyl 2-(2-fluoro-6-nitrophenoxy)-2-methylpropanoate 1,2-Difluoro-3-nitrobenzene (2 g, 12.57 mmol) was dissolved in DMF (40 mL) and caesium carbonate (6.2 g, 19.03 mmol) was added, followed by ethyl 2-hydroxy-2-methylpropanoate (2.5 mL, 18.16 mmol). The reaction mixture was heated at 80° C. with continuous stirring for 16 h, then allowed to cool to room temperature. The mixture was diluted with ethyl acetate (50 mL) and washed with water (30 mL) and brine (2×20 mL), then dried over sodium sulfate and concentrated in vacuo. The crude residue was purified on silica gel, eluting with 0-20% ethyl acetate in heptane, to afford the title compound (1.94 g, 56.9%) as a yellow oil. $\delta_H$ (500 MHz, CDCl$_3$) 7.54 (dt, J 8.2, 1.4 Hz, 1H), 7.29 (ddd, J 10.4, 8.4, 1.7 Hz, 1H), 7.15 (td, J 8.3, 5.0 Hz, 1H), 4.26 (q, J 7.1 Hz, 2H), 1.61 (s, 6H), 1.31 (t, J 7.1 Hz, 3H).

Intermediate 57

8-Fluoro-2,2-dimethyl-3,4-dihydro-2H-1,4-benzoxazin-3-one

Prepared from Intermediate 56 by a method analogous to that used to prepare Intermediate 15. $\delta_H$ (500 MHz, DMSO-d$_6$) 10.81 (s, 1H), 6.90 (dt, J 23.6, 7.0 Hz, 2H), 6.71 (d, J 7.0 Hz, 1H), 1.42 (s, 6H).

Intermediate 58

4[(6-Bromo-7-fluoro-2-methylimidazo[1,2-a]pyridin-3-yl)methyl]-8-fluoro-2,2-dimethyl-3,4-dihydro-2H-1,4-benzoxazin-3-one Prepared from Intermediate 57 and Intermediate 34 by a method analogous to that used to prepare Intermediate 21. $\delta_H$ (500 MHz, CDCl$_3$) 8.39 (d, J 6.6 Hz, 1H), 7.20 (d, J 8.5 Hz, 1H), 6.91-6.84 (m, 1H), 6.84-6.77 (m, 2H), 5.44 (s, 2H), 2.56 (s, 3H), 1.61 (s, 6H).

Intermediate 59 tert-Butyl 3-[5-(7-fluoro-3-{[(2R)-8-fluoro-2-methyl-3-oxo-3,4-dihydro-2H-1,4-benzoxazin-4-yl]methyl}-2-methylimidazo[1,2-a]pyridin-6-yl)pyrimidin-2-yl]-3-hydroxyazetidine-1-carboxylate Prepared from Intermediate 35 and Intermediate 46 by a method analogous to that used to prepare Intermediate 3, followed by treatment with 1M TBAF in THF. LCMS: MH+m/z 593.

Intermediate 60

(2R)-8-Fluoro-4-({7-fluoro-6-[2-(3-hydroxyazetidin-3-yl)pyrimidin-5-yl]-2-methyl-imidazo[1,2-a]pyridin-3-yl}methyl)-2-methyl-3,4-dihydro-2H-1,4-benzoxazin-3-one hydrochloride Intermediate 59 (300 mg, 0.51 mmol) was dissolved in 1,4-dioxane (2.5 mL) and 4M hydrogen chloride in 1,4-dioxane (2.5 mL) was added. The resulting suspension was stirred under nitrogen for 90 minutes. The reaction mixture was concentrated in vacuo and the residue was triturated with dichloromethane (3 mL) to afford the title compound (195 mg, 72.8%) as a pale yellow solid. $\delta_H$ (500 MHz, DMSO-d$_6$) 9.57 (s, 1H), 9.24 (s, 2H), 8.11-7.99 (m, 1H), 7.67-7.49 (m, 1H), 7.28 (d, J 7.3 Hz, 1H), 7.15-6.98 (m, 2H), 5.80-5.60 (m, 2H), 4.95 (q, J 6.6 Hz, 1H), 4.63-4.45 (m, 2H), 4.27-4.11 (m, 2H), 2.39 (s, 3H), 1.50 (d, J 6.7 Hz, 3H).

Intermediate 61

Ethyl (2R)-2-[(6-chloro-5-nitropyrimidin-4-yl)oxy]propanoate

To a solution of ethyl (2R)-2-hydroxypropanoate (2.01 g, 0.02 mol) in DMF (40 mL), cooled to 0° C., was added sodium hydride (60%, 0.68 g, 0.02 mol) portionwise and stirring was continued for 20 minutes. 4,6-Dichloro-5-nitropyrimidine (3 g, 0.02 mol) and DMF (20 mL) were charged in a separate flask and the reaction mixture was cooled to 0° C. The sodium lactate solution was added dropwise to the nitropyrimidine solution over 15 minutes at 0° C. The reaction mixture was stirred at ambient temperature for 20 h, then diluted with dichloromethane (100 mL). The organic phase was washed with water (3×100 mL) and brine (100 mL), then dried over sodium sulphate and filtered. The solvent was removed in vacuo. The residue was purified on silica gel, eluting with 10-65% dichloromethane in heptanes, to afford the title compound (0.91 g, 21%) as a yellow oil. $\delta_H$ (500 MHz, CDCl$_3$) 8.58 (s, 1H), 5.48 (q, J 7.1 Hz, 1H), 4.22 (q, J 7.1 Hz, 2H), 1.66 (d, J 7.1 Hz, 3H), 1.26 (t, J 7.1 Hz, 3H).

Intermediate 62

(7R)-7-Methyl-5H,6H,7H-pyrimido[4,5-b][1,4]oxazin-6-one

To a solution of Intermediate 61 (900 mg, 3.27 mmol) in ethanol (9 mL) was added palladium on charcoal (10% w/w, 50% wet, 90 mg, 5 wt %). The reaction mixture was flushed with nitrogen gas three times, then with hydrogen gas three times. The reaction mixture was stirred at ambient temperature under a hydrogen gas atmosphere for 16 h. The reaction mixture was filtered over Celite and the solvent was removed in vacuo. The residue was diluted with acetic acid (9 mL) and iron powder (183 mg, 3.27 mmol) was added. The reaction mixture was then heated at 80° C. for 2 h, then filtered over a pad of Celite, rinsing the pad with ethyl acetate (3×9 mL). The solvent was removed in vacuo and the residue was diluted with water (10 mL). The aqueous phase was extracted with isopropanol/chloroform (1:1, 2×50 mL), dried over sodium sulphate and filtered. The solvent was removed in vacuo to give the title compound (260 mg, 48%) as a grey solid. $\delta_H$ (500 MHz, DMSO-d$_6$) 11.04 (s, 1H), 8.42 (s, 1H), 8.13 (s, 1H), 5.10 (q, J 6.9 Hz, 1H), 1.51 (d, J 6.9 Hz, 3H).

Intermediate 63

(7R)-5-[(6-Bromo-2-methylimidazo[1,2-a]pyrazin-3-yl)methyl]-7-methyl-5H,6H,7H-pyrimido[4,5-b][1,4]oxazin-6-one Prepared from Intermediate 62 and Intermediate 98 by a method analogous to that used to prepare Intermediate 21. $\delta_H$ (500 MHz, DMSO-d$_6$) 8.80 (d, J 1.1 Hz, 1H), 8.78 (d, J 1.2 Hz, 1H), 8.58 (s, 1H), 8.50 (s, 1H), 5.61 (dd, J 16.6, 3.0 Hz, 1H), 5.57-5.49 (m, 1H), 5.28 (q, J 6.8 Hz, 1H), 2.36 (s, 3H), 1.56 (d, J 6.8 Hz, 3H).

Intermediate 64

(2R)-4-[(6-Bromo-2-methylimidazo[1,2-a]pyrazin-3-yl)methyl]-6,8-difluoro-2-methyl-3,4-dihydro-2H-1,4-benzoxazin-3-one Prepared from Intermediate 37 and Intermediate 98 by a method analogous to that used to prepare Intermediate 21. $\delta_H$ (500 MHz, DMSO-d$_6$) 9.10-8.72 (m, 2H), 7.24 (dt, J 10.5, 2.0 Hz, 1H), 7.11 (td, J 8.1, 2.8 Hz, 1H), 5.62 (d, J 16.6 Hz, 1H), 5.48 (d, J 16.6 Hz, 1H), 4.96-4.88 (m, 1H), 2.31 (s, 3H), 1.49 (d, J 6.7 Hz, 3H).

Intermediate 65

3-[5-(4,4,5,5-Tetramethyl-1,3,2-dioxaborolan-2-yl)pyrimidin-2-yl]oxetan-3-ol Prepared from Intermediate 41 by a method analogous to that used to prepare Intermediate 43 (reaction time 15 h). $\delta_H$ (500 MHz, DMSO-$d_6$) 8.99 (s, 2H), 4.96 (d, J 6.5 Hz, 2H), 4.68 (d, J 6.5 Hz, 2H), 1.33 (s, 12H).

Intermediate 66

(2R)-4-[(6-Bromo-2-methylimidazo[1,2-a]pyrazin-3-yl)methyl]-8-fluoro-2-methyl-3,4-dihydro-2H-1,4-benzoxazin-3-one Prepared from Intermediate 28 and Intermediate 98 by a method analogous to that used to prepare Intermediate 21. $\delta_H$ (500 MHz, CDCl$_3$) 8.75 (d, J 1.2 Hz, 1H), 8.36 (d, J 1.2 Hz, 1H), 6.97-6.90 (m, 1H), 6.90-6.82 (m, 1H), 6.83-6.76 (m, 1H), 5.56 (d, J 16.2 Hz, 1H), 5.31 (d, J 16.2 Hz, 1H), 4.78 (q, J 6.7 Hz, 1H), 2.61 (s, 3H), 1.67 (d, J 6.7 Hz, 3H), 1.59 (s, 3H).

Intermediate 67

4-[(6-Bromo-2-methylimidazo[1,2-a]pyrazin-3-yl)methyl]-8-fluoro-2,2-dimethyl-3,4-dihydro-2H-1,4-benzoxazin-3-one Prepared from Intermediate 57 and Intermediate 98 by a method analogous to that used to prepare Intermediate 21. $\delta_H$ (500 MHz, DMSO-$d_6$) 8.77 (d, J 10.8 Hz, 1H), 8.65 (d, J 18.2 Hz, 1H), 7.19-6.88 (m, 3H), 5.54 (s, 2H), 2.31 (d, J 6.0 Hz, 3H), 1.45 (s, 6H).

Intermediate 68

1-(5-Bromopyrimidin-2-yl)ethan-1-one

5-Bromo-2-iodopyrimidine (10 g, 35.1 mmol) and tributyl(1-ethoxyethenyl)-stannane (15.85 g, 43.88 mmol) were dissolved in anhydrous toluene (500 mL) and purged with nitrogen for 10 minutes. Dichlorobis(triphenylphosphine)palladium(II) (1.23 g, 1.76 mmol) was added and the mixture was stirred at 130° C. for 16 h. The reaction mixture was cooled to room temperature and water (29 mL) was added, followed by 6M HCl (106 mL), then the mixture was stirred vigorously at room temperature for 4 h. The solvent was removed in vacuo and the pH of the mixture was adjusted to pH 7 by the addition of saturated aqueous sodium hydrogencarbonate solution (500 mL). The mixture was extracted with ethyl acetate (3×350 mL). The combined organic extracts were dried over magnesium sulfate, filtered and concentrated in vacuo. The crude material was purified on silica gel, eluting with 20-100% ethyl acetate in heptane, to afford the title compound (2.99 g, 66%) as a gold-coloured solid. LCMS m/z 201/203.

Intermediate 69

5-Bromo-2-(1,1-difluoroethyl)pyrimidine

Intermediate 68 (0.59 g, 2.62 mmol) was stirred in anhydrous dichloromethane (30 mL) at 0° C. under an atmosphere of nitrogen gas. BAST (50% solution in toluene; 3.87 mL, 10.5 mmol) was added dropwise. The mixture was warmed to room temperature and stirred for 16 h, then added dropwise to stirred ice/saturated aqueous sodium hydrogencarbonate solution (50 mL). The organic layer was separated and the crude residue further extracted with dichloromethane (2×50 mL). The combined organic phase was dried over magnesium sulfate and concentrated in vacuo to afford the title compound (585 mg, 90%) as a brown solution in toluene, which was used directly in the subsequent step. $\delta_H$ (500 MHz, CDCl$_3$) 8.91 (s, 2H), 2.06 (t, J 18.6 Hz, 3H).

Intermediate 70

2-(1,1-Difluoroethyl)-5-(4,4,5,5-tetramethyl-1,3,2-dioxaborolan-2-yl)pyrimidine

Prepared from Intermediate 69 by a method analogous to that used to prepare Intermediate 43. $\delta_H$ (500 MHz, CDCl$_3$) 9.10 (s, 2H), 2.06 (t, J 18.6 Hz, 3H), 1.36 (s, 12H).

Intermediate 71

4-[(6-Bromo-2-methylimidazo[1,2-a]pyrazin-3-yl)methyl]-2H,3H,4H-pyrido[4,3-b][1,4]-oxazin-3-one Prepared from 2H,3H,4H-pyrido[4,3-b][1,4]oxazin-3-one and Intermediate 98 by a method analogous to that used to prepare Intermediate 21. $\delta_H$ (500 MHz, CD$_3$OD) 8.74 (d, J 1.2 Hz, 1H), 8.71 (d, J 1.2 Hz, 1H), 8.41 (s, 1H), 8.15 (d, J 5.3 Hz, 1H), 7.06 (d, J 5.3 Hz, 1H), 5.65 (s, 2H), 4.88 (s, 2H), 2.53 (s, 3H).

Intermediate 72

2H,3H,4H-Pyrido[3,2-b][1,4]oxazin-3-one

Prepared from 6-bromo-2H,3H,4H-pyrido[3,2-b][1,4]oxazin-3-one by a method analogous to that used to prepare Intermediate 12. $\delta_H$ (500 MHz, DMSO-$d_6$) 11.19 (s, 1H), 7.89 (dd, J 4.9, 1.4 Hz, 1H), 7.33 (dd, J 7.9, 1.4 Hz, 1H), 6.97 (dd, J 7.9, 4.9 Hz, 1H), 4.64 (s, 2H).

Intermediate 73

4-[(6-Bromo-7-fluoro-2-methylimidazo[1,2-a]pyridin-3-yl)methyl]-2H,3H,4H-pyrido-[3,2-b][1,4]oxazin-3-one Prepared from Intermediate 34 and Intermediate 72 by a method analogous to that used to prepare Intermediate 88. $\delta_H$ (500 MHz, DMSO-$d_6$) 9.14 (d, J 6.9 Hz, 1H), 8.02 (dd, J 4.8, 1.4 Hz, 1H), 7.51 (d, J 9.6 Hz, 1H), 7.39 (dd, J 7.9, 1.4 Hz, 1H), 7.07 (dd, J 7.9, 4.8 Hz, 1H), 5.52 (s, 2H), 4.82 (s, 2H), 2.41 (s, 3H).

Intermediate 74

4-[(6-Bromo-2-methylimidazo[1,2-a]pyrazin-3-yl)methyl]-2H,3H,4H-pyrido[3,2-b][1,4]-oxazin-3-one Prepared from Intermediate 72 and Intermediate 98 by a method analogous to that used to prepare Intermediate 88. $\delta_H$ (500 MHz, DMSO-$d_6$) 9.05-8.91 (m, 1H), 8.73 (dd, J 36.8, 1.2 Hz, 1H), 8.01 (dd, J 4.8, 1.4 Hz, 1H), 7.41 (dd, J 7.9, 1.4 Hz, 1H), 7.12-7.05 (m, 1H), 5.57 (s, 2H), 4.85 (s, 2H), 2.47 (d, J 32.4 Hz, 3H).

Intermediate 75

Ethyl 2-(2,4-difluoro-6-nitrophenoxy)acetate

Prepared from 2,4-difluoro-6-nitrophenol by a method analogous to that used to prepare Intermediate 19. $\delta_H$ (500

Intermediate 76

6,8-Difluoro-3,4-dihydro-2H-1,4-benzoxazin-3-one

Prepared from Intermediate 75 by a method analogous to that used to prepare Intermediate 15. $\delta_H$ (500 MHz, DMSO-d$_6$) 10.99 (s, 1H), 6.95 (ddd, J 11.1, 9.2, 2.9 Hz, 1H), 6.56 (dt, J 9.2, 2.3 Hz, 1H), 4.66 (s, 2H).

Intermediate 77

4-[(6-Bromo-7-fluoro-2-methylimidazo[1,2-a]pyridin-3-yl)methyl]-6,8-difluoro-3,4-dihydro-2H-1,4-benzoxazin-3-one Prepared from Intermediate 34 and Intermediate 76 by a method analogous to that used to prepare Intermediate 88. $\delta_H$ (500 MHz, DMSO-d$_6$) 8.81 (d, J 6.7 Hz, 1H), 7.57 (s, 1H), 7.23-7.19 (m, 1H), 7.10 (ddd, J 11.5, 9.0, 2.8 Hz, 1H), 5.53 (s, 2H), 4.83 (s, 2H), 2.29 (s, 3H).

Intermediate 78

[2-(5-Oxo-1,4-diazepan-1-yl)pyrimidin-5-yl]boronic acid

Prepared from 2-chloropyrimidin-5-ylboronic acid and 1,4-diazepan-5-one by a method analogous to that used to prepare Intermediate 90. LCMS MH+ m/z 237.

Intermediate 79

Ethyl 2-(2,4-difluoro-6-nitrophenoxy)-2-methylpropanoate

Prepared from 2,4-difluoro-6-nitrophenol and ethyl 2-bromo-2-methylpropanoate by a method analogous to that used to prepare Intermediate 19. $\delta_H$ (500 MHz, DMSO-d$_6$) 7.88-7.79 (m, 2H), 4.14 (q, J 7.1 Hz, 2H), 1.47 (s, 6H), 1.21 (t, J 7.1 Hz, 3H).

Intermediate 80

6,8-Difluoro-2,2-dimethyl-3,4-dihydro-2H-1,4-benzoxazin-3-one

Prepared from Intermediate 79 by a method analogous to that used to prepare Intermediate 15. $\delta_H$ (500 MHz, DMSO-d$_6$) 10.92 (s, 1H), 6.95 (ddd, J 11.1, 9.4, 2.8 Hz, 1H), 6.55 (dt, J 9.1, 2.2 Hz, 1H), 1.42 (s, 6H).

Intermediate 81

4-[(6-Bromo-7-fluoro-2-methylimidazo[1,2-a]pyridin-3-yl)methyl]-6,8-difluoro-2,2-dimethyl-3,4-dihydro-2H-1,4-benzoxazin-3-one Prepared from Intermediate 34 and Intermediate 80 by a method analogous to that used to prepare Intermediate 88. $\delta_H$ (500 MHz, DMSO-d$_6$) 8.70 (d, J 6.7 Hz, 1H), 7.55 (d, J 9.6 Hz, 1H), 7.17 (d, J 10.3 Hz, 1H), 7.13-7.07 (m, 1H), 5.53 (s, 2H), 2.28 (s, 3H), 1.46 (s, 6H).

Intermediate 82

Methyl (2S)-2-(2,4-difluoro-6-nitrophenoxy)propanoate

Prepared from 2,4-difluoro-6-nitrophenol and methyl (2R)-2-hydroxypropanoate by a method analogous to that used to prepare Intermediate 14. $\delta_H$ (500 MHz, CDCl$_3$) 7.43-7.33 (m, 1H), 7.12 (ddd, J 10.8, 7.7, 3.1 Hz, 1H), 4.83 (q, J 6.8 Hz, 1H), 3.73 (s, 3H), 1.67 (d, J 6.8 Hz, 4H), 1.43 (d, J 6.3 Hz, 1H), 1.26 (d, J 6.3 Hz, 1H).

Intermediate 83

(2S)-6,8-Difluoro-2-methyl-3,4-dihydro-2H-1,4-benzoxazin-3-one

Prepared from Intermediate 82 by a method analogous to that used to prepare Intermediate 15. $\delta_H$ (500 MHz, CDCl$_3$) 8.50 (s, 1H), 6.66-6.52 (m, 1H), 6.40 (d, J 8.3 Hz, 1H), 4.69 (q, J 6.8 Hz, 1H), 1.62 (d, J 6.8 Hz, 3H), 1.26 (d, J 6.2 Hz, 2H).

Intermediate 84

(2S)-4-[(6-Bromo-2-methylimidazo[1,2-a]pyrazin-3-yl)methyl]-6,8-difluoro-2-methyl-3,4-dihydro-2H-1,4-benzoxazin-3-one Prepared from Intermediate 83 and Intermediate 98 by a method analogous to that used to prepare Intermediate 88. $\delta_H$ (500 MHz, DMSO-d$_6$) 8.79 (s, 2H), 7.27-7.21 (m, 1H), 7.15-7.07 (m, 1H), 5.62 (d, J 16.6 Hz, 1H), 5.48 (d, J 16.6 Hz, 1H), 4.92 (q, J 6.7 Hz, 1H), 2.31 (s, 3H), 1.49 (d, J 6.7 Hz, 3H).

Intermediate 85

4-[(6-Bromo-2-methylimidazo[1,2-a]pyrazin-3-yl)methyl]-6,8-difluoro-3,4-dihydro-2H-1,4-benzoxazin-3-one Prepared from Intermediate 76 and Intermediate 98 by a method analogous to that used to prepare Intermediate 88. $\delta_H$ (500 MHz, DMSO-d$_6$) 9.03 (s, 1H), 8.78 (d, J 7.3 Hz, 1H), 7.56 (d, J 11.2 Hz, 1H), 7.27-7.20 (m, 1H), 7.12 (ddd, J 11.5, 9.1, 2.7 Hz, 1H), 5.58 (s, 2H), 5.20 (s, 1H), 2.29 (s, 3H), 1.56 (s, 6H), 1.45 (s, 6H).

Intermediate 86

4-[(6-Bromo-2-methylimidazo[1,2-a]pyrazin-3-yl)methyl]-6,8-difluoro-2,2-dimethyl-3,4-dihydro-2H-1,4-benzoxazin-3-one Prepared from Intermediate 80 and Intermediate 98 by a method analogous to that used to prepare Intermediate 88. $\delta_H$ (500 MHz, DMSO-d$_6$) 8.80 (d, J 1.2 Hz, 1H), 8.76 (d, J 1.2 Hz, 1H), 7.23 (dt, J 10.4, 2.2 Hz, 1H), 7.12 (ddd, J 11.6, 9.1, 2.7 Hz, 1H), 5.56 (s, 2H), 2.32 (s, 3H), 1.46 (s, 6H).

Intermediate 87

(2S)-6,8-Difluoro-4-({6-[2-(3-hydroxyoxetan-3-yl)pyrimidin-5-yl]-2-methylimidazo[1,2-a]pyrazin-3-yl}methyl)-2-methyl-3,4-dihydro-2H-1,4-benzoxazin-3-one Prepared from Intermediate 65 and Intermediate 84 by a method analogous to that used to prepare Intermediate 3. LCMS MH+ m/z 495.

Intermediate 88

(2S)-4-[(6-Bromo-7-fluoro-2-methylimidazo[1,2-a]pyridin-3-yl)methyl]-6,8-difluoro-2-methyl-3,4-dihydro-2H-1,4-benzoxazin-3-one Intermediate 83 (1 g, 3.77 mmol), Intermediate 34 (1.17 g, 4.52 mmol) and triphenylphosphine (1.19 g, 4.52 mmol) were suspended in anhydrous dichloromethane (40 mL) and the external temperature of the mixture was cooled to −20° C. A solution of diisopropyl azadicarboxylate (0.90 mL, 4.52 mmol) in anhydrous dichloromethane (20 mL) was added to the mixture dropwise over 5 minutes and the reaction mixture was stirred for 10 minutes whilst the temperature was maintained at −20° C. The reaction mixture was allowed to warm gradually towards room temperature over 1.5 h, then diluted with dichloromethane (20 mL) and methanol (20 mL) and dry-loaded onto silica. The crude material was purified on silica gel, eluting with 15-80% ethyl acetate-heptane, to afford the title compound (1.06 g, 63%) as a beige powder. $\delta_H$ (500 MHz, DMSO-d$_6$) 8.76 (d, J 6.7 Hz, 1H), 7.55 (d, J 9.6 Hz, 1H), 7.21 (dt, J 10.4, 2.2 Hz, 1H), 7.10 (ddd, J 11.6, 9.0, 2.8 Hz, 1H), 5.62 (d, J 16.6 Hz, 1H), 5.44 (d, J 16.6 Hz, 1H), 4.91 (q, J 6.7 Hz, 1H), 2.28 (s, 3H), 1.49 (d, J 6.7 Hz, 3H).

Intermediate 89

3-[(6-Bromo-7-fluoro-2-methylimidazo[1,2-a]pyridin-3-yl)methyl]-7-fluoro-2,3-dihydro-1,3-benzoxazol-2-one Intermediate 22 (0.97 g, 6.34 mmol), Intermediate 34 (1.97 g, 7.61 mmol) and triphenylphosphine (1.99 g, 7.61 mmol) were suspended in anhydrous dichloromethane (45 mL) and the external temperature of the mixture was cooled to −20° C. A solution of diisopropyl azadicarboxylate (1.51 mL, 7.61 mmol) in anhydrous dichloromethane (15 mL) was added to the mixture dropwise over 15-20 minutes. The reaction mixture was stirred for 45 minutes whilst the temperature was maintained below −10° C., then allowed to warm gradually towards room temperature. The reaction mixture was concentrated onto silica in vacuo and purified on silica (Biotage, 100 g), eluting with 50-100% ethyl acetate in heptane, to afford the title compound (1.44 g, 50%) as a pale yellow solid. $\delta_H$ (500 MHz, CDCl$_3$) 8.64 (d, J 6.4 Hz, 1H), 7.24 (d, J 8.5 Hz, 1H), 7.10 (td, J 8.3, 4.6 Hz, 1H), 6.92 (t, J 9.2 Hz, 1H), 6.72 (d, J 7.9 Hz, 1H), 5.27 (s, 2H), 2.66 (s, 3H), 1.66-1.37 (m, 4H).

Intermediate 90

2-(Morpholin-4-yl)pyrimidin-5-ylboronic acid

2-Chloropyrimidin-5-ylboronic acid (1 g, 6.32 mmol), morpholine (2.19 mL, 25.26 mmol) and triethylamine (0.88 mL, 6.32 mmol) were stirred in ethanol (25 mL) at 20° C. for 1 h. Water (50 mL) was slowly added to the reaction mixture. The resulting precipitate was filtered and washed with water to afford the title compound (950 mg, 70%) as a cream solid. $\delta_H$ (250 MHz, DMSO-d$_6$) 8.63 (s, 2H), 8.05 (s, 2H), 3.68 (ddd, J 23.4, 5.7, 3.9 Hz, 8H).

Intermediate 91

2-Bromo-N-(3,5-difluoro-2-hydroxyphenyl)-2,2-difluoroacetamide

2-Amino-4,6-difluorophenol (5 g, 34.46 mmol) was stirred in dichloromethane (7 mL) under an atmosphere of nitrogen at 0° C. Bromo(difluoro)acetyl chloride (3.89 mL, 41.35 mmol) was added, followed by triethylamine (7.20 mL, 51.69 mmol). The reaction mixture was warmed to room temperature and stirred for 12 h. The reaction mixture was diluted using dichloromethane (10 mL), then washed using water (2×40 mL) and brine (20 mL). The organic phase was dried over sodium sulfate and concentrated in vacuo to afford the title compound (11.02 g, 83%) as a black oil. $\delta_H$ (500 MHz, DMSO-d$_6$) 7.06 (ddd, J 11.4, 8.9, 3.0 Hz, 1H), 6.98 (dt, J 9.8, 2.3 Hz, 1H).

Intermediate 92

2,2,6,8-Tetrafluoro-3,4-dihydro-2H-1,4-benzoxazin-3-one

Intermediate 91 (11.04 g, 28.88 mmol) was dissolved in anhydrous DMF (100 mL). Potassium carbonate (1.84 g, 13.34 mmol) was added and the reaction mixture was heated at 50° C. for 12 h, then cooled to room temperature and concentrated in vacuo. Ethyl acetate (100 mL) was added, then the reaction mixture was washed with 1M HCl (50 mL), saturated aqueous sodium hydrogencarbonate solution (50 mL) and brine (50 mL). The pH of the aqueous phase was adjusted to ensure that it was acidic, then re-extracted using isopropanol:chloroform (30 mL). The combined organic layers were dried over sodium sulfate and concentrated in vacuo. The resulting crude viscous black oil was purified over silica gel, eluting with 0-50% ethyl acetate in heptane, to afford the title compound (4.55 g, 71.2%) as a pale pink solid. $\delta_H$ (500 MHz, DMSO-d$_6$) 12.30 (s, 1H), 7.27 (ddd, J 11.0, 9.1, 2.9 Hz, 1H), 6.79-6.74 (m, 1H).

Intermediate 93

4-[(6-Bromo-7-fluoro-2-methylimidazo[1,2-a]pyridin-3-yl)methyl]-2,2,6,8-tetrafluoro-3,4-dihydro-2H-1,4-benzoxazin-3-one Prepared from Intermediate 34 and Intermediate 92 by a method analogous to that used to prepare Intermediate 88. $\delta_H$ (500 MHz, CDCl$_3$) 8.36 (d, J 6.3 Hz, 1H), 7.25 (d, J 8.5 Hz, 1H), 6.86-6.70 (m, 2H), 5.47 (s, 2H), 2.60 (s, 3H).

Intermediate 94

2-{2,4-Difluoro-6-[({7-fluoro-6-[2-(3-hydroxy-3-methylazetidin-1-yl)pyrimidin-5-yl]-2-methylimidazo[1,2-a]pyridin-3-yl}methyl)amino]phenoxy}-2,2-difluoroacetic acid Prepared from Intermediate 93 and Intermediate 149 by a method analogous to that used to prepare Intermediate 3, followed by treatment with 4M HCl in 1,4-dioxane. LCMS m/z 565.

Intermediate 95

2-(2,4-Difluoro-6-{[(7-fluoro-6-{2-[3-hydroxy-3-(trifluoromethyl)azetidin-1-yl]-pyrimidin-5-yl}-2-methylimidazo[1,2-a]pyridin-3-yl)methyl]amino}phenoxy)-2,2-difluoroacetic acid Prepared from Intermediate 93 and Intermediate 148 by a method analogous to that used to prepare Intermediate 3, followed by treatment with 4M HCl in 1,4-dioxane. LCMS m/z 619.

Intermediate 96

(2R)-4-[(6-Bromo-2-methylimidazo[1,2-a]pyrazin-3-yl)methyl]-2-methyl-2H,3H,4H-pyrido[3,2-b][1,4]oxazin-3-one Prepared from Intermediate 15 and Intermediate 98 by a method analogous to that used to prepare Intermediate 88. $\delta_H$ (500 MHz, DMSO-d$_6$) 9.01 (d, J 1.2 Hz, 1H), 8.76 (d, J 1.1 Hz, 1H), 8.03 (dd, J 4.9, 1.4 Hz, 1H), 7.43 (dd, J 7.9, 1.4 Hz, 1H), 7.09 (ddd, J 7.8, 4.9, 1.5 Hz, 1H), 5.57 (s, 2H), 4.95 (q, J 6.7 Hz, 1H), 2.48 (s, 3H), 1.48 (d, J 6.7 Hz, 3H).

Intermediate 97

4-[(6-Bromo-7-fluoro-2-methylimidazo[1,2-a]pyridin-3-yl)methyl]pyrido[4,3-b][1,4]-oxazin-3-one Prepared from Intermediate 34 and 2H,3H,4H-pyrido[4,3-b][1,4]oxazin-3-one by a method analogous to that used to prepare Intermediate 21. $\delta_H$ (500 MHz, CD$_3$OD) 8.78 (d, J 6.6 Hz, 1H), 8.42 (s, 1H), 8.13 (d, J 5.3 Hz, 1H), 7.31 (d, J 8.9 Hz, 1H), 7.04 (d, J 5.5 Hz, 1H), 5.62 (s, 2H), 4.88 (s, 2H), 2.49 (s, 3H).

Intermediate 98

(6-Bromo-2-methylimidazo[1,2-a]pyrazin-3-yl)methanol

6-Bromo-2-methylimidazo[1,2-a]pyrazine (5 g, 23.58 mmol) and sodium acetate (9.67 g, 117.9 mmol) were dissolved in acetic acid (25 mL) and water (25 mL). Aqueous formaldehyde (37%, 18 mL, 241.77 mmol) was added and the reaction mixture was stirred at 80° C. for 1 h, then left to stand at room temperature for 15 h. The reaction mixture was stirred at 80° C. for a further 4 h, then left to stand room temperature for 15 h. The solid that formed was collected by filtration and washed with water (30 mL). A second batch of solid was obtained from the filtrate and washed with water (30 mL). A third batch of solid was obtained from the filtrate and washed with water (30 mL). The solids were combined and dried in vacuo to afford the title compound (4.31 g, 75.5%) as a white solid. $\delta_H$ (500 MHz, DMSO-d$_6$) 8.80 (d, J 1.1 Hz, 1H), 8.68 (d, J 1.2 Hz, 1H), 5.29 (t, J 5.5 Hz, 1H), 4.81 (d, J 5.2 Hz, 2H), 2.43 (s, 3H). LCMS m/z 242.

Intermediate 99

1-(5-Bromopyrimidin-2-yl)-3,3-difluorocyclobutan-1-ol

Prepared from 5-bromo-2-iodopyrimidine and 3,3-difluorocyclobutanone by a method analogous to that used to prepare Intermediate 41. $\delta_H$ (500 MHz, CDCl$_3$) 8.83 (s, 2H), 4.72 (s, 1H), 3.54-3.18 (m, 2H), 3.16-2.83 (m, 2H).

Intermediate 100

5-Bromo-2-{3,3-difluoro-1-[(trimethylsilyl)oxy]cyclobutyl}pyrimidine

Prepared from Intermediate 99 by a method analogous to that used to prepare Intermediate 42. $\delta_H$ (500 MHz, CDCl$_3$) 8.82 (s, 2H), 3.47 (ddd, J 14.7, 12.3, 9.3 Hz, 2H), 2.99 (ddd, J 14.6, 13.6, 12.1 Hz, 2H), 0.00 (s, 9H).

Intermediate 101

2-{3,3-Difluoro-1-[(trimethylsilyl)oxy]cyclobutyl}-5-(4,4,5,5-tetramethyl-1,3,2-dioxaborolan-2-yl)pyrimidine Prepared from Intermediate 100 by a method analogous to that used to prepare Intermediate 43. $\delta_H$ (500 MHz, CDCl$_3$) 9.04 (s, 2H), 3.58-3.47 (m, 2H), 2.98 (td, J 14.2, 11.7 Hz, 2H), 1.37 (s, 6H), 1.26 (s, 16H).

Intermediate 102

5-Bromo-2-{1-[(tert-butyldimethylsilyl)oxy]ethenyl}pyrimidine

Intermediate 68 (6.87 g, 34.16 mmol) and triethylamine (7.14 mL, 51.23 mmol) were stirred in anhydrous dichloromethane (300 mL) and the reaction mixture was cooled to 0° C. tert-Butyl(dimethyl)silyl trifluoromethanesulfonate (13.54 g, 51.23 mmol) was added dropwise. After 30 minutes, the mixture was allowed to warm to room temperature, then left standing for 16 h. The reaction mixture was quenched by the addition of water (300 mL). The two phases were separated and the organic phase was washed with brine (200 mL), then dried over magnesium sulfate, filtered and concentrated in vacuo. The crude material was purified on silica gel, eluting with 1-8% ethyl acetate in heptane, to afford the title compound (10.22 g, 82%) as a light yellow oil. LCMS m/z 315/317.

Intermediate 103

5-Bromo-2-{1-[(tert-butyldimethylsilyl)oxy]cyclopropyl}pyrimidine

To a stirred solution of potassium tert-butoxide (4.07 g, 0.04 mol) in anhydrous DMSO (100 mL) was added trimethylsulfoxonium iodide (8.4 g, 38.19 mmol) portionwise and the mixture was heated at 50° C. for 30 minutes. A solution of Intermediate 102 (3.01 g, 9.55 mmol) in anhydrous DMSO (100 mL) was added dropwise to the mixture. The reaction mixture was stirred at 50° C. for 85 minutes, then left standing for 16 h at room temperature. The reaction mixture was poured into a saturated aqueous solution of ammonium chloride (400 mL), then ethyl acetate (350 mL) was added and the two phases were separated. The aqueous phase was extracted with ethyl acetate (3×350 mL). The combined organic extracts were washed with water (2×400 mL) and brine (400 mL), then dried over magnesium sulfate, filtered and concentrated in vacuo. The residue was purified on silica gel, eluting with 5-40% dichloromethane in hep-

Intermediate 104

2-{1-[(tert-Butyldimethylsilyl)oxy]cyclopropyl}-5-(4,4,5,5-tetramethyl-1,3,2-dioxaborolan-2-yl)pyrimidine Prepared from Intermediate 103 by a method analogous to that used to prepare Intermediate 43. $\delta_H$ (500 MHz, CDCl$_3$) 8.88 (s, 2H), 1.53-1.48 (m, 2H), 1.35 (s, 12H), 1.34-1.31 (m, 2H), 0.91 (s, 9H), 0.14 (s, 6H).

Intermediate 105

(2R)-4-{[6-(2-{1-[(tert-Butyldimethylsilyl)oxy]cyclopropyl}pyrimidin-5-yl)-7-fluoro-2-methylimidazo[1,2-a]pyridin-3-yl]methyl}-8-fluoro-2-methyl-3,4-dihydro-2H-1,4-benzoxazin-3-one Prepared from Intermediate 35 and Intermediate 104 by a method analogous to that used to prepare Intermediate 3. $\delta_H$ (250 MHz, DMSO-d$_6$) 8.76 (d, J 1.6 Hz, 2H), 8.53 (d, J 7.3 Hz, 1H), 7.36 (d, J 11.4 Hz, 1H), 7.09-6.71 (m, 3H), 5.52 (d, J 16.6 Hz, 1H), 5.35 (d, J 16.6 Hz, 1H), 4.76 (q, J 6.6 Hz, 1H), 2.15 (s, 3H), 1.34 (d, J 6.7 Hz, 3H), 1.30 (m, 2H), 1.23-1.04 (m, 2H), 0.76 (s, 9H), 0.00 (s, 6H).

Intermediate 106

9-[5-(4,4,5,5-Tetramethyl-1,3,2-dioxaborolan-2-yl)pyrimidin-2-yl]-3,7-dioxa-9-azabicyclo[3.3.1]nonane Prepared from 2-chloro-5-(4,4,5,5-tetramethyl-1,3,2-dioxaborolan-2-yl)pyrimidine and 3,7-dioxa-9-azabicyclo[3.3.1]nonane by a method analogous to that used to prepare Intermediate 90. $\delta_H$ (500 MHz, CDCl$_3$) 8.62 (s, 2H), 4.63 (s, 2H), 4.13 (d, J 11.2 Hz, 4H), 3.92 (dd, J 10.8, 2.1 Hz, 4H), 1.33 (s, 12H).

Intermediate 107

2-{5-[7-Fluoro-3-(hydroxymethyl)-2-methylimidazo[1,2-a]pyridin-6-yl]pyrimidin-2-yl}-propan-2-ol Prepared from Intermediate 34 and 2-[5-(4,4,5,5-tetramethyl-1,3,2-dioxaborolan-2-yl)pyrimidin-2-yl]propan-2-ol by a method analogous to that used to prepare Intermediate 3. $\delta_H$ (500 MHz, DMSO-d$_6$) 9.05 (s, 1H), 9.05 (s, 1H), 8.68 (d, J 7.5 Hz, 1H), 7.54 (d, J 11.4 Hz, 1H), 5.17 (s, 1H), 5.14 (t, J 5.6 Hz, 1H), 4.81 (d, J 5.6 Hz, 2H), 2.35 (s, 3H), 1.55 (s, 6H).

Intermediate 108

(2R)-4-[(6-Bromo-7-fluoro-2-methylimidazo[1,2-a]pyridin-3-yl)methyl]-2-methyl-2H,3H,4H-pyrido[3,2-b][1,4]oxazin-3-one Prepared from Intermediate 15 and Intermediate 34 by a method analogous to that used to prepare Intermediate 88. $\delta_H$ (500 MHz, DMSO-d$_6$) 9.14 (d, J 6.9 Hz, 1H), 8.04 (dd, J 4.8, 1.3 Hz, 1H), 7.51 (d, J 9.6 Hz, 1H), 7.43 (dd, J 7.9, 1.3 Hz, 1H), 7.09 (dd, J 7.9, 4.9 Hz, 1H), 5.53 (d, J 2.3 Hz, 2H), 4.93 (q, J 6.7 Hz, 1H), 2.40 (s, 3H), 1.47 (d, J 6.7 Hz, 3H).

Intermediate 109

Ethyl (2R)-2-(3,4,6-trifluoro-2-nitrophenoxy)propanoate

Prepared from 1,2,4,5-tetrafluoro-3-nitrobenzene and ethyl (2R)-2-hydroxy-propanoate by a method analogous to that used to prepare Intermediate 56. LCMS m/z 294.

Intermediate 110

(2R)-5,6,8-Trifluoro-2-methyl-4H-1,4-benzoxazin-3-one

Prepared from Intermediate 109 by a method analogous to that used to prepare Intermediate 15. $\delta_H$ (400 MHz, DMSO-d$_6$) 11.30 (s, 1H), 7.23-7.31 (m, 1H), 4.81 (q, J 6.8 Hz, 1H), 1.47 (d, J 6.8 Hz, 3H).

Intermediate 111

(2R)-4-[(6-Bromo-2-methylimidazo[1,2-a]pyrazin-3-yl)methyl]-5,6,8-trifluoro-2-methyl-1,4-benzoxazin-3-one Prepared from Intermediate 98 and Intermediate 110 by a method analogous to that used to prepare Intermediate 21. LCMS m/z 448.

Intermediate 112

4-Benzyl-8-fluoro-1,4-benzoxazin-3-one

To a solution of Intermediate 20 (1 g, 5.98 mmol) at 0° C. was added, portionwise, sodium hydride (0.20 g, 8.37 mmol). After 5 minutes, benzyl bromide (1.64 g, 9.57 mmol) was added dropwise. The mixture was stirred at 0° C. for 3 h, then quenched with water and extracted with three portions of EtOAc. The combined organic layers were washed with three portions of brine, dried over magnesium sulphate and concentrated in vacuo. The residue was purified by gradient silica column chromatography, eluting with 0-80% ethyl acetate in DCM, to afford the title compound (400 mg, 30%) as a white solid. LCMS m/z 258.

Intermediate 113

4-Benzyl-8-fluoro-3-methyl-2,3-dihydro-1,4-benzoxazine

To a solution of Intermediate 112 (0.4 g, 1.56 mmol) in THF at 0-5° C. was added, dropwise, methylmagnesium bromide (0.74 g, 6.21 mmol). The mixture was allowed to warm to room temperature and stirred for 2 h, then cooled to 0-5° C. Acetic acid (2 mL) was added, followed by sodium borohydride (0.09 g, 2.33 mmol), added portionwise. The mixture was warmed to room temperature and stirred for 2 h, then cooled again to 0° C. The mixture was quenched with water, stirred overnight at room temperature and extracted with three portions of EtOAc. The combined organic layers were washed with three portions of brine, dried over magnesium sulphate and concentrated in vacuo. The residue was purified by gradient silica column chromatography, eluting with 0-80% ethyl acetate in DCM, to afford a clear oil containing ~50% of the title compound (336 mg). The mixture was used in the next step without further purification. LCMS m/z 258.

Intermediate 114

8-Fluoro-3-methyl-3,4-dihydro-2H-1,4-benzoxazine

To a solution of Intermediate 113 (0.336 g, 1.3 mmol) in ethanol was added palladium (0.12 g, 1.1 mmol) on charcoal (Degussa, 10%, 50% $H_2O$ w/w). The mixture was flushed with nitrogen and placed under a hydrogen atmosphere. After stirring at room temperature for 2 h, the mixture was filtered through celite and the filter cake was washed with methanol. The combined organic layers were concentrated in vacuo. The residue was purified by gradient silica column chromatography, eluting with 0-80% ethyl acetate in DCM, to afford the title compound (100 mg, 50%) as a pale yellow oil. $\delta_H$ (400 MHz, $CDCl_3$) 6.64-6.72 (m, 1H), 6.50 (ddd, J 10.6, 8.3, 1.4 Hz, 1H), 6.40 (dt, J 8.0, 1.4 Hz, 1H), 4.28 (dd, J 10.5, 2.8 Hz, 1H), 3.80-3.89 (m, 1H), 3.55-3.68 (m, 1H), 1.23 (d, J 6.4 Hz, 3H).

Intermediate 115

4-[(6-Bromo-7-fluoro-2-methylimidazo[1,2-a]pyridin-3-yl)methyl]-8-fluoro-3-methyl-2,3-dihydro-1,4-benzoxazine Prepared from Intermediate 34 by treatment with thionyl chloride, followed by reaction of the resulting material with Intermediate 114 in the presence of potassium carbonate, utilising a method analogous to that described for Example 2. The title compound (20 mg, 10%) was obtained as a white solid. $\delta_H$ (400 MHz, $CDCl_3$) 8.08 (d, J 6.4 Hz, 1H), 7.37 (d, J 8.4 Hz, 1H), 6.74-6.80 (m, 1H), 6.57-6.63 (m, 2H), 4.66 (d, J 15.0 Hz, 1H), 4.35 (d, J 15.0 Hz, 1H), 4.04 (q, J 8.9 Hz, 2H), 2.87-2.92 (m, 1H), 2.47 (s, 3H), 1.05 (d, J 6.6 Hz, 3H). LCMS m/z 409.

Intermediate 116

4-[(6-Bromo-2-methylimidazo[1,2-a]pyridin-3-yl)methyl]-1,4-benzoxazin-3-one

To a solution of Intermediate 6 (0.15 g, 0.58 mmol) in DMF at 0° C. were added cesium carbonate (0.94 g, 2.9 mmol) and 2H-1,4-benzoxazin-3(4H)-one (0.172 g, 1.15 mmol). The mixture was stirred at room temperature overnight and quenched with water. The precipitate was filtered off and washed with water to afford the title compound (165 mg, 77%) as an off-white solid, which was used directly in the next step without further purification.

Intermediate 117

Spiro[4H-1,4-benzoxazine-2,1'-cyclopropane]-3-one

A solution of 6-bromospiro[4H-1,4-benzoxazine-2,1'-cyclopropane]-3-one (1.7 g, 6.7 mmol) in THF (36 mL) was added to a suspension of palladium on charcoal (0.17 g, 1.6 mmol) in ethanol (18 mL). The reaction mixture was degassed, then stirred at room temperature under a hydrogen balloon for 3 h. A further portion of palladium on charcoal (0.02 g) was added and the reaction mixture was stirred at room temperature under a hydrogen balloon for 3 days. The reaction mixture was filtered through celite and washed with EtOAc. The filtrate was diluted with EtOAc and washed with water. The organic layer was dried over sodium sulphate and concentrated under reduced pressure to afford the title compound (980 mg, 84%) as an off-white solid, which was used directly in the next stage without further purification. $\delta_H$ (300 MHz, DMSO-$d_6$) 10.70 (br s, 1H), 7.00-6.85 (m, 4H), 1.26-1.12 (m, 4H).

Intermediate 118

4-[(6-Bromo-7-fluoro-2-methylimidazo[1,2-a]pyridin-3-yl)methyl]spiro[1,4-benzoxazine-2,1'-cyclopropane]-3-one Prepared from Intermediate 34 and Intermediate 117 by a method analogous to that used to prepare Intermediate 21. $\delta_H$ (300 MHz, DMSO-$d_6$) 8.75 (d, J 6.8 Hz, 1H), 7.57 (d, J 9.6 Hz, 1H), 7.28 (dd, J 8.0, 1.2 Hz, 1H), 7.10-7.00 (m, 2H), 6.95 (dd, J 7.8, 1.4 Hz, 1H), 5.55 (s, 2H), 2.25 (s, 3H), 1.35-1.25 (m, 4H).

Intermediate 119

Methyl (2R)-2-(4-bromo-2-fluoro-6-nitrophenoxy)propanoate

Prepared from 4-bromo-2-fluoro-6-nitrophenol and (S)-methyl lactate by a method analogous to that used to prepare Intermediate 14. $\delta_H$ (300 MHz, $CDCl_3$) 7.74 (d, 1H), 7.47 (dd, 1H), 4.90 (q, 1H), 3.72 (s, 3H), 1.66 (d, 3H).

Intermediate 120

(2R)-6-Bromo-8-fluoro-2-methyl-4H-1,4-benzoxazin-3-one

Prepared from Intermediate 119 by a method analogous to that used to prepare Intermediate 15. $\delta_H$ (300 MHz, DMSO-$d_6$) 10.95 (br s, 1H), 7.21 (d, 1H), 6.88 (s, 1H), 4.80 (q, 1H), 1.45 (d, 3H).

Intermediate 121

Methyl (2R)-8-fluoro-2-methyl-3-oxo-4H-1,4-benzoxazine-6-carboxylate

A mixture of Intermediate 120 (0.3 g, 1.15 mmol), Hermann's catalyst (0.055 g, 0.06 mmol), tri-tert-butylphosphonium tetrafluoroborate (0.067 g, 0.23 mmol), molybdenum hexacarbonyl (0.621 g, 2.31 mmol), DBU (0.53 g, 3.46 mmol), MeOH (6 mL) and 1,4-dioxane (6 mL) was heated at 150° C. for 30 minutes under microwave irradiation. The reaction mixture was filtered and the filtrate was concentrated under reduced pressure. The residue was purified by flash column chromatography (EtOAc: hexane, 0-50%) to afford the title compound (320 mg, quantitative) as a white solid, which was used directly in the next step without further purification. $\delta_H$ (300 MHz, DMSO-$d_6$) 11.00 (br s, 1H), 7.42 (dd, J 10.8, 1.9 Hz, 1H), 7.36-7.35 (m, 1H), 4.91 (dd, J 13.6, 6.7 Hz, 1H), 3.83 (s, 3H), 1.48 (d, J 6.8 Hz, 3H).

Intermediate 122

Methyl (2R)-4-[(6-bromo-7-fluoro-2-methylimidazo[1,2-a]pyridin-3-yl)methyl]-8-fluoro-2-methyl-3-oxo-1,4-benzoxazine-6-carboxylate Prepared from Intermediate 34 and Intermediate 121 by a method analogous to that used to prepare Intermediate 21. LCMS m/z 480.

Intermediate 123

Ethyl (2R)-2-(2,3-difluoro-6-nitrophenoxy)propanoate

Prepared from 2,3,4-trifluoronitrobenzene and (+)-ethyl D-lactate by a method analogous to that used to prepare Intermediate 56. LCMS m/z 276.

Intermediate 124

(2R)-7,8-Difluoro-2-methyl-4H-1,4-benzoxazin-3-one

Prepared from Intermediate 123 by a method analogous to that used to prepare Intermediate 15. $\delta_H$ (300 MHz, DMSO-$d_6$) 10.80 (br s, 1H), 7.01 (ddd, J 10.5, 9.1, 7.9 Hz, 1H), 6.68 (ddd, J 9.0, 5.0, 2.3 Hz, 1H), 4.82 (q, J 6.8 Hz, 1H), 1.46 (d, J 6.8 Hz, 3H).

Intermediate 125

(2R)-4-[(6-Bromo-7-fluoro-2-methylimidazo[1,2-a]pyridin-3-yl)methyl]-7,8-difluoro-2-methyl-1,4-benzoxazin-3-one Prepared from Intermediate 34 and Intermediate 124 by a method analogous to that used to prepare Intermediate 21. LCMS m/z 440.

Intermediate 126

Ethyl 1-(2-fluoro-6-nitrophenoxy)cyclopropanecarboxylate

Prepared from 2,3-difluoronitrobenzene and ethyl 1-hydroxycyclopropane-carboxylate by a method analogous to that used to prepare Intermediate 56. $\delta_H$ (300 MHz, DMSO-$d_6$) 7.73 (dt, J 8.2, 1.5 Hz, 1H), 7.64 (ddd, J 12.7, 8.4, 1.6 Hz, 1H), 7.27 (dt, J 8.3, 4.8 Hz, 1H), 4.17 (q, J 7.1 Hz, 2H), 1.50-1.37 (m, 4H), 1.16 (t, J 7.1 Hz, 3H).

Intermediate 127

8-Fluorospiro[4H-1,4-benzoxazine-2,1'-cyclopropane]-3-one

Prepared from Intermediate 126 by a method analogous to that used to prepare Intermediate 15. $\delta_H$ (300 MHz, DMSO-$d_6$) 10.00 (br s, 1H), 7.00-6.85 (m, 2H), 6.75 (dt, J 7.9, 1.4 Hz, 1H), 1.32-1.20 (m, 4H).

Intermediate 128

4-[(6-Bromo-7-fluoro-2-methylimidazo[1,2-a]pyridin-3-yl)methyl]-8-fluorospiro[1,4-benzoxazine-2,1'-cyclopropane]-3-one Prepared from Intermediate 34 and Intermediate 127 by a method analogous to that used to prepare Intermediate 21. LCMS m/z 434.

Intermediate 129

Ethyl (2R)-2-(2-chloro-4-fluoro-6-nitrophenoxy)propanoate

Prepared from 2-chloro-4-fluoro-6-nitrophenol and (−)-ethyl L-lactate by a method analogous to that used to prepare Intermediate 14. LCMS m/z 292.

Intermediate 130 (2R)-8-Chloro-6-fluoro-2-methyl-4H-1,4-benzoxazin-3-one

Prepared from Intermediate 129 by a method analogous to that used to prepare Intermediate 15. LCMS (negative ion) m/z 214.

Intermediate 131

(2R)-4-[(6-Bromo-2-methylimidazo[1,2-a]pyrazin-3-yl)methyl]-8-chloro-6-fluoro-2-methyl-1,4-benzoxazin-3-one Prepared from Intermediate 98 and Intermediate 130 by a method analogous to that used to prepare Intermediate 21. LCMS (negative ion) m/z 439/441.

Intermediate 132

Ethyl (2R)-2-(2-chloro-6-nitrophenoxy)propanoate

Prepared from 2-chloro-6-nitrophenol and (−)-ethyl L-lactate by a method analogous to that used to prepare Intermediate 14. LCMS m/z 274.

Intermediate 133

(2R)-8-Chloro-2-methyl-4H-1,4-benzoxazin-3-one

Prepared from Intermediate 132 by a method analogous to that used to prepare Intermediate 15. LCMS (negative ion) m/z 196.

Intermediate 134

(2R)-4-[(6-Bromo-2-methylimidazo[1,2-a]pyrazin-3-yl)methyl]-8-chloro-2-methyl-1,4-benzoxazin-3-one Prepared from Intermediate 98 and Intermediate 133 by a method analogous to that used to prepare Intermediate 21. LCMS m/z 421/423.

Intermediate 135

2-{5-[3-(Hydroxymethyl)-2-methylimidazo[1,2-a]pyrazin-6-yl]pyrimidin-2-yl}propan-2-ol Prepared from Intermediate 98 and 2-[5-(4,4,5,5-tetramethyl-1,3,2-dioxaborolan-2-yl)pyrimidin-2-yl]propan-2-ol by a method analogous to that used to prepare Intermediate 3. LCMS m/z 300.

Intermediate 136

Ethyl (2R)-2-{[6-chloro-2-nitro-4-(trifluoromethyl)pyridin-3-yl]oxy}propanoate

Prepared from 6-chloro-2-nitro-4-(trifluoromethyl)pyridin-3-ol and (−)-ethyl L-lactate by a method analogous to that used to prepare Intermediate 14. LCMS (negative ion) m/z 311.

Intermediate 137

(2R)-6-Chloro-2-methyl-8-(trifluoromethyl)-4H-pyrido[3,2-b][1,4]oxazin-3-one

Prepared from Intermediate 136 by a method analogous to that used to prepare Intermediate 15. LCMS (negative ion mode) m/z 265.

Intermediate 138

(2R)-2-Methyl-8-(trifluoromethyl)-4H-pyrido[3,2-b][1,4]oxazin-3-one

Prepared from Intermediate 137 by a method analogous to that used to prepare Intermediate 12. LCMS m/z 233.

Intermediate 139

(2R)-4[(6-Bromo-2-methylimidazo[1,2-a]pyrazin-3-yl)methyl]-2-methyl-8-(trifluoromethyl)pyrido[3,2-b][1,4]oxazin-3-one Prepared from Intermediate 98 and Intermediate 138 by a method analogous to that used to prepare Intermediate 21. LCMS m/z 456/458.

Intermediate 140

(2R)-8-Fluoro-2-methyl-3-oxo-4H-1,4-benzoxazine-6-carbonitrile

Intermediate 120 (300 mg, 1.15 mmol) was heated with copper(I) cyanide (207 mg, 2.30 mmol) in 1-methyl-2-pyrrolidinone (6 mL) at 220° C. under microwave irradiation for 40 minutes. After cooling, the reaction mixture was diluted with EtOAc (×5,) washed with water, 1:1 water/brine, and brine (three portions), then dried over $Na_2SO_4$, concentrated onto silica and purified by column chromatography (gradient, 0-40% EtOAc in hexane), to give the title compound (140 mg, 58.9%) as a white, crystalline solid. $\delta_H$ (400 MHz, DMSO-$d_6$) 10.95 (s, 1H), 7.22 (dd, 1H, J 10.1, 2.2 Hz), 6.88 (t, 1H, J 1.9 Hz), 4.81 (q, 1H, J 6.8 Hz), 1.46 (d, 3H, J 6.8 Hz). LCMS m/z 205.

Intermediate 141

Ethyl (2S)-2-(2-fluoro-6-nitrophenoxy)propanoate

Prepared from 2-fluoro-6-nitrophenol and ethyl (2R)-2-hydroxypropanoate by a method analogous to that used to prepare Intermediate 14. $\delta_H$ (300 MHz, DMSO-$d_6$) 7.77 (dt, 1H, J 8.3, 1.6 Hz), 7.66 (ddd, 1H, J 11.8, 8.4, 1.6 Hz), 7.32 (td, 1H, J 8.3, 5.0 Hz), 4.99 (qd, 1H, J 6.8, 1.0 Hz), 4.10 (qd, 2H, J 7.1, 1.2 Hz), 1.50 (dd, 3H, J 6.8, 0.5 Hz), 1.14 (t, 3H, J 7.1 Hz).

Intermediate 142

(2S)-8-Fluoro-2-methyl-4H-1,4-benzoxazin-3-one

Prepared from Intermediate 141 by a method analogous to that used to prepare Intermediate 15. $\delta_H$ (300 MHz, DMSO-$d_6$) 10.86 (s, 1H), 6.91 (m, 2H), 6.63 (m, 1H), 4.76 (q, 1H, J 6.8 Hz), 1.44 (d, 3H, J 6.8 Hz).

Intermediate 143

(2S)-4-[(6-Bromo-7-fluoro-2-methylimidazo[1,2-a]pyridin-3-yl)methyl]-8-fluoro-2-methyl-1,4-benzoxazin-3-one Prepared from Intermediate 34 and Intermediate 142 by a method analogous to that used to prepare Intermediate 21. $\delta_H$ (400 MHz, DMSO-$d_6$) 8.76 (d, 1H, J 6.7 Hz), 7.73 (m, 2H), 7.56 (d, 1H, J 9.6 Hz), 5.65 (m, 1H, J 6.8 Hz), 5.50 (m, 1H, J 6.8 Hz), 5.10 (q, 1H, J 6.8 Hz), 2.30 (s, 3H), 1.55 (d, 3H, J 6.8 Hz).

Intermediate 144

4-[(6-Bromo-2-methylimidazo[1,2-a]pyrazin-3-yl)methyl]-8-fluoro-1,4-benzoxazin-3-one Prepared from Intermediate 20 and Intermediate 98 by a method analogous to that used to prepare Intermediate 21. LCMS m/z 391.

Intermediate 145

4-[(6-Bromo-2-methylimidazo[1,2-a]pyrazin-3-yl)methyl]spiro[1,4-benzoxazine-2,1'-cyclopropane]-3-one Prepared from Intermediate 98 and Intermediate 117 by a method analogous to that used to prepare Intermediate 21. LCMS m/z 399.

Intermediate 146

4-[(6-Bromo-2-methylimidazo[1,2-a]pyrazin-3-yl)methyl]-8-fluorospiro[1,4-benzoxazine-2,1'-cyclopropane]-3-one Prepared from Intermediate 98 and Intermediate 127 by a method analogous to that used to prepare Intermediate 21. LCMS m/z 417.

Intermediate 147

2-(3-Oxopiperazin-1-yl)pyrimidin-5-ylboronic acid

Prepared from 2-chloropyrimidin-5-ylboronic acid and piperazin-2-one by a method analogous to that used to prepare Intermediate 90. $\delta_H$ (400 MHz, DMSO-$d_6$) 8.65 (s, 2H), 8.14 (s, 2H), 8.11 (m, 1H), 4.19 (s, 2H), 3.92 (m, 2H), 3.26 (m, 2H).

Intermediate 148

1-[5-(4,4,5,5-Tetramethyl-1,3,2-dioxaborolan-2-yl)pyrimidin-2-yl]-3-(trifluoromethyl)-azetidin-3-ol

Prepared from 2-chloro-5-(4,4,5,5-tetramethyl-1,3,2-dioxaborolan-2-yl)pyrimidine and 3-(trifluoromethyl)azetidin-3-ol by a method analogous to that used to prepare Intermediate 90. $\delta_H$ (400 MHz, DMSO-$d_6$) 8.53 (s, 2H), 7.46 (s, 1H), 4.32 (d, J 10.8 Hz, 2H), 4.10 (d, J 10.8 Hz, 2H), 1.29 (s, 12H).

Intermediate 149

3-Methyl-1-[5-(4,4,5,5-tetramethyl-1,3,2-dioxaborolan-2-yl)pyrimidin-2-yl]azetidin-3-ol

Prepared from 2-chloro-5-(4,4,5,5-tetramethyl-1,3,2-dioxaborolan-2-yl)pyrimidine and 3-methylazetidin-3-ol by a method analogous to that used to prepare Intermediate 90. $\delta_H$ (400 MHz, DMSO-$d_6$) 8.45 (s, 2H), 5.67 (s, 1H), 3.92 (m, 4H), 1.43 (s, 3H), 1.28 (s, 12H).

Intermediate 150

2-(3,3-Difluoroazetidin-1-yl)pyrimidin-5-ylboronic acid

Prepared from 2-chloropyrimidin-5-ylboronic acid and 3,3-difluoroazetidine by a method analogous to that used to prepare Intermediate 90.

Intermediate 151

(6-Choro-2-methylimidazo[1,2-b]pyridazin-3-yl)methanol

A mixture of 6-chloro-2-methylimidazo[1,2-b]pyridazine (2.5 g, 15 mmol) and sodium acetate (6.2 g, 75 mmol) in water (15 mL) and acetic acid (15 mL) was treated with a solution of formaldehyde (4.15 mL, 150 mmol) in water (8 mL). The resulting suspension was heated at 80° C. for 16 h. The reaction mixture was treated with HCl (6N, 15 mL) and the resulting mixture was heated at 60° C. for 1 h. The reaction mixture was treated with aqueous NaOH solution (2N, 15 mL) and saturated aqueous NaHCO$_3$ solution until pH 8, then extracted into DCM (three portions), dried over NaSO$_4$ and evaporated. The resulting crude white solid was purified by column chromatography on silica gel (eluting with 0-10% MeOH in DCM) to give the title compound (700 mg, 24%) as a white powder. $\delta_H$ (300 MHz, DMSO-$d_6$) 8.09 (d, 1H, J 9.4 Hz), 7.30 (d, 1H, J 9.4 Hz), 5.13 (t, 1H, J 5.5 Hz), 4.76 (d, 2H, J 5.4 Hz), 2.40 (s, 3H). LCMS m/z 198.

Intermediate 152

(2R)-4-[(6-Chloro-2-methylimidazo[1,2-b]pyridazin-3-yl)methyl]-8-fluoro-2-methyl-1,4-benzoxazin-3-one

Prepared from Intermediate 28 and Intermediate 151 by a method analogous to that used to prepare Intermediate 21. LCMS m/z 361.

Intermediate 153

Ethyl 4-methyl-1-[5-(4,4,5,5-tetramethyl-1,3,2-dioxaborolan-2-yl)pyrimidin-2-yl]-piperidine-4-carboxylate

Prepared from 2-chloro-5-(4,4,5,5-tetramethyl-1,3,2-dioxaborolan-2-yl)pyrimidine and ethyl 4-methylpiperidine-4-carboxylate by a method analogous to that used to prepare Intermediate 90.

Intermediate 154

2-[(1R,5S)-8-Methoxycarbonyl-3-azabicyclo[3.2.1]octan-3-yl]pyrimidin-5-ylboronic acid

(1R,5S)-3-(tert-Butoxycarbonyl)-3-azabicyclo[3.2.1]octane-8-carboxylic acid (9.0 g, 35.3 mmol) was suspended in HCl solution (2.25M in MeOH) and the reaction mixture was heated at reflux for 4 h. The reaction mixture was allowed to cool to room temperature, then concentrated in vacuo. To the resulting white solid was added 2-chloropyrimidin-5-ylboronic acid (5.58 g, 35.2 mmol) and the mixture was suspended in EtOH (130 mL). Triethylamine (9.90 mL, 70.5 mmol) was added and the reaction mixture was heated at 80° C. for 5 h. The reaction mixture was allowed to cool to room temperature, then water (30 mL) was added. The reaction mixture was concentrated to around one-third volume, then more water (100 mL) was added. The off-white solid precipitate was filtered and washed with water (2×30 mL) to afford the title compound (8.9 g, 86%) as an off-white powder. $\delta_H$ (300 MHz, DMSO-$d_6$) 8.59 (2H, s), 8.02 (2H, s), 4.45 (2H, dd, J 13.1, 3.4 Hz), 3.62 (3H, s), 2.98 (2H, br d, J 12.4 Hz), 2.77 (1H, s), 2.59 (2H, br s), 1.66-1.63 (2H, m), 1.38-1.33 (2H, m). LCMS m/z 292.

Intermediate 155

Ethyl 4-(4,4,5,5-tetramethyl-1,3,2-dioxaborolan-2-yl)cyclohex-3-ene-1-carboxylate

Lithium hexamethyldisilazide in THF/ethylbenzene (1M, 5.55 mL) was added dropwise to a stirred solution of ethyl 4-oxocyclohexanecarboxylate (900 mg, 5.29 mmol) in anhydrous THF (5 mL) under an inert atmosphere at −78° C., and the mixture was stirred for 1 h. 1,1,1-Trifluoro-N-phenyl-N-[(trifluoromethyl)sulfonyl]methanesulfonamide (1.98 g, 5.55 mmol) in THF (5 mL) was added over 5 minutes, and the mixture was stirred for 30 minutes. The reaction mixture was then warmed to room temperature and stirred for 12 h. The mixture was quenched with NaHSO$_4$ and diluted with ethyl acetate (250 mL), then washed with 0.5M aqueous NaOH solution (2×20 mL), saturated aqueous NH$_4$Cl solution (20 mL) and brine (20 mL). The organic fraction was dried over MgSO₄ and concentrated under reduced pressure. The resulting material (1.9 g, 83%) was dissolved in 1,4-dioxane (30 mL), then bis(pinacolato)diboron (1.68 g, 6.6 mmol) and 1,1'-bis(diphenylphosphino)ferrocene (73 mg, 0.13 mmol) were added and the mixture was degassed with nitrogen for 5 minutes. Bis[3-(diphenylphosphanyl)-cyclopenta-2,4-dien-1-yl]iron-dichloropalladium-dichloromethane complex (108 mg, 0.13 mmol) was added and the mixture was heated at 90° C. for 18 h. The mixture was diluted with water (100 mL) and extracted with ethyl acetate (2×100 mL). The combined organic layers were washed with brine (50 mL), dried over MgSO₄ and concentrated under reduced pressure. The residue was purified by silica gel chromatography, eluting with 10-20% ethyl acetate in heptane, to afford the title compound in two batches (440 mg, 26% yield, 73% purity; and 362 mg, 12% yield, 42% purity) as a colourless oil. LCMS m/z 281.

Intermediate 156

Ethyl 4-(5-bromopyrimidin-2-yl)cyclohex-3-ene-1-carboxylate

Prepared from Intermediate 155 and 5-bromo-2-iodopyrimidine by a method analogous to that used to prepare Intermediate 3.

Intermediate 157

Ethyl 4-[5-(4,4,5,5-tetramethyl-1,3,2-dioxaborolan-2-yl)pyrimidin-2-yl]cyclohex-3-ene-1-carboxylate Prepared from Intermediate 156 by a method analogous to that used to prepare Intermediate 43.

Intermediate 158

2-(6-Oxa-3-azabicyclo[3.1.1]heptan-3-yl)pyrimidin-5-ylboronic acid

Prepared from 2-chloropyrimidin-5-ylboronic acid and 6-oxa-3-azabicyclo-[3.1.1]heptane by a method analogous to that used to prepare Intermediate 90. $\delta_H$ (300 MHz, DMSO-d₆) 1.84 (d, J 8.9 Hz, 1H), 3.10 (m, 1H), 3.63 (d, J 14.2 Hz, 2H), 3.85 (d, J 14.2 Hz, 2H), 4.68 (d, J 6.1 Hz, 2H), 8.08 (s, 2H), 8.67 (s, 2H).

Intermediate 159

2-(6,6-Dioxo-6λ⁶-thia-2-azaspiro[3.3]heptan-2-yl)pyrimidin-5-ylboronic acid

Prepared from 2-chloropyrimidin-5-ylboronic acid and 6,6-dioxo-6λ⁶-thia-2-aza-spiro[3.3]heptane by a method analogous to that used to prepare Intermediate 90. $\delta_H$ (300 MHz, DMSO-d₆) 8.61 (2H, s), 8.10 (2H, s), 4.50 (4H, s), 4.28 (4H, s).

Intermediate 160

6-[5-(4,4,5,5-Tetramethyl-1,3,2-dioxaborolan-2-yl)pyrimidin-2-yl]-3-oxa-6-azaspiro[3.3]-heptane Prepared from 2-chloro-5-(4,4,5,5-tetramethyl-1,3,2-dioxaborolan-2-yl)pyrimidine and 3-oxa-6-azaspiro[3.3]heptane by a method analogous to that used to prepare Intermediate 90. $\delta_H$ (300 MHz, DMSO-d₆) 8.41 (s, 2H), 4.46 (t, 2H, J 7.5 Hz), 4.32 (dd, 2H, J 10.7, 1.5 Hz), 4.15 (dd, 2H, J 10.8, 1.7 Hz), 2.87 (t, 2H, J 7.5 Hz), 1.27 (s, 12H).

Intermediate 161

(2R)-8-Fluoro-6-(1-hydroxy-1-methylethyl)-2-methyl-4H-1,4-benzoxazin-3-one

A solution of Intermediate 120 (0.3 g, 1.15 mmol) in THF (3 mL) was added dropwise to a solution of n-butyllithium (1.6 mL of a 1.6M solution in cyclohexane, 1.15 mmol) in THF (1 mL) at −78° C. The reaction mixture was allowed to stir at −78° C. for 10 minutes, then acetone (0.19 mL, 2.54 mmol) was added dropwise. After further stirring for 1 h at −78° C. the reaction was quenched with water and allowed to warm to room temperature. The reaction mixture was diluted with EtOAc and washed with brine. The organic layer was dried over sodium sulfate and concentrated under reduced pressure. The residue was purified by flash column chromatography (EtOAc:hexanes, 0-100%) to afford the title compound (132 mg, 47%) as an off-white solid. $\delta_H$ (300 MHz, DMSO-d₆) 10.70 (br s, 1H), 6.93-6.88 (m, 1H), 6.86-6.85 (m, 1H), 5.07 (s, 1H), 4.72 (q, J 6.8 Hz, 1H), 1.43 (d, J 6.8 Hz, 3H), 1.36 (s, 6H). LCMS m/z 238.

Intermediate 162

(2R)-4-[(6-Bromo-7-fluoro-2-methylimidazo[1,2-a]pyridin-3-yl)methyl]-8-fluoro-6-(1-hydroxy-1-methylethyl)-2-methyl-1,4-benzoxazin-3-one Prepared from Intermediate 34 and Intermediate 161 by a method analogous to that used to prepare Intermediate 21. The title compound was obtained as a brown oil which was used directly in the next step without further purification. LCMS m/z 480.

Intermediate 163

(2R)-4-[(6-Bromo-2-methylimidazo[1,2-a]pyrazin-3-yl)methyl]-7,8-difluoro-2-methyl-1,4-benzoxazin-3-one Prepared from Intermediate 98 and Intermediate 124 by a method analogous to that used to prepare Intermediate 21. $\delta_H$ (300 MHz, DMSO-d₆) 8.80 (m, 1H), 8.74 (m, 1H), 7.14 (m, 2H), 5.64 (d, 1H, J 16.7 Hz), 5.51 (d, 1H, J 16.7 Hz), 5.00 (q, 1H, J 6.7 Hz), 2.30 (s, 3H), 1.52 (d, 3H, J 6.7 Hz). LCMS m/z 427.8.

Intermediate 164

4-[(6-Bromo-7-fluoro-2-methylimidazo[1,2-a]pyridin-3-yl)methyl]-8-fluoro-3,4-dihydro-2H-1,4-benzoxazin-3-one Intermediate 20 (2.97 g, 17.77 mmol) and Intermediate 34 (5.06 g, 19.55 mmol) were suspended in toluene (45 mL), then a solution of (tributyl-λ⁵-phosphanylidene)-acetonitrile (6.06 mL, 23.1 mmol) in toluene (10 mL) was added. The reaction mixture was stirred at 95° C. for 2 h, then allowed to cool to room temperature. The resulting slurry was diluted with tert-butyl methyl ether (90 mL) and stirred for 1 h at room temperature. The resulting solid was collected by filtration and the filter cake was washed with tert-butyl methyl ether (2×30 mL), then dried in a vacuum oven, to afford the title compound (4.05 g, 56%) as a beige solid. $\delta_H$ (250 MHz, DMSO-d$_6$) 8.82 (d, J 6.7 Hz, 1H), 7.55 (d, J 9.6 Hz, 1H), 7.19-7.08 (m, 1H), 7.08-6.93 (m, 2H), 5.55 (s, 2H), 4.85 (s, 2H), 2.30 (s, 3H).

Intermediate 165 (2R)-4-[(6-Bromo-7-fluoro-2-methylimidazo[1,2-a]pyridin-3-yl)methyl]-8-chloro-2-methyl-3,4-dihydro-2H-1,4-benzoxazin-3-one Prepared from Intermediate 34 and Intermediate 133 by a method analogous to that used to prepare Intermediate 164. δ$_H$ (500 MHz, CD$_3$OD) 8.72 (d, J 6.5 Hz, 1H), 8.67 (d, J 6.5 Hz, 1H), 7.28 (dd, J 16.2, 8.9 Hz, 2H), 7.21 (dd, J 8.2, 1.3 Hz, 1H), 7.09 (dd, J 8.2, 1.3 Hz, 1H), 7.01 (t, J 8.2 Hz, 1H), 5.65 (d, J 16.5 Hz, 1H), 5.42 (d, J 16.5 Hz, 1H), 4.78 (q, J 6.7 Hz, 1H), 2.42 (s, 3H), 1.59 (d, J 6.8 Hz, 3H).

Intermediate 166

(2R)-8-Fluoro-4-{[7-fluoro-6-(4-methanesulfinyl-phenyl)-2-methylimidazo[1,2-a]pyridin-3-yl]methyl}-2-methyl-3,4-dihydro-2H-1,4-benzoxazin-3-one Prepared from Intermediate 35 and 4-(methanesulfinyl)phenylboronic acid by a method analogous to that used to prepare Example 1. LCMS m/z 482.

Intermediate 167

2,2,2-Trifluoro-N-{[4-(7-fluoro-3-{[(2R)-8-fluoro-2-methyl-3-oxo-3,4-dihydro-2H-1,4-benzoxazin-4-yl]methyl}-2-methylimidazo[1,2-a]pyridin-6-yl)phenyl](methyl)oxo-λ$^6$-sulfanylidene}acetamide To a suspension of Intermediate 166 (84%, 200 mg, 0.35 mmol), MgO (57 mg, 1.4 mmol), tetrakis(acetato-κO)dirhodium(Rh—Rh) (4 mg, 0.01 mmol) and 2,2,2-trifluoro-acetamide (79 mg, 0.7 mmol) in DCM (3 mL) was added bis(acetyloxy)(phenyl)-λ$^3$-iodane (170 mg, 0.52 mmol) at room temperature. The resulting mixture was stirred at room temperature for 18 h. The reaction mixture was filtered over a celite pad, then washed with DCM/MeOH and concentrated. The crude residue was purified by chromatography on silica gel, eluting with ethyl acetate:heptane, followed by a DCM: 10% MeOH in DCM flush, to yield the title compound (42 mg, 19%) as a white solid. LCMS m/z 593.

Intermediate 168

N-1-[(4-Bromophenyl)(methyl)oxo-λ$^6$-sulfanylidene]-2,2,2-trifluoroacetamide

To a suspension of 1-bromo-4-(methanesulfinyl)benzene (5 g, 22.82 mmol), MgO (3.68 g, 91.28 mmol), tetrakis(acetato-κO)dirhodium(Rh—Rh) (0.25 g, 0.57 mmol) and 2,2,2-trifluoroacetamide (5.16 g, 45.64 mmol) in anhydrous DCM (150 mL) was added bis(acetyloxy)(phenyl)-λ$^3$-iodane (11.0 g, 34.23 mmol) at room temperature. The reaction mixture was stirred at room temperature overnight, then filtered over celite. The filter cake was washed with DCM (30 mL). The filtrate was concentrated in vacuo and purified by chromatography on silica gel, eluting with 0-100% EtOAc in heptanes, giving the title compound (5.7 g, 97%) as a light yellow oil which crystallized on standing. LCMS m/z 332.

Intermediate 169

(4-Bromophenyl)(imino)methyl-λ$^6$-sulfanone

Prepared from Intermediate 168 by a method analogous to that used to prepare Example 137. LCMS m/z 236.

Intermediate 170

Imino(methyl)[4-(4,4,5,5-tetramethyl-1,3,2-dioxaborolan-2-yl)phenyl]-λ$^6$-sulfanone Prepared from Intermediate 169 by a method analogous to that used to prepare Intermediate 43. δ$_H$ (500 MHz, CDCl$_3$) 8.00 (q, J 8.0 Hz, 4H), 3.09 (s, 3H), 1.36 (s, 12H).

Intermediate 171 tert-Butyl 2-{[methyl(oxo)[4-(4,4,5,5-tetramethyl-1,3,2-dioxaborolan-2-yl)phenyl]-λ$^6$-sulfanylidene]amino}acetate NaH (60%, 0.11 g, 2.67 mmol) was added to a stirred solution of Intermediate 170 (0.5 g, 1.78 mmol) in anhydrous DMF (10 mL) at 0° C. The mixture was stirred for 10 minutes, then treated with tert-butyl 2-bromoacetate (0.32 mL, 2.67 mmol). After warming to room temperature, the mixture was stirred overnight, then quenched with water (20 mL) and extracted with EtOAc (30 mL). The aqueous phase was further extracted with EtOAc (2×20 mL). The combined organic phase was washed with water (2×50 mL) and brine (50 mL), then dried (Na$_2$SO$_4$) and reduced in vacuo. Trituration of the resulting brown gum with heptanes gave the title compound (0.34 g, 48%) as a tan solid. LCMS m/z 314.

Intermediate 172

5-Bromo-2-(methanesulfinyl)pyridine

NaIO$_4$ (9.56 g, 44.69 mmol) was added as a slurry in water (10 mL) to a stirred solution of 5-bromo-2-(methylsulfanyl)pyridine (2.4 g, 11.76 mmol) in acetic acid (40 mL) at room temperature. The mixture was stirred at room temperature for 2 h. After this time, a colourless precipitate had formed. The mixture was treated with water (50 mL), upon which the precipitate dissolved. The aqueous acidic mixture was basified through addition of saturated aqueous potassium carbonate solution and the resulting material was extracted with EtOAc (3×50 mL). The combined organic phase was washed with 10% aqueous sodium thiosulfate solution (50 mL), then dried (Na$_2$SO$_4$) and reduced in vacuo. The resulting crude amber glass (2.52 g) solidified on standing. Purification by chromatography on silica gel, eluting with 0-100% EtOAc in heptanes, afforded the title compound (2.04 g, 79%) as a pale yellow oil which solidified on standing. δ$_H$ (500 MHz, CDCl$_3$) 8.68 (d, J 2.0 Hz, 1H), 8.08 (dd, J 8.3, 2.2 Hz, 1H), 7.93 (d, J 8.3 Hz, 1H), 2.84 (s, 3H).

Intermediate 173

N-1-[(5-Bromopyridin-2-yl)(methyl)oxo-λ$^6$-sulfanylidene]-2,2,2-trifluoroacetamide Prepared from Intermediate 172 by a method analogous to that used to prepare Intermediate 168. δ$_H$ (500 MHz, CDCl$_3$) 8.79 (d, J 1.4 Hz, 1H), 8.22-8.19 (m, 1H), 8.18 (dd, J 8.4, 2.0 Hz, 1H), 3.56 (s, 3H).

Intermediate 174

(5-Bromopyridin-2-yl)(imino)methyl-$\lambda^6$-sulfanone

Prepared from Intermediate 173 by a method analogous to that used to prepare Example 137. $\delta_H$ (500 MHz, DMSO-$d_6$) 8.88 (d, J 2.2 Hz, 1H), 8.37 (dd, J 8.4, 2.3 Hz, 1H), 8.01 (d, J 8.4 Hz, 1H), 4.54 (s, 1H), 3.17 (s, 3H).

Intermediate 175

Imino(methyl)[5-(4,4,5,5-tetramethyl-1,3,2-dioxaborolan-2-yl)pyridin-2-yl]-$\lambda^6$-sulfanone Prepared from Intermediate 174 by a method analogous to that used to prepare Intermediate 43. $\delta_H$ (250 MHz, CDCl$_3$) 8.77 (s, 1H), 8.30 (d, J 6.5 Hz, 1H), 8.04 (d, J 5.3 Hz, 1H), 3.25 (s, 3H), 1.36 (s, 12H).

Intermediate 176

5-Bromo-2-(methanesulfinyl)-4-methylpyridine

Prepared from 5-bromo-2-(methanesulfanyl)-4-methylpyridine by a method analogous to that used to prepare Intermediate 172. $\delta_H$ (500 MHz, CDCl$_3$) 8.62 (s, 1H), 7.87 (s, 1H), 2.82 (s, 3H), 2.50 (s, 3H).

Intermediate 177

N-[(5-Bromo-4-methylpyridin-2-yl)(methyl)oxo-$\lambda^6$-sulfanylidene]-2,2,2-trifluoro-acetamide Prepared from Intermediate 176 by a method analogous to that used to prepare Intermediate 168. $\delta_H$ (500 MHz, CDCl$_3$) 8.74 (s, 1H), 8.16 (s, 1H), 3.54 (s, 3H), 2.57 (s, 3H).

Intermediate 178

1-Bromo-4-[(trifluoromethane)sulfinyl]benzene m-CPBA (73%, 600 mg, 2.54 mmol) was added portionwise to a solution of 1-bromo-4-[(trifluoromethyl)sulfanyl]benzene (500 mg, 1.94 mmol) in DCM (25 mL) at 0° C. and the reaction mixture was allowed to warm to room temperature with stirring for 18 h. The mixture was diluted with water (50 mL), then extracted with DCM (2×25 mL). The combined organic layers were washed with saturated aqueous NaHCO$_3$ solution (50 mL) and dried over sodium sulfate, then filtered and concentrated under reduced pressure. The resulting colourless oil was purified by chromatography on silica gel, eluting with 0-100% ethyl acetate in heptanes, to afford the title compound (417 mg, 74.6%) as a colourless oil that solidified upon standing. $\delta_H$ (500 MHz, CDCl$_3$) 7.78-7.75 (m, 2H), 7.66 (d, J 8.4 Hz, 2H).

Intermediate 179

N-1-[(4-Bromophenyl)(oxo)(trifluoromethyl)-$\lambda^6$-sulfanylidene]acetamide

Trifluoromethanesulfonic anhydride (1M, 1.7 mL) was added to a solution of Intermediate 178 (300 mg, 1.1 mmol) in acetonitrile (60 µL) at −15° C. The reaction mixture was stirred at room temperature for 18 h. Water (0.5 mL), potassium permanganate (175 mg, 1.11 mmol) and sodium hydroxide (90 mg, 2.25 mmol) were added, then the reaction mixture was stirred at 110° C. for 4 h. The reaction mixture was cleared with sodium hydrosulfite and diluted with water (15 mL), then extracted with DCM (3×20 mL). The organic layers were dried over sodium sulfate, filtered and concentrated under reduced pressure. The resulting off-white solid was purified by chromatography on silica gel, eluting with 0-100% ethyl acetate in heptanes, to afford the title compound (170 mg, 42.2%) as an off-white solid. $\delta_H$ (500 MHz, CDCl$_3$) 7.90 (d, J 8.7 Hz, 2H), 7.82 (d, J 8.8 Hz, 2H), 2.26 (s, 3H).

Intermediate 180

(4-Bromophenyl)(imino)(trifluoromethyl)-$\lambda^6$-sulfanone

Prepared from Intermediate 179 by a method analogous to that used to prepare Example 137. $\delta_H$ (500 MHz, CDCl$_3$) 8.00 (d, J 8.6 Hz, 2H), 7.79 (d, J 8.7 Hz, 2H), 3.62 (s, 1H).

Intermediate 181

Imino[4-(4,4,5,5-tetramethyl-1,3,2-dioxaborolan-2-yl)phenyl](trifluoromethyl)-$\lambda^6$-sulfanone Prepared from Intermediate 180 by a method analogous to that used to prepare Intermediate 43. $\delta_H$ (500 MHz, CDCl$_3$) 8.12 (d, J 8.2 Hz, 2H), 8.04 (d, J 8.3 Hz, 2H), 3.59 (s, 1H), 1.36 (s, 12H).

Intermediate 182

5-Bromo-2-(ethanesulfinyl)pyridine

Prepared from 5-bromo-2-(ethylsulfanyl)pyridine by a method analogous to that used to prepare Intermediate 172. $\delta_H$ (250 MHz, CDCl$_3$) 8.68 (d, J 2.2 Hz, 1H), 8.06 (dd, J 8.3, 2.2 Hz, 1H), 7.88 (d, J 8.3 Hz, 1H), 3.28-3.07 (m, 1H), 3.01-2.80 (m, 1H), 1.20 (t, J 7.4 Hz, 3H).

Intermediate 183

N-[(5-Bromopyridin-2-yl)(ethyl)oxo-$\lambda^6$-sulfanylidene]-2,2,2-trifluoroacetamide Prepared from Intermediate 182 by a method analogous to that used to prepare Intermediate 168. $\delta_H$ (500 MHz, CDCl$_3$) 8.80-8.77 (m, 1H), 8.22-8.15 (m, 2H), 3.86-3.72 (m, 2H), 1.36 (t, J 7.4 Hz, 3H).

Intermediate 184

3-Bromo-6-(methanesulfinyl)-2-methylpyridine

Prepared from 3-bromo-2-methyl-6-(methylsulfanyl)pyridine by a method analogous to that used to prepare Intermediate 172. $\delta_H$ (500 MHz, CDCl$_3$) 8.04 (d, J 8.2 Hz, 1H), 7.72 (d, J 8.2 Hz, 1H), 2.84 (s, 3H), 2.68 (s, 3H).

Intermediate 185

N-[(5-Bromo-6-methylpyridin-2-yl)(methyl)oxo-$\lambda^6$-sulfanlidene]-2,2,2-trifluoro-acetamide Prepared from Intermediate 184 by a method analogous to that used to prepare Intermediate 168. $\delta_H$ (500 MHz, CDCl$_3$) 8.14 (d, J 8.2 Hz, 1H), 8.00 (d, J 8.2 Hz, 1H), 3.55 (s, 3H), 2.75 (s, 3H).

Intermediate 186

1,3-Dimethyl 2-[(2-fluoro-6-nitrophenyl)methyl]-2-methylpropanedioate

To a stirred suspension of sodium hydride (60%, 2.89 g, 72.23 mmol) in anhydrous DMF (100 mL) at 0° C. was added 1,3-dimethyl 2-methylpropanedioate (7.65 mL, 57.48 mmol) portionwise. The reaction mixture was stirred at 0° C. for 10 minutes. A solution of 2-(bromomethyl)-1-fluoro-3-nitrobenzene (13.0 g, 55.6 mmol) in DMF (40 mL) was added dropwise to the stirred reaction mixture and stirring was continued at 0° C. for 45 minutes. The reaction mixture was diluted with saturated aqueous ammonium chloride solution (50 mL) and extracted with EtOAc (2×200 mL). The combined organic extracts were washed with water (2×100 mL) and brine (50 mL), then dried over MgSO$_4$ and concentrated under vacuum, to give the title compound (15.84 g, 90.5%) as an orange oil. $\delta_H$ (500 MHz, CDCl$_3$) 7.65-7.60 (m, 1H), 7.32 (td, J 8.2, 5.5 Hz, 1H), 7.25-7.20 (m, 1H), 3.68 (d, J 2.2 Hz, 2H), 3.65 (s, 6H), 1.26 (d, J 1.7 Hz, 3H).

Intermediate 187

Methyl 5-fluoro-3-methyl-2-oxo-1,2,3,4-tetrahydroquinoline-3-carboxylate

To a solution of Intermediate 186 (95%, 15.8 g, 50 mmol) in acetic acid (250 mL) was added iron (11.2 g, 0.2 mol) portionwise. The reaction mixture was stirred at 75° C. for 2.5 h. After cooling to room temperature, the mixture was filtered through Celite, washing with EtOAc, then concentrated under vacuum. Water (300 mL) was added to the residue, followed by 2M HCl until approximately pH 2. EtOAc (300 mL) was added and the layers were separated. The aqueous layer was further extracted with EtOAc (2×100 mL). The combined organic layers were washed with water (100 mL) and brine (50 mL), then dried (MgSO$_4$) and concentrated under reduced pressure, to afford the title compound (11.3 g, 90%) as a beige solid. $\delta_H$ (500 MHz, CDCl$_3$) 7.96 (s, 1H), 7.14 (td, J 8.2, 5.9 Hz, 1H), 6.79-6.72 (m, 1H), 6.56 (d, J 7.9 Hz, 1H), 3.68 (s, 4H), 3.59 (d, J 16.3 Hz, 1H), 2.82 (d, J 16.3 Hz, 1H), 1.55 (s, 4H).

Intermediate 188

5-Fluoro-3-methyl-3,4-dihydro-1H-quinolin-2-one

Intermediate 187 (5.00 g, 21.08 mmol) was dissolved in methanol (20 mL) and aqueous potassium hydroxide solution (2M, 42 mL) was added. The mixture was heated at 90° C. for 30 minutes before cooling to room temperature. The mixture was acidified with 3M HCl and the residue was extracted with EtOAc (150 mL). The organic layer was washed with water (2×50 mL), dried (MgSO$_4$) and concentrated under reduced pressure. The crude residue was heated at 170° C. under N$_2$ until gas evolution had ceased. The reaction mixture was cooled to room temperature, then the crude brown solid was recrystallised from boiling EtOAc, to afford the title compound (2.42 g, 60.9%) as a beige solid. $\delta_H$ (500 MHz, CDCl$_3$) 7.96 (s, 1H), 7.13 (td, J 8.1, 6.0 Hz, 1H), 6.74 (t, J 8.6 Hz, 1H), 6.55 (d, J 7.9 Hz, 1H), 3.21-3.05 (m, 1H), 2.72-2.51 (m, 2H), 1.31 (d, J 6.5 Hz, 3H).

Intermediate 189

1-[(6-Bromo-7-fluoro-2-methylimidazo[1,2-a]pyridin-3-yl)methyl]-5-fluoro-3-methyl-1,2,3,4-tetrahydroquinolin-2-one Prepared from Intermediate 34 and Intermediate 188 by a method analogous to that used to prepare Intermediate 164. $\delta_H$ (250 MHz, CDCl$_3$) 8.44 (d, J 6.5 Hz, 1H), 7.22-7.09 (m, 2H), 6.86 (d, J 8.3 Hz, 1H), 6.77 (t, J 8.5 Hz, 1H), 5.71 (d, J 16.4 Hz, 1H), 5.24 (d, J 16.3 Hz, 1H), 3.06 (dd, J 15.6, 5.6 Hz, 1H), 2.82-2.64 (m, 1H), 2.51 (s, 4H), 1.36 (d, J 6.8 Hz, 3H).

Intermediate 190

1-[(6-Bromo-7-fluoro-2-methylimidazo[1,2-a]pyridin-3-yl)methyl]-5-fluoro-3-methyl-1,2,3,4-tetrahydroquinolin-2-one (Enantiomer A)

Prepared from Intermediate 189 by SFC using ChiralPak AD (250 mm×20 mm, 5 µm) column. The eluent was 40% MeOH/CO$_2$ (diethylamine was added as a modifier). The flow rate was 50 mL/minute at a wavelength of 234 nm. $\delta_H$ (500 MHz, CDCl$_3$) 8.43 (d, J 6.5 Hz, 1H), 7.18 (d, J 8.7 Hz, 1H), 7.16-7.11 (m, 1H), 6.86 (d, J 8.3 Hz, 1H), 6.76 (t, J 8.4 Hz, 1H), 5.70 (d, J 16.3 Hz, 1H), 5.24 (d, J 16.3 Hz, 1H), 3.06 (dd, J 15.9, 5.7 Hz, 1H), 2.73 (tt, J 12.7, 6.8 Hz, 1H), 2.50 (s, 3H), 2.49 (dd, J 16.0, 11.2 Hz, 4H), 1.36 (d, J 6.9 Hz, 3H).

Intermediate 191

1-[(6-Bromo-7-fluoro-2-methylimidazo[1,2-a]pyridin-3-yl)methyl]-5-fluoro-3-methyl-1,2,3,4-tetrahydroquinolin-2-one (Enantiomer B)

Prepared from Intermediate 189 by SFC using ChiralPak AD (250 mm×20 mm, 5 µm) column. The eluent was 40% MeOH/CO$_2$ (diethylamine was added as a modifier). The flow rate was 50 mL/minute at a wavelength of 234 nm. $\delta_H$ (500 MHz, CDCl$_3$) 8.43 (d, J 6.5 Hz, 1H), 7.18 (d, J 8.7 Hz, 1H), 7.16-7.12 (m, 1H), 6.86 (d, J 8.3 Hz, 1H), 6.76 (t, J 8.4 Hz, 1H), 5.70 (d, J 16.3 Hz, 1H), 5.24 (d, J 16.3 Hz, 1H), 3.06 (dd, J 15.9, 5.6 Hz, 1H), 2.73 (tt, J 12.8, 6.8 Hz, 1H), 2.50 (s, 3H), 2.49 (dd, J 16.0, 11.1 Hz, 4H), 1.36 (d, J 6.9 Hz, 3H).

Intermediate 192

2,2-Dichloro-3-oxocyclobutyl 2,2-dimethylpropanoate

To a stirred mixture of vinyl pivalate (30 g, 234 mmol) and zinc (31 g, 474 mmol) in diethyl ether (250 mL) was added a solution of 2,2,2-trichloroacetyl chloride (34 mL, 304 mmol) in diethyl ether (250 mL) dropwise over 2.5 h in a water bath whilst maintaining the reaction temperature at 15-30° C. The reaction mixture was filtered through Celite and washed through with ethyl acetate (200 mL). The filtrate was washed with water (200 mL) and brine (200 mL), then dried over sodium sulfate and concentrated under vacuum, to afford the title compound (68 g, 97% at 80% purity) as an orange liquid. $\delta_H$ (500 MHz, CDCl$_3$) 5.40 (dd, J 8.4, 6.2 Hz, 1H), 3.70 (dd, J 18.9, 8.4 Hz, 1H), 3.39 (dd, J 18.9, 6.2 Hz, 1H), 1.28 (s, 9H).

Intermediate 193

3-Oxocyclobutyl 2,2-dimethylpropanoate

Zinc (74 g, 1.1 mol) was added to acetic acid (200 mL) with stirring and the suspension was cooled in an ice bath. Intermediate 192 (80%, 68 g, 228 mmol) in acetic acid (300 mL) was added dropwise over 2 h. The reaction mixture was warmed to room temperature and stirred for 1.5 h, then filtered and washed with DCM (100 mL). The filtrate was diluted with ethyl acetate (800 mL), then washed sequentially with water (3×250 mL), saturated aqueous NaHCO$_3$ solution (3×250 mL) and brine (50 mL). The organic phase was dried over sodium sulfate and concentrated under vacuum. The resulting brown oil (30 g) was purified by dry flash chromatography on silica gel, eluting with 0-10% ethyl acetate in heptanes, to afford the title compound (11 g, 28%) as a clear colourless oil. $\delta_H$ (500 MHz, CDCl$_3$) 5.26-5.19 (m, 1H), 3.51-3.40 (m, 2H), 3.19-3.07 (m, 2H), 1.22 (s, 9H).

Intermediate 194

3-(5-Bromopyrimidin-2-yl)-3-hydroxycyclobutyl 2,2-dimethylpropanoate

5-Bromo-2-iodopyrimidine (16.7 g, 58.8 mmol) was dissolved in DCM (200 mL) with stirring and cooled to −78° C. under N$_2$. n-Butyllithium in hexane (2.5M, 23.5 mL) was added dropwise and the mixture was stirred for 20 minutes at −78° C. Intermediate 193 (10 g, 58.8 mmol) in DCM (50 mL) was cooled in a dry-ice bath and added in one portion. The reaction mixture was stirred at −78° C. for 10 minutes, then quenched by addition of saturated aqueous NH$_4$Cl solution (20 mL). The mixture was allowed to warm to room temperature, then saturated aqueous NH$_4$Cl solution (50 mL) was added and the mixture was extracted with DCM (2×100 mL). The combined organic extracts were dried over sodium sulfate and concentrated under vacuum. The crude residue was purified by column chromatography, using 0-30% ethyl acetate in heptane, to afford the title compound (7.6 g, 35%) as a yellow solid. $\delta_H$ (500 MHz, CDCl$_3$) 8.78 (s, 2H), 5.22-5.14 (m, 1H), 3.03-2.93 (m, 2H), 2.67-2.58 (m, 2H), 1.22 (s, 9H).

Intermediate 195

1-(5-Bromopyrimidin-2-yl)cyclobutane-1,3-diol

Intermediate 194 (90%, 6 g, 16.4 mmol) was dissolved in MeOH (120 mL) and K$_2$CO$_3$ (11.3 g, 82 mmol) was added. The reaction mixture was stirred for 18 h at room temperature, then diluted with DCM (400 mL) and washed with water (150 mL). The aqueous phase was extracted with DCM (200 mL). The combined organic extracts were dried over sodium sulfate and concentrated under vacuum to afford the title compound (2.94 g, 73%) as an off-white solid. $\delta_H$ (500 MHz, DMSO-d$_6$) 8.98 (s, 2H), 5.63 (s, 1H), 5.08 (d, J 6.2 Hz, 1H), 4.09-3.92 (m, 1H), 2.87-2.79 (m, 2H), 2.28-2.14 (m, 2H).

Intermediate 196

3-(5-Bromopyrimidin-2-yl)-3-hydroxycyclobutan-1-one

To a stirred solution of Intermediate 195 (2 g, 8.1 mmol) in DCM (200 mL) was added Dess-Martin periodinane (4.1 g, 9.8 mmol). The reaction mixture was stirred for 18 h, then the resulting suspension was diluted with DCM (100 mL) and washed with saturated aqueous NaHCO$_3$ solution (100 mL). The aqueous layer was re-extracted with DCM (100 mL), then the combined organic extracts were dried over sodium sulfate and concentrated. The crude residue was purified by chromatography on silica gel, eluting with 0-30% ethyl acetate in heptanes, to afford the title compound (1.37 g, 69%) as an off-white solid. $\delta_H$ (500 MHz, DMSO-d$_6$) 9.04 (s, 2H), 6.41 (s, 1H), 3.69-3.55 (m, 2H), 3.37-3.21 (m, 2H).

Intermediate 197

3-(5-Bromopyrimidin-2-yl)-3-[(tert-butyldimethylsilyl)oxy]cyclobutan-1-one

Intermediate 196 (1.37 g, 5.64 mmol) was dissolved in dry DMF (20 mL) with stirring under N$_2$ and cooled to 0° C. 1H-Imidazole (1.9 g, 28.18 mmol) was added, followed by tert-butyl(chloro)dimethylsilane (2.0 g, 13.5 mmol). The reaction mixture was stirred at room temperature for 20 h, then diluted with DCM (150 mL) and washed with water (3×50 mL). The aqueous phase was re-extracted with DCM (50 mL). The combined organic extracts were dried over sodium sulfated and concentrated. The crude residue was purified by chromatography on silica gel, eluting with 0-20% ethyl acetate in heptanes, to afford the title compound (1.6 g 79%) as a pale orange oil. $\delta_H$ (500 MHz, DMSO-d$_6$) 9.06 (s, 2H), 3.78-3.66 (m, 2H), 3.44-3.34 (m, 2H), 0.88 (s, 9H), 0.00 (s, 6H).

Intermediate 198

3-(5-Bromopyrimidin-2-yl)-3-[(tert-butyldimethylsilyl)oxy]-1-methylcyclobutan-1-ol Intermediate 197 (1.35 g, 3.78 mmol) was dissolved in dry diethyl ether (40 mL) under N$_2$ with stirring, then cooled to 0° C. using an ice bath. Methylmagnesium bromide in diethyl ether (3M, 2.52 mL) was added dropwise. The reaction mixture was stirred for 30 minutes at 0° C., then quenched with saturated aqueous NH$_4$Cl solution (20 mL) and water (20 mL). The mixture was extracted with ethyl acetate (2×50 mL), then dried over sodium sulfate and concentrated. The resulting yellow oil was purified by chromatography on silica gel, eluting with 0-100% DCM in heptane followed by 0-20% ethyl acetate in DCM, to afford the title compound (1.19 g, 84%), mixture of cis and trans isomers, as a clear oil.

Major isomer, approximately 70% abundance: $\delta_H$ (500 MHz, CDCl$_3$) 8.79 (s, 2H), 3.10-3.03 (m, 2H), 2.59-2.51 (m, 2H), 1.18 (s, 3H), 0.87 (s, 9H), −0.14 (s, 6H).

Minor isomer, approximately 30% abundance: $\delta_H$ (500 MHz, CDCl$_3$) 8.79 (s, 2H), 2.78-2.63 (m, 4H), 1.49 (s, 3H), 0.95 (s, 9H), 0.04 (s, 6H).

Intermediate 199

5-Bromo-2-{(1s,3s)-1,3-bis[(tert-butyldimethylsilyl)oxy]cyclobutyl}pyrimidine Prepared from Intermediate 195 by a method analogous to that used to prepare Intermediate 197. $\delta_H$ (500 MHz, CDCl$_3$) 8.76 (s, 2H), 4.07 (p, J 7.1 Hz, 1H), 3.07 (ddd, J 9.5, 6.9, 3.0

Hz, 2H), 2.42 (ddd, J 12.2, 6.3, 2.5 Hz, 2H), 0.90 (s, 9H), 0.89 (s, 9H), 0.03 (s, 6H), −0.06 (s, 6H).

Intermediate 200

2-{(1s,3s)-1,3-Bis[(tert-butyldimethylsilyl)oxy]cyclobutyl}-5-(4,4,5,5-tetramethyl-1,3,2-dioxaborolan-2-yl)pyrimidine Prepared from Intermediate 199 by a method analogous to that used to prepare Intermediate 43. $\delta_H$ (500 MHz, CDCl$_3$) 8.76 (s, 2H), 4.07 (p, J 7.1 Hz, 1H), 3.07 (ddd, J 9.5, 6.9, 3.0 Hz, 2H), 2.42 (ddd, J 12.2, 6.3, 2.5 Hz, 2H), 0.90 (s, 9H), 0.89 (s, 9H), 0.03 (s, 6H), −0.06 (s, 6H).

Intermediate 201

3-[(tert-Butyldimethylsilyl)oxy]-1-methyl-3-[5-(4,4,5,5-tetramethyl-1,3,2-dioxaborolan-2-yl)pyrimidin-2-yl]cyclobutan-1-ol Prepared from Intermediate 198 by a method analogous to that used to prepare Intermediate 43. $\delta_H$ (500 MHz, CDCl$_3$) 9.02 (s, 2H), 3.15-3.08 (m, 2H), 2.58-2.50 (m, 2H), 1.37 (s, 12H), 1.27 (s, 3H), 0.87 (s, 9H), −0.16 (s, 6H).

Intermediate 202

(R)—N-{3-(5-Bromopyrimidin-2-yl)-3-[(tert-butyldimethylsilyl)oxy]cyclobutylidene}-2-methylpropane-2-sulfinamide (R)-2-Methylpropane-2-sulfinamide (1.12 g, 9.24 mmol) was dissolved in anhydrous 1,2-dichloroethane (5 mL) and treated with Intermediate 197 (3 g, 8.4 mmol), followed by titanium(IV) ethoxide (2.1 g, 9.21 mmol). The reaction mixture was heated at 80° C. and stirred under N$_2$ overnight. After cooling to room temperature, the mixture was diluted with DCM (150 mL) and poured onto stirring saturated aqueous sodium bicarbonate solution (150 mL). The resulting heavy emulsion was stirred for 5 minutes, then passed over a pad of celite under vacuum. The filtrate was transferred to a separating funnel and the layers were separated. The aqueous phase was further extracted with DCM (2×100 mL), then the combined organic phase was dried over Na$_2$SO$_4$, filtered and reduced in vacuo. The resulting crude yellow oil was purified by chromatography on silica gel, eluting with 15-50% ethyl acetate in heptanes, to afford the title compound (2.91 g, 72.3%) as a yellow-coloured oil. $\delta_H$ (500 MHz, CDCl$_3$) 8.78 (d, J 6.6 Hz, 2H), 4.16 (dddd, J 90.0, 18.2, 5.5, 2.5 Hz, 1H), 3.86-3.59 (m, 2H), 3.52-3.43 (m, 1H), 1.26 (d, J 7.0 Hz, 9H), 0.92 (d, J 1.2 Hz, 9H), 0.03-0.03 (m, 6H).

Intermediate 203

(R)—N-{3-(5-Bromopyrimidin-2-yl)-3-[(tert-butyldimethylsilyl)oxy]cyclobutyl}-2-methyl-propane-2-sulfinamide Intermediate 202 (1.5 g, 3.26 mmol) was dissolved in THF (150 mL) under N$_2$ and cooled to −50° C. prior to addition of sodium borohyride (350 mg, 9.25 mmol). The reaction mixture was stirred at −50° C. for 30 minutes, then warmed to room temperature and stirred for a further 1 h. The reaction mixture was concentrated under reduced pressure and diluted with DCM (50 mL), then washed with aqueous NH$_4$Cl solution (40 mL) and aqueous NaHCO$_3$ solution (40 mL). The aqueous layers were recombined and re-extracted with DCM (2×30 mL). The organic layers were combined, dried over Na$_2$SO$_4$ and filtered, then concentrated under reduced pressure, to afford the title compound (1.15 g, 61.1%) as a viscous brown/orange oil. $\delta_H$ (500 MHz, CDCl$_3$) 8.77 (s, 2H), 3.78-3.70 (m, 1H), 3.40 (d, J 7.1 Hz, 1H), 3.24-3.12 (m, 2H), 2.39 (ddd, J 16.2, 11.4, 8.5 Hz, 2H), 1.22 (s, 9H), 0.90 (s, 9H), −0.06 (d, J 8.4 Hz, 6H).

Intermediate 204

(R)—N-{3-[(tert-Butyldimethylsilyl)oxy]-3-[5-(4,4,5,5-tetramethyl-1,3,2-dioxaborolan-2-yl)pyrimidin-2-yl]cyclobutyl}-2-methylpropane-2-sulfinamide Prepared from Intermediate 203 by a method analogous to that used to prepare Intermediate 43. $\delta_H$ (500 MHz, CDCl$_3$) 9.00 (s, 2H), 3.78 (h, J 7.6 Hz, 1H), 3.40 (d, J 7.1 Hz, 1H), 3.21 (ddt, J 23.9, 12.7, 5.8 Hz, 2H), 2.39 (ddd, J 16.4, 11.4, 8.5 Hz, 2H), 1.36 (s, 12H), 1.22 (s, 9H), 0.90 (s, 9H), −0.08 (d, J 8.4 Hz, 6H).

Intermediate 205

3-(5-Bromopyridin-2-yl)-3-hydroxycyclobutyl 2,2-dimethylpropanoate

Prepared from 5-bromo-2-iodopyridine and Intermediate 193 by a method analogous to that used to prepare Intermediate 194. $\delta_H$ (500 MHz, CDCl$_3$) 8.59-8.57 (m, 1H), 7.86 (dd, J 8.4, 2.3 Hz, 1H), 7.36 (dd, J 8.4, 0.6 Hz, 1H), 5.00 (p, J 7.2 Hz, 1H), 2.97-2.90 (m, 2H), 2.66-2.59 (m, 2H), 1.22 (s, 9H).

Intermediate 206

3-(5-Bromopyridin-2-yl)-3-[(tert-butyldimethylsilyl)oxy]cyclobutyl 2,2-dimethyl-propanoate Prepared from Intermediate 205 by a method analogous to that used to prepare Intermediate 197. $\delta_H$ (500 MHz, CDCl$_3$) 8.59-8.57 (m, 1H), 7.76 (dd, J 8.5, 2.4 Hz, 1H), 7.45 (dd, J 8.5, 0.6 Hz, 1H), 4.96 (p, J 7.1 Hz, 1H), 3.07 (ddd, J 10.1, 7.2, 2.8 Hz, 2H), 2.49 (ddd, J 10.0, 7.0, 3.0 Hz, 2H), 1.21 (s, 9H), 0.94 (s, 9H), 0.06 (s, 6H).

Intermediate 207

3-(5-Bromopyridin-2-yl)-3-[(tert-butylmethylsilyl)oxy]cyclobutan-1-ol

Prepared from Intermediate 206 by a method analogous to that used to prepare Intermediate 195. $\delta_H$ (500 MHz, CDCl$_3$) 8.57-8.55 (m, 1H), 7.77 (dd, J 8.5, 2.4 Hz, 1H), 7.47 (dd, J 8.5, 0.5 Hz, 1H), 4.27 (p, J 7.1 Hz, 1H), 3.01 (ddd, J 9.6, 6.9, 2.9 Hz, 2H), 2.44-2.37 (m, 2H), 0.92 (s, 9H), 0.00 (s, 6H).

Intermediate 208

3-(5-Bromopyridin-2-yl)-3-[(tert-butyldimethylsilyl)oxy]cyclobutan-1-one

Prepared from Intermediate 207 by a method analogous to that used to prepare Intermediate 196. $\delta_H$ (500 MHz, CDCl$_3$)

8.60 (d, J 2.3 Hz, 1H), 7.84 (dd, J 8.4, 2.3 Hz, 1H), 7.58 (d, J 8.4 Hz, 1H), 3.80-3.72 (m, 2H), 3.42-3.34 (m, 2H), 0.95 (s, 9H), 0.06 (s, 6H).

Intermediate 209

(1s,3r)-3-(5-Bromopyridin-2-yl)-3-[(tert-butyldimethylsilyl)oxy]-1-methylcyclobutan-1-ol Prepared from Intermediate 208 by a method analogous to that used to prepare Intermediate 198. $\delta_H$ (500 MHz, CDCl$_3$) 8.59 (d, J 2.3 Hz, 1H), 7.79 (dd, J 8.4, 2.4 Hz, 1H), 7.40 (d, J 8.4 Hz, 1H), 2.99-2.94 (m, 2H), 2.55-2.50 (m, 2H), 2.36 (s, 1H), 1.23 (s, 3H), 0.86 (s, 9H), −0.16 (s, 6H).

Intermediate 210

(1s,3r)-3-[(tert-Butyldimethylsilyl)oxy]-1-methyl-3-[5-(4,4,5,5-tetramethyl-1,3,2-dioxaborolan-2-yl)pyridin-2-yl]cyclobutan-1-ol Prepared from Intermediate 209 by a method analogous to that used to prepare Intermediate 43. $\delta_H$ (500 MHz, CDCl$_3$) 8.88 (s, 1H), 8.03 (dd, J 7.9, 1.6 Hz, 1H), 7.47 (d, J 7.9 Hz, 1H), 3.02-2.98 (m, 2H), 2.52 (d, J 13.1 Hz, 2H), 2.05 (s, 1H), 1.36 (s, 12H), 1.21 (s, 3H), 0.86 (s, 9H), −0.20 (s, 6H).

Intermediate 211

(1s,3r)-3-(5-Bromopyrimidin-2-yl)-3-[(tert-butyldimethylsilyl)oxy]-1-ethylcyclobutan-1-ol Prepared from Intermediate 197 and ethylmagnesium bromide by a method analogous to that used to prepare Intermediate 198. $\delta_H$ (500 MHz, CDCl$_3$) 8.78 (s, 2H), 3.08-3.02 (m, 2H), 2.48-2.43 (m, 2H), 1.38 (q, J 7.4 Hz, 2H), 0.87 (s, 9H), 0.84 (t, J 7.4 Hz, 3H), −0.14 (s, 6H).

Intermediate 212

(1s,3r)-3-[(tert-Butyldimethylsilyl)oxy]-1-ethyl-3-[5-(4,4,5,5-tetramethyl-1,3,2-dioxaborolan-2-yl)pyrimidin-2-yl]cyclobutan-1-ol Prepared from Intermediate 211 by a method analogous to that used to prepare Intermediate 43. $\delta_H$ (500 MHz, CDCl$_3$) 9.01 (s, 2H), 3.13-3.07 (m, 2H), 2.48-2.43 (m, 2H), 1.37 (s, 14H), 0.88 (s, 9H), 0.83 (t, J 7.4 Hz, 3H), −0.16 (s, 6H).

Intermediate 213

N-(5-Bromopyridin-2-yl)dimethylsulfoximine

A dry 25 mL two-neck flask equipped with a magnetic stir bar, a septum inlet and a reflux condenser was charged with palladium(II) acetate (78 mg, 0.35 mmol) and 1,1'-binaphthalene-2,2'-diylbis(diphenylphosphane) (326 mg, 0.52 mmol) under a N$_2$ atmosphere and stirred in anhydrous toluene (40 mL) for 20 minutes. 5-Bromo-2-iodo-pyridine (99%, 2 g, 6.97 mmol), sulfoximine (0.81 g, 8.72 mmol) and caesium carbonate (3.18 g) were then added. The mixture was heated under reflux for 24 h, then allowed to cool to room temperature, diluted with tert-butyl methyl ether (100 mL) and filtered through a plug of Celite. The solvents were removed in vacuo, and the resulting oily residue was purified by chromatography on silica gel, eluting 20-100% EtOAc in heptanes, to afford the title compound (1.57 g, 87.6%) as a yellow solid. $\delta_H$ (500 MHz, CD$_3$OD) 8.18-8.15 (m, 1H), 7.66 (dd, J 8.7, 2.6 Hz, 1H), 6.68 (dd, J 8.7, 0.5 Hz, 1H), 3.38 (s, 6H).

Intermediate 214

Dimethyl-N-[5-(4,4,5,5-tetramethyl-1,3,2-dioxaborolan-2-yl)pyridin-2-yl]sulfoximine Intermediate 213 (1.57 g, 6.3 mmol), 4,4,4',4',5,5,5',5'-octamethyl-2,2'-bi-1,3,2-dioxaborolane (1.92 g, 7.56 mmol) and potassium acetate (1.86 g, 18.91 mmol) were suspended in anhydrous 1,4-dioxane (35 mL). The mixture was degassed thoroughly under a stream of N$_2$ for 10 minutes, then treated with bis[3-(diphenylphosphanyl)-cyclopenta-2,4-dien-1-yl]iron; dichloromethane; dichloropalladium (257 mg, 0.32 mmol) and heated at 85° C. for 3 h with stirring. The reaction mixture was allowed to cool to room temperature, then diluted with dichloromethane and filtered through Celite, washing through with further dichloromethane. The filtrate was concentrated under vacuum. The resulting crude dark oily solid was repeatedly triturated in diethyl ether/heptane and concentrated in vacuo, followed by a final trituration in heptane. The residue was filtered, washing through with more heptane, to give the title compound (3.2 g, 68.6%, approximately 40% purity) as a pale brown solid. $\delta_H$ (500 MHz, CD$_3$OD) 8.42 (s, 1H), 7.84 (d, J 7.9 Hz, 1H), 6.75 (d, J 7.3 Hz, 1H), 3.40 (s, 6H), 1.32 (s, 12H).

Intermediate 215

Ethyl (2R)-2-(4-bromo-2-chloro-6-nitrophenoxy)propanoate

Prepared from commercially available starting materials by a method analogous to that used to prepare Intermediate 14. $\delta_H$ (500 MHz, CDCl$_3$) 7.85 (d, J 2.4 Hz, 1H), 7.73 (d, J 2.4 Hz, 1H), 4.89 (q, J 6.8 Hz, 1H), 4.16 (q, J 7.0 Hz, 2H), 1.66 (d, J 6.8 Hz, 3H), 1.23 (t, J 7.2 Hz, 3H).

Intermediate 216

(2R)-6-Bromo-8-chloro-2-methyl-3,4-dihydro-2H-1,4-benzoxazin-3-one

Prepared from Intermediate 215 by a method analogous to that used to prepare Intermediate 15. $\delta_H$ (500 MHz, CDCl$_3$) 8.22 (s, 1H), 7.20 (d, J 2.2 Hz, 1H), 6.87 (d, J 2.1 Hz, 1H), 4.75 (q, J 6.9 Hz, 1H), 1.27 (d, J 6.3 Hz, 3H).

Intermediate 217

2-Methyl-6-{methyl(oxo)[(trifluoroacetyl)imino]-λ$^6$-sulfanyl}pyridin-3-ylboronic acid Prepared from Intermediate 185 by a method analogous to that used to prepare Intermediate 43. $\delta_H$ (500 MHz, CD$_3$OD) 8.19-8.09 (m, 1H), 8.05 (t, J 6.5 Hz, 2H), 3.59 (s, 2H), 2.65 (s, 2H).

Intermediate 218

5-Bromo-2-[(3-chloropropyl)sulfanyl]pyridine

Powdered sodium methoxide (1.08 g, 19.95 mmol) and 1-bromo-3-chloropropane (2.87 mL, 28.7 mmol) were added to a stirred suspension of 5-bromopyridine-2-thiol (3.16 g, 16.63 mmol) in anhydrous methanol (80 mL). The mixture was heated at 60° C. and stirred under $N_2$ for 1.5 h. After cooling to room temperature, the mixture was quenched with water-brine (1:1, 100 mL) and extracted with EtOAc (2×100 mL). The combined organic fraction was washed with brine (50 mL), then dried ($MgSO_4$) and reduced in vacuo, to give the title compound (3.92 g, 88%) as a yellow solid. $\delta_H$ (500 MHz, $CDCl_3$) 8.50-8.44 (m, 1H), 7.58 (dd, J 8.5, 2.4 Hz, 1H), 7.07 (dd, J 8.5, 0.6 Hz, 1H), 3.67 (t, J 6.4 Hz, 2H), 3.29 (t, J 6.9 Hz, 2H), 2.17 (p, J 6.6 Hz, 2H).

Intermediate 219

5-Bromo-2-(3-chloropropanesulfinyl)pyridine $NaIO_4$ (9.56 g, 44.7 mmol) was added as a slurry in water (10 mL) to a stirred solution of Intermediate 218 (80%, 3.92 g, 11.76 mmol) in acetic acid (60 mL) at room temperature. The mixture was stirred at room temperature overnight, after which time a tan precipitate had formed. The mixture was treated with water (50 mL), upon which the precipitate partially dissolved. The aqueous acidic mixture was transferred carefully onto saturated aqueous potassium carbonate solution (250 mL), giving a final pH of approximately 7. The resulting mixture extracted with EtOAc (2×100 mL). The combined organic phase was washed with 10% aqueous sodium thiosulfate solution (2×100 mL), dried ($MgSO_4$) and reduced in vacuo. The resulting crude brown oil (4.9 g) was purified by chromatography on silica gel, eluting with 0-100% EtOAc in heptanes. The resulting orange oil was re-dissolved in EtOAc (50 mL) and washed with further 10% aqueous sodium thiosulfate solution (50 mL). The colourless organic phase was separated, dried ($MgSO_4$) and reduced in vacuo to give the title compound (2.4 g, 72%) as a pale yellow oil. $\delta_H$ (500 MHz, $CDCl_3$) 8.76-8.61 (m, 1H), 8.07 (dd, J 8.3, 2.3 Hz, 1H), 7.89 (d, J 8.3 Hz, 1H), 3.71-3.53 (m, 2H), 3.29 (ddd, J 13.5, 9.6, 5.8 Hz, 1H), 3.04 (ddd, J 13.5, 9.4, 5.4 Hz, 1H), 2.43-2.28 (m, 1H), 2.03-1.91 (m, 1H).

Intermediate 220

5-Bromo-2-(cyclopropanesulfinyl)pyridine

NaH (60% on mineral oil; 0.37 g, 9.13 mmol) was added portionwise to a stirred solution of Intermediate 219 (2.15 g, 7.61 mmol) in DMF (35 mL) at 0° C. The mixture was stirred for 10 minutes, then warmed to room temperature and stirred under $N_2$ overnight. The mixture was re-cooled to 0° C. and further treated with NaH (60% on mineral oil; 0.37 g, 9.13 mmol). After stirring for 3 h at room temperature, the mixture was re-cooled to 0° C. and further treated with NaH (60% on mineral oil; 0.37 g, 9.13 mmol). After a further 1 h at room temperature, the mixture was cooled to 0° C. and quenched with water (50 mL). The mixture was extracted with EtOAc (150 mL). The layers were separated and the organic fraction was washed successively with water (2×100 mL) and brine (50 mL), then dried ($MgSO_4$) and reduced in vacuo to leave a pale yellow oil. In order to wash out residual mineral oil, the crude residue was dissolved in acetonitrile (100 mL) and washed with heptane (2×100 mL). The acetonitrile fraction was reduced in vacuo. Purification of the resulting orange oil on Biotage isolera 4 (C18, SNAP, 120 g), eluting with 0-23% MeCN in water spiked with 0.1% formic acid, afforded the title compound (0.730 g, 39%) as a pale yellow oil. $\delta_H$ (500 MHz, $CDCl_3$) 8.68 (d, J 2.2 Hz, 1H), 8.04 (dd, J 8.3, 2.3 Hz, 1H), 7.84-7.80 (m, 1H), 2.41 (tt, J 8.1, 4.9 Hz, 1H), 1.19-1.05 (m, 2H), 1.04-0.96 (m, 1H), 0.79-0.69 (m, 1H).

Intermediate 221

N-1-[(5-Bromopyridin-2-yl)(cyclopropyl)oxo-$\lambda^6$-sulfanylidene]-2,2,2-trifluoroacetamide Prepared from Intermediate 220 by a method analogous to that used to prepare Intermediate 168. $\delta_H$ (250 MHz, $CDCl_3$) 8.78 (d, J 1.5 Hz, 1H), 8.15 (dd, J 8.4, 2.1 Hz, 1H), 8.08 (d, J 7.9 Hz, 1H), 3.05 (tt, J 7.9, 4.8 Hz, 1H), 1.74 (ddt, J 10.1, 7.1, 5.2 Hz, 1H), 1.48-1.22 (m, 2H), 1.21-1.02 (m, 1H).

Intermediate 222

Ethyl 2-(2-chloro-6-nitrophenoxy)acetate

Prepared from 2-chloro-6-nitrophenol and ethyl bromoacetate by a method analogous to that used to prepare Intermediate 19. $\delta_H$ (250 MHz, $CD_3OD$) 7.87-7.73 (m, 2H), 7.35 (t, J 8.2 Hz, 1H), 4.80 (s, 2H), 4.26 (q, J 7.2 Hz, 2H), 1.30 (t, J 7.1 Hz, 3H).

Intermediate 223

8-Chloro-3,4-dihydro-2H-1,4-benzoxazin-3-one

Prepared from Intermediate 222 by a method analogous to that used to prepare Intermediate 20. $\delta_H$ (500 MHz, DMSO-$d_6$) 10.89 (s, 1H), 7.04 (d, J 6.5 Hz, 1H), 6.94 (t, J 7.6 Hz, 1H), 6.86 (d, J 6.1 Hz, 1H), 4.69 (s, 2H).

Intermediate 224

3-Hydroxy-3-methylcyclobutyl 2,2-dimethylpropanoate

Intermediate 193 (25 g, 146.88 mmol) was dissolved in anhydrous diethyl ether (300 mL) under $N_2$ and the solution was cooled to −30° C. Methylmagnesium bromide (3M, 100 mL) was added dropwise, then the reaction mixture was allowed to warm to room temperature for 1.5 h with stirring. The reaction mixture was quenched with saturated aqueous $NH_4Cl$ solution (300 mL) and diluted with water (100 mL), then the mixture was extracted with ethyl acetate (3×150 mL). The combined organic extracts were dried over $MgSO_4$, filtered and concentrated under reduced pressure to afford crude title compound (18 g, 32.9%), which was used without further purification. $\delta_H$ (500 MHz, $CDCl_3$) 4.66-4.59 (m, 1H), 2.60-2.53 (m, 2H), 2.18-2.12 (m, 2H), 1.38 (s, 3H), 1.19 (s, 9H).

Intermediate 225

3-[(tert-Butyldimethylsilyl)oxy]-3-methylcyclobutyl 2,2-dimethylpropanoate

Intermediate 224 (50%, 18 g, 48.32 mmol) was dissolved in DMF (300 mL) under $N_2$ and the solution was cooled to 0° C. with stirring. Imidazole (16.45 g, 0.24 mol) was added, followed by tert-butyl(chloro)dimethylsilane (17.48 g, 0.12 mol). The reaction mixture was stirred at room temperature for 5 hours at 50° C., then cooled, diluted with tert-butyl methyl ether (500 mL) and washed with 1:1 brine/water (6×600 mL). The organic phase was dried over sodium sulfate and concentrated under reduced pressure. The crude residue was purified by chromatography on silica gel, eluting with 0-15% ethyl acetate in heptanes, to afford the title compound (12.8 g, 79.3%) as a yellow oil. $\delta_H$ (500 MHz, CD$_3$OD) 4.63-4.56 (m, 1H), 2.55-2.49 (m, 2H), 2.18-2.11 (m, 2H), 1.36 (s, 3H), 1.18 (s, 9H), 0.90 (d, J 1.8 Hz, 9H), 0.10 (s, 6H).

Intermediate 226

3-[(tert-Butyldimethylsilyl)oxy]-3-methylcyclobutan-1-ol

Prepared from Intermediate 225 by a method analogous to that used to prepare Intermediate 195. $\delta_H$ (500 MHz, CD$_3$OD) 3.84 (s, 1H), 2.42-2.36 (m, 2H), 2.09-2.03 (m, 2H), 1.29 (s, 3H), 0.89 (s, 9H), 0.09 (s, 6H).

Intermediate 227

3-[(tert-Butyldimethylsilyl)oxy]-3-methylcyclobutan-1-one

Prepared from Intermediate 226 by a method analogous to that used to prepare Intermediate 196. $\delta_H$ (500 MHz, CD$_3$OD) 3.12 (s, 2H), 3.04 (s, 2H), 1.61 (s, 3H), 0.91 (s, 9H), 0.15 (s, 6H).

Intermediate 228

(R)—N-{3-[(tert-Butyldimethylsilyl)oxy]-3-methylcyclobutylidene}-2-methylpropane-2-sulfinamide Prepared from Intermediate 227 by a method analogous to that used to prepare Intermediate 201. $\delta_H$ (500 MHz, CD$_3$OD) 3.52-3.42 (m, 1H, mixed isomers), 3.30-3.15 (m, 2H, mixed isomers), 3.14-3.06 (m, 1H, mixed isomers), 1.54 (s, 3H, isomer 1), 1.52 (s, 3H, isomer 2), 1.24 (t, J 1.3 Hz, 9H, mixed isomers), 0.92-0.90 (m, 9H, mixed isomers), 0.14 (s, 6H, mixed isomers).

Intermediate 229

(R)—N-{1-(5-Bromopyrimidin-2-yl)-3-[(tert-butyldimethylsilyl)oxy]-3-methylcyclobutyl}-2-methylpropane-2-sulfinamide n-Butyllithium in hexanes (2.5M, 1.76 mL) was added dropwise to a solution of 5-bromo-2-iodopyrimidine (1.1 g, 3.85 mmol) in anhydrous toluene (50 mL) under an atmosphere of N$_2$ at −50° C. After 20 minutes at −50° C., Intermediate 228 (95%, 1.4 g, 4.19 mmol) was added dropwise as a solution in anhydrous toluene (30 mL). The reaction mixture was stirred at −50° C. for 30 minutes, then warmed to room temperature and stirred for 2 h. The mixture was diluted with water (100 mL) and EtOAc (150 mL), then poured into brine (100 mL). The aqueous phase was partitioned and extracted with EtOAc (4×150 mL). The combined organic extracts were dried (MgSO$_4$) and reduced in vacuo. The resulting dark orange gum (2 g) was purified by chromatography on silica gel, eluting with 0-100% EtOAc in heptanes. The product-containing fractions were combined and concentrated to afford the title compound (380 mg, 11%) as a mixture of diastereoisomers. $\delta_H$ (500 MHz, CD$_3$OD) 8.89 (s, 2H, isomer 2), 8.86 (s, 2H, isomer 1), 3.29-3.22 (m, 2H, isomer 1), 2.96 (dd, J 12.8, 4.9 Hz, 1H, isomer 2), 2.74-2.69 (m, 2H, mixed isomers), 2.69-2.60 (m, 2H mixed isomers), 1.56 (s, 3H), 1.21 (s, 9H, isomer 1), 1.19 (s, 9H, isomer 2), 0.91 (s, 6H, isomer 2), 0.78 (s, 6H, isomer 1), 0.12 (s, 3H, isomer 2), 0.03 (s, 3H, isomer 1).

Intermediate 230

(2R)-8-Fluoro-2-methyl-6-(methylsulfanyl)-4H-1,4-benzoxazin-3-one

A suspension of Intermediate 216 (455 mg, 1.75 mmol), zinc fluoride (410 mg, 3.92 mmol) and cuprous iodide (210 mg, 1.08 mmol) in DMSO (4 mL) was heated at 160° C. for 20 h, then allowed to cool to ambient temperature. The crude mixture was partitioned between water (70 mL) and EtOAc (70 mL). The aqueous layer was extracted with further EtOAc (70 mL) and the combined organic layers were washed with water (70 mL) and brine (2×30 mL), then dried over MgSO$_4$ and concentrated in vacuo. Purification of the residue by chromatography on silica gel gave the title compound as a white solid. m/z 226 [M−H]$^-$.

Intermediate 231

(2R)-8-Chloro-N-isopropyl-2-methyl-3-oxo-4H-1,4-benzoxazine-6-carboxamide

Intermediate 216 (0.6 g, 2 mmol) was dissolved in 1-methyl-2-pyrrolidinone (20 mL). Triethylamine (0.6 mL, 4 mmol) and isopropylamine (0.4 mL, 5 mmol) were added, followed by dibromo[(S)-(−)-2,2'-bis(diphenylphosphino)-1,1'-binaphthyl]-palladium(II) (0.1 mmol). The mixture was heated at 80° C. for 16 h under an atmosphere of 5 bars of CO, then filtered through a Celite pad and washed with ethyl acetate. The solvent was concentrated in vacuo. The residue was dissolved in ethyl acetate (50 mL) and washed with water (20 mL), then dried over magnesium sulphate and concentrated to dryness. The residue was triturated with diethyl ether, then filtered, to afford the title compound (309 mg, 52%) as a white solid. $\delta_H$ (400 MHz, DMSO-d$_6$) 10.90 (s, 1H), 8.22 (s, 1H), 7.62 (s, 1H), 7.35 (s, 1H), 4.87 (m, 1H), 4.04 (m, 1H), 1.46 (m, 3H), 1.14 (m, 6H). LCMS 283 [M+H]$^+$.

Intermediate 232

[2-(2-Methyl-5-oxo-1,4-diazepan-1-yl)pyrimidin-5-yl]boronic acid

Prepared from 2-chloropyrimidin-5-ylboronic acid and 2-methyl-1,4-diazepan-5-one by a method analogous to that used to prepare Intermediate 90. LCMS m/z 251, RT 0.31 minutes.

Intermediate 233

[2-(7-Methyl-5-oxo-1,4-diazepan-1-yl)pyrimidin-5-yl]boronic acid

Prepared from 2-chloropyrimidin-5-ylboronic acid and 7-methyl-1,4-diazepan-5-one by a method analogous to that used to prepare Intermediate 90. LCMS m/z 251, RT 0.35 minutes.

Intermediate 234

(2R)-6-Bromo-4-[(6-bromo-7-fluoro-2-methylimidazo[1,2-a]pyridin-3-yl)methyl]-8-fluoro-2-methyl-1,4-benzoxazin-3-one Prepared from Intermediates 34 and 120 by a method analogous to that used to prepare Intermediate 21, 89 or 164. LCMS m/z 502, RT 2.34 minutes.

Intermediate 235

Methyl 8-fluoro-4-({7-fluoro-6-[2-(1-hydroxy-1-methylethyl)pyrimidin-5-yl]-2-methyl-imidazo[1,2-a]pyridin-3-yl}methyl)-3-oxo-1,4-benzoxazine-6-carboxylate Prepared from Intermediates 107 and 239 by a method analogous to that used to prepare Intermediate 21, 89 or 164. LCMS m/z 524, RT 2.24 minutes.

Intermediate 236

(2R)-4-[(6-Bromo-7-fluoro-2-methylimidazo[1,2-a]pyridin-3-yl)methyl]-8-fluoro-6-(3-hydroxyoxetan-3-yl)-2-methyl-1,4-benzoxazin-3-one Prepared from Intermediates 34 and 238 by a method analogous to that used to prepare Intermediate 21, 89 or 164. LCMS m/z 496, RT 1.76 minutes.

Intermediate 237

(2S)-4-[(6-Bromo-7-fluoro-2-methylimidazo[1,2-a]pyridin-3-yl)methyl]-8-fluoro-6-(1-hydroxy-1-methylethyl)-2-methyl-1,4-benzoxazin-3-one Prepared from Intermediates 34 and 243 by a method analogous to that used to prepare Intermediate 21, 89 or 164. LCMS m/z 482, RT 2.40 minutes.

Intermediate 238

(2R)-8-Fluoro-6-(3-hydroxyoxetan-3-yl)-2-methyl-4H-1,4-benzoxazin-3-one

Prepared from Intermediate 120 and oxetan-3-one by a method analogous to that used to prepare Intermediate 194. LCMS m/z 252, RT 2.48 minutes.

Intermediate 239

Methyl 8-fluoro-3-oxo-4H-1,4-benzoxazine-6-carboxylate

Prepared from 6-bromo-8-fluoro-4H-1,4-benzoxazin-3-one by a method analogous to that used to prepare Intermediate 121. LCMS: [M–H]+ m/z 224, RT 1.10 minutes.

Intermediate 240

8-Fluoro-4-({7-fluoro-6-[2-(1-hydroxy-1-methylethyl)pyrimidin-5-yl]-2-methyl-imidazo[1,2-a]pyridin-3-yl}methyl)-3-oxo-1,4-benzoxazine-6-carboxylic acid Prepared from Intermediate 235 by a method analogous to that used to prepare Example 131. LCMS: MH+ m/z 510, RT 0.94 minutes.

Intermediate 241

N-Isopropyl-2-methyl-3-oxo-4H-pyrido[3,2-b][1,4]oxazine-6-carboxamide

Prepared from (2R)-6-chloro-2-methyl-4H-pyrido[3,2-b][1,4]oxazin-3-one and isopropylamine by a method analogous to that used to prepare Intermediate 231. LCMS: MH+ m/z 251, RT 0.91 minutes.

Intermediate 242

(2R)-4[(6-Bromo-7-fluoro-2-methylimidazo[1,2-a]pyridin-3-yl)methyl]-8-fluoro-6-(3-methoxyoxetan-3-yl)-2-methyl-1,4-benzoxazin-3-one Intermediate 236 (83 mg, 0.17 mmol) was dissolved in DMF (1.5 mL) and cooled to 0° C. Sodium hydride (7.3 mg, 0.18 mmol) was added and the reaction mixture was allowed to stir for 1 h before iodomethane (12 μL, 0.20 mmol) was added. The reaction mixture was allowed to warm to room temperature overnight, then diluted with EtOAc and washed with brine. The organic layer was dried over sodium sulfate and concentrated under reduced pressure. The crude residue was purified by flash column chromatography (MeOH:EtOAc, 0-15%) to give the title compound (50 mg, 58%) as a white solid. HPLC-MS: MH+ m/z 508, RT 1.91 minutes.

Intermediate 243

(2S)-8-Fluoro-6-(1-hydroxy-1-methylethyl)-2-methyl-4H-1,4-benzoxazin-3-one

Prepared from (2S)-6-bromo-8-fluoro-2-methyl-4H-1,4-benzoxazin-3-one by a method analogous to that used to prepare Intermediate 161. LCMS: MH+ m/z 240, RT 1.99 minutes.

Intermediate 244

3-Methyl-1,2,3,4-tetrahydroquinolin-2-one

To a stirred solution of lithium diisopropylamide (2M in THF, 61.15 mL, 122.3 mmol) and anhydrous tetrahydrofuran (100 mL), previously cooled to 0° C., was added 3,4-dihydroquinolin-2(1H)-one (9 g, 61.15 mmol) over 10 minutes. The reaction mixture was stirred at ambient temperature for 2 h, then cooled to −78° C. Iodomethane (3.81 mL, 61.15 mmol) was added in one portion and the reaction mixture was allowed to warm to ambient temperature over 16 h. The reaction mixture was diluted with ethyl acetate (200 mL), then washed with water (2×100 mL) and brine (100 mL). The organic layer was dried over sodium sulphate and filtered, then the solvent was removed in vacuo. The residue was purified by chromatography on silica gel, using an ethyl acetate/heptane gradient (0-30% ethyl acetate), to give the title compound (4.60 g, 45% yield) as a yellow oil. $\delta_H$ (500 MHz, DMSO-$d_6$) 10.01 (s, 1H), 7.15 (d, J 8.0 Hz, 1H), 7.11 (d, J 7.7 Hz, 1H), 6.89 (td, J 7.4, 0.9 Hz, 1H), 6.84 (d, J 7.8 Hz, 1H), 2.92 (dd, J 15.6, 5.9 Hz, 1H), 2.62 (dd, J 15.5, 11.6 Hz, 1H), 2.56-2.44 (m, 1H), 1.11 (d, J 6.9 Hz, 3H). Method C HPLC-MS: MH+ m/z 162, RT 1.04 minutes (96%).

Intermediate 245

1-[(6-Bromo-7-fluoro-2-methylimidazo[1,2-a]pyridin-3-yl)methyl]-3-methyl-1,2,3,4-tetrahydroquinolin-2-one Prepared from Intermediates 34 and 244 by a method analogous to that used to prepare Intermediate 21, 89 or 164. $\delta_H$ (500 MHz, DMSO-$d_6$) 8.69 (d, J 6.8 Hz, 1H), 7.51 (d, J 9.6 Hz, 1H), 7.24-7.20 (m, 2H), 7.18 (d, J 7.7 Hz, 1H), 6.98 (ddd, J 8.2, 5.3, 3.2 Hz, 1H), 5.66 (d, J 16.5 Hz, 1H), 5.39 (d, J 16.5 Hz, 1H), 2.88 (dd, J 15.2, 5.3 Hz, 1H), 2.69 (dq, J 12.2, 6.3, 5.6 Hz, 1H), 2.58-2.53 (m, 1H), 2.27 (s, 3H), 1.19 (d, J 6.8 Hz, 3H).

Intermediate 246

(1R,5S,8R)-3-[5-(4,4,5,5-Tetramethyl-1,3,2-dioxaborolan-2-yl)pyrimidin-2-yl]-3-azabicyclo[3.2.1]octane-8-carboxylic acid Prepared from 2-chloro-5-(4,4,5,5-tetramethyl-1,3,2-dioxaborolan-2-yl)pyrimidine and (1R,5S)-3-azabicyclo[3.2.1]octane-8-carboxylic acid by a method analogous to that used to prepare Intermediate 90. $\delta_H$ (500 MHz, CDCl$_3$) 8.58 (s, 2H), 4.60 (dd, J 13.2, 3.4 Hz, 2H), 3.03 (d, J 12.5 Hz, 2H), 2.72 (s, 2H), 2.69 (s, 1H), 1.83 (dd, J 8.0, 3.5 Hz, 2H), 1.52 (q, J 6.1 Hz, 2H), 1.31 (s, 12H).

Intermediate 247

4-(5-Bromopyridin-2-yl)oxan-4-ol

Prepared from 2,5-dibromopyridine and tetrahydro-4H-pyran-4-one by a method analogous to that used to prepare Intermediate 194. MS m/z 258.0/260.0 (M+H)$^+$.

Intermediate 248

[4-(5-Bromopyridin-2-yl)tetrahydropyran-4-yl]oxy(trimethyl)silane

Prepared from Intermediate 247 by a method analogous to that used to prepare Intermediate 42. $\delta_H$ (500 MHz, CDCl$_3$) 8.60 (d, J 2.0 Hz, 1H), 7.81 (dd, J 8.5, 2.4 Hz, 1H), 7.44-7.38 (m, 1H), 3.95-3.76 (m, 4H), 2.18 (ddd, J 14.7, 11.0, 4.8 Hz, 2H), 1.89 (dd, J 14.2, 2.5 Hz, 2H), 0.00 (s, 9H).

Intermediate 249

{4-[5-(4,4,5,5-Tetramethyl-1,3,2-dioxaborolan-2-yl)pyridin-2-yl]tetrahydropyran-4-yl}oxy(trimethyl)silane Prepared from Intermediate 248 by a method analogous to that used to prepare Intermediate 43. $\delta_H$ (500 MHz, CDCl$_3$) 8.89 (s, 1H), 8.05 (dd, J 7.9, 1.5 Hz, 1H), 7.48 (d, J 7.9 Hz, 1H), 3.90 (td, J 11.1, 2.2 Hz, 2H), 3.82 (dt, J 11.3, 4.0 Hz, 2H), 2.22 (ddd, J 15.1, 11.3, 4.7 Hz, 2H), 1.91 (d, J 11.9 Hz, 2H), 1.35 (s, 12H), 0.00 (s, 9H).

Intermediate 250

5-Bromo-4-methylpyrimidine-2-carbonitrile

To a solution of sodium cyanide (6.18 g, 126.2 mmol) and DABCO (2.17 g, 19.41 mmol) in DMSO:H$_2$O (1:1, 200 mL) was added 5-bromo-2-chloro-4-methylpyrimidine (20 g, 97.08 mmol in DMSO). The reaction mixture was stirred at room temperature for 12 h, then diluted with water and extracted with ethyl acetate. The organic layer was separated and dried over sodium sulphate, then concentrated under reduced pressure. The residue was purified by silica gel column chromatography, using 20% ethyl acetate in hexanes as eluent, to afford the title compound (19 g, 67%) as a colourless oil. $\delta_H$ (500 MHz, CDCl$_3$) 8.80 (s, 1H), 2.62-2.80 (m, 3H).

Intermediate 251

5-Bromo-4-methylpyrimidine-2-carboxylic acid

Intermediate 250 (25 g, 127 mmol) was dissolved in aqueous sodium hydroxide solution (15.2 g, 380.7 mmol in 100 mL water) and heated at 60° C. for 2 h. The reaction mixture was acidified by the addition of 1N aqueous HCl to pH 2, then the compound was extracted with 10% methanol in dichloromethane. The organic layer was separated and dried over sodium sulphate, then evaporated under reduced pressure, to afford the title compound (19 g, 69%) as an off-white solid. $\delta_H$ (400 MHz, CDCl$_3$) 8.87-9.02 (m, 1H), 2.79 (s, 3H).

Intermediate 252

Ethyl 5-bromo-4-methylpyrimidine-2-carboxylate

To a solution of Intermediate 251 (19 g, 87.9 mmol) in ethanol (200 mL) was added concentrated sulfuric acid (8 mL) dropwise. The reaction mixture was stirred at 80° C. for 12 h, then concentrated under reduced pressure. The residue was extracted with ethyl acetate. The organic layer was washed with saturated aqueous sodium bicarbonate solution, water and brine, then separated, dried over sodium sulphate and concentrated under reduced pressure. The residue was purified by silica gel (100:200 mesh) column chromatography, using 30% ethyl acetate in hexanes as eluent, to afford the title compound (14 g, 65%) as an off-white solid. $\delta_H$ (400 MHz, CDCl$_3$) 8.79-9.01 (m, 1H), 4.54 (q, J 7.14 Hz, 2H), 2.67-2.83 (s, 3H) 1.46 (t, J 7.14 Hz, 3H). LCMS m/z 245 [M+1]$^+$.

Intermediate 253

2-(5-Bromo-4-methylpyrimidin-2-yl)propan-2-ol

To a solution of Intermediate 252 (13.8 g, 56.55 mmol) in diethyl ether (150 mL) at 0° C. was added methylmagnesium bromide (3M solution, 56 mL, 169.6 mmol). The reaction mixture was warmed to room temperature and stirred for 30 minutes, then quenched by the addition of saturated aqueous ammonium chloride solution and extracted with ethyl acetate. The organic layer was washed with water and brine, then dried over sodium sulphate and concentrated under reduced pressure. The residue was purified by silica gel column chromatography, using 20% ethyl acetate in hexanes as eluent, to afford the title compound (8.9 g, 68%) as a yellow oil. δ$_H$ (400 MHz, CDCl$_3$) 8.67 (s, 1H), 2.65 (s, 3H), 1.48-1.65 (m, 6H). LCMS m/z 233 [M+H]$^+$.

Intermediate 254

(2R)-4-[(6-Bromo-7-fluoro-2-methylimidazo[1,2-a]pyridin-3-yl)methyl]-8-fluoro-2-methyl-6-nitro-3,4-dihydro-2H-1,4-benzoxazin-3-one Intermediate 35 (500 mg, 1.18 mmol) was dissolved in glacial acetic acid (5 mL) and cooled to 0° C. Red fuming nitric acid (1.5 mL, 28 mmol) was added portionwise at 0° C. and the resulting solution was stirred for 5 minutes, then allowed to warm to room temperature and stirred for 24 h. The reaction mixture was poured onto ice (melted volume approximately 80 mL) and neutralised with saturated aqueous NaHCO$_3$ solution to approximately pH 7. The solid that formed was collected by filtration and purified by column chromatography on silica gel, eluting with a gradient of EtOAc in heptane, to yield the title compound (179 mg, 32%) as an off-white solid. δ$_H$ (500 MHz, CD$_3$OD) 8.68 (d, J 6.6 Hz, 1H), 8.01 (dd, J 2.5, 1.8 Hz, 1H), 7.86 (dd, J 9.8, 2.5 Hz, 1H), 7.30 (d, J 8.9 Hz, 1H), 5.79 (d, J 16.6 Hz, 1H), 5.56 (d, J 16.6 Hz, 1H), 5.02 (q, J 6.8 Hz, 1H), 2.59 (s, 3H), 1.68 (d, J 6.7 Hz, 3H).

Intermediate 255

(2R)-6-Amino-4-[(6-bromo-7-fluoro-2-methylimidazo[1,2-a]pyridin-3-yl)methyl]-8-fluoro-2-methyl-3,4-dihydro-2H-1,4-benzoxazin-3-one Intermediate 254 (163 mg, 0.35 mmol) was dissolved in acetic acid (4 mL) and iron powder (300 mg, 5.37 mmol) was added. The resulting mixture was stirred at 50° C. in a sealed tube for 2 h, then allowed to cool to room temperature and diluted with water (8 mL). The pH was adjusted to approximately pH 8 by the addition of saturated aqueous NaHCO$_3$ solution. The resulting suspension was extracted with EtOAc (10 mL). The organic layer was dried (Na$_2$SO$_4$) and concentrated to dryness under vacuum to yield the title compound (116 mg, 62%) as an off-white solid. δ$_H$ (500 MHz, CD$_3$OD) 8.67 (d, J 6.6 Hz, 1H), 7.29 (d, J 8.9 Hz, 1H), 6.41 (s, 1H), 6.24 (dd, J 12.1, 2.1 Hz, 1H), 5.56 (d, J 16.3 Hz, 1H), 5.31 (d, J 16.5 Hz, 1H), 4.60 (q, J 6.6 Hz, 1H), 2.44 (s, 3H), 1.54 (d, J 6.7 Hz, 3H).

Intermediate 256

N-{(2R)-4-[(6-Bromo-7-fluoro-2-methylimidazo[1,2-a]pyridin-3-yl)methyl]-8-fluoro-2-methyl-3-oxo-3,4-dihydro-2H-1,4-benzoxazin-6-yl}-2-methylpropanamide Intermediate 255 (102 mg, 0.23 mmol) was dissolved in DCM (2 mL) and isobutyryl chloride (30 μL, 0.29 mmol) was added, followed by DIPEA (80 μL, 0.46 mmol). The resulting mixture was stirred under nitrogen for 1 h, then washed with water (3 mL). The aqueous layer was re-extracted with DCM (2×3 mL). The combined organic layers were dried (Na$_2$SO$_4$) and concentrated to dryness under vacuum. The residue was triturated with DCM (3 mL), and the resulting solid was washed with DCM (3 mL), to yield the title compound (70 mg, 59%) as an off-white solid. δ$_H$ (500 MHz, DMSO-d$_6$) 9.85 (s, 1H), 8.76 (d, J 6.7 Hz, 1H), 7.54 (d, J 9.6 Hz, 1H), 7.37 (s, 1H), 7.11 (dd, J 12.4, 2.1 Hz, 1H), 5.53 (d, J 16.6 Hz, 1H), 5.34 (d, J 16.6 Hz, 1H), 4.87 (q, J 6.6 Hz, 1H), 2.24 (s, 3H), 1.50 (d, J 6.7 Hz, 3H), 1.05 (d, J 6.7 Hz, 6H). MI-1' 506.90.

Intermediate 257

4-[(6-Bromo-2-methylimidazo[1,2-a]pyrazin-3-yl)methyl]-8-chloro-3,4-dihydro-2H-1,4-benzoxazin-3-one Prepared from Intermediate 98 and Intermediate 223 by a method analogous to that used to prepare Intermediate 21 or 89. δ$_H$ (500 MHz, DMSO-d$_6$) 8.85-8.74 (m, 2H), 7.59 (d, J 30.6 Hz, 1H), 7.20 (d, J 38.2 Hz, 2H), 5.58 (s, 2H), 4.89 (s, 2H), 2.33 (s, 3H).

Intermediate 258

4-[(6-Bromo-7-fluoro-2-methylimidazo[1,2-a]pyridin-3-yl)methyl]-8-chloro-3,4-dihydro-2H-1,4-benzoxazin-3-one Prepared from Intermediate 34 and Intermediate 223 by a method analogous to that used to prepare Intermediate 164. δ$_H$ (500 MHz, CDCl$_3$) 8.51 (d, J 5.4 Hz, 1H), 7.21 (d, J 8.0 Hz, 1H), 7.06 (dd, J 24.7, 7.5 Hz, 2H), 6.94 (d, J 7.9 Hz, 1H), 5.43 (s, 2H), 4.79 (s, 2H), 2.55 (s, 3H). HPLC-MS: MH$^+$ m/z 426, RT 1.07 minutes.

Example 1

4-{[6-(6-Methanesulfonylpyridin-3-yl)-2-methylimidazo[1,2-a]pyridin-3-yl]methyl}-2H,3H,4H-pyrido[3,2-b][1,4]oxazin-3-one Intermediate 7 (100 mg, 0.27 mmol), 6-(methylsulfonyl)pyridin-3-ylboronic acid (53 mg, 0.27 mmol) and 2M aqueous sodium carbonate solution (0.4 mL, 0.80 mmol) were dissolved in anhydrous 1,4-dioxane (6 mL) and the mixture was degassed under nitrogen for 15 minutes. Further 2M aqueous sodium carbonate solution (0.4 mL, 0.80 mmol) and Pd(dppf)Cl$_2$ (11 mg, 0.01 mmol) were added and the mixture was degassed with nitrogen for 5 minutes before stirring with heating at 100° C. for 2 h. The reaction mixture was cooled to room temperature and diluted with ethyl acetate (10 mL), then filtered through a pad of celite and concentrated in vacuo. The crude material was purified using preparative HPLC to afford the title compound (52 mg, 43.3%) as an off-white solid. δ$_H$ (250 MHz, DMSO-d$_6$) 9.32 (s, 1H), 9.13 (d, J 1.6 Hz, 1H), 8.45 (dd, J 8.2, 2.3 Hz, 1H), 8.18 (d, J 8.2 Hz, 1H), 8.01 (dd, J 4.8, 1.4 Hz, 1H), 7.87 (d, J 8.1 Hz, 1H), 7.71 (d, J 9.2 Hz, 1H), 7.38 (dd, J 7.9, 1.4 Hz, 1H), 7.05 (dd, J 7.9, 4.8 Hz, 1H), 5.64 (s, 2H), 4.83 (s, 2H), 2.88 (s, 3H), 2.52 (s, 3H). LCMS MH+ m/z 450.

Example 2

3-{[6-(4-Methanesulfonylphenyl)-2-methylimidazo[1,2-a]pyridin-3-yl]methyl}-2,3-dihydro-1,3-benzoxazol-2-one Intermediate 4 (300 mg, 0.95 mmol) was suspended in dichloromethane (10 mL). Thionyl chloride (0.34 mL, 4.74 mmol) was added dropwise with continuous stirring at room temperature. The reaction mixture was stirred at room temperature for 30 minutes. The solvent was removed in vacuo and the resultant chloride was slurried in dichloromethane (15 mL). The suspension was sonicated and the solvent was removed in vacuo. 1,3-Benzoxazol-2(3H)-one (0.11 g, 0.79 mmol) and caesium carbonate (0.74 g, 2.28 mmol) were stirred in DMF (5 mL) and the prepared chloride was added as a suspension in DMF (10 mL). The reaction mixture was stirred at 70° C. for 30 minutes, then poured onto water (75 mL). The resulting solid was collected by filtration and washed with heptane. The crude residue was purified on silica gel, eluting with 0-5% methanol in dichloromethane, followed by trituration using dichloromethane and heptane, to afford the title compound (67 mg, 20%) as a yellow solid. $\delta_H$ (250 MHz, DMSO-$d_6$) 8.91 (s, 1H), 8.04 (d, J 8.4 Hz, 2H), 7.95 (d, J 8.5 Hz, 2H), 7.68 (dd, J 9.4, 1.4 Hz, 1H), 7.60 (d, J 9.4 Hz, 1H), 7.33 (d, J 7.9 Hz, 1H), 7.23 (d, J 4.2 Hz, 2H), 7.17-7.06 (m, 1H), 5.54 (s, 2H), 3.27 (s, 3H), 2.55 (s, 3H). LCMS m/z 434.

Example 3

8-Fluoro-4-{[6-(4-methanesulfonylphenyl)-2-methylimidazo[1,2-a]pyridin-3-yl]methyl}-3,4-dihydro-2H-1,4-benzoxazin-3-one Intermediate 4 (300 mg, 0.95 mmol) was suspended in dichloromethane (10 mL). Thionyl chloride (0.34 mL, 4.74 mmol) was added dropwise with continuous stirring at room temperature. The reaction mixture was stirred at room temperature for 30 minutes. The solvent was removed in vacuo and the resultant chloride was slurried in dichloromethane (15 mL). The suspension was sonicated, then the solvent was removed in vacuo. Intermediate 20 (0.16 g, 0.95 mmol) and caesium carbonate (0.74 g, 2.28 mmol) were stirred in DMF (5 mL) and the prepared chloride was added as a suspension in DMF (10 mL). The reaction mixture was stirred at 70° C. for 30 minutes, then poured onto water (75 mL). The resulting solid was collected by filtration and washed with heptane. The crude residue was purified on silica gel, eluting with 0-25% methanol in dichloromethane, followed by dichloromethane/methanol/ammonia (90:9:1). The material was further purified on silica (Biotage: KP-NH cartridge), eluting with 0-2% methanol in dichloro-methane, to afford the title compound (28 mg, 7%) as a white solid. $\delta_H$ (250 MHz, DMSO-$d_6$) 8.77 (s, 1H), 8.04 (d, J 8.6 Hz, 2H), 7.93 (d, J 8.6 Hz, 2H), 7.65 (dd, J 9.3, 1.6 Hz, 1H), 7.57 (d, J 8.8 Hz, 1H), 7.19 (dd, J 7.6, 1.7 Hz, 1H), 7.11-6.94 (m, 2H), 5.64 (s, 2H), 4.87 (s, 2H), 3.27 (s, 3H), 2.38 (s, 3H). LCMS MH+ m/z 466.1.

Example 4

3-{[6-(4-Methanesulfonylphenyl)-2-methylimidazo[1,2-a]pyridin-3-yl]methyl}-2H,3H-[1,3]oxazolo[4,5-b]pyridin-2-one Prepared from Intermediate 8 and 4-(methanesulfonyl)phenylboronic acid by a method analogous to that used to prepare Example 1. $\delta_H$ (500 MHz, DMSO-$d_6$) 9.25 (s, 1H), 8.24 (dd, J 5.3, 1.1 Hz, 1H), 8.08 (d, J 8.5 Hz, 2H), 7.99 (d, J 8.5 Hz, 2H), 7.71 (dd, J 7.9, 1.1 Hz, 1H), 7.69 (dd, J 9.4, 1.8 Hz, 1H), 7.60 (d, J 9.2 Hz, 1H), 7.21 (dd, J 7.9, 5.3 Hz, 1H), 5.47 (s, 2H), 3.29 (s, 3H), 2.59 (s, 3H). LCMS m/z 435.

Example 5

8-{[6-(4-Methanesulfonylphenyl)-2-methylimidazo[1,2-a]pyridin-3-yl]methyl}-6H,7H,8H-pyrimido[5,4-b][1,4]oxazin-7-one Prepared from Intermediate 13 and 4-(methanesulfonyl)phenylboronic acid by a method analogous to that used to prepare Example 1. $\delta_H$ (500 MHz, DMSO-$d_6$) 9.13 (s, 1H), 8.69 (s, 1H), 8.36 (s, 1H), 8.06 (d, J 8.5 Hz, 2H), 7.96 (d, J 8.5 Hz, 2H), 7.66 (dd, J 9.3, 1.7 Hz, 1H), 7.58 (d, J 9.3 Hz, 1H), 5.60 (s, 2H), 4.94 (s, 2H), 3.29 (s, 3H), 2.53 (s, 3H). LCMS m/z 449.

Example 6

1-{[6-(4-Methylsulfonylphenyl)-2-methylimidazo[1,2-a]pyridin-3-yl]methyl}quinolin-2-one Prepared from Intermediate 17 and 4-(methanesulfonyl)phenylboronic acid by a method analogous to that used to prepare Example 1. $\delta_H$ (500 MHz, DMSO-$d_6$) 8.96 (s, 1H), 8.08-7.97 (m, 5H), 7.77 (dd, J 7.8, 1.3 Hz, 1H), 7.66 (dd, J 9.4, 1.7 Hz, 1H), 7.62-7.56 (m, 2H), 7.53 (d, J 8.6 Hz, 1H), 7.28 (t, J 7.4 Hz, 1H), 6.80 (d, J 9.5 Hz, 1H), 5.98 (s, 2H), 3.29 (s, 3H), 2.17 (s, 3H). LCMS m/z 444.

Example 7

(2R)-4-{[6-(4-Methanesulfonylphenyl)-2-methylimidazo[1,2-a]pyridin-3-yl]methyl}-2-methyl-2H,3H,4H-pyrido[3,2-b][1,4]oxazin-3-one Prepared from Intermediate 16 and 4-(methanesulfonyl)phenylboronic acid by a method analogous to that used to prepare Example 1. $\delta_H$ (500 MHz, DMSO-$d_6$) 9.16 (s, 1H), 8.11-8.07 (m, 1H), 8.05 (d, J 8.4 Hz, 2H), 7.94 (d, J 8.4 Hz, 2H), 7.64 (d, J 9.3 Hz, 1H), 7.56 (d, J 9.3 Hz, 1H), 7.43 (d, J 7.1 Hz, 1H), 7.10 (dd, J 7.9, 4.9 Hz, 1H), 5.64 (s, 2H), 4.95 (q, J 6.7 Hz, 1H), 3.28 (s, 3H), 2.48 (s, 3H), 1.48 (d, J 6.7 Hz, 3H). LCMS m/z 463.

Example 8

1-{[6-(4-Methanesulfonylphenyl)-2-methylimidazo[1,2-a]pyridin-3-yl]methyl}-1,2,3,4-tetrahydroquinolin-2-one Prepared from Intermediate 18 and 4-(methanesulfonyl)phenylboronic acid by a method analogous to that used to prepare Example 1. $\delta_H$ (500 MHz, CD$_3$OD) 8.68 (s, 1H), 8.04 (d, J 8.4 Hz, 2H), 7.82 (d, J 8.4 Hz, 2H), 7.66 (dd, J 9.3, 1.6 Hz, 1H), 7.53 (d, J 9.3 Hz, 1H), 7.37 (d, J 8.2 Hz, 1H), 7.27 (t, J 7.8 Hz, 1H), 7.19 (d, J 7.3 Hz, 1H), 7.04 (t, J 7.4 Hz, 1H), 5.64 (s, 2H), 3.18 (s, 3H), 2.78 (dd, J 8.5, 5.4 Hz, 2H), 2.70 (dd, J 8.7, 5.2 Hz, 2H), 2.49 (s, 3H). LCMS m/z 446.

Example 9

8-Fluoro-4-({6-[2-(2-hydroxypropan-2-yl)pyrimidin-5-yl]-2-methylimidazo[1,2-a]-pyridin-3-yl}methyl)-3,4-dihydro-2H-1,4-benzoxazin-3-one Prepared from Intermediate 21 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-$d_6$) 9.14 (s, 2H), 8.88 (s, 1H), 7.70 (dd, J 9.3, 1.7 Hz, 1H), 7.61 (d, J 9.3 Hz, 1H), 7.15 (d, J 8.2 Hz, 1H), 7.10-6.94 (m, 2H), 5.63 (s, 2H), 5.16 (s, 1H), 4.88 (s, 2H), 2.37 (s, 3H), 1.55 (s, 6H). LCMS m/z 448.

Example 10

7-Fluoro-3-({6-[2-(2-hydroxypropan-2-yl)pyrimidin-5-yl]-2-methylimidazo[1,2-a]-pyridin-3-yl}methyl)-2,3-dihydro-1,3-benzoxazol-2-one Prepared from Intermediate 23 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-d$_6$) 9.14 (s, 2H), 8.89 (s, 1H), 7.74 (dd, J 9.3, 1.7 Hz, 1H), 7.65 (d, J 9.3 Hz, 1H), 7.24 (td, J 8.3, 4.9 Hz, 1H), 7.10 (dd, J 10.0, 9.1 Hz, 1H), 7.01 (d, J 7.9 Hz, 1H), 5.54 (s, 2H), 5.15 (s, 1H), 2.57 (s, 3H), 1.55 (s, 6H). LCMS m/z 443.

Example 11

3-({6-[2-(2-Hydroxypropan-2-yl)pyrimidin-5-yl]-2-methylimidazo[1,2-a]pyridin-3-yl}methyl)-2H,3H-[1,3]oxazolo[4,5-d]pyrimidin-2-one Prepared from Intermediate 26 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, CD$_3$OD) 9.26 (s, 1H), 9.13 (br s, 2H), 8.78 (s, 1H), 8.42 (br s, 1H), 7.71 (d, J 9.3 Hz, 1H), 7.59 (d, J 9.3 Hz, 1H), 5.54 (s, 2H), 3.31 (s, 3H), 1.65 (s, 6H). LCMS m/z 449.

Example 12

8-Fluoro-4-{[6-(6-methanesulfonylpyridin-3-yl)-2-methylimidazo[1,2-a]pyridin-3-yl]-methyl}-3,4-dihydro-2H-1,4-benzoxazin-3-one Prepared from Intermediate 21 and 6-(methanesulfonyl)pyridin-3-ylboronic acid by a method analogous to that used to prepare Example 1. $\delta_H$ (250 MHz, CDCl$_3$) 8.94 (d, J 1.5 Hz, 1H), 8.80 (s, 1H), 8.21 (d, J 8.0 Hz, 1H), 8.17-8.09 (m, 1H), 7.73 (s, 1H), 7.53 (d, J 8.5 Hz, 1H), 6.98 (t, J 3.3 Hz, 2H), 6.94-6.83 (m, 1H), 5.54 (s, 2H), 4.75 (s, 2H), 3.30 (s, 3H), 2.68 (s, 3H). LCMS m/z 467.

Example 13 tert-Butyl 4-(5-{3-[(8-Fluoro-3-oxo-3,4-dihydro-2H-1,4-benzoxazin-4-yl)methyl]-2-methylimidazo[1,2-a]pyridin-6-yl}pyrimidin-2-yl)piperazine-1-carboxylate Prepared from Intermediate 21 and tert-butyl 4-[5-(4,4,5,5-tetramethyl-1,3,2-dioxaborolan-2-yl)pyrimidin-2-yl]piperazine-1-carboxylate by a method analogous to that used to prepare Example 1. $\delta_H$ (500 MHz, DMSO-d$_6$) 8.72 (s, 2H), 8.65 (s, 1H), 7.56 (dd, J 9.3, 1.6 Hz, 1H), 7.53 (d, J 9.1 Hz, 1H), 7.14 (d, J 8.2 Hz, 1H), 7.07-6.94 (m, 2H), 5.61 (s, 2H), 4.87 (s, 2H), 3.83-3.75 (m, 4H), 3.48-3.41 (m, 4H), 2.37 (s, 3H), 1.44 (s, 9H). LCMS m/z 579.

Example 14

8-Fluoro-4-({2-methyl-6-[2-(morpholin-4-yl)pyrimidin-5-yl]imidazo[1,2-a]pyridin-3-yl}methyl)-3,4-dihydro-2H-1,4-benzoxazin-3-one Prepared from Intermediate 21 and Intermediate 90 by a method analogous to that used to prepare Example 1. $\delta_H$ (500 MHz, DMSO-d$_6$) 8.72 (s, 2H), 8.66 (s, 1H), 7.56 (dd, J 9.3, 1.6 Hz, 1H), 7.53 (d, J 9.2 Hz, 1H), 7.14 (d, J 8.2 Hz, 1H), 7.08-6.94 (m, 2H), 5.61 (s, 2H), 4.87 (s, 2H), 3.80-3.75 (m, 4H), 3.72-3.67 (m, 4H), 2.37 (s, 3H). LCMS m/z 475.

Example 15

8-Fluoro-4-({2-methyl-6-[2-(piperazin-1-yl)pyrimidin-5-yl]imidazo[1,2-a]pyridin-3-yl}-methyl)-3,4-dihydro-2H-1,4-benzoxazin-3-one hydrochloride Example 13 (79 mg, 0.138 mmol) was dissolved in 1,4-dioxane (1.1 mL). HCl in 1,4-dioxane (4M, 0.35 mL, 1.38 mmol) was added dropwise and the reaction mixture was heated with stirring at 50° C. for 1 h. The solvent was removed in vacuo and the residue was dried under high vacuum to afford the title compound (71.4 mg, 96%) as a beige solid. $\delta_H$ (500 MHz, DMSO-d$_6$) 9.33 (s, 2H), 9.12 (s, 1H), 8.90 (s, 2H), 8.29 (d, J 9.4 Hz, 1H), 8.00 (d, J 9.3 Hz, 1H), 7.27 (d, J 7.5 Hz, 1H), 7.13-7.03 (m, 2H), 5.72 (s, 2H), 4.88 (s, 2H), 4.11-4.03 (m, 4H), 3.21 (m, 4H), 2.47 (s, 3H). LCMS MH+ m/z 474.

Example 16

(2R)-8-Fluoro-4-({6-[2-(2-hydroxypropan-2-yl)pyrimidin-5-yl]-2-methylimidazo[1,2-a]-pyridin-3-yl}methyl)-2-methyl-3,4-dihydro-2H-1,4-benzoxazin-3-one Prepared from Intermediate 29 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-d$_6$) 9.14 (s, 2H), 8.86 (s, 1H), 7.70 (dd, J 9.3, 1.6 Hz, 1H), 7.61 (d, J 9.3 Hz, 1H), 7.16 (d, J 8.2 Hz, 1H), 7.05 (td, J 8.3, 5.8 Hz, 1H), 7.03-6.97 (m, 1H), 5.71 (d, J 16.5 Hz, 1H), 5.59 (d, J 16.5 Hz, 1H), 5.17 (s, 1H), 4.97 (q, J 6.7 Hz, 1H), 2.35 (s, 3H), 1.56 (s, 6H), 1.52 (d, J 6.7 Hz, 3H). LCMS m/z 462.

Example 17

Ethyl 1-(5-{3-[(8-Fluoro-3-oxo-3,4-dihydro-2H-1,4-benzoxazin-4-yl)methyl]-2-methyl-imidazo[1,2-a]pyridin-6-yl}pyrimidin-2-yl)-4-methylpiperidine-4-carboxylate Prepared from Intermediate 21 and Intermediate 153 by a method analogous to that used to prepare Example 1. $\delta_H$ (500 MHz, DMSO-d$_6$) 8.68 (s, 2H), 8.64 (s, 1H), 7.55 (dd, J 9.3, 1.5 Hz, 1H), 7.52 (d, J 9.2 Hz, 1H), 7.14 (d, J 8.2 Hz, 1H), 7.07-6.96 (m, 2H), 5.61 (s, 2H), 4.87 (s, 2H), 4.28 (dt, J 13.4, 4.3 Hz, 2H), 4.15 (q, J 7.1 Hz, 2H), 3.36-3.33 (m, 2H), 2.37 (s, 3H), 2.04 (d, J 13.7 Hz, 2H), 1.44 (ddd, J 13.7, 10.2, 3.9 Hz, 2H), 1.22 (t, J 7.1 Hz, 3H), 1.20 (s, 3H). LCMS m/z 559.

Example 18

8-Fluoro-4-({6-[6-(2-hydroxypropan-2-yl)pyridin-3-yl]-2-methylimidazo[1,2-a]pyridin-3-yl}methyl)-3,4-dihydro-2H-1,4-benzoxazin-3-one Prepared from Intermediate 21 and 5-(4,4,5,5-tetramethyl-1,3,2-dioxaborolan-2-yl)-2-{2-[(trimethylsilyl)oxy]propan-2-yl}pyridine by a method analogous to that used to prepare Example 1, followed by treatment with TBAF at room temperature. $\delta_H$ (500 MHz, DMSO-d$_6$) 8.82 (d, J 2.2

Hz, 1H), 8.75 (s, 1H), 8.04 (dd, J 8.3, 2.4 Hz, 1H), 7.78 (d, J 8.2 Hz, 1H), 7.63 (dd, J 9.3, 1.7 Hz, 1H), 7.57 (d, J 9.3 Hz, 1H), 7.19 (d, J 8.3 Hz, 1H), 7.06 (td, J 8.3, 5.7 Hz, 1H), 7.00 (t, J 8.7 Hz, 1H), 5.64 (s, 2H), 5.31 (s, 1H), 4.88 (s, 2H), 2.39 (s, 3H), 1.50 (s, 6H). LCMS m/z 447.

Example 19

8-Fluoro-4-({2-methyl-6-[2-(3-oxopiperazin-1-yl)pyrimidin-5-yl]imidazo[1,2-a]pyridin-3-yl}methyl)-3,4-dihydro-2H-1,4-benzoxazin-3-one Prepared from Intermediate 21 and Intermediate 147 by a method analogous to that used to prepare Example 1. $\delta_H$ (500 MHz, DMSO-$d_6$) 8.76 (s, 2H), 8.67 (s, 1H), 8.14 (s, 1H), 7.57 (dd, J 9.3, 1.5 Hz, 1H), 7.54 (d, J 9.2 Hz, 1H), 7.15 (d, J 8.2 Hz, 1H), 7.07-6.96 (m, 2H), 5.61 (s, 2H), 4.87 (s, 2H), 4.25 (s, 2H), 4.00-3.95 (m, 2H), 3.32-3.29 (m, 2H, under water peak), 2.37 (s, 3H). LCMS m/z 488.

Example 20

1-(5-{3-[(8-Fluoro-3-oxo-3,4-dihydro-2H-1,4-benzoxazin-4-yl)methyl]-2-methylimidazo-[1,2-a]pyridin-6-yl}pyridin-2-yl)-4-methylpiperidine-4-carboxylic acid Example 17 (150 mg, 0.27 mmol) and 1,4-dioxane (4.7 mL) were stirred in a pressure tube. Aqueous lithium hydroxide solution (2M, 1.34 mL, 2.7 mmol) was added portionwise and the reaction mixture was heated with continuous stirring at 100° C. for 2 h. The solution was cooled to room temperature and acidified to pH 2-3 with 4M HCl in 1,4-dioxane. The solvent was removed in vacuo. The solid was azeotroped with toluene (3×20 mL). The residue was partitioned between water (3 mL) and isopropanol/chloroform (1:1, 3 mL). The organic phase was decanted off and the aqueous phase was further extracted with isopropanol/chloroform (1:1, 3 mL). The organic phases were combined and dried over sodium sulphate, then the solvent was removed in vacuo, to afford the title compound (114.1 mg, 80%) as a beige solid. $\delta_H$ (500 MHz, DMSO-$d_6$) 12.48 (s, 1H), 9.05 (s, 1H), 8.79 (s, 2H), 8.22 (d, J 9.2 Hz, 1H), 7.95 (d, J 9.3 Hz, 1H), 7.25 (d, J 7.8 Hz, 1H), 7.12-7.03 (m, 2H), 5.70 (s, 2H), 4.88 (s, 2H), 4.30 (dt, J 13.3, 4.3 Hz, 2H), 3.39-3.35 (m, 2H, under water peak), 2.45 (s, 3H), 2.06-2.00 (m, 2H), 1.40 (ddd, J 13.7, 10.3, 3.9 Hz, 2H), 1.20 (s, 3H). LCMS MH+ m/z 531.

Example 21

(2R)-8-Fluoro-2-methyl-4-({2-methyl-6-[2-(3-oxopiperazin-1-yl)pyrimidin-5-yl]imidazo-[1,2-a]pyridin-3-yl}methyl)-3,4-dihydro-2H-1,4-benzoxazin-3-one Intermediate 29 (150 mg, 0.37 mmol) and Intermediate 147 (91 mg, 0.41 mmol) were dissolved in anhydrous 1,4-dioxane (4.5 mL). Aqueous sodium carbonate solution (2M, 0.56 mL, 1.11 mmol) was added and the reaction mixture was degassed with nitrogen gas for 10 minutes. Bis[3-(diphenylphosphanyl)cyclopenta-2,4-dien-1-yl]irondichloropalladium-dichloromethane complex (15 mg, 0.019 mmol) was added and the reaction mixture was degassed with nitrogen gas for another 5 minutes. The reaction mixture was heated with stirring in a pressure tube at 100° C. for 1 h, then cooled to room temperature. The precipitate which formed was collected by filtration. Ethyl acetate (25 mL) and water (20 mL) were added to the filtrate. The aqueous layer was extracted with ethyl acetate (20 mL). The organic phases were combined, washed with brine (15 mL) and dried over sodium sulphate, then the solvent was removed in vacuo. The residue and precipitate were combined and purified on silica (Biotage, 10 g), eluting with 0-10% methanol in dichloromethane, to afford the title compound (82.7 mg, 44%) as an off-white solid. $\delta_H$ (500 MHz, DMSO-$d_6$) 8.75 (s, 2H), 8.63 (s, 1H), 8.14 (s, 1H), 7.57 (dd, J 9.3, 1.5 Hz, 1H), 7.53 (d, J 9.3 Hz, 1H), 7.14 (d, J 8.2 Hz, 1H), 7.04 (td, J 8.3, 5.8 Hz, 1H), 6.99 (t, J 8.9 Hz, 1H), 5.69 (d, J 16.5 Hz, 1H), 5.55 (d, J 16.5 Hz, 1H), 4.96 (q, J 6.7 Hz, 1H), 4.24 (s, 2H), 4.00-3.94 (m, 2H), 3.36-3.30 (m, 2H, under water peak), 2.35 (s, 3H), 1.51 (d, J 6.7 Hz, 3H). LCMS MH+ m/z 502.

Example 22

8-Fluoro-4-({2-methyl-6-[6-(piperazin-1-yl)pyridin-3-yl]imidazo[1,2-a]pyridin-3-yl}-methyl)-3,4-dihydro-2H-1,4-benzoxazin-3-one Intermediate 30 (258 mg, 0.43 mmol) was stirred in 1,4-dioxane (4 mL) and 4M HCl in 1,4-dioxane (1 mL) was added. The reaction mixture was stirred and heated at 50° C. for 45 minutes. The reaction mixture was concentrated in vacuo to approximately 1 mL and 4M HCl in 1,4-dioxane (2 mL) was added. The reaction mixture was heated at 70° C. for 30 minutes, then stirred at room temperature for 12 h. The reaction mixture was concentrated in vacuo and purified on silica (SCX cartridge, 2 g), eluting with methanol and 7M methanolic ammonia, then concentrated in vacuo, to afford the title compound (66 mg, 32%) as a cream solid. $\delta_H$ (500 MHz, CD$_3$OD) 8.50 (s, 1H), 8.35 (d, J 2.5 Hz, 1H), 7.78 (dd, J 8.9, 2.5 Hz, 1H), 7.54 (dd, J 9.3, 1.4 Hz, 1H), 7.48 (d, J 9.3 Hz, 1H), 7.14 (d, J 8.4 Hz, 1H), 7.02 (td, J 8.4, 5.4 Hz, 1H), 6.89 (dd, J 20.4, 9.2 Hz, 2H), 5.62 (s, 2H), 4.77 (s, 2H), 4.59 (s, 1H), 3.62-3.56 (m, 4H), 3.02-2.95 (m, 4H), 2.52 (s, 3H). LCMS MH+ m/z 473.

Example 23

Methyl (1S,5R)-3-(5-{3-[(8-fluoro-3-oxo-3,4-dihydro-2H-1,4-benzoxazin-4-yl)methyl]-2-methylimidazo[1,2-a]pyridin-6-yl}pyrimidin-2-yl)-3-azabicyclo[3.2.1]octane-8-carboxylate Intermediate 21 (0.2 g, 0.51 mmol) and Intermediate 154 (0.31 g, 1.08 mmol) were dissolved in 1,4-dioxane (15 mL). Aqueous sodium carbonate solution (2M, 0.75 mL, 1.50 mmol) was added and the resulting mixture was degassed with nitrogen for 30 minutes. Dichlorobis(triphenylphosphine)palladium(II) (18 mg, 0.03 mmol) was added, then the reaction mixture was stirred and heated at 120° C. under an atmosphere of nitrogen for 1 h. The reaction mixture was cooled to room temperature and water (50 mL) was added, then the mixture was extracted using ethyl acetate (70 mL). Brine (30 mL) was added and the aqueous phase was re-extracted using ethyl acetate (3×50 mL). The combined organic layers were dried over sodium sulfate and concentrated in vacuo The crude residue was purified on silica (Biotage, 25 g), eluting with 0-10% methanol in dichloromethane, followed by trituration using heptane in ethyl acetate, to afford the title compound (121.5 mg, 42%) as a white solid. $\delta_H$ (500 MHz, CDCl$_3$) 8.49 (s, 2H), 8.43 (s, 1H), 7.61 (d, J 9.2 Hz, 1H), 7.35 (d, J 9.2 Hz, 1H), 6.97-6.90 (m, 2H), 6.88-6.79 (m, 1H), 5.51 (s, 2H), 4.75 (s, 2H), 4.55 (dd, J 13.0, 2.9 Hz, 2H), 3.71 (s, 3H), 3.07 (d, J 12.6 Hz, 2H), 2.75 (s, 2H), 2.67 (s, 1H), 2.63 (s, 3H), 1.94-1.74 (m, 2H), 1.58 (d, J 7.9 Hz, 2H). LCMS MH+ m/z 556.

Example 24

(2R)-8-Fluoro-4-{[6-(3-methanesulfonylphenyl)-2-methylimidazo[1,2-a]pyridin-3-yl]-methyl}-2-methyl-3,4-dihydro-2H-1,4-benzoxazin-3-one Intermediate 29 (160 mg, 0.4 mmol) and 3-(methanesulfonyl)phenylboronic acid (87 mg, 0.44 mmol) were dissolved in anhydrous 1,4-dioxane (3 mL). Aqueous sodium carbonate solution (2M, 0.59 mL, 1.18 mmol) was added and the reaction mixture was degassed with nitrogen gas for 10 minutes. Bis[3-(diphenylphosphanyl)cyclopenta-2,4-dien-1-yl]iron-dichloropalladium-dichloromethane complex (16 mg, 0.02 mmol) was added and the reaction mixture was degassed with nitrogen gas for another 5 minutes. The reaction mixture was continuously stirred and heated in a pressure tube at 100° C. for 1 h, then cooled to room temperature, diluted with ethyl acetate (30 mL), filtered and concentrated in vacuo. The crude residue was purified by preparative HPLC to afford the title compound (41.6 mg, 22%) as a white solid. $\delta_H$ (500 MHz, DMSO-$d_6$) 8.74 (s, 1H), 8.20 (s, 1H), 8.01 (d, J 8.0 Hz, 1H), 7.95 (d, J 7.8 Hz, 1H), 7.80 (t, J 7.8 Hz, 1H), 7.68 (dd, J 9.3, 1.7 Hz, 1H), 7.58 (d, J 9.3 Hz, 1H), 7.18 (d, J 8.2 Hz, 1H), 7.06 (ddd, J 5, 10, 15 Hz, 1H), 6.99 (t, J 8.9 Hz, 1H), 5.71 (d, J 16.5 Hz, 1H), 5.60 (d, J 16.4 Hz, 1H), 4.96 (q, J 6.7 Hz, 1H), 2.37 (s, 3H), 1.52 (d, J 6.7 Hz, 3H); Me peak under DMSO. LCMS MH+m/z 480.

Example 25

(1r,4r)-4-(5-{3-[8-Fluoro-3-oxo-1,4-benzoxazin-4-yl)methyl]-2-methylimidazo[1,2-a]-pyridin-6-yl}pyrimidin-2-yl)cyclohexanecarboxylic acid Intermediate 32 (140 mg, 0.26 mmol) and 2M sodium ethoxide in ethanol (0.64 mL) [freshly prepared by dissolving sodium metal (1.15 g) in ethanol (25 mL) and heating under reflux at 80° C. for 1 h] was stirred in ethanol (10 mL) and heated at 80° C. for 16 h. The reaction mixture was quenched with saturated aqueous ammonium chloride solution and concentrated in vacuo. Water (2 mL) was added and the mixture was acidified with 4N HCl (20 eq) in 1,4-dioxane, then concentrated in vacuo. The mixture was dissolved in toluene (5 mL) and concentrated in vacuo. The residue was acidified to pH 2 with 4M HCl in 1,4-dioxane, then partitioned between 2-propanol:chloroform (1:1; 50 mL) and water (3 mL). The aqueous layer was separated and further extracted into 2-propanol:chloroform (2×10 mL). The combined organic extracts were washed with brine (10 mL), dried over sodium sulfate and concentrated in vacuo. The residue was purified by preparative HPLC to afford the title compound (14 mg, 10.5%) as a cream solid. $\delta_H$ (500 MHz, DMSO-$d_6$) 9.02 (s, 2H), 8.79 (s, 1H), 7.63 (dd, J 9.3, 1.6 Hz, 1H), 7.54 (d, J 9.3 Hz, 1H), 7.10 (d, J 8.2 Hz, 1H), 6.98 (ddd, J 5.0, 10.0, 15.0 Hz, 1H), 6.94 (t, J 5.0 Hz, 1H), 5.58 (s, 2H), 4.82 (s, 2H), 2.82 (tt, J 5.0, 11.8 Hz, 1H), 2.31 (s, 3H), 2.23 (tt, J 5.0, 10.0 Hz, 1H), 2.04-1.97 (m, 4H), 1.66-1.55 (m, 2H), 1.51-1.40 (m, 2H). LCMS MH+m/z 498.

Example 26

(2R)-8-Fluoro-4-({7-fluoro-6-[2-(2-hydroxypropan-2-yl)pyrimidin-5-yl]-2-methyl-imidazo[1,2-a]pyridin-3-yl}methyl)-2-methyl-3,4-dihydro-2H-1,4-benzoxazin-3-one Intermediate 35 (278 mg, 0.5 mmol) and 2-[5-(4,4,5,5-tetramethyl-1,3,2-dioxaborolan-2-yl)pyrimidin-2-yl]propan-2-ol (146 mg, 0.55 mmol) were dissolved in anhydrous 1,4-dioxane (5 mL). Aqueous sodium carbonate solution (2M, 0.75 mL, 1.5 mmol) was added and the reaction mixture was degassed with nitrogen gas for 10 minutes. Bis[3-(diphenylphosphanyl)cyclopenta-2,4-dien-1-yl]iron-dichloropalladium-dichloromethane complex (20 mg, 0.025 mmol) was added and the reaction mixture was degassed with nitrogen gas for another 5 minutes. The reaction mixture was heated with continuous stirring in a pressure tube at 100° C. for 1 h, then cooled to room temperature. Ethyl acetate (25 mL) and water (20 mL) were added to the solution, and the aqueous layer was extracted with ethyl acetate (20 mL). The organic phases were combined, washed with brine (15 mL), dried over sodium sulphate and filtered, then the solvent was removed in vacuo. The residue was purified on silica (Biotage, 10 g), eluting with 0-10% methanol in dichloromethane, followed by preparative HPLC. The residue was triturated in ether to give the title compound (73.1 mg, 30%) as a white solid. $\delta_H$ (500 MHz, DMSO-$d_6$) 9.03 (d, J 1.1 Hz, 2H), 8.77 (d, J 7.4 Hz, 1H), 7.55 (d, J 11.2 Hz, 1H), 7.15 (d, J 8.2 Hz, 1H), 7.05 (td, J 8.3, 5.8 Hz, 1H), 7.03-6.97 (m, 1H), 5.65 (d, J 16.6 Hz, 1H), 5.54 (d, J 16.6 Hz, 1H), 5.20 (s, 1H), 4.94 (q, J 6.6 Hz, 1H), 2.30 (s, 3H), 1.56 (s, 6H), 1.50 (d, J 6.7 Hz, 3H). LCMS MH+ m/z 480.5.

Example 27

(2R)-6,8-Fluoro-4-({7-fluoro-6-[2-(2-hydroxypropan-2-yl)pyrimidin-5-yl]-2-methyl-imidazo[1,2-a]pyridin-3-yl}methyl)-2-methyl-3,4-dihydro-2H-1,4-benzoxazin-3-one Intermediate 38 (220 mg, 0.45 mmol) and 2-[5-(4,4,5,5-tetramethyl-1,3,2-dioxaborolan-2-yl)pyrimidin-2-yl]propan-2-ol (131 mg, 0.49 mmol) were dissolved in anhydrous 1,4-dioxane (5 mL). Aqueous sodium carbonate solution (2M, 0.67 mL, 1.35 mmol) was added and the reaction mixture was degassed with nitrogen gas for 10 minutes. Bis[3-(diphenylphosphanyl)cyclopenta-2,4-dien-1-yl]iron-dichloropalladium-dichloromethane complex (18 mg, 0.022 mmol) was added and the reaction mixture was degassed with nitrogen gas for another 5 minutes. The reaction mixture was heated with continuous stirring at 100° C. for 1 h, then cooled to room temperature. Ethyl acetate (25 mL) and water (20 mL) were added to the reaction mixture. The aqueous layer was extracted with ethyl acetate (20 mL). The organic phases were combined, washed with brine (20 mL), dried over sodium sulphate and filtered, then the solvent was removed in vacuo. The residue was purified on silica (Biotage, 10 g), eluting with 0-10% methanol in dichloromethane, then triturated in diethyl ether, to afford the title compound (139.1 mg, 60%) as a white solid. $\delta_H$ (500 MHz, DMSO-$d_6$) 9.03 (d, J 0.8 Hz, 2H), 8.79 (d, J 7.3 Hz, 1H), 7.56 (d, J 11.2 Hz, 1H), 7.24 (dt, J 10.5, 2.0 Hz, 1H), 7.15-7.07 (m, 1H), 5.65 (d, J 16.6 Hz, 1H), 5.51 (d, J 16.6 Hz, 1H), 5.19 (s, 1H), 4.93 (q, J 6.6 Hz, 1H), 2.30 (s, 3H), 1.56 (s, 6H), 1.48 (d, J 6.7 Hz, 3H). LCMS MH+ m/z 498.

Example 28

4-(5-{3-[(8-Fluoro-2-methyl-3-oxo-3,4-dihydro-2H-1,4-benzoxazin-4-yl)methyl]-2-methylimidazo[1,2-a]pyridin-6-yl}pyrimidin-2-yl)cyclohexane-1-carboxylic acid Intermediate 40 (223 mg, 0.4 mmol) and sodium ethoxide [freshly prepared by dissolving sodium metal (1.15 g) in ethanol (25 mL) and heating under reflux at 80° C. for 1 h] were dissolved in ethanol (10 mL) and heated with stirring at 80° C. overnight. The reaction mixture was quenched with saturated ammonium chloride solution and concentrated in vacuo. Water (2 mL) was added and the solution was acidified with 4M HCl (20 eq) in 1,4-dioxane, then concentrated in vacuo. The mixture was dissolved in toluene (5 mL) and concentrated in vacuo. The reaction mixture was acidified to pH 2 with 4M HCl in 1,4-dioxane, then partitioned between 2-propanol:chloroform (1:1, 50 mL) and water (3 mL). The aqueous layer was further extracted into 2-propanol:chloro-form (2×10 mL). The combined organic extracts were washed with brine (10 mL), dried over sodium sulfate and concentrated in vacuo. The residue was purified by preparative HPLC to afford the title compound (20 mg, 9.5%) as a pale yellow solid. $\delta_H$ (500 MHz, DMSO-$d_6$) 9.06 (s, 2H), 8.81 (s, 1H), 7.67 (dd, J 9.3, 1.7 Hz, 1H), 7.59 (d, J 9.2 Hz, 1H), 7.16 (s, 1H), 7.08-7.01 (m, 1H), 6.99 (t, J 9.2 Hz, 1H), 5.70 (d, J 16.5 Hz, 1H), 5.57 (d, J 16.5 Hz, 1H), 4.96 (q, J 6.7 Hz, 1H), 2.87 (tt, J 11.9, 3.1 Hz, 1H), 2.33 (s, 3H), 2.27 (tt, J 11.9, 2.8 Hz, 1H), 2.10-2.00 (m, 4H), 1.65 (qd, J 14.7, 14.0, 3.8 Hz, 2H), 1.56-1.44 (m, 5H). LCMS MH+ m/z 530.

Example 29

(2R)-6,8-Difluoro-4-({7-fluoro-6-[2-(3-hydroxyoxetan-3-yl)pyrimidin-5-yl]-2-methyl-imidazo[1,2-a]pyridin-3-yl}methyl)-2-methyl-3,4-dihydro-2H-1,4-benzoxazin-3-one Prepared from Intermediate 38 and Intermediate 43 by a method analogous to that used to prepare Example 1, followed by treatment with TBAF at room temperature. $\delta_H$ (500 MHz, DMSO-$d_6$) 9.12 (d, J 1.2 Hz, 2H), 8.81 (d, J 7.3 Hz, 1H), 7.58 (d, J 11.2 Hz, 1H), 7.24 (d, J 10.4 Hz, 1H), 7.15-7.07 (m, 1H), 6.48 (s, 1H), 5.66 (d, J 16.6 Hz, 1H), 5.52 (d, J 16.6 Hz, 1H), 5.05 (d, J 6.6 Hz, 2H), 4.93 (q, J 6.7 Hz, 1H), 4.74 (d, J 6.6 Hz, 2H), 2.31 (s, 3H), 1.49 (d, J 6.7 Hz, 3H). LCMS m/z 512.

Example 30

(2R)-8-Fluoro-4-({7-fluoro-2-methyl-6-[2-(3-oxopiperazin-1-yl)pyrimidin-5-yl]imidazo-[1,2-a]pyridin-3-yl}methyl)-2-methyl-3,4-dihydro-2H-1,4-benzoxazin-3-one Prepared from Intermediate 35 and Intermediate 147 by a method analogous to that used to prepare Example 1. $\delta_H$ (500 MHz, DMSO-$d_6$) 8.62 (d, J 1.2 Hz, 2H), 8.57 (d, J 7.4 Hz, 1H), 8.16 (s, 1H), 7.48 (d, J 11.1 Hz, 1H), 7.15 (d, J 8.2 Hz, 1H), 7.09-6.98 (m, 2H), 5.65 (d, J 16.5 Hz, 1H), 5.53 (d, J 16.5 Hz, 1H), 4.94 (q, J 6.7 Hz, 1H), 4.26 (s, 2H), 4.02-3.95 (m, 2H), 3.44-3.36 (m, 2H), 2.32 (s, 3H), 1.50 (d, J 6.7 Hz, 3H); CH$_2$ peak assumed to be under solvent. LCMS m/z 520.

Example 31

(2R)-8-Fluoro-4-({7-fluoro-6-[2-(3-hydroxyoxetan-3-yl)pyrimidin-5-yl]-2-methyl-imidazo[1,2-a]pyridin-3-yl}methyl)-2-methyl-3,4-dihydro-2H-1,4-benzoxazin-3-one Prepared from Intermediate 35 and Intermediate 43 by a method analogous to that used to prepare Example 1, followed by treatment with TBAF at room temperature. $\delta_H$ (500 MHz, DMSO-$d_6$) 9.12 (d, J 1.1 Hz, 2H), 8.79 (d, J 7.3 Hz, 1H), 7.57 (d, J 11.3 Hz, 1H), 7.16 (d, J 8.2 Hz, 1H), 7.06 (td, J 8.3, 5.8 Hz, 1H), 7.01 (t, J 8.7 Hz, 1H), 6.48 (s, 1H), 5.65 (d, J 16.6 Hz, 1H), 5.55 (d, J 16.6 Hz, 1H), 5.05 (d, J 6.6 Hz, 2H), 4.95 (q, J 6.7 Hz, 1H), 4.74 (d, J 6.6 Hz, 2H), 2.32 (s, 3H), 1.50 (d, J 6.7 Hz, 3H). LCMS m/z 494.

Example 32

(2R)-6,8-Difluoro-4-({7-fluoro-6-[2-(3-hydroxyazetidin-3-yl)pyrimidin-5-yl]-2-methyl-imidazo[1,2-a]pyridin-3-yl}methyl)-2-methyl-3,4-dihydro-2H-1,4-benzoxazin-3-one Intermediate 47 (145 mg, 0.23 mmol) was suspended in dichloromethane (1.5 mL) and cooled to 0° C. with stirring. Trifluoroacetic acid (0.2 mL, 2.59 mmol) was added dropwise and the reaction mixture was allowed to warm to ambient temperature. Stirring was continued for another 2 h. The solvent was removed in vacuo and the residue was triturated in diethyl ether to afford the title compound (130.1 mg, 92%) trifluoroacetate salt as a pink solid. $\delta_H$ (500 MHz, DMSO-$d_6$) 9.28-9.12 (m, 3H), 8.95 (d, J 7.0 Hz, 1H), 8.83 (s, 1H), 7.79 (d, J 10.7 Hz, 1H), 7.30 (d, J 10.2 Hz, 1H), 7.19-7.11 (m, 1H), 7.00 (s, 1H), 5.68 (d, J 16.7 Hz, 1H), 5.57 (d, J 16.7 Hz, 1H), 4.94 (q, J 6.7 Hz, 1H), 4.59 (dt, J 11.6, 7.0 Hz, 2H), 4.22-4.12 (m, 2H), 2.37 (s, 3H), 1.50 (d, J 6.7 Hz, 3H). LCMS MH+ m/z 511.

Example 33

(2R)-6,8-Difluoro-4-({7-fluoro-6-[2-(4-hydroxytetrahydropyran-4-yl)pyrimidin-5-yl]-2-methylimidazo[1,2-a]pyridin-3-yl}methyl)-2-methyl-1,4-benzoxazin-3-one Prepared from Intermediate 38 and Intermediate 50 by a method analogous to that used to prepare Example 1, followed by treatment with TBAF at room temperature. $\delta_H$ (500 MHz, DMSO-$d_6$) 9.07 (d, J 1.3 Hz, 2H), 8.79 (d, J 7.3 Hz, 1H), 7.57 (d, J 11.2 Hz, 1H), 7.27-7.20 (m, 1H), 7.15-7.07 (m, 1H), 5.65 (d, J 16.7 Hz, 1H), 5.51 (d, J 16.6 Hz, 1H), 5.35 (s, 1H), 4.93 (q, J 6.7 Hz, 1H), 3.81 (td, J 11.0, 2.2 Hz, 2H), 3.71 (dt, J 10.7, 3.7 Hz, 2H), 2.30 (s, 3H), 2.27-2.20 (m, 2H), 1.77 (d, J 12.1 Hz, 2H), 1.48 (d, J 6.7 Hz, 3H). LCMS m/z 540.

Example 34

(2R)-8-Fluoro-4-({7-fluoro-6-[2-(1-hydroxycyclobutyl)pyrimidin-5-yl]-2-methylimidazo-[1,2-a]pyridin-3-yl}methyl)-2-methyl-3,4-dihydro-2H-1,4-benzoxazin-3-one Prepared from Intermediate 35 and Intermediate 53 by a method analogous to that used to prepare Example 1, followed by treatment with TBAF at room temperature. $\delta_H$ (500 MHz, DMSO-d$_6$) 9.06 (d, J 1.3 Hz, 2H), 8.77 (d, J 7.3 Hz, 1H), 7.56 (d, J 11.2 Hz, 1H), 7.15 (d, J 8.2 Hz, 1H), 7.05 (td, J 8.3, 5.8 Hz, 1H), 7.00 (t, J 9.3 Hz, 1H), 5.70 (s, 1H), 5.65 (d, J 16.6 Hz, 1H), 5.54 (d, J 16.6 Hz, 1H), 4.94 (q, J 6.7 Hz, 1H), 2.72-2.65 (m, 2H), 2.35-2.33 (m, 2H), 2.32 (s, 3H), 1.96-1.87 (m, 1H), 1.81-1.70 (m, 1H), 1.50 (d, J 6.7 Hz, 3H). LCMS m/z 492.

Example 35

(2R)-8-Fluoro-4-(1-{7-fluoro-6-[2-(2-hydroxypropan-2-yl)pyrimidin-5-yl]-2-methyl-imidazo[1,2-a]pyridin-3-yl}ethyl)-2-methyl-3,4-dihydro-2H-1,4-benzoxazin-3-one Single unknown diastereoisomer prepared from Intermediate 55 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, CDCl$_3$) 8.81 (s, 2H), 7.92 (d, J 7.0 Hz, 1H), 7.30 (d, J 10.4 Hz, 1H), 6.91 (d, J 7.9 Hz, 1H), 6.87-6.74 (m, 2H), 6.60 (q, J 7.2 Hz, 1H), 4.72 (q, J 6.9 Hz, 1H), 4.59 (s, 1H), 2.72 (s, 3H), 2.06 (d, J 7.3 Hz, 3H), 1.65 (s, 6H), 1.61 (d, J 6.9 Hz, 3H). LCMS m/z 494.

Example 36

(2R)-8-Fluoro-4-(1-{7-fluoro-6-[2-(2-hydroxypropan-2-yl)pyrimidin-5-yl]-2-methyl-imidazo[1,2-a]pyridin-3-yl}ethyl)-2-methyl-3,4-dihydro-2H-1,4-benzoxazin-3-one Single unknown diastereoisomer prepared from Intermediate 55 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, CDCl$_3$) 8.81 (s, 2H), 8.20 (d, J 6.4 Hz, 1H), 7.60 (d, J 10.1 Hz, 1H), 6.98-6.82 (m, 3H), 6.45 (q, J 7.0 Hz, 1H), 4.66 (q, J 6.7 Hz, 1H), 2.69 (s, 3H), 2.01 (d, J 7.3 Hz, 3H), 1.67 (s, 6H), 1.61 (d, J 6.7 Hz, 3H). LCMS m/z 494.

Example 37

8-Fluoro-4-({7-fluoro-6-[2-(2-hydroxypropan-2-yl)pyrimidin-5-yl]-2-methylimidazo[1,2-a]pyridin-3-yl}methyl)-2,2-dimethyl-3,4-dihydro-2H-1,4-benzoxazin-3-one Intermediate 58 (200 mg, 0.28 mmol) and 2-[5-(4,4,5,5-tetramethyl-1,3,2-dioxaborolan-2-yl)pyrimidin-2-yl]propan-2-ol (100 mg, 0.38 mmol) were dissolved in 1,4-dioxane (3 mL) and 2M aqueous sodium carbonate solution (0.44 mL, 0.88 mmol) was added. The resulting mixture was degassed with a stream of nitrogen for 5 minutes, then bis[3-(diphenylphosphanyl)cyclopenta-2,4-dien-1-yl]irondichloropalladium-dichloromethane complex (12 mg, 0.01 mmol) was added. The reaction mixture was heated with continual stirring in a sealed tube at 100° C. for 1 h, then diluted with ethyl acetate (5 mL) and washed with water (3 mL). The aqueous layer was re-extracted with ethyl acetate (3 mL), then the combined organic layers were dried over sodium sulfate and concentrated in vacuo. The crude residue was purified on silica (Biotage, 10 g), eluting with 0-5% methanol in dichloromethane. The residue was suspended in water (15 mL) and sonicated for 30 minutes, then filtered, to afford the title compound (65 mg, 46.3%) as a white solid. $\delta_H$ (500 MHz, DMSO-d$_6$) 9.03 (s, 2H), 8.75 (d, J 7.2 Hz, 1H), 7.55 (d, J 11.1 Hz, 1H), 7.14 (d, J 7.9 Hz, 1H), 7.08-6.95 (m, 2H), 5.60 (s, 2H), 5.20 (s, 1H), 2.29 (s, 3H), 1.56 (s, 6H), 1.46 (s, 6H). LCMS MH+ m/z 494.

Example 38

(2R)-8-Fluoro-4-({7-fluoro-6-[2-(3-hydroxy-1-methylazetidin-3-yl)pyrimidin-5-yl]-2-methylimidazo[1,2-a]pyridin-3-yl}methyl)-2-methyl-3,4-dihydro-2H-1,4-benzoxazin-3-one formic acid salt Intermediate 60 (195 mg, 0.37 mmol) was suspended in ethanol (4 mL) and 37% aqueous formaldehyde (0.12 mL, 1.67 mmol) was added. The resulting solution was stirred at room temperature for 20 minutes, then sodium triacetoxyborohydride (200 mg, 0.94 mmol) was added, followed by acetic acid (0.1 mL). The reaction mixture was stirred under nitrogen for 16 h, then treated with additional 37% aqueous formaldehyde (0.12 mL, 1.67 mmol) and additional sodium triacetoxyborohydride (200 mg, 0.94 mmol). The reaction mixture was stirred under nitrogen for 7 h, heated with continuous stirring at 50° C. for 2 h, then allowed to cool to room temperature. The mixture was re-treated with sodium triacetoxyborohydride (200 mg, 0.94 mmol) and stirred under nitrogen for 2 h, then quenched with saturated aqueous sodium hydrogencarbonate solution (15 mL). The resulting solution was extracted with dichloromethane (2×20 mL). The precipitate which formed was isolated by filtration. The aqueous layer was re-extracted with dichloromethane (2×20 mL). The precipitate which formed was isolated by filtration. The solids and the organic layers were combined and concentrated in vacuo. The crude residue was purified by preparative HPLC to afford the title compound (26 mg, 12.8%) as a white solid. $\delta_H$ (500 MHz, CD$_3$OD) 9.12 (s, 2H), 8.76 (d, J 7.0 Hz, 1H), 8.40 (s, 1H), 7.35 (d, J 10.8 Hz, 1H), 7.17 (d, J 8.4 Hz, 1H), 7.05 (td, J 8.4, 5.4 Hz, 1H), 6.90 (t, J 8.8 Hz, 1H), 5.69 (d, J 16.5 Hz, 1H), 5.54 (d, J 16.6 Hz, 1H), 4.82-4.71 (m, 3H), 4.40 (d, J 11.4 Hz, 2H), 3.12 (s, 3H), 2.48 (s, 3H), 1.55 (d, J 6.7 Hz, 3H). LCMS MH+ m/z 507.

Example 39

(7R)-5-({6-[2-(2-Hydroxypropan-2-yl)pyrimidin-5-yl]-2-methylimidazo[1,2-a]pyrazin-3-yl}methyl)-7-methyl-5H,6H,7H-pyrimido[4,5-b][1,4]oxazin-6-one Prepared from Intermediate 63 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-d$_6$) 9.36 (s, 2H), 9.22 (d, J 1.3 Hz, 1H), 9.10 (d, J 1.3 Hz, 1H), 8.61 (s, 1H), 8.51 (s, 1H), 5.69 (d, J 16.6 Hz, 1H), 5.64 (d, J 16.6 Hz, 1H), 5.32 (q, J 6.8 Hz, 1H), 5.19 (s, 1H), 2.39 (s, 3H), 1.58 (d, J 6.8 Hz, 3H), 1.55 (s, 6H). LCMS m/z 447.

Example 40

(2R)-6,8-Difluoro-4-({6-[2-(2-hydroxypropan-2-yl)pyrimidin-5-yl]-2-methylimidazo[1,2-a]pyrazin-3-yl}methyl)-2-methyl-3,4-dihydro-2H-1,4-benzoxazin-3-one Prepared from Intermediate 64 and 2-[5-(4,4,5,5-tetramethyl-1,3,2-dioxaborolan-2-yl)pyrimidin-2-yl]propan-2-ol by a method analogous to that used to prepare Example 1.

$\delta_H$ (500 MHz, DMSO-d$_6$) 9.37 (s, 2H), 9.25 (d, J 1.2 Hz, 1H), 9.09 (d, J 1.2 Hz, 1H), 7.30-7.25 (m, 1H), 7.12 (ddd, J 11.5, 9.2, 2.7 Hz, 1H), 5.71 (d, J 16.7 Hz, 1H), 5.59 (d, J 16.6 Hz, 1H), 5.19 (s, 1H), 4.95 (q, J 6.7 Hz, 1H), 2.34 (s, 3H), 1.56 (s, 6H), 1.50 (d, J 6.7 Hz, 3H). LCMS m/z 481.

Example 41

(2R)-8-Fluoro-4-({6-[2-(3-hydroxyoxetan-3-yl)pyrimidin-5-yl]-2-methylimidazo[1,2-a]-pyrazin-3-yl}methyl)-2-methyl-3,4-dihydro-2H-1,4-benzoxazin-3-one Prepared from Intermediate 65 and Intermediate 66 by a method analogous to that used to prepare Example 1. $\delta_H$ (500 MHz, DMSO-d$_6$) 9.46 (s, 2H), 9.29 (s, 1H), 9.10 (s, 1H), 7.14 (d, J 7.6 Hz, 1H), 7.09-6.95 (m, 2H), 6.46 (s, 1H), 5.73 (d, J 16.6 Hz, 1H), 5.64 (d, J 16.6 Hz, 1H), 5.05 (d, J 6.4 Hz, 2H), 4.98 (q, J 6.6 Hz, 1H), 4.74 (d, J 6.4 Hz, 2H), 2.33 (s, 3H), 1.53 (d, J 6.7 Hz, 3H). LCMS m/z 521.

Example 42

8-Fluoro-4-({6-[2-(2-hydroxypropan-2-yl)pyrimidin-5-yl]-2-methylimidazo[1,2-a]pyrazin-3-yl}methyl)-2,2-dimethyl-3,4-dihydro-2H-1,4-benzoxazin-3-one Prepared from Intermediate 67 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-d$_6$) 9.38 (s, 2H), 9.25 (d, J 1.3 Hz, 1H), 9.09 (d, J 1.3 Hz, 1H), 7.15-7.11 (m, 1H), 7.06-7.00 (m, 2H), 5.68 (s, 2H), 5.19 (s, 1H), 2.31 (s, 3H), 1.55 (s, 6H), 1.49 (s, 6H). LCMS m/z 477.

Example 43

(2R)-8-Fluoro-4-({6-[2-(4-hydroxytetrahydropyran-4-yl)pyrimidin-5-yl]-2-methyl-imidazo[1,2-a]pyrazin-3-yl}methyl)-2-methyl-1,4-benzoxazin-3-one Prepared from Intermediate 50 and Intermediate 66 by a method analogous to that used to prepare Example 1, followed by treatment with TBAF at room temperature. $\delta_H$ (500 MHz, DMSO-d$_6$) 9.41 (s, 2H), 9.26 (d, J 1.1 Hz, 1H), 9.09 (d, J 1.1 Hz, 1H), 7.14 (d, J 7.5 Hz, 1H), 7.08-6.97 (m, 2H), 5.72 (d, J 16.6 Hz, 1H), 5.63 (d, J 16.6 Hz, 1H), 5.34 (s, 1H), 4.98 (q, J 6.7 Hz, 1H), 3.81 (td, J 11.0, 2.1 Hz, 2H), 3.74-3.66 (m, 2H), 2.33 (s, 3H), 2.29-2.20 (m, 2H), 1.79-1.72 (m, 2H), 1.52 (d, J 6.7 Hz, 3H).

Example 44

(2R)-4-({6-[2-(1,1-Difluoroethyl)pyrimidin-5-yl]-2-methylimidazo[1,2-a]pyrazin-3-yl}methyl)-8-fluoro-2-methyl-3,4-dihydro-2H-1,4-benzoxazin-3-one Prepared from Intermediate 66 and Intermediate 70 by a method analogous to that used to prepare Example 1. $\delta_H$ (500 MHz, CD$_3$OD) 9.48 (s, 2H), 9.22 (d, J 1.4 Hz, 1H), 9.02 (d, J 1.4 Hz, 1H), 7.21-7.14 (m, 1H), 7.06 (td, J 8.4, 5.5 Hz, 1H), 6.93 (ddd, J 9.7, 8.5, 1.2 Hz, 1H), 5.75 (d, J 16.5 Hz, 1H), 5.63 (d, J 16.6 Hz, 1H), 4.80 (q, J 6.8 Hz, 1H), 2.50 (s, 3H), 2.10 (t, J 18.6 Hz, 3H), 1.59 (d, J 6.7 Hz, 3H). LCMS m/z 469.

Example 45

(2R)-6,8-Difluoro-4-({7-fluoro-2-methyl-6-[2-(3-oxopiperazin-1-yl)pyrimidin-5-yl]-imidazo[1,2-a]pyridin-3-yl}methyl)-2-methyl-3,4-dihydro-2H-1,4-benzoxazin-3-one Prepared from Intermediate 38 and Intermediate 147 by a method analogous to that used to prepare Example 1. $\delta_H$ (500 MHz, DMSO-d$_6$) 8.62 (d, J 1.2 Hz, 2H), 8.59 (d, J 7.4 Hz, 1H), 8.15 (s, 1H), 7.48 (d, J 11.1 Hz, 1H), 7.25-7.19 (m, 1H), 7.13-7.08 (m, 1H), 5.65 (d, J 16.5 Hz, 1H), 5.50 (d, J 16.4 Hz, 1H), 4.92 (q, J 6.7 Hz, 1H), 4.25 (s, 2H), 4.00-3.95 (m, 2H), 3.35-3.30 (m, 2H, under water peak), 2.31 (s, 3H), 1.48 (d, J 6.7 Hz, 3H). LCMS m/z 538.

Example 46

4-({6-[2-(2-Hydroxypropan-2-yl)pyrimidin-5-yl]-2-methylimidazo[1,2-a]pyrazin-3-yl}-methyl)-2H,3H,4H-pyrido[4,3-b][1,4]oxazin-3-one Prepared from Intermediate 71 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, CD$_3$OD) 9.36 (s, 2H), 9.17 (d, J 1.4 Hz, 1H), 9.02 (d, J 1.4 Hz, 1H), 8.47 (s, 1H), 8.15 (d, J 5.3 Hz, 1H), 7.05 (d, J 5.3 Hz, 1H), 5.76 (s, 2H), 4.92 (s, 2H), 2.59 (s, 3H), 1.65 (s, 6H). LCMS m/z 432.

Example 47

4-({7-Fluoro-6-[2-(2-hydroxypropan-2-yl)pyrimidin-5-yl]-2-methylimidazo[1,2-a]-pyridin-3-yl}methyl)-2H,3H,4H-pyrido[3,2-b][1,4]oxazin-3-one Prepared from Intermediate 73 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-d$_6$) 9.07 (d, J 7.5 Hz, 1H), 9.04 (d, J 1.3 Hz, 2H), 8.00 (dd, J 4.8, 1.4 Hz, 1H), 7.51 (d, J 11.3 Hz, 1H), 7.39 (dd, J 7.9, 1.4 Hz, 1H), 7.06 (dd, J 7.9, 4.9 Hz, 1H), 5.59 (s, 2H), 5.19 (s, 1H), 4.85 (s, 2H), 2.47 (s, 3H), 1.56 (s, 6H). LCMS m/z 449.

Example 48

4-({6-[2-(2-Hydroxypropan-2-yl)pyrimidin-5-yl]-2-methylimidazo[1,2-a]pyrazin-3-yl}-methyl)-2H,3H,4H-pyrido[3,2-b][1,4]oxazin-3-one Prepared from Intermediate 74 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-d$_6$) 9.38 (d, J 1.3 Hz, 1H), 9.30 (s, 2H), 9.02 (d, J 1.3 Hz, 1H), 7.95 (dd, J 4.8, 1.4 Hz, 1H), 7.36 (dd, J 7.9, 1.4 Hz, 1H), 7.02 (dd, J 7.9, 4.9 Hz, 1H), 5.62 (s, 2H), 5.14 (s, 1H), 4.84 (s, 2H), 2.50 (s, 3H), 1.52 (s, 6H). LCMS m/z 432.

Example 49

6,8-Difluoro-4-[7-fluoro-6-{2-[3-hydroxy-3-(trifluoromethyl)azetidin-1-yl]pyrimidin-5-yl}-2-methyl-imidazo[1,2-a]pyridin-3-yl)methyl]-3,4-dihydro-2H-1,4-benzoxazin-3-one Prepared from Intermediate 77 and Intermediate 148 by a method analogous to that used to prepare Example 1. $\delta_H$ (500 MHz, DMSO-d$_6$) 8.65-8.60 (m, 3H), 7.56-7.41 (m, 2H), 7.23-7.17 (m, 1H), 7.10 (td, J 11.3, 10.2, 2.7 Hz, 1H), 5.57 (s, 2H), 4.84 (s, 2H), 4.36 (d, J 10.4 Hz, 2H), 4.14 (d, J 10.2 Hz, 2H), 2.34 (s, 3H). LCMS m/z 565.

Example 50

(2R)-6,8-Difluoro-2-methyl-4-({2-methyl-6-[2-(5-oxo-1,4-diazepan-1-yl)pyrimidin-5-yl]-imidazo[1,2-a]pyrazin-3-yl}methyl)-3,4-dihydro-2H-1,4-benzoxazin-3-one Prepared from Intermediate 64 and Intermediate 78 by a method analogous to that used to prepare Example 1. δ$_H$ (500 MHz, DMSO-d$_6$) 9.01-8.94 (m, 4H), 7.70 (t, J 5.3 Hz, 1H), 7.24 (d, J 10.4 Hz, 1H), 7.15-7.06 (m, 1H), 5.69 (d, J 16.5 Hz, 1H), 5.56 (d, J 16.5 Hz, 1H), 4.94 (q, J 6.7 Hz, 1H), 4.00 (t, J 7.7 Hz, 4H), 3.28-3.21 (m, 2H), 2.56-2.53 (m, 2H), 2.33 (s, 3H), 1.50 (d, J 6.7 Hz, 3H). LCMS m/z 536.

Example 51

(2R)-4-{[6-(2-{3,7-Dioxa-9-azabicyclo[3.3.1]nonan-9-yl}pyrimidin-5-yl)-7-fluoro-2-methylimidazo[1,2-a]pyridin-3-yl]methyl}-8-fluoro-2-methyl-3,4-dihydro-2H-1,4-benzoxazin-3-one Prepared from Intermediate 35 and Intermediate 106 by a method analogous to that used to prepare Example 1. δ$_H$ (500 MHz, DMSO-d$_6$) 8.62 (d, J 1.2 Hz, 2H), 8.60 (d, J 7.4 Hz, 1H), 7.48 (d, J 11.2 Hz, 1H), 7.15 (d, J 8.2 Hz, 1H), 7.06 (td, J 8.3, 5.8 Hz, 1H), 7.01 (t, J 8.7 Hz, 1H), 5.65 (d, J 16.6 Hz, 1H), 5.53 (d, J 16.5 Hz, 1H), 4.95 (q, J 6.7 Hz, 1H), 4.55 (s, 2H), 4.06 (s, 2H), 4.04 (s, 2H), 3.79 (d, J 2.2 Hz, 2H), 3.77 (d, J 2.3 Hz, 2H), 2.32 (s, 3H), 1.50 (d, J 6.7 Hz, 3H). LCMS m/z 549.

Example 52

6,8-Difluoro-4-[(7-fluoro-6-{2-[3-hydroxy-3-(trifluoromethyl)azetidin-1-yl]pyrimidin-5-yl}-2-methylimidazo[1,2-a]pyridin-3-yl)methyl]-2,2-dimethyl-3,4-dihydro-2H-1,4-benzoxazin-3-one Prepared from Intermediate 81 and Intermediate 148 by a method analogous to that used to prepare Example 1. δ$_H$ (500 MHz, DMSO-d$_6$) 8.62 (d, J 1.3 Hz, 2H), 8.58 (d, J 7.4 Hz, 1H), 7.49 (d, J 11.1 Hz, 2H), 7.21 (d, J 10.0 Hz, 1H), 7.12 (ddd, J 11.5, 9.0, 2.7 Hz, 1H), 5.58 (s, 2H), 4.37 (d, J 10.7 Hz, 2H), 4.15 (d, J 10.3 Hz, 2H), 2.31 (s, 3H), 1.46 (s, 6H); OH under doublet at 7.49 ppm. LCMS m/z 428.

Example 53

(2R)-6,8-Difluoro-4-[(6-{2-[3-hydroxy-3-(trifluoromethyl)azetidin-1-yl]pyrimidin-5-yl}-2-methyl-imidazo[1,2-a]pyrazin-3-yl)methyl]-2-methyl-3,4-dihydro-2H-1,4-benzoxazin-3-one Prepared from Intermediate 64 and Intermediate 148 by a method analogous to that used to prepare Example 1. δ$_H$ (500 MHz, DMSO-d$_6$) 9.03-8.98 (m, 4H), 7.48 (s, 1H), 7.24 (d, J 10.4 Hz, 1H), 7.11 (ddd, J 11.4, 9.2, 2.7 Hz, 1H), 5.69 (d, J 16.6 Hz, 1H), 5.56 (d, J 16.5 Hz, 1H), 4.94 (q, J 6.7 Hz, 1H), 4.37 (d, J 10.2 Hz, 2H), 4.15 (d, J 10.2 Hz, 2H), 2.33 (s, 3H), 1.50 (d, J 6.7 Hz, 3H). LCMS m/z 562.

Example 54

(2S)-6,8-Difluoro-4-[(6-{2-[3-hydroxy-3-(trifluoromethyl)azetidin-1-yl]pyrimidin-5-yl}-2-methyl-imidazo[1,2-a]pyrazin-3-yl)methyl]-2-methyl-3,4-dihydro-2H-1,4-benzoxazin-3-one Prepared from Intermediate 84 and Intermediate 148 by a method analogous to that used to prepare Example 1. δ$_H$ (500 MHz, CD$_3$OD) 8.95 (s, 2H), 8.93 (d, J 1.0 Hz, 1H), 8.86 (d, J 1.0 Hz, 1H), 7.06 (dt, J 10.0, 2.2 Hz, 1H), 6.81 (ddd, J 11.2, 8.9, 2.6 Hz, 1H), 5.73 (d, J 16.6 Hz, 1H), 5.54 (d, J 16.6 Hz, 1H), 4.78 (q, J 6.7 Hz, 1H), 4.44 (d, J 10.5 Hz, 2H), 4.16 (d, J 10.2 Hz, 2H), 2.52 (s, 3H), 1.59 (d, J 6.7 Hz, 3H). LCMS m/z 562.

Example 55

(2R)-6,8-Difluoro-4-({7-fluoro-6-[2-(3-fluorooxetan-3-yl)pyrimidin-5-yl]-2-methyl-imidazo[1,2-a]pyridin-3-yl}methyl)-2-methyl-3,4-dihydro-2H-1,4-benzoxazin-3-one To a stirred solution of Example 29 (0.31 g, 0.61 mmol) in anhydrous dichloro-methane (21 mL) under nitrogen at 0° C. was added BAST (50% solution in toluene, 0.45 mL, 1.22 mmol) dropwise over 2 minutes. After 10 minutes, the cooling bath was removed and the reaction mixture was stirred at room temperature. The reaction mixture was cooled to 0° C., quenched with water (30 mL) and basified to pH 8 using saturated aqueous sodium bicarbonate solution with continual stirring. The two phases were separated and the aqueous layer was further extracted with dichloromethane (3×30 mL). The combined organic extracts were washed with brine (30 mL), dried over magnesium sulfate, filtered and concentrated in vacuo. The crude material was purified using preparative HPLC to afford the title compound (110 mg, 36%) as an off-white solid. δ$_H$ (500 MHz, DMSO-d$_6$) 9.20 (s, 2H), 8.84 (d, J 7.3 Hz, 1H), 7.59 (d, J 11.3 Hz, 1H), 7.27-7.20 (m, 1H), 7.16-7.08 (m, 1H), 5.65 (d, J 16.6 Hz, 1H), 5.52 (d, J 16.6 Hz, 1H), 5.19 (dd, J 8.2, 1.2 Hz, 1H), 5.15 (dd, J 8.2, 1.2 Hz, 1H), 5.03 (dd, J 8.2, 1.2 Hz, 1H), 4.99 (dd, J 8.2, 1.1 Hz, 1H), 4.93 (q, J 6.7 Hz, 1H), 2.31 (s, 3H), 1.49 (d, J 6.7 Hz, 3H). LCMS MH+ m/z 514.

Example 56

6,8-Difluoro-4-({6-[2-(2-hydroxypropan-2-yl)pyrimidin-5-yl]-2-methylimidazo[1,2-a]-pyrazin-3-yl}methyl)-3,4-dihydro-2H-1,4-benzoxazin-3-one Prepared from Intermediate 85 and 2-[5-(4,4,5,5-tetramethyl-1,3,2-dioxaborolan-2-yl)pyrimidin-2-yl]propan-2-ol by a method analogous to that used to prepare Example 1. δ$_H$ (500 MHz, DMSO-d$_6$) 9.36 (s, 2H), 9.24 (d, J 1.2 Hz, 1H), 9.10 (d, J 1.2 Hz, 1H), 7.24 (d, J 10.2 Hz, 1H), 7.16-7.07 (m, 1H), 5.66 (s, 2H), 5.19 (s, 1H), 4.87 (s, 2H), 2.37 (s, 3H), 1.56 (s, 6H). LCMS m/z 467.

Example 57

(2R)-6,8-Difluoro-2-methyl-4-({2-methyl-6-[2-(3-oxopiperazin-1-yl)pyrimidin-5-yl]-imidazo[1,2-a]pyrazin-3-yl}methyl)-3,4-dihydro-2H-1,4-benzoxazin-3-one Prepared from Intermediate 64 and Intermediate 147 by a method analogous to that used to prepare Example 1. δ$_H$ (500 MHz, DMSO-d$_6$) 9.02-8.96 (m, 4H), 8.15 (s, 1H), 7.24 (d, J 10.4 Hz, 1H), 7.15-7.06 (m, 1H), 5.69 (d, J 16.6 Hz, 1H), 5.56 (d, J 16.6 Hz, 1H), 4.94 (q, J 6.6 Hz, 1H), 4.26 (s, 2H), 4.04-3.94 (m, 2H), 2.32 (s, 3H), 1.50 (d, J 6.6 Hz, 3H). LCMS m/z 521.

Example 58

6,8-Difluoro-4-({6-[2-(3-hydroxy-3-methylazetidin-1-yl)pyrimidin-5-yl]-2-methyl-imidazo[1,2-a] pyrazin-3-yl}methyl)-2,2-dimethyl-3,4-dihydro-2H-1,4-benzoxazin-3-one Prepared from Intermediate 86 and Intermediate 149 by a method analogous to that used to prepare Example 1. δ$_H$ (500 MHz, DMSO-d$_6$) 8.99 (d, J 1.2 Hz, 1H), 8.94 (d, J 1.2 Hz, 1H), 8.93 (s, 2H), 7.23 (d, J 10.2 Hz, 1H), 7.17-7.06 (m, 1H), 5.67 (s, 1H), 5.63 (s, 2H), 3.99 (d, J 9.1 Hz, 2H), 3.95 (d, J 9.1 Hz, 2H), 2.32 (s, 3H), 1.47 (s, 6H), 1.45 (s, 3H). LCMS m/z 552.

Example 59

(2R)-6,8-Difluoro-4-({6-[2-(3-fluorooxetan-3-yl) pyrimidin-5-yl]-2-methylimidazo[1,2-a]-pyrazin-3-yl}methyl)-2-methyl-3,4-dihydro-2H-1,4-benzoxazin-3-one To a stirred solution of Intermediate 87 (0.17 g, 0.34 mmol) in anhydrous dichloromethane (12 mL) in a two-neck flask, under nitrogen at 0° C., was added BAST (50% in toluene, 0.25 mL, 0.67 mmol) dropwise. After 10 minutes, the cooling bath was removed and the reaction mixture was stirred at room temperature for 35 minutes. The reaction mixture was cooled to 0° C., quenched by adding water (12 mL), then basified to pH 8 using saturated aqueous sodium bicarbonate solution (5.5 mL) with continual stirring. The two phases were separated and the aqueous layer was further extracted with dichloromethane (3×15 mL). The combined organic extracts were washed with brine (15 mL), dried over magnesium sulfate, filtered and concentrated in vacuo. The crude material was purified using preparative HPLC to afford the title compound (74 mg, 44%) as a beige solid. δ$_H$ (500 MHz, DMSO-d$_6$) 9.53 (s, 2H), 9.34 (s, 1H), 9.12 (s, 1H), 7.33-7.22 (m, 1H), 7.18-7.07 (m, 1H), 5.71 (d, J 16.7 Hz, 1H), 5.60 (d, J 16.7 Hz, 1H), 5.21-5.18 (m, 1H), 5.17-5.13 (m, 1H), 5.05-5.01 (m, 1H), 5.00-4.97 (m, 1H), 4.98-4.93 (m, 1H), 2.33 (s, 3H), 1.50 (d, J 6.7 Hz, 3H). LCMS MH+ m/z 497.

Example 60

(2S)-6,8-Difluoro-4-({7-fluoro-6-[2-(3-hydroxy-3-methylazetidin-1-yl)pyrimidin-5-yl]-2-methylimidazo[1,2-a]pyridin-3-yl}methyl)-2-methyl-3,4-dihydro-2H-1,4-benzoxazin-3-one Prepared from Intermediate 88 and Intermediate 149 by a method analogous to that used to prepare Example 1. δ$_H$ (500 MHz, DMSO-d$_6$) 8.54 (d, J 7.4 Hz, 1H), 8.53 (s, 1H), 8.52 (s, 1H), 7.46 (d, J 11.1 Hz, 1H), 7.21 (dt, J 10.6, 1.5 Hz, 1H), 7.10 (ddd, J 11.5, 9.0, 2.7 Hz, 1H), 5.68 (s, 1H), 5.65 (d, J 16.5 Hz, 1H), 5.49 (d, J 16.5 Hz, 1H), 4.92 (q, J 6.7 Hz, 1H), 3.98 (d, J 9.0 Hz, 2H), 3.95 (d, J 9.1 Hz, 2H), 2.32 (s, 3H), 1.48 (d, J 6.7 Hz, 3H), 1.45 (s, 3H). LCMS m/z 524.

Example 61

(2R)-6,8-Difluoro-4-[7-fluoro-6-{2-[3-hydroxy-3-(trifluoromethyl)azetidin-1-yl]-pyrimidin-5-yl}-2-methylimidazo[1,2-a]pyridin-3-yl)methyl]-2-methyl-3,4-dihydro-2H-1,4-benzoxazin-3-one Prepared from Intermediate 38 and Intermediate 148 by a method analogous to that used to prepare Example 1. δ$_H$ (500 MHz, DMSO-d$_6$) 8.61 (d, J 1.3 Hz, 2H), 8.59 (d, J 7.4 Hz, 1H), 7.60-7.43 (m, 2H), 7.27-7.16 (m, 1H), 7.10 (ddd, J 11.6, 9.0, 2.8 Hz, 1H), 5.65 (d, J 16.6 Hz, 1H), 5.50 (d, J 16.5 Hz, 1H), 4.92 (q, J 6.7 Hz, 1H), 4.36 (d, J 10.9 Hz, 2H), 4.14 (d, J 10.2 Hz, 2H), 2.31 (s, 3H), 1.48 (d, J 6.7 Hz, 3H). LCMS m/z 496.

Example 62

7-Fluoro-3-({7-fluoro-6-[2-(3-hydroxy-3-methylazetidin-1-yl)pyrimidin-5-yl]-2-methyl-imidazo[1,2-a]pyridin-3-yl}methyl)-2,3-dihydro-1,3-benzoxazol-2-one formate Prepared from Intermediate 89 and Intermediate 149 by a method analogous to that used to prepare Example 1. δ$_H$ (500 MHz, DMSO-d$_6$) 8.59 (d, J 7.5 Hz, 1H), 8.54 (d, J 1.2 Hz, 2H), 7.49 (d, J 11.3 Hz, 1H), 7.23 (td, J 8.3, 5.0 Hz, 1H), 7.15-7.05 (m, 1H), 7.01 (d, J 7.9 Hz, 1H), 5.68 (s, 1H), 5.48 (s, 2H), 4.01-3.90 (m, 5H), 2.53 (s, 3H), 1.45 (s, 3H). LCMS m/z 479.

Example 63

(2R)-6,8-Difluoro-2-methyl-4-({2-methyl-6-[2-(morpholin-4-yl)pyrimidin-5-yl]imidazo-[1,2-a]pyrazin-3-yl}methyl)-3,4-dihydro-2H-1,4-benzoxazin-3-one Prepared from Intermediate 64 and Intermediate 90 by a method analogous to that used to prepare Example 1. δ$_H$ (500 MHz, DMSO-d$_6$) 9.00 (d, J 0.9 Hz, 3H), 8.98 (s, 2H), 8.97 (d, J 0.9 Hz, 3H), 7.24 (dt, J 10.3, 1.7 Hz, 1H), 7.11 (td, J 10.5, 2.6 Hz, 1H), 5.70 (d, J 16.6 Hz, 1H), 5.56 (d, J 16.5 Hz, 1H), 4.95 (q, J 6.7 Hz, 1H), 3.80 (dd, J 4.5 Hz, 4H), 3.70 (dd, J 4.9 Hz, 4H), 2.33 (s, 3H), 1.50 (d, J 6.7 Hz, 3H). LCMS m/z 508.

Example 64

(2R)-6,8-Difluoro-4-({6-[2-(3-hydroxy-3-methylazetidin-1-yl)pyrimidin-5-yl]-2-methyl-imidazo[1,2-a]pyrazin-3-yl}methyl)-2-methyl-3,4-dihydro-2H-1,4-benzoxazin-3-one Prepared from Intermediate 64 and Intermediate 149 by a method analogous to that used to prepare Example 1. δ$_H$ (500 MHz, DMSO-d$_6$) 8.99 (d, J 1.1 Hz, 1H), 8.94 (d, J 1.2 Hz, 1H), 8.92 (s, 2H), 7.27-7.21 (m, 1H), 7.11 (ddd, J 11.5, 9.1, 2.8 Hz, 1H), 5.75-5.65 (m, 2H), 5.56 (d, J 16.5 Hz, 1H), 4.94 (q, J 6.7 Hz, 1H), 3.99 (d, J 9.0 Hz, 2H), 3.96 (d, J 9.2 Hz, 2H), 2.33 (s, 3H), 1.50 (d, J 6.7 Hz, 3H), 1.46 (s, 3H). LCMS m/z 508.

Example 65

6,8-Difluoro-4-({7-fluoro-6-[2-(3-hydroxy-3-methylazetidin-1-yl)pyrimidin-5-yl]-2-methylimidazo[1,2-a]pyridin-3-yl}methyl)-2,2-dimethyl-3,4-dihydro-2H-1,4-benzoxazin-3-one Prepared from Intermediate 81 and Intermediate 149 by a method analogous to that used to prepare Example 1. δ$_H$ (500 MHz, DMSO-$d_6$) 8.60-8.41 (m, 3H), 7.46 (d, J 11.1 Hz, 1H), 7.19 (dt, J 15.2, 10.0 Hz, 1H), 7.10 (ddd, J 11.6, 9.0, 2.8 Hz, 1H), 5.68 (s, 1H), 5.57 (s, 2H), 3.97 (d, J 9.2 Hz, 3H), 3.94 (d, J 9.1 Hz, 3H), 2.30 (s, 3H), 1.45 (s, 9H). LCMS m/z 539.

Example 66

(2R)-8-Fluoro-4-({7-fluoro-6-[2-(3-hydroxy-3-methylazetidin-1-yl)pyrimidin-5-yl]-2-methylimidazo[1,2-a]pyridin-3-yl}methyl)-2-methyl-3,4-dihydro-2H-1,4-benzoxazin-3-one Prepared from Intermediate 35 and Intermediate 149 by a method analogous to that used to prepare Example 1. $\delta_H$ (500 MHz, DMSO-$d_6$) 8.55-8.49 (m, 3H), 7.46 (d, J 11.1 Hz, 1H), 7.14 (d, J 8.2 Hz, 1H), 7.05 (td, J 8.3, 5.7 Hz, 1H), 7.00 (t, J 8.7 Hz, 1H), 5.68 (s, 1H), 5.64 (d, J 16.5 Hz, 1H), 5.52 (d, J 16.5 Hz, 1H), 4.94 (q, J 6.7 Hz, 1H), 3.98 (d, J 9.0 Hz, 2H), 3.95 (d, J 9.1 Hz, 2H), 2.32 (s, 3H), 1.49 (d, J 6.7 Hz, 3H), 1.46 (s, 3H). LCMS m/z 507.

Example 67

6,8-Difluoro-4-({7-fluoro-6-[2-(3-hydroxy-3-methylazetidin-1-yl)pyrimidin-5-yl]-2-methylimidazo[1,2-a]pyridin-3-yl}methyl)-3,4-dihydro-2H-1,4-benzoxazin-3-one Prepared from Intermediate 77 and Intermediate 149 by a method analogous to that used to prepare Example 1. $\delta_H$ (500 MHz, DMSO-$d_6$) 8.58 (d, J 7.4 Hz, 1H), 8.54 (s, 2H), 7.47 (d, J 11.1 Hz, 1H), 7.25-7.16 (m, 1H), 7.15-7.05 (m, 1H), 5.68 (s, 1H), 5.57 (s, 2H), 4.84 (s, 2H), 3.98 (d, J 9.0 Hz, 2H), 3.95 (d, J 9.0 Hz, 2H), 2.35 (s, 3H), 1.46 (s, 3H). LCMS m/z 511.

Example 68

2,2,6,8-Tetrafluoro-4-({7-fluoro-6-[2-(2-hydroxypropan-2-yl)pyrimidin-5-yl]-2-methyl-imidazo[1,2-a]pyridin-3-yl}methyl)-3,4-dihydro-2H-1,4-benzoxazin-3-one Prepared from Intermediate 93 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, CDCl$_3$) 8.88 (s, 2H), 8.52 (dd, J 23.1, 6.0 Hz, 1H), 7.54-7.40 (m, 1H), 6.89 (d, J 8.9 Hz, 1H), 6.82 (t, J 8.7 Hz, 1H), 5.54 (s, 2H), 4.54 (s, 1H), 2.68 (s, 3H), 1.67 (s, 6H). LCMS m/z 520.

Example 69

(2S)-6,8-Difluoro-4-({6-[2-(2-hydroxypropan-2-yl)pyrimidin-5-yl]-2-methylimidazo[1,2-a]pyrazin-3-yl}methyl)-2-methyl-3,4-dihydro-2H-1,4-benzoxazin-3-one Prepared from Intermediate 84 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, CD$_3$OD) 9.36 (s, 2H), 9.12 (d, J 1.4 Hz, 1H), 9.01 (d, J 1.2 Hz, 1H), 7.10 (dt, J 10.0, 2.2 Hz, 1H), 6.82 (ddd, J 11.4, 8.9, 2.8 Hz, 1H), 5.74 (d, J 16.6 Hz, 1H), 5.58 (d, J 16.5 Hz, 1H), 4.79 (q, J 6.7 Hz, 1H), 2.52 (s, 3H), 1.65 (s, 6H), 1.59 (d, J 6.7 Hz, 3H). LCMS m/z 481.

Example 70

2,2,6,8-Tetrafluoro-4-({7-fluoro-6-[2-(3-hydroxy-3-methylazetidin-1-yl)pyrimidin-5-yl]-2-methylimidazo[1,2-a]pyridin-3-yl}methyl)-3,4-dihydro-2H-1,4-benzoxazin-3-one Intermediate 94 (69 mg, 0.1 mmol) was dissolved in THF (3 mL), then DIPEA (0.07 mL, 0.40 mmol) was added and the reaction mixture was cooled to −10° C. 2,4,6-Tripropyl-1,3,5,2,4,6-trioxatriphosphinane 2,4,6-trioxide (0.18 mL, 0.30 mmol) was added and the reaction mixture was warmed to room temperature and stirred continuously for 16 h. Water (10 mL) was added to the reaction mixture, followed by dilution with ethyl acetate (10 mL). The organic layer was washed with water (2×10 mL), then the aqueous layer was extracted using ethyl acetate (10 mL). The combined organic layers were dried over sodium sulfate and concentrated in vacuo. The crude material was purified using preparative HPLC, followed by re-crystallisation from methanol and water, to afford the title compound (6 mg, 10%) as a white solid. $\delta_H$ (500 MHz, CD$_3$OD) 8.52 (d, J 7.1 Hz, 3H), 7.31 (d, J 10.6 Hz, 1H), 7.24 (d, J 9.9 Hz, 1H), 7.09-7.02 (m, 1H), 5.69 (s, 2H), 4.08 (q, J 9.3 Hz, 4H), 2.48 (s, 3H), 1.56 (s, 3H). LCMS MH+ m/z 547.

Example 71

(2S)-6,8-Difluoro-4-[(7-fluoro-6-{2-[3-hydroxy-3-(trifluoromethyl)azetidin-1-yl]-pyrimidin-5-yl}-2-methylimidazo[1,2-a]pyridin-3-yl)methyl]-2-methyl-3,4-dihydro-2H-1,4-benzoxazin-3-one Prepared from Intermediate 88 and Intermediate 148 by a method analogous to that used to prepare Example 1. $\delta_H$ (500 MHz, DMSO-$d_6$) 8.61 (s, 1H), 8.59 (d, J 7.4 Hz, 1H), 7.48 (d, J 11.1 Hz, 1H), 7.48 (s, 1H), 7.21 (dt, J 10.4, 2.2 Hz, 1H), 7.10 (ddd, J 11.6, 9.0, 2.8 Hz, 1H), 5.65 (d, J 16.6 Hz, 1H), 5.50 (d, J 16.5 Hz, 1H), 4.92 (q, J 6.7 Hz, 1H), 4.36 (d, J 10.8 Hz, 2H), 4.14 (d, J 10.2 Hz, 2H), 2.31 (s, 3H), 1.48 (d, J 6.7 Hz, 3H). LCMS m/z 578.

Example 72

(2R)-6,8-Difluoro-4-({7-fluoro-2-methyl-6-[2-(morpholin-4-yl)pyrimidin-5-yl]imidazo-[1,2-a]pyridin-3-yl}methyl)-2-methyl-3,4-dihydro-2H-1,4-benzoxazin-3-one Prepared from Intermediate 38 and Intermediate 90 by a method analogous to that used to prepare Example 1. $\delta_H$ (500 MHz, DMSO-$d_6$) 8.59 (s, 1H), 8.58 (s, 1H), 8.57 (d, J 7.5 Hz, 2H), 7.47 (d, J 11.1 Hz, 1H), 7.25-7.18 (m, 1H), 7.10 (ddd, J 11.4, 9.2, 2.8 Hz, 1H), 5.65 (d, J 16.6 Hz, 1H), 5.49 (d, J 16.5 Hz, 1H), 4.92 (q, J 6.7 Hz, 1H), 3.79 (t, J 4.3 Hz, 4H), 3.69 (t, J 4.5 Hz, 5H), 2.31 (s, 3H), 1.48 (d, J 6.7 Hz, 3H). LCMS m/z 525.

Example 73

6,8-Difluoro-4-[(6-{2-[3-hydroxy-3-(trifluoromethyl)azetidin-1-yl]pyrimidin-5-yl}-2-methylimidazo[1,2-a]pyrazin-3-yl)methyl]-2,2-dimethyl-3,4-dihydro-2H-1,4-benzoxazin-3-one Prepared from Intermediate 86 and Intermediate 148 by a method analogous to that used to prepare Example 1. $\delta_H$ (500 MHz, DMSO-d$_6$) 9.05-8.96 (m, 4H), 7.47 (s, 1H), 7.29-7.21 (m, 1H), 7.17-7.07 (m, 1H), 5.63 (s, 2H), 4.37 (d, J 10.5 Hz, 2H), 4.15 (d, J 10.2 Hz, 2H), 2.32 (s, 3H), 1.47 (s, 6H). LCMS m/z 576.

Example 74

7-Fluoro-3-({7-fluoro-6-[2-(2-hydroxypropan-2-yl)pyrimidin-5-yl]-2-methylimidazo[1,2-a]pyridin-3-yl}methyl)-2,3-dihydro-1,3-benzoxazol-2-one Prepared from Intermediate 89 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-d$_6$) 9.03 (d, J 1.2 Hz, 2H), 8.78 (d, J 7.3 Hz, 1H), 7.59 (d, J 11.3 Hz, 1H), 7.24 (td, J 8.3, 4.9 Hz, 1H), 7.14-7.05 (m, 1H), 7.01 (d, J 7.9 Hz, 1H), 5.51 (s, 2H), 5.19 (s, 1H), 2.55 (s, 3H), 1.56 (s, 6H). LCMS m/z 452.

Example 75

(2R)-6,8-Difluoro-4-({7-fluoro-2-methyl-6-[2-(3-oxopiperazin-1-yl)pyrimidin-5-yl]-imidazo[1,2-a]pyridin-3-yl}methyl)-2-methyl-3,4-dihydro-2H-1,4-benzoxazin-3-one Prepared from Intermediate 38 and Intermediate 147 by a method analogous to that used to prepare Example 1. $\delta_H$ (500 MHz, DMSO-d$_6$) 8.62 (s, 1H), 8.58 (d, J 7.4 Hz, 1H), 8.15 (s, 1H), 7.48 (d, J 11.1 Hz, 1H), 7.21 (d, J 10.7 Hz, 1H), 7.10 (td, J 11.4, 10.5, 2.6 Hz, 1H), 5.65 (d, J 16.5 Hz, 1H), 5.50 (d, J 16.6 Hz, 1H), 4.92 (q, J 6.7 Hz, 1H), 4.25 (s, 2H), 3.98 (t, J 5.1 Hz, 2H), 2.53-2.51 (m, 2H), 2.31 (s, 3H), 1.48 (d, J 6.7 Hz, 3H). LCMS m/z 536.

Example 76

2,2,6,8-Tetrafluoro-4-[(7-fluoro-6-{2-[3-hydroxy-3-(trifluoromethyl)azetidin-1-yl]-pyrimidin-5-yl}-2-methylimidazo[1,2-a]pyridin-3-yl)methyl]-3,4-dihydro-2H-1,4-benzoxazin-3-one Intermediate 95 (200 mg, 0.31 mmol) was dissolved in THF (5 mL), then DIPEA (0.22 mL, 1.25 mmol) was added and the reaction mixture was cooled to −10° C. 2,4,6-Tripropyl-1,3,5,2,4,6-trioxatriphosphinane 2,4,6-trioxide (0.55 mL, 0.94 mmol) was added and the reaction mixture was warmed to room temperature and stirred continuously for 16 h. Water (10 mL) was added to the reaction mixture, followed by dilution with ethyl acetate (10 mL). The layers were shaken and separated. The organic layer was washed with water (2×10 mL), then the aqueous layer was extracted using ethyl acetate (10 mL). The combined organic layers were dried over sodium sulfate and concentrated in vacuo. The crude material was purified on silica (Biotage, 10 g), eluting with 0-6% methanol in dichloromethane, followed by triturating from ethyl acetate in heptanes, to afford the title compound (38 mg, 19%) as a white solid. $\delta_H$ (500 MHz, DMSO-d$_6$) 8.67-8.56 (m, 3H), 7.47 (td, J 20.5, 19.0, 10.0 Hz, 4H), 5.67 (s, 2H), 4.36 (d, J 10.3 Hz, 2H), 4.14 (d, J 10.2 Hz, 2H), 2.33 (s, 3H). LCMS MH+ m/z 601.

Example 77

(2R)-4-({6-[2-(2-Hydroxypropan-2-yl)pyrimidin-5-yl]-2-methylimidazo[1,2-a]pyrazin-3-yl}methyl)-2-methyl-2H,3H,4H-pyrido[3,2-b][1,4]oxazin-3-one Prepared from Intermediate 96 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-d$_6$) 9.46 (d, J 1.4 Hz, 1H), 9.36 (s, 2H), 9.06 (d, J 1.3 Hz, 1H), 8.02 (dd, J 4.9, 1.4 Hz, 1H), 7.44 (dd, J 7.9, 1.4 Hz, 1H), 7.08 (dd, J 7.9, 4.9 Hz, 1H), 5.70 (d, J 15.3 Hz, 2H), 5.66 (d, J 16.5 Hz, 2H), 5.20 (s, 1H), 4.99 (d, J 6.7 Hz, 1H), 2.54 (s, 3H), 1.56 (s, 6H), 1.51 (d, J 6.7 Hz, 3H). LCMS m/z 446.

Example 78

4-({7-Fluoro-6-[2-(2-hydroxypropan-2-yl)pyrimidin-5-yl]-2-methylimidazo[1,2-a]-pyridin-3-yl}methyl)-2H,3H,4H-pyrido[4,3-b][1,4]oxazin-3-one Prepared from Intermediate 97 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, CD$_3$OD) 9.01 (s, 2H), 8.79 (d, J 7.2 Hz, 1H), 8.48 (s, 1H), 8.14 (d, J 5.5 Hz, 1H), 7.36 (d, J 10.8 Hz, 1H), 7.04 (d, J 5.5 Hz, 1H), 5.69 (s, 2H), 4.88 (s, 2H), 2.55 (s, 3H), 1.65 (s, 6H). LCMS m/z 449.

Example 79

(2R)-6,8-Difluoro-4-({7-fluoro-6-[2-(3-hydroxy-3-methylazetidin-1-yl)pyrimidin-5-yl]-2-methylimidazo[1,2-a]pyridin-3-yl}methyl)-2-methyl-3,4-dihydro-2H-1,4-benzoxazin-3-one Prepared from Intermediate 38 and Intermediate 149 by a method analogous to that used to prepare Example 1. $\delta_H$ (500 MHz, DMSO-d$_6$) 8.54 (d, J 7.4 Hz, 1H), 8.52 (d, J 1.4 Hz, 2H), 7.46 (d, J 11.1 Hz, 1H), 7.24-7.17 (m, 1H), 7.13-7.05 (m, 1H), 5.68 (s, 1H), 5.65 (d, J 16.6 Hz, 1H), 5.49 (d, J 16.5 Hz, 1H), 4.92 (q, J 6.7 Hz, 1H), 3.98 (d, J 9.0 Hz, 2H), 3.95 (d, J 9.1 Hz, 2H), 2.32 (s, 3H), 1.48 (d, J 6.7 Hz, 3H), 1.45 (s, 3H). LCMS m/z 525.

Example 80

(2R)-8-Fluoro-4-[(7-fluoro-6-{2-[3-hydroxy-3-(trifluoromethyl)azetidin-1-yl]pyrimidin-5-yl}-2-methylimidazo[1,2-a]pyridin-3-yl)methyl]-2-methyl-3,4-dihydro-2H-1,4-benzoxazin-3-one Prepared from Intermediate 35 and Intermediate 148 by a method analogous to that used to prepare Example 1. $\delta_H$ (500 MHz, DMSO-d$_6$) 8.62 (d, J 1.2 Hz, 2H), 8.58 (d, J 7.4 Hz, 1H), 7.49 (d, J 7.4 Hz, 1H), 7.48 (s, 1H), 7.15 (d, J 8.2 Hz, 1H), 7.06 (td, J 8.3, 5.7 Hz, 1H), 7.03-6.97 (m, 1H), 5.65 (d, J 16.5 Hz, 1H), 5.53 (d, J 16.5 Hz, 1H), 4.94 (q, J 6.7 Hz, 1H), 4.37 (d, J 10.6 Hz, 2H), 4.15 (d, J 10.2 Hz, 2H), 2.32 (s, 3H), 1.50 (d, J 6.7 Hz, 3H). LCMS m/z 561.

Example 81

6,8-Difluoro-4-({7-fluoro-6-[2-(2-hydroxypropan-2-yl)pyrimidin-5-yl]-2-methylimidazo-[1,2-a]pyridin-3-yl}methyl)-2,2-dimethyl-3,4-dihydro-2H-1,4-benzoxazin-3-one Prepared from Intermediate 80 and Intermediate 107 by a method analogous to that used to prepare Intermediate 88. $\delta_H$ (500 MHz, DMSO-d$_6$) 9.03 (s, 1H), 8.78 (d, J 7.3 Hz, 1H), 7.56 (d, J 11.2 Hz, 1H), 7.27-7.20 (m, 1H), 7.12 (ddd, J 11.5, 9.1, 2.7 Hz, 1H), 5.58 (s, 2H), 5.20 (s, 1H), 2.29 (s, 3H), 1.56 (s, 6H), 1.45 (s, 6H). LCMS m/z 512.

Example 82

(2R)-4-({6-[2-(3,7-Dioxa-9-azabicyclo[3.3.1]nonan-9-yl)pyrimidin-5-yl]-2-methyl-imidazo[1,2-a]pyrazin-3-yl}methyl)-6,8-difluoro-2-methyl-3,4-dihydro-2H-1,4-benzoxazin-3-one Prepared from Intermediate 64 and Intermediate 106 by a method analogous to that used to prepare Example 1. $\delta_H$ (500 MHz, DMSO-d$_6$) 9.02-8.98 (m, 4H), 7.27-7.22 (m, 1H), 7.15-7.07 (m, 1H), 5.69 (d, J 16.6 Hz, 1H), 5.56 (d, J 16.5 Hz, 1H), 4.95 (q, J 6.6 Hz, 1H), 4.55 (s, 2H), 4.04 (d, J 11.1 Hz, 4H), 3.78 (dd, J 10.8, 1.6 Hz, 4H), 2.33 (s, 3H), 1.50 (d, J 6.7 Hz, 3H). LCMS m/z 549.

Example 83

(2R)-6,8-Difluoro-4-({7-fluoro-2-methyl-6-[2-(5-oxo-1,4-diazepan-1-yl)pyrimidin-5-yl]-imidazo[1,2-a]pyridin-3-yl}methyl)-2-methyl-3,4-dihydro-2H-1,4-benzoxazin-3-one Prepared from Intermediate 38 and Intermediate 78 by a method analogous to that used to prepare Example 1. $\delta_H$ (500 MHz, DMSO-d$_6$) 8.62-8.55 (m, 3H), 7.70 (t, J 5.2 Hz, 1H), 7.47 (d, J 11.1 Hz, 1H), 7.21 (d, J 10.5 Hz, 1H), 7.14-7.04 (m, 1H), 5.64 (d, J 16.5 Hz, 1H), 5.49 (d, J 16.5 Hz, 1H), 4.92 (q, J 6.7 Hz, 1H), 3.99 (t, J 7.4 Hz, 4H), 3.26-3.22 (m, 2H), 2.57-2.53 (m, 2H), 2.30 (s, 3H), 1.48 (d, J 6.7 Hz, 3H). LCMS m/z 552.

Example 84

(2R)-8-Fluoro-4-({7-fluoro-6-[2-(1-hydroxycyclopropyl)pyrimidin-5-yl]-2-methyl-imidazo[1,2-a]pyridin-3-yl}methyl)-2-methyl-3,4-dihydro-2H-1,4-benzoxazin-3-one To a solution of Intermediate 105 (190 mg, 0.32 mmol) in 1,4-dioxane (2 mL) was added TBAF (1N, 0.96 mL, 0.96 mmol). The reaction mixture was stirred for 1 h at room temperature. Ethyl acetate (15 mL) and water (20 mL) were added to the reaction mixture. The aqueous layer was extracted with ethyl acetate (10 mL). The organic phases were combined, dried over sodium sulfate, and filtered, then the solvent was removed in vacuo. The residue was dissolved in ethyl acetate (4 mL) and washed with water (3×4 mL), then dried over sodium sulphate and filtered. The solvent was removed in vacuo to afford the title compound (79.3 mg, 51%) as an off white solid. $\delta_H$ (500 MHz, DMSO-d$_6$) 8.93 (s, 1H), 8.92 (s, 1H), 8.71 (d, J 7.3 Hz, 1H), 7.53 (d, J 11.2 Hz, 1H), 7.15 (d, J 8.2 Hz, 1H), 7.09-7.02 (m, 1H), 7.00 (td, J 9.3, 8.5, 1.3 Hz, 1H), 6.16 (s, 1H), 5.65 (d, J 16.5 Hz, 1H), 5.54 (d, J 16.5 Hz, 1H), 4.93 (q, J 6.7 Hz, 1H), 2.31 (s, 3H), 1.49 (d, J 6.7 Hz, 3H), 1.36 (q, J 4.1 Hz, 2H), 1.22 (q, J 4.1 Hz, 2H). LCMS MH+ m/z 478.2.

Example 85

4-({6-[2-(3,3-Difluoro-1-hydroxycyclobutyl)pyrimidin-5-yl]-2-methylimidazo[1,2-a]-pyrazin-3-yl}methyl)-6,8-difluoro-2,2-dimethyl-3,4-dihydro-2H-1,4-benzoxazin-3-one Prepared from Intermediate 86 and Intermediate 101 by a method analogous to that used to prepare Example 1, followed by treatment with TBAF at room temperature. 6H (500 MHz, CDCl$_3$) 9.33 (s, 2H), 9.08 (d, J 1.3 Hz, 1H), 8.86 (d, J 1.4 Hz, 1H), 6.71-6.67 (m, 1H), 6.67-6.61 (m, 1H), 5.50 (s, 2H), 5.08 (s, 1H), 3.52-3.37 (m, 2H), 3.10-2.97 (m, 2H), 2.70 (s, 3H), 1.60 (s, 6H). LCMS m/z 543.

Example 86

(2R)-4-({7-Fluoro-6-[2-(2-hydroxypropan-2-yl)pyrimidin-5-yl]-2-methylimidazo[1,2-d]-pyridin-3-yl}methyl)-2-methyl-2H,3H,4H-pyrido[3,2-b][1,4]oxazin-3-one Prepared from Intermediate 108 and 2-[5-(4,4,5,5-tetramethyl-1,3,2-dioxaborolan-2-yl)pyrimidin-2-yl]propan-2-ol by a method analogous to that used to prepare Example 1. $\delta_H$ (500 MHz, DMSO-d$_6$) 9.08 (d, J 7.5 Hz, 1H), 9.03 (d, J 1.3 Hz, 2H), 8.01 (dd, J 4.9, 1.4 Hz, 1H), 7.51 (d, J 11.3 Hz, 1H), 7.42 (dd, J 7.9, 1.4 Hz, 1H), 7.07 (dd, J 7.9, 4.9 Hz, 1H), 5.60 (s, 2H), 5.20 (s, 1H), 4.96 (q, J 6.7 Hz, 1H), 2.43 (s, 3H), 1.56 (s, 6H), 1.48 (d, J 6.7 Hz, 3H). LCMS m/z 463.

Example 87

4-({7-Fluoro-6-[2-(1-hydroxy-1-methylethyl)pyrimidin-5-yl]-2-methylimidazo[1,2-a]-pyridin-3-yl}methyl)spiro[1,4-benzoxazine-2,1'-cyclopropane]-3-one Prepared from Intermediate 118 and 2-[5-(4,4,5,5-tetramethyl-1,3,2-dioxaborolan-2-yl)pyrimidin-2-yl]propan-2-ol by a method analogous to that used to prepare Example 1. $\delta_H$ (300 MHz, DMSO-d$_6$) 9.03 (d, J 1.5 Hz, 2H), 8.77 (d, J 7.4 Hz, 1H), 7.57 (d, J 11.3 Hz, 1H), 7.30 (dd, J 8.0, 1.4 Hz, 1H), 7.10-7.01 (m, 2H), 6.96 (dd, J 7.8, 1.6 Hz, 1H), 5.60 (s, 2H), 5.19 (s, 1H), 2.28 (s, 3H), 1.57 (s, 6H), 1.34-1.24 (m, 4H). LCMS m/z 474.

Example 88

Methyl (2R)-8-fluoro-4-({7-fluoro-6-[2-(1-hydroxy-1-methylethyl)pyrimidin-5-yl]-2-methylimidazo[1,2-a]pyridin-3-yl}methyl)-2-methyl-3-oxo-1,4-benzoxazine-6-carboxylate Prepared from Intermediate 122 and 2-[5-(4,4,5,5-tetramethyl-1,3,2-dioxaborolan-2-yl)pyrimidin-2-yl]propan-2-ol by a method analogous to that used to prepare Example 1. $\delta_H$ (300 MHz, DMSO-d$_6$) 9.03 (d, J 1.6 Hz, 2H), 8.74 (d, J 7.3 Hz, 1H), 7.70-7.69 (m, 1H), 7.58-7.50 (m, 2H), 5.72 (d, J 16.8 Hz, 1H), 5.64 (d, J 16.6 Hz, 1H), 5.18 (s, 1H), 5.12 (q, J 6.8 Hz, 1H), 3.79 (s, 3H), 2.43 (s, 3H), 1.56 (s, 6H), 1.55 (d, J 7.9 Hz, 3H). LCMS m/z 538.

Example 89

(2R)-7,8-Difluoro-4-({7-fluoro-6-[2-(1-hydroxy-1-methylethyl)pyrimidin-5-yl]-2-methyl-imidazo[1,2-a]pyridin-3-yl}methyl)-2-methyl-1,4-benzoxazin-3-one Prepared from Intermediate 125 and 2-[5-(4,4,5,5-tetramethyl-1,3,2-dioxaborolan-2-yl)pyrimidin-2-yl]propan-2-ol by a method analogous to that used to prepare Example 1. $\delta_H$ (300 MHz, DMSO-d$_6$) 9.03 (d, J 1.6 Hz, 2H), 8.76 (d, J 7.3 Hz, 1H), 7.55 (d, J 11.3 Hz, 1H), 7.21-7.09 (m, 2H), 5.65 (d, J 16.6 Hz, 1H), 5.53 (d, J 16.6 Hz, 1H), 5.18 (s, 1H), 5.01 (q, J 6.7 Hz, 1H), 2.30 (s, 3H), 1.56 (s, 6H), 1.51 (d, J 6.7 Hz, 3H). LCMS m/z 498.

Example 90

8-Fluoro-4-({7-fluoro-6-[2-(1-hydroxy-1-methylethyl)pyrimidin-5-yl]-2-methylimidazo-[1,2-a]pyridin-3-yl}methyl)spiro[1,4-benzoxazine-2,1'-cyclopropane]-3-one Prepared from Intermediate 128 and 2-[5-(4,4,5,5-tetramethyl-1,3,2-dioxaborolan-2-yl)pyrimidin-2-yl]propan-2-ol by a method analogous to that used to prepare Example 1. $\delta_H$ (300 MHz, DMSO-$d_6$) 9.04 (d, J 1.6 Hz, 2H), 8.77 (d, J 7.4 Hz, 1H), 7.56 (d, J 11.3 Hz, 1H), 7.15-6.98 (m, 3H), 5.60 (s, 2H), 5.17 (s, 1H), 2.27 (s, 3H), 1.56 (s, 6H), 1.36-1.33 (m, 4H). LCMS m/z 492.

Example 91

8-Fluoro-4-({7-fluoro-6-[2-(3-hydroxy-3-methylazetidin-1-yl)pyrimidin-5-yl]-2-methyl-imidazo[1,2-a]pyridin-3-yl}methyl)spiro[1,4-benzoxazine-2,1'-cyclopropane]-3-one Prepared from Intermediate 128 and Intermediate 149 by a method analogous to that used to prepare Example 1. $\delta_H$ (300 MHz, DMSO-$d_6$) 8.52-8.50 (m, 3H), 7.47 (d, J 11.2, 1H), 7.15-6.98 (m, 3H), 5.66 (s, 1H), 5.59 (s, 2H), 4.00-3.93 (m, 4H), 2.29 (s, 3H), 1.45 (s, 3H), 1.34 (br s, 4H). LCMS m/z 519.

Example 92

8-Fluoro-4-[(7-fluoro-6-{2-[3-hydroxy-3-(trifluoromethyl)azetidin-1-yl]pyrimidin-5-yl}-2-methyl-imidazo[1,2-a]pyridin-3-yl)methyl]spiro[1,4-benzoxazine-2,1'-cyclopropane]3-one Prepared from Intermediate 128 and Intermediate 148 by a method analogous to that used to prepare Example 1. $\delta_H$ (300 MHz, DMSO-$d_6$) 8.62 (d, J 1.5 Hz, 2H), 8.57 (d, J 7.4 Hz, 1H), 7.50 (d, J 11.1 Hz, 1H), 7.46 (s, 1H), 7.15-7.00 (m, 3H), 5.60 (s, 2H), 4.37 (d, J 10.9 Hz, 2H), 4.15 (d, J 10.3 Hz, 2H), 2.29 (s, 3H), 1.37-1.34 (m, 4H). LCMS m/z 573.

Example 93

(2R)-5,6,8-Trifluoro-4-[(6-{2-[3-hydroxy-3-(trifluoromethyl)azetidin-1-yl]pyrimidin-5-yl}-2-methyl-imidazo[1,2-a]pyrazin-3-yl)methyl]-2-methyl-1,4-benzoxazin-3-one Prepared from Intermediate 111 and Intermediate 148 by a method analogous to that used to prepare Example 1. $\delta_H$ (400 MHz, DMSO-$d_6$) 9.01 (m, 2H), 8.93 (d, J 1.1 Hz, 1H), 7.47 (m, 2H), 5.83 (d, J 16.5 Hz, 1H), 5.57 (d, J 16.5 Hz, 1H), 4.95 (m, 1H), 4.38 (d, J 10.5 Hz, 1H), 4.16 (d, J 10.6 Hz, 2H), 2.24 (s, 2H), 1.50 (d, J 6.7 Hz, 3H), 1.50 (d, J 6.7 Hz, 3H). LCMS m/z 442.

Example 94

4-{[2-Methyl-6-(4-methylsulfonylphenyl)imidazo[1,2-a]pyridin-3-yl]methyl}-1,4-benzoxazin-3-one Prepared from Intermediate 116 and 4-(methylsulfonyl) phenylboronic acid by a method analogous to that used to prepare Example 1. $\delta_H$ (400 MHz, CDCl$_3$/CD$_3$OD) 8.63 (s, 1H), 8.01 (d, J 8.4 Hz, 2H), 7.73 (d, J 8.5 Hz, 2H), 7.52 (q, J 9.0 Hz, 2H), 7.20-7.22 (m, 1H), 6.92-7.10 (m, 3H), 5.52 (s, 2H), 4.64 (s, 1H), 3.11 (s, 3H), 2.58 (s, 3H). LCMS m/z 448.

Example 95

2-(5-{7-Fluoro-3-[(8-fluoro-3-methyl-2,3-dihydro-1,4-benzoxazin-4-yl)methyl]-2-methylimidazo[1,2-a] pyridin-6-yl}pyrimidin-2-yl)propan-2-ol Prepared from Intermediate 115 and 2-[5-(4,4,5,5-tetramethyl-1,3,2-dioxaborolan-2-yl)pyrimidin-2-yl]propan-2-ol by a method analogous to that used to prepare Example 1. $\delta_H$ (400 MHz, CDCl$_3$) 1.82 (d, J 6.4 Hz, 3H), 1.65 (s, 6H), 2.66 (s, 3H), 3.06-3.84 (m, 1H), 4.04 (d, J 10.8 Hz, 1H), 4.15 (d, J 10.8 Hz, 1H), 4.44 (s, 1H), 4.56 (d, J 5.3 Hz, 1H), 4.85 (d, J 5.3 Hz, 1H), 6.66-6.73 (m, 2H), 6.83-6.96 (m, 1H), 7.78 (d, J 9.5 Hz, 1H), 8.18 (d, J 6.6 Hz, 1H), 8.82 (s, 2H). LCMS m/z 466.

Example 96

(2R)-8-Chloro-6-fluoro-4-({6-[2-(3-hydroxy-3-methylazetidin-1-yl)pyrimidin-5-yl]-2-methylimidazo[1,2-a]pyrazin-3-yl}methyl)-2-methyl-1,4-benzoxazin-3-one Prepared from Intermediate 131 and Intermediate 149 by a method analogous to that used to prepare Example 1. $\delta_H$ (300 MHz, DMSO-$d_6$) 8.94 (m, 1H), 8.92 (m, 3H), 7.37 (dd, 1H, J 10.3, 2.8 Hz), 7.21 (dd, 1H, J 8.4, 2.8 Hz), 5.64 (m, 3H), 4.97 (q, 1H, J 6.7 Hz), 3.98 (m, 4H), 2.33 (s, 3H), 1.50 (d, 3H, J 6.7 Hz), 1.46 (s, 3H). LCMS m/z 524.

Example 97

(2R)-8-Chloro-4-({6-[2-(3-hydroxy-3-methylazetidin-1-yl)pyrimidin-5-yl]-2-methyl-imidazo[1,2-a] pyrazin-3-yl}methyl)-2-methyl-1,4-benzoxazin-3-one Prepared from Intermediate 134 and Intermediate 149 by a method analogous to that used to prepare Example 1. $\delta_H$ (300 MHz, DMSO-$d_6$) 8.98 (m, 1H), 8.92 (m, 3H), 7.27 (dd, 1H, J 8.3, 1.0 Hz), 7.17 (m, 1H), 7.05 (m, 1H), 5.65 (m, 3H), 5.00 (q, J 6.9 Hz), 3.98 (m, 4H), 2.33 (s, 3H), 1.52 (d, 3H, J 6.7 Hz), 1.46 (s, 3H). LCMS m/z 506.

Example 98

(2S)-8-Fluoro-4-({6-[2-(1-hydroxy-1-methylethyl) pyrimidin-5-yl]-2-methylimidazo[1,2-a]pyrazin-3-yl}methyl)-2-methyl-1,4-benzoxazin-3-one Prepared from Intermediate 135 and Intermediate 142 by a method analogous to that used to prepare Intermediate 21. $\delta_H$ (300 MHz, DMSO-$d_6$) 9.37 (s, 2H), 9.24 (d, 1H, J 1.4 Hz), 9.09 (d, 1H, J 1.3 Hz), 7.06 (m, 3H), 5.68 (q, 2H, J 16.6

Hz), 5.18 (s, 1H), 4.98 (q, 1H, J 6.7 Hz), 2.34 (s, 3H), 1.56 (s, 6H), 1.53 (d, 3H, J 6.7 Hz). LCMS m/z 464.

Example 99

(2S)-8-Fluoro-4-[(7-fluoro-6-{2-[3-hydroxy-3-(trifluoromethyl)azetidin-1-yl]pyrimidin-5-yl}-2-methyl-imidazo[1,2-a]pyridin-3-yl)methyl]-2-methyl-1,4-benzoxazin-3-one Prepared from Intermediate 143 and Intermediate 148 by a method analogous to that used to prepare Example 1. $\delta_H$ (300 MHz, DMSO-$d_6$) 8.58 (m, 3H), 7.47 (m, 2H), 7.07 (m, 3H), 5.58 (m, 2H), 4.94 (d, 1H, J 6.7 Hz), 4.25 (m, 4H), 2.32 (s, 3H), 1.49 (d, 3H, J 6.7 Hz). LCMS m/z 562.

Example 100

(2S)-8-Fluoro-4-({7-fluoro-6-[2-(3-hydroxy-3-methylazetidin-1-yl)pyrimidin-5-yl]-2-methylimidazo[1,2-a]pyridin-3-yl}methyl)-2-methyl-1,4-benzoxazin-3-one Prepared from Intermediate 143 and Intermediate 149 by a method analogous to that used to prepare Example 1. $\delta_H$ (300 MHz, DMSO-$d_6$) 8.53 (m, 3H), 7.45 (d, 1H, J 11.2 Hz), 7.06 (m, 3H), 5.58 (m, 3H), 4.94 (q, J 6.9 Hz), 3.99 (m, 4H), 2.32 (s, 3H), 1.48 (m, 6H). LCMS m/z 507.

Example 101

(2R)-4-({7-Fluoro-6-[2-(1-hydroxy-1-methylethyl)pyrimidin-5-yl]-2-methylimidazo[1,2-a]pyridin-3-yl}methyl)-2-methyl-8-(trifluoromethyl)pyrido[3,2-b][1,4]oxazin-3-one Prepared from Intermediate 107 and Intermediate 138 by a method analogous to that used to prepare Intermediate 21. $\delta_H$ (400 MHz, DMSO-$d_6$) 9.04 (m, 3H), 8.20 (d, 1H, J 5.1 Hz), 7.53 (d, 1H, J 11.4 Hz), 7.37 (d, 1H, J 5.2 Hz), 5.63 (s, 2H), 5.19 (m, 2H), 2.46 (s, 3H), 1.58 (s, 6H), 1.53 (d, 3H, J 6.8 Hz). LCMS m/z 531.

Example 102

(2R)-4-({6-[2-(1-Hydroxy-1-methylethyl)pyrimidin-5-yl]-2-methylimidazo[1,2-a]-pyrazin-3-yl}methyl)-2-methyl-8-(trifluoromethyl)pyrido[3,2-b][1,4]oxazin-3-one Prepared from Intermediate 139 and 2-[5-(4,4,5,5-tetramethyl-1,3,2-dioxaborolan-2-yl)pyrimidin-2-yl]propan-2-ol by a method analogous to that used to prepare Example 1. $\delta_H$ (400 MHz, DMSO-$d_6$) 9.41 (d, 1H, J 1.2 Hz), 9.37 (s, 2H), 9.07 (d, 1H, J 1.1 Hz), 8.19 (d, 1H, J 5.1 Hz), 7.37 (d, 1H, J 5.2 Hz), 5.71 (s, 2H), 5.20 (m, 2H), 2.49 (s, 3H), 1.55 (m, 9H). LCMS m/z 514.

Example 103

(2R)-4-[(6-Bromo-2-methylimidazo[1,2-a]pyrazin-3-yl)methyl]-8-fluoro-2-methyl-1,4-benzoxazin-3-one Prepared from Intermediate 28 and Intermediate 98 by a method analogous to that used to prepare Intermediate 21. $\delta_H$ (400 MHz, DMSO-$d_6$) 8.79 (d, 2H, J 1.7 Hz), 7.12 (m, 1H), 7.03 (m, 2H), 5.65 (m, 1H), 5.52 (m, 1H), 4.95 (q, 1H, J 6.6 Hz), 2.32 (s, 3H), 1.52 (d, 3H, J 6.7 Hz). LCMS m/z 407.

Example 104

(2R)-8-Fluoro-4-({6-[2-(1-hydroxy-1-methylethyl)pyrimidin-5-yl]-2-methylimidazo[1,2-a]pyrazin-3-yl}methyl)-2-methyl-1,4-benzoxazin-3-one Prepared from Example 103 and 2-[5-(4,4,5,5-tetramethyl-1,3,2-dioxaborolan-2-yl)pyrimidin-2-yl]propan-2-ol by a method analogous to that used to prepare Example 1. $\delta_H$ (400 MHz, DMSO-$d_6$) 9.38 (s, 2H), 9.25 (d, 1H, J 1.3 Hz), 9.09 (d, 1H, J 1.2 Hz), 7.14 (m, 1H), 7.04 (m, 2H), 5.73 (m, 1H), 5.64 (m, 1H), 5.18 (s, 1H), 4.99 (d, 1H, J 6.7 Hz), 2.34 (s, 3H), 1.57 (s, 6H), 1.52 (d, 3H, J 6.7 Hz). LCMS m/z 463.

Example 105

(2R)-4-[(6-Bromo-7-fluoro-2-methylimidazo[1,2-a]pyridin-3-yl)methyl]-8-fluoro-2-methyl-3-oxo-1,4-benzoxazine-6-carbonitrile Prepared from Intermediate 34 and Intermediate 140 by a method analogous to that used to prepare Intermediate 21. $\delta_H$ (400 MHz, DMSO-$d_6$) 8.76 (d, 1H, J 6.7 Hz), 7.75 (s, 1H), 7.72 (m, 1H), 7.56 (d, 1H, J 9.6 Hz), 5.66 (m, 1H), 5.50 (m, 1H), 5.10 (q, 1H, J 6.8 Hz), 2.30 (s, 3H), 1.55 (d, 3H, J 6.8 Hz). LCMS m/z 450.

Example 106

(2R)-8-Fluoro-4-({7-fluoro-6-[2-(1-hydroxy-1-methylethyl)pyrimidin-5-yl]-2-methyl-imidazo[1,2-a]pyridin-3-yl}methyl)-2-methyl-3-oxo-1,4-benzoxazine-6-carbonitrile Prepared from Example 105 and 2-[5-(4,4,5,5-tetramethyl-1,3,2-dioxaborolan-2-yl)pyrimidin-2-yl]propan-2-ol by a method analogous to that used to prepare Example 1. $\delta_H$ (300 MHz, DMSO-$d_6$) 9.27 (s, 1H), 9.02 (d, 2H, J 1.5 Hz), 8.76 (d, 1H, J 7.3 Hz), 7.70 (m, 2H), 7.47 (d, 1H, J 11.2 Hz), 5.61 (m, 2H), 5.09 (m, 1H), 2.27 (s, 3H), 1.56 (s, 6H). LCMS m/z 506.

Example 107

(2S)-8-Fluoro-4-({7-fluoro-6-[6-(1-hydroxy-1-methylethyl)pyridin-3-yl]-2-methyl-imidazo[1,2-a]pyridin-3-yl}methyl)-2-methyl-1,4-benzoxazin-3-one Prepared from Intermediate 143 and 5-(4,4,5,5-tetramethyl-1,3,2-dioxaborolan-2-yl)-2-{2-[(trimethylsilyl)oxy]propan-2-yl}pyridine by a method analogous to that used to prepare Example 1, followed by treatment with TBAF at room temperature. $\delta_H$ (300 MHz, DMSO-$d_6$) 8.67 (t, 1H, J 1.6 Hz), 8.58 (d, 1H, J 7.5 Hz), 7.95 (m, 1H), 7.80 (dd, 1H, J 8.2, 0.6 Hz), 7.49 (d, 1H, J 11.3 Hz), 7.16 (m, 1H), 7.03 (m, 2H), 5.67 (m, 1H), 5.52 (d, 1H, J 6.7 Hz), 5.32 (s, 1H), 4.93 (q, 1H, J 6.7 Hz), 2.32 (s, 3H), 1.49 (m, 9H). LCMS m/z 480.

Example 108

(2R)-8-Fluoro-4-({6-[2-(1-hydroxycyclobutyl)pyrimidin-5-yl]-2-methylimidazo[1,2-a]-pyrazin-3-yl}methyl)-2-methyl-1,4-benzoxazin-3-one Prepared from Intermediate 53 and Intermediate 66 by a method analogous to that used to prepare Example 1. $\delta_H$ (300 MHz, DMSO-$d_6$) 9.40 (s, 2H), 9.25 (d, 1H, J 1.4 Hz), 9.09 (d, 1H, J 1.4 Hz), 7.14 (m, 1H), 7.03 (m, 2H), 5.73 (d, 1H, J 16.8 Hz), 5.66 (s, 1H), 5.63 (d, 1H, J 16.6 Hz) 4.98 (q, 1H, J 6.7 Hz), 2.69 (m, 2H), 2.34 (s, 4H), 2.27 (m, 2H), 1.92 (m, 1H), 1.76 (m, 1H), 1.53 (d, 3H, J 6.7 Hz). LCMS m/z 476.

Example 109

(2R)-8-Fluoro-4-[(6-{2-[3-hydroxy-3-(trifluoromethyl)azetidin-1-yl]pyrimidin-5-yl}-2-methylimidazo[1,2-a]pyrazin-3-yl)methyl]-2-methyl-1,4-benzoxazin-3-one Prepared from Intermediate 66 and Intermediate 148 by a method analogous to that used to prepare Example 1. $\delta_H$ (300 MHz, DMSO-$d_6$) 8.99 (m, 4H), 7.46 (s, 1H), 7.07 (m, 3H), 5.71 (d, 1H, J 16.5 Hz), 5.60 (d, 1H, J 16.4 Hz), 4.97 (q, 1H, J 6.7 Hz), 4.37 (d, 2H, J 10.0 Hz), 4.15 (d, 2H, J 10 Hz), 2.35 (s, 3H), 1.52 (d, 3H, J 6.7 Hz). LCMS m/z 545.

Example 110

(2R)-8-Fluoro-2-methyl-4-({2-methyl-6-[2-(morpholin-4-yl)pyrimidin-5-yl]imidazo[1,2-a]pyrazin-3-yl}methyl)-1,4-benzoxazin-3-one Prepared from Intermediate 66 and Intermediate 90 by a method analogous to that used to prepare Example 1. $\delta_H$ (300 MHz, DMSO-$d_6$) 8.94 (m, 4H), 7.21 (dd, 1H, J 2.2, 0.7 Hz), 7.02 (m, 2H), 5.87 (d, 2H, J 16.7 Hz), 5.60 (d, 1H, J 16.7 Hz), 4.97 (q, 1H, J 6.7 Hz), 3.87 (m, 4H), 3.70 (m, 4H), 2.33 (s, 3H), 1.52 (d, 3H, J 6.7 Hz). LCMS m/z 491.

Example 111

(2R)-8-Fluoro-2-methyl-4-{[2-methyl-6-(4-methylsulfonylphenyl)imidazo[1,2-a]pyrazin-3-yl]methyl}-1,4-benzoxazin-3-one Prepared from Intermediate 66 and 2-(4-methylsulfonylphenyl)-1,3,2-dioxaborolane by a method analogous to that used to prepare Example 1. $\delta_H$ (300 MHz, DMSO-$d_6$) 9.18 (d, 1H, J 1.4 Hz), 9.06 (d, 1H, J 1.3 Hz), 8.30 (d, 2H, J 8.7 Hz), 8.08 (d, 2H, J 8.7 Hz), 7.18 (m, 1H), 7.04 (m, 2H), 5.76 (d, 1H, J 16.6 Hz), 5.65 (d, 1H, J 16.5 Hz), 4.97 (q, 1H, J 6.7 Hz), 3.29 (m, 3H), 2.35 (s, 3H), 1.52 (d, 3H, J 6.7 Hz). LCMS m/z 482.

Example 112

(2R)-8-Fluoro-4-({6-[2-(3-hydroxy-3-methylazetidin-1-yl)pyrimidin-5-yl]-2-methyl-imidazo[1,2-a]pyrazin-3-yl}methyl)-2-methyl-1,4-benzoxazin-3-one Prepared from Intermediate 66 and Intermediate 149 by a method analogous to that used to prepare Example 1. $\delta_H$ (300 MHz, DMSO-$d_6$) 9.12 (d, 1H, J 1.3 Hz), 8.98 (s, 3H), 7.26 (m, 1H), 7.08 (m, 2H), 5.85 (d, 1H, J 16.5 Hz), 5.73 (s, 1H), 5.63 (d, 1H, J 16.5 Hz), 5.03 (q, 1H, J 6.7 Hz), 4.04 (dd, 4H, J 12.0, 8.9 Hz), 2.40 (s, 3H), 1.71 (d, 3H, J 6.7 Hz), 1.52 (s, 3H). LCMS m/z 491.

Example 113

(2R)-8-Fluoro-4-({6-[6-(1-hydroxy-1-methylethyl)pyridin-3-yl]-2-methylimidazo[1,2-a]-pyrazin-3-yl}methyl)-2-methyl-1,4-benzoxazin-3-one Prepared from Intermediate 66 and 5-(4,4,5,5-tetramethyl-1,3,2-dioxaborolan-2-yl)-2-{2-[(trimethylsilyl)oxy]propan-2-yl}pyridine by a method analogous to that used to prepare Example 1, followed by treatment with TBAF at room temperature. $\delta_H$ (300 MHz, DMSO-$d_6$) 9.12 (dd, 1H, J 2.3, 0.7 Hz), 9.08 (d, 1H, J 1.4 Hz), 9.04 (d, 1H, J 1.4 Hz), 8.35 (dd, 1H, J 8.3, 2.4 Hz), 7.80 (dd, 1H, J 8.3, 0.7 Hz), 7.17 (m, 1H), 7.03 (m, 2H), 5.74 (d, 1H, J 16.5 Hz), 5.63 (d, 1H, J 16.6 Hz), 5.30 (s, 1H), 4.97 (q, 1H, J 6.6 Hz), 2.35 (s, 4H), 1.55 (d, 3H, J 6.7 Hz), 1.50 (s, 7H). LCMS m/z 462.

Example 114

(2R)-8-Fluoro-2-methyl-4-({2-methyl-6-[2-(6-oxa-3-azabicyclo[3.1.1]heptan-3-yl)-pyrimidin-5-yl]imidazo[1,2-a]pyrazin-3-yl}methyl)-1,4-benzoxazin-3-one Prepared from Intermediate 66 and Intermediate 158 by a method analogous to that used to prepare Example 1. $\delta_H$ (400 MHz, DMSO-$d_6$) 9.02 (s, 2H), 9.01 (d, 1H, J 1.2 Hz), 8.97 (d, 1H, J 1.2 Hz), 7.16 (dd, 1H, J 7.9, 1.8 Hz), 7.04 (m, 2H), 5.79 (d, 1H, J 16.5 Hz), 5.61 (d, 1H, J 16.5 Hz), 4.98 (q, 1H, J 6.6 Hz), 4.74 (d, 2H, J 6.4 Hz), 3.94 (d, 2H, J 13.1 Hz), 3.74 (d, 2H, J 13.1 Hz), 3.15 (q, 1H, J 7.3 Hz), 2.35 (s, 3H), 1.91 (d, 1H, J 8.9 Hz), 1.54 (d, 3H, J 6.7 Hz). LCMS m/z 503.

Example 115

8-Fluoro-4-[(6-{2-[3-hydroxy-3-(trifluoromethyl)azetidin-1-yl]pyrimidin-5-yl}-2-methyl-imidazo[1,2-a]pyrazin-3-yl)methyl]-1,4-benzoxazin-3-one Prepared from Intermediate 144 and Intermediate 148 by a method analogous to that used to prepare Example 1. $\delta_H$ (400 MHz, DMSO-$d_6$) 9.02 (d, 1H, J 1.4 Hz), 9.00 (s, 2H), 8.99 (d, 1H, J 1.4 Hz), 7.47 (s, 1H), 7.12 (m, 1H), 7.03 (m, 2H), 5.66 (s, 2H), 4.90 (s, 2H), 4.38 (d, 2H, J 10.5 Hz), 4.16 (d, 2H, J 10.5 Hz), 2.32 (s, 3H). LCMS m/z 531.

Example 116

(2R)-6-Bromo-8-fluoro-4-({6-[2-(1-hydroxy-1-methylethyl)pyrimidin-5-yl]-2-methyl-imidazo[1,2-a]pyrazin-3-yl}methyl)-2-methyl-1,4-benzoxazin-3-one Prepared from Intermediate 120 and Intermediate 135 by a method analogous to that used to prepare Intermediate 21. $\delta_H$ (300 MHz, DMSO-$d_6$) 9.37 (s, 2H), 9.24 (d, 1H, J 1.4 Hz), 9.10 (d, 1H, J 1.3 Hz), 7.48 (t, 1H, J 1.9 Hz), 7.36 (dd, 1H, J 9.7, 2.0 Hz), 5.76 (d, 1H, J 16.6 Hz), 5.64 (d, 1H, J 16.5 Hz), 5.20 (s, 1H), 5.01 (q, 1H, J 6.6 Hz), 2.40 (s, 3H), 1.56 (s, 6H), 1.53 (d, 3H, J 6.7 Hz). LCMS m/z 524.

Example 117

(2R)-8-Fluoro-2-methyl-4-{[2-methyl-6-(6-methylsulfonylpyridin-3-yl)imidazo[1,2-a]-pyrazin-3-yl]methyl}-1,4-benzoxazin-3-one Prepared from Intermediate 66 and 2-(methylsulfonyl)-5-(4,4,5,5-tetramethyl-1,3,2-dioxaborolan-2-yl)pyridine by a method analogous to that used to prepare Example 1. $\delta_H$ (300 MHz, DMSO-d$_6$) 9.51 (dd, 1H, J 2.2, 0.6 Hz), 9.35 (d, 1H, J 1.4 Hz), 9.10 (d, 1H, J 1.3 Hz), 8.74 (dd, 1H, J 8.3, 2.2 Hz), 8.24 (dd, 1H, J 8.3, 0.6 Hz), 7.24 (m, 1H), 7.03 (m, 2H), 5.75 (s, 1H), 5.74 (d, 1H, J 16.5 Hz), 5.65 (d, 1H, J 16.5 Hz), 4.98 (q, 1H, J 6.7 Hz), 3.40 (s, 3H), 2.32 (s, 3H), 1.52 (d, 3H, J 6.7 Hz). LCMS m/z 483.

Example 118

(2R)-8-Fluoro-2-methyl-4-({2-methyl-6-[4-(pentafluoro-$\lambda^6$-sulfanyl)phenyl]imidazo[1,2-a]pyrazin-3-yl}methyl)-1,4-benzoxazin-3-one Prepared from Intermediate 66 and pentafluoro-[4-(4,4,5,5-tetramethyl-1,3,2-dioxaborolan-2-yl)phenyl]-$\lambda^6$-sulfane by a method analogous to that used to prepare Example 1. $\delta_H$ (300 MHz, DMSO-d$_6$) 9.19 (d, 1H, J 1.2 Hz), 9.06 (d, 1H, J 0.8 Hz), 8.26 (d, 2H, J 8.8 Hz), 8.09 (d, 2H, J 9.0 Hz), 7.16 (dd, 1H, J 1.4, 0.9 Hz), 7.04 (m, 2H), 5.75 (d, 1H, J 16.5 Hz), 5.65 (d, 1H, J 16.5 Hz), 4.97 (d, 1H, J 6.7 Hz), 2.34 (s, 3H), 1.52 (d, 3H, J 6.7 Hz). LCMS m/z 530.

Example 119

(2R)-4-({6-[2-(6,6-Dioxo-$\lambda^6$-thia-2-azaspiro[3.3]heptan-2-yl)pyrimidin-5-yl]-2-methyl-imidazo[1,2-a]pyrazin-3-yl}methyl)-8-fluoro-2-methyl-1,4-benzoxazin-3-one Prepared from Intermediate 66 and Intermediate 159 by a method analogous to that used to prepare Example 1. $\delta_H$ (300 MHz, DMSO-d$_6$) 9.03 (d, 1H, J 1.4 Hz), 8.96 (s, 2H), 8.94 (d, 1H, J 1.4 Hz), 7.13 (m, 1H), 7.02 (m, 2H), 5.70 (d, 1H, J 16.5 Hz), 5.59 (d, 1H, J 16.5 Hz), 4.97 (q, 1H, J 6.6 Hz), 4.54 (s, 4H), 4.37 (s, 4H), 2.33 (s, 3H), 1.52 (d, 3H, J 6.7 Hz). LCMS m/z 551.

Example 120

(2R)-8-Fluoro-2-methyl-4-({2-methyl-6-[2-(3-oxa-6-azaspiro[3.3]heptan-6-yl)pyrimidin-5-yl]imidazo[1,2-a]pyrazin-3-yl}methyl)-1,4-benzoxazin-3-one Prepared from Intermediate 66 and Intermediate 160 by a method analogous to that used to prepare Example 1. $\delta_H$ (300 MHz, DMSO-d$_6$) 9.02 (s, 1H), 8.92 (m, 3H), 7.16 (m, 1H), 6.99 (m, 2H), 5.76 (s, 1H), 5.70 (d, 1H, J 16.8 Hz), 5.55 (d, 1H, J 16.8 Hz), 5.01 (q, 1H, J 6.8 Hz), 4.52 (t, 1H, J 7.6 Hz), 4.33 (d, 2H, J 10.5 Hz), 4.18 (d, 2H, J 10.5 Hz), 2.89 (t, 1H, J 7.6 Hz), 2.32 (s, 3H), 1.52 (d, 3H, J 6.8 Hz). LCMS m/z 503.

Example 121

(2R)-8-Fluoro-2-methyl-4-{[2-methyl-6-(1-methylpyrazol-4-yl)imidazo[1,2-a]pyrazin-3-yl]methyl}-1,4-benzoxazin-3-one Prepared from Intermediate 66 and 1-methyl-4-(4,4,5,5-tetramethyl-1,3,2-dioxaborolan-2-yl)pyrazole by a method analogous to that used to prepare Example 1. $\delta_H$ (300 MHz, DMSO-d$_6$) 8.88 (d, 1H, J 1.4 Hz), 8.70 (d, 1H, J 1.4 Hz), 8.15 (s, 1H), 7.86 (d, 1H, J 0.7 Hz), 7.05 (m, 3H), 5.77 (d, 1H, J 16.5 Hz), 5.55 (d, 1H, J 16.5 Hz), 4.97 (q, 1H, J 6.7 Hz), 3.90 (s, 3H), 2.32 (s, 3H), 1.52 (d, 3H, J 6.7 Hz). LCMS m/z 408.

Example 122

(2R)-7,8-Difluoro-4-[(6-{2-[3-hydroxy-3-(trifluoromethyl)azetidin-1-yl]pyrimidin-5-yl}-2-methylimidazo[1,2-a]pyrazin-3-yl)methyl]-2-methyl-1,4-benzoxazin-3-one Prepared from Intermediate 148 and Intermediate 163 by a method analogous to that used to prepare Example 1. $\delta_H$ (400 MHz, DMSO-d$_6$) 9.02 (d, 1H, J 1.4 Hz), 9.01 (s, 2H), 8.99 (d, 1H, J 1.3 Hz), 7.50 (s, 1H), 7.13 (m, 2H), 5.71 (d, 1H, J 16.7 Hz), 5.55 (d, 1H, J 16.7 Hz), 5.03 (d, 1H, J 6.8 Hz), 4.38 (d, 2H, J 10.3 Hz), 4.16 (m, 2H), 2.31 (s, 3H), 1.54 (d, 3H, J 6.7 Hz). LCMS m/z 563.

Example 123

4-({6-[2-(1-Hydroxy-1-methylethyl)pyrimidin-5-yl]-2-methylimidazo[1,2-a]pyrazin-3-yl}methyl)spiro[1,4-benzoxazine-2,1'-cyclopropane]-3-one Prepared from Intermediate 145 and 2-[5-(4,4,5,5-tetramethyl-1,3,2-dioxaborolan-2-yl)pyrimidin-2-yl]propan-2-ol by a method analogous to that used to prepare Example 1. $\delta_H$ (300 MHz, DMSO-d$_6$) 9.44 (s, 2H), 9.23 (d, 1H, J 1.4 Hz), 9.09 (d, 10H, J 1.3 Hz), 7.27 (m, 1H), 7.01 (m, 3H), 5.68 (s, 2H), 5.17 (s, 1H), 2.32 (s, 3H), 1.60 (s, 6H), 1.32 (m, 4H). LCMS m/z 476.

Example 124

8-Fluoro-4-({6-[2-(1-hydroxy-1-methylethyl)pyrimidin-5-yl]-2-methylimidazo[1,2-a]-pyrazin-3-yl}methyl)spiro[1,4-benzoxazine-2,1'-cyclopropane]-3-one Prepared from Intermediate 146 and 2-[5-(4,4,5,5-tetramethyl-1,3,2-dioxaborolan-2-yl)pyrimidin-2-yl]propan-2-ol by a method analogous to that used to prepare Example 1. $\delta_H$ (300 MHz, DMSO-d$_6$) 9.39 (s, 2H), 9.24 (d, 1H, J 1.4 Hz), 9.10 (d, 1H, J 1.4 Hz), 7.07 (m, 3H), 5.69 (s, 2H), 5.17 (s, 1H), 2.32 (s, 3H), 1.55 (s, 6H), 1.37 (m, 4H). LCMS m/z 476.

Example 125

(2R)-8-Fluoro-2-methyl-4-{[2-methyl-6-(morpholin-4-yl)imidazo[1,2-a]pyrazin-3-yl]-methyl}-1,4-benzoxazin-3-one A mixture of Intermediate 66 (230 mg, 0.5676 mmol) and morpholine in DMSO was heated under microwave irradiation at 180° C. for 5 minutes, then at 200° C. for 10 minutes. The crude mixture was diluted with EtOAc (20 mL) and washed with water (50 mL). The water layer was extracted with EtOAc (2×40 mL). The combined organic layers were washed with water (2×50 mL) and brine (2×50 mL), then dried over MgSO$_4$. Removal of solvent in vacuo and purification of the residue by preparative HPLC gave the title compound (2 mg, 1%) as a white solid. $\delta_H$ (400 MHz, DMSO-d$_6$) 8.67 (s, 1H), 7.56 (s, 1H), 7.13-6.96 (m, 3H), 5.64 (d, 1H), 5.49 (d, 1H), 4.94 (q, 1H), 3.76 (m, 4H), 3.19 (m, 4H), 2.38 (s, 3H), 1.51 (d, 3H). LCMS MH+ m/z 413.

Example 126

(2R)-8-Fluoro-2-methyl-4-({2-methyl-6-[2-(3-oxopiperazin-1-yl)pyrimidin-5-yl]imidazo-[1,2-a]pyrazin-3-yl}methyl)-1,4-benzoxazin-3-one Prepared from Intermediate 66 and Intermediate 147 by a method analogous to that used to prepare Example 1. $\delta_H$ (400 MHz, DMSO-d$_6$) 8.99 (m, 4H), 8.14 (br s, 1H), 7.12 (m, 1H), 7.02 (m, 2H), 5.65 (q, J 16.6 Hz, 2H), 4.97 (m, 1H), 4.26 (s, 2H), 3.99 (m, 2H), 2.50 (m, overlapping with DMSO signal, 2H), 2.32 (s, 3H), 1.52 (d, J 6.7 Hz, 3H). LCMS m/z 504.

Example 127

(2R)-4-({6-[2-(3,3-Difluoroazetidin-1-yl)pyrimidin-5-yl]-2-methylimidazo[1,2-a]pyrazin-3-yl}methyl)-8-fluoro-2-methyl-1,4-benzoxazin-3-one Prepared from Intermediate 66 and Intermediate 150 by a method analogous to that used to prepare Example 1. LCMS m/z 497.

Example 128

(2R)-8-Fluoro-4-({7-fluoro-2-hydroxymethyl)-6-[2-(1-hydroxy-1-methylethyl)-pyrimidin-5-yl]imidazo[1,2-a]pyridin-3-yl}methyl)-2-methyl-1,4-benzoxazin-3-one To a solution of Example 26 (150 mg, 0.31 mmol) in acetonitrile (10 mL) was added Selectfluor™ (0.122 g, 0.34 mmol). The mixture was stirred at room temperature for 18 h, then partitioned between aqueous sodium carbonate solution (50 mL) and ethyl acetate (75 mL). The organic layer was concentrated in vacuo. The crude residue was purified by chromatography on silica (0-7% MeOH in DCM), followed by preparative HPLC, to give, after freeze-drying, the title compound (5 mg, 3.2%) as a white solid. $\delta_H$ (300 MHz, DMSO-d$_6$) 9.01 (d, 2H, J 1.6 Hz), 8.74 (d, 1H, J 7.3 Hz), 7.60 (d, 1H, J 11.3 Hz), 7.39 (m, 1H), 7.01 (m, 2H), 5.70 (m, 2H), 5.42 (t, 1H, J 5.4 Hz), 5.19 (s, 1H), 4.92 (m, 1H), 4.68 (d, 2H, J 5.1 Hz), 1.56 (s, 6H), 1.49 (d, 3H, J 6.7 Hz). LCMS m/z 500.

Example 129

(2R)-8-Fluoro-4-({6-[2-(1-hydroxy-1-methylethyl)pyrimidin-5-yl]-2-methylimidazo[1,2-b]pyridazin-3-yl}methyl)-2-methyl-1,4-benzoxazin-3-one Prepared from Intermediate 152 and 2-[5-(4,4,5,5-tetramethyl-1,3,2-dioxaborolan-2-yl)pyrimidin-2-yl]propan-2-ol by a method analogous to that used to prepare Example 1. $\delta_H$ (400 MHz, DMSO-d$_6$) 9.39 (s, 2H), 8.17 (d, 1H, J 9.5 Hz), 7.89 (d, 1H, J 9.5 Hz), 7.13 (d, 1H, J 7.8 Hz), 6.92 (m, 2H), 5.79 (d, 1H, J 16.1 Hz), 5.57 (d, 1H, J 16.1 Hz), 5.19 (s, 1H), 4.87 (q, 1H, J 6.6 Hz), 2.49 (s, 3H), 1.59 (s, 6H), 1.50 (d, 3H, J 6.7 Hz). LCMS m/z 464.

Example 130

(2R)-8-Fluoro-2-methyl-4-({2-methyl-6-[2-(5-oxo-1,4-diazepan-1-yl)pyrimidin-5-yl]-imidazo[1,2-a]pyrazin-3-yl}methyl)-1,4-benzoxazin-3-one Prepared from Intermediate 66 and Intermediate 78 by a method analogous to that used to prepare Example 1. $\delta_H$ (300 MHz, DMSO-d$_6$) 9.00 (d, J 1.3 Hz, 1H), 8.97 (s, 2H), 8.96 (d, J 1.5 Hz, 1H), 7.96 (br s, 1H), 7.14-7.11 (m, 1H), 7.05-6.99 (m, 2H), 5.65 (dd, J 16.7, 16.4 Hz, 2H), 4.97 (q, J 6.7 Hz, 1H), 4.01-3.98 (m, 4H), 3.27-3.22 (m, 2H), 2.56-2.53 (m, 2H), 2.33 (s, 3H), 1.52 (d, J 6.7 Hz, 3H). LCMS m/z 517.

Example 131

(2R)-8-Fluoro-4-({7-fluoro-6-[2-(1-hydroxy-1-methylethyl)pyrimidin-5-yl]-2-methyl-imidazo[1,2-a]pyridin-3-yl}methyl)-2-methyl-3-oxo-1,4-benzoxazine-6-carboxylic acid Example 88 (115 mg, 0.21 mmol) was dissolved in THF (2.5 mL) and water (0.5 mL). Lithium hydroxide monohydrate (12 mg, 0.28 mmol) was added and the reaction mixture was stirred at room temperature for 4 days, then quenched with saturated ammonium chloride solution and concentrated under reduced pressure. The residue was taken up in water (5 mL) and HCl (1 mL of a 4M solution in 1,4-dioxane, 4.3 mmol), then the solution was concentrated under reduced pressure. The residue was distributed between water and isopropanol:CHCl$_3$ (1:1) and the phases were separated. The organic phase was dried over sodium sulfate and concentrated under reduced pressure. The residue was purified by flash column chromatography (MeOH:DCM 0-20%) to afford the title compound (70 mg, 62%) as a white solid. $\delta_H$ (300 MHz, DMSO-d$_6$) 9.17 (d, J 6.7 Hz, 1H), 9.11 (d, J 1.3 Hz, 2H), 8.01 (d, J 9.6 Hz, 1H), 7.71 (s, 1H), 7.52 (dd, J 10.4, 1.6 Hz, 1H), 5.77 (dd, J 16.9, 16.9 Hz, 2H), 5.10 (q, J 6.7 Hz, 1H), 2.50 (s, 3H), 1.57 (s, 6H), 1.54 (d, J 6.5 Hz, 3H). LCMS MH+ m/z 524.

Example 132

(2R)-8-Fluoro-4-({7-fluoro-6-[2-(1-hydroxy-1-methylethyl)pyrimidin-5-yl]-2-methyl-imidazo[1,2-a]pyridin-3-yl}methyl)-N,2-dimethyl-3-oxo-1,4-benzoxazine-6-carboxamide Example 131 (42 mg, 0.08 mmol), HATU (34 mg, 0.09 mmol), methylamine (0.05 mL of a 2M solution in THF, 0.10 mmol) and DIPEA (0.03 mL, 0.16 mmol) were dissolved in DMF (1 mL). The reaction mixture was stirred at room temperature for 2 h, then diluted with EtOAc and washed with brine. The organic layer was dried over sodium sulfate and concentrated under reduced pressure. The crude residue was purified by flash column chromatography (MeOH:DCM, 0-10%) to afford the title compound (15 mg, 35%) as a white solid. $\delta_H$ (300 MHz, DMSO-d$_6$) 8.98 (d, J 1.5 Hz, 2H), 8.71 (d, J 7.3 Hz, 1H), 8.33 (d, J 4.6 Hz, 1H), 7.60 (s, 1H), 7.48 (d, J 11.3 Hz, 1H), 7.43 (dd, J 11.0, 1.6 Hz, 1H), 5.56 (dd, J 17.1, 16.6 Hz, 2H), 5.11 (s, 1H), 4.97 (q, J 6.7 Hz, 1H), 2.67 (d, J 4.5 Hz, 3H), 2.32 (s, 3H), 1.49 (s, 6H), 1.45 (d, J 6.7 Hz, 3H). LCMS MH+ m/z 537.

Example 133

(2S)-6,8-Difluoro-4-({7-fluoro-6-[2-(2-hydroxypropan-2-yl)pyrimidin-5-yl]-2-methyl-imidazo[1,2-a]pyridin-3-yl}methyl)-2-methyl-3,4-dihydro-2H-1,4-benzoxazin-3-one To stirred solution of Intermediate 88 (500 mg, 1.14 mmol) and 2-[5-(4,4,5,5-tetramethyl-1,3,2-dioxaborolan-2-yl)pyrimidin-2-yl]propan-2-ol (360 mg, 1.36 mmol) in 1,4-dioxane (12.5 mL) was added 2M aqueous sodium carbonate solution (1.7 mL, 3.41 mmol) and the reaction mixture was degassed with nitrogen gas for 10 minutes. Pd(dppf)Cl$_2$ (47 mg, 0.057 mmol) was added and the reaction mixture was degassed with nitrogen gas for another 5 minutes. The reaction mixture was heated at 100° C. for 1 h, then cooled to room temperature. Ethyl acetate (75 mL) and water (70 mL) were added to the reaction mixture. The aqueous layer was back-extracted with ethyl acetate (75 mL). The organic phases were combined, washed with brine (70 mL), dried over sodium sulphate and filtered, then the solvent was removed in vacuo. The residue was purified by column chromatography using a methanol/dichloromethane gradient. The residue was triturated in diethyl ether to give the title compound (358 mg, 63%) as a white solid. $\delta_H$ (500 MHz, DMSO-d$_6$) 9.03 (s, 2H), 8.78 (d, J 7.3 Hz, 1H), 7.56 (d, J 11.2 Hz, 1H), 7.23 (d, J 10.3 Hz, 1H), 7.14-7.07 (m, 1H), 5.65 (d, J 16.6 Hz, 1H), 5.51 (d, J 16.6 Hz, 1H), 5.18 (s, 1H), 4.93 (q, J 6.7 Hz, 1H), 2.30 (s, 3H), 1.56 (s, 6H), 1.48 (d, J 6.7 Hz, 3H). LCMS MH+ m/z 498.

Example 134

(2S)-8-Fluoro-4-({7-fluoro-6-[2-(2-hydroxypropan-2-yl)pyrimidin-5-yl]-2-methyl-imidazo[1,2-a]pyridin-3-yl}methyl)-2-methyl-3,4-dihydro-2H-1,4-benzoxazin-3-one A mixture of Intermediate 143 (0.150 g, 0.355 mmol), 2-[5-(4,4,5,5-tetramethyl-1,3,2-dioxaborolan-2-yl)pyrimidin-2-yl]propan-2-ol (141 mg, 0.533 mmol) and Pd(dppf)Cl$_2$ (13 mg, 0.018 mmol) in 1,4-dioxane (3.8 mL) and aqueous sodium carbonate solution (1 mL) was de-gassed and stirred at 110° C. under nitrogen for 1 h. The reaction mixture was partitioned between EtOAc and brine. The organic layer was dried (MgSO$_4$) and evaporated onto silica, then purified by column chromatography on silica gel (0-100% EtOAc in hexane), to give the title compound (18 mg, 12%) as a white solid. $\delta_H$ (300 MHz, DMSO-d$_6$) 8.99 (d, 2H, J 1.6 Hz), 8.71 (d, 1H, J 7.4 Hz), 7.50 (d, 1H, J 11.3 Hz), 7.13 (m, 1H), 6.97 (m, 2H), 5.59 (d, 1H, J 16.5 Hz), 5.47 (d, 1H, J 16.5 Hz), 5.15 (s, 1H), 4.88 (q, 1H, J 6.7 Hz), 2.24 (s, 3H), 1.50 (s, 6H), 1.43 (d, 3H, J 6.7 Hz). LCMS MH+m/z 480.8.

Example 135

(2R)-8-Fluoro-4-({7-fluoro-6-[2-(1-hydroxy-1-methylethyl)pyrimidin-5-yl]-2-methyl-imidazo[1,2-a]pyridin-3-yl}methyl)-6-(1-hydroxy-1-methyl-ethyl)-2-methyl-1,4-benzoxazin-3-one Prepared from Intermediate 162 and 2-[5-(4,4,5,5-tetramethyl-1,3,2-dioxaborolan-2-yl)pyrimidin-2-yl]propan-2-ol by a method analogous to that used to prepare Example 1. The title compound (106 mg, 36%) was obtained as a white solid. $\delta_H$ (300 MHz, DMSO-d$_6$) 9.03 (d, J 1.5 Hz, 2H), 8.82 (d, J 7.3 Hz, 1H), 7.55 (d, J 11.3 Hz, 1H), 7.11 (br s, 1H), 7.02 (dd, J 11.8, 1.7 Hz, 1H), 5.69 (d, J 16.4 Hz, 1H), 5.56 (d, J 16.4 Hz, 1H), 5.18 (s, 1H), 5.05 (s, 1H), 4.91 (q, J 6.7 Hz, 1H), 2.32 (s, 3H), 1.56 (s, 6H), 1.49 (d, J 6.7 Hz, 3H), 1.25 (d, J 3.3 Hz, 6H). LCMS MH+ m/z 538.

Example 136

8-Fluoro-4-({6-[6-(methanesulfonyl)pyridin-3-yl]-2-methylimidazo[1,2-a]pyridin-3-yl}-methyl)-3,4-dihydro-2H-1,4-benzoxazin-3-one Prepared from Intermediate 21 and 6-(methylsulfonyl)pyridin-3-ylboronic acid by a method analogous to that used to prepare Example 1. The title compound (106 mg, 36%) was obtained as a white solid. LCMS m/z 467, RT 1.29 minutes.

Example 137

(2R)-8-Fluoro-4-[(7-fluoro-6-{4-[imino(methyl)oxo-$\lambda^6$-sulfanyl]phenyl}-2-methyl-imidazo[1,2-a]pyridin-3-yl)methyl]-2-methyl-3,4-dihydro-2H-1,4-benzoxazin-3-one Intermediate 167 (91%, 42 mg, 0.06 mmol) was dissolved in MeOH (1 mL) and K$_2$CO$_3$ (45 mg, 0.32 mmol) was added. The reaction mixture was stirred at room temperature for 1 h, then purified by preparative HPLC to afford the title compound (6 mg, 18.4%) as a white solid. $\delta_H$ (500 MHz, CDCl$_3$) 8.41 (d, J 7.1 Hz, 1H), 8.11 (d, J 8.4 Hz, 2H), 7.68 (d, J 7.6 Hz, 2H), 7.25-7.22 (m, 1H), 6.98-6.90 (m, 2H), 6.88-6.81 (m, 1H), 5.64 (dd, J 16.3, 5.8 Hz, 1H), 5.35 (dd, J 16.3, 5.0 Hz, 1H), 4.73 (q, J 6.5 Hz, 1H), 3.17 (s, 3H), 2.75 (s, 1H), 2.60 (s, 3H), 1.62 (d, J 6.8 Hz, 3H). LCMS m/z 497.

Examples 138 to 147

The following compounds were prepared from the specified starting materials. Examples 138-142, 144 and 145 were prepared by a method analogous to that used to prepare Example 1. Example 143 was prepared by a method analogous to that used to prepare Example 32. Examples 146 and 147 were prepared by chiral resolution.

| Ex. | Name | Starting Material | LCMS RT | LCMS m/z |
|---|---|---|---|---|
| 138 | (2R)-8-Fluoro-4-({7-fluoro-6-[4-(methanesulfonyl)-phenyl]-2-methylimidazo[1,2-a]pyridin-3-yl}methyl)-2-methyl-3,4-dihydro-2H-1,4-benzoxazin-3-one | Int. 35 | 1.41 | 498 |
| 139 | (2S)-8-Fluoro-4-[(7-fluoro-6-{4-[imino(methyl)oxo-$\lambda^6$-sulfanyl]phenyl}-2-methylimidazo[1,2-a]pyridin-3-yl)methyl]-2-methyl-3,4-dihydro-2H-1,4-benzoxazin-3-one | Int. 143 and Int. 170 | 1.28 | 497 |

| Ex. | Name | Starting Material | LCMS RT | LCMS m/z |
|---|---|---|---|---|
| 140 | (2R)-6,8-Difluoro-4-[(6-{4-[imino(methyl)oxo-$\lambda^6$-sulfanyl]phenyl}-2-methylimidazo[1,2-a]pyrazin-3-yl)methyl]-2-methyl-3,4-dihydro-2H-1,4-benzoxazin-3-one | Int. 64 and Int. 170 | 1.29 | 498 |
| 141 | (2R)-8-Fluoro-4-[(6-{4-[imino(methyl)oxo-$\lambda^6$-sulfanyl]phenyl}-2-methylimidazo[1,2-a]pyrazin-3-yl)methyl]-2-methyl-3,4-dihydro-2H-1,4-benzoxazin-3-one | Int. 66 and Int. 170 | 1.25 | 480 |
| 142 | tert-Butyl 2-({[4-(7-fluoro-3-{[(2S)-8-fluoro-2-methyl-3-oxo-3,4-dihydro-2H-1,4-benzoxazin-4-yl]methyl}-2-methylimidazo[1,2-a]pyridin-6-yl)phenyl](methyl)-oxo-$\lambda^6$-sulfanylidene}amino)acetate | Int. 143 and Int. 171 | 1.54 | 611 |
| 143 | 2-({[4-(7-Fluoro-3-{[(2S)8-fluoro-2-methyl-3-oxo-3,4-dihydro-2H-1,4-benzoxazin-4-yl]methyl}-2-methylimidazo[1,2-a]pyridin-6-yl)phenyl](methyl)-oxo-$\lambda^6$-sulfanylidene}amino)acetic acid | Ex. 142 | 1.16 | 555 |
| 144 | (2R)-8-Fluoro-4-[(7-fluoro-6-{6-[imino(methyl)oxo-$\lambda^6$-sulfanyl]pyridin-3-yl}-2-methylimidazo[1,2-a]-pyridin-3-yl)methyl]-2-methyl-3,4-dihydro-2H-1,4-benzoxazin-3-one | Int. 35 and Int. 175 | 1.24 | 498 |
| 145 | 8-Fluoro-4-[(7-fluoro-6-{4-[imino(methyl)oxo-$\lambda^6$-sulfanyl]phenyl}-2-methylimidazo[1,2-a]pyridin-3-yl)methyl]-3,4-dihydro-2H-1,4-benzoxazin-3-one | Int. 164 and Int. 170 | 1.26 | 483 |
| 146 | (2S)-8-Fluoro-4-[(7-fluoro-6-{4-[imino(methyl)oxo-$\lambda^6$-sulfanyl]phenyl}-2-methylimidazo[1,2-a]pyridin-3-yl)-methyl]-2-methyl-3,4-dihydro-2H-1,4-benzoxazin-3-one Isomer 1 | Ex. 139 | 1.31 | 497 |
| 147 | (2S)-8-Fluoro-4-[(7-fluoro-6-{4-[imino(methyl)oxo-$\lambda^6$-sulfanyl]phenyl}-2-methylimidazo[1,2-a]pyridin-3-yl)-methyl]-2-methyl-3,4-dihydro-2H-1,4-benzoxazin-3-one Isomer 2 | Ex. 139 | 1.31 | 497 |

Example 148

(2S)-8-Fluoro-4-[(7-fluoro-6-{6-[imino(methyl)oxo-$\lambda^6$-sulfanyl]pyridin-3-yl}-2-methyl-imidazo[1,2-a]pyridin-3-yl)methyl]-2-methyl-3,4-dihydro-2H-1,4-benzoxazin-3-one A multi-neck round-bottom flask containing a suspension of Intermediate 173 (98%, 0.5 g, 1.48 mmol), 4,4,4',4',5,5,5',5'-octamethyl-2,2'-bi-1,3,2-dioxaborolane (0.45 g, 1.78 mmol) and potassium acetate (0.44 g, 4.44 mmol) in anhydrous 1,4-dioxane (10 mL) was degassed under a stream of nitrogen gas for 15 minutes prior to the addition of Pd(dppf)Cl$_2$ (0.06 g, 0.07 mmol). The mixture was stirred at 80° C. for 3 h, then cooled to room temperature and treated with Intermediate 143 (169 mg, 0.4 mmol) and 2M K$_2$CO$_3$ in water (0.89 mL). The mixture was stirred at 80° C. overnight, then cooled to room temperature, diluted with EtOAc (40 mL) and passed over a pad of celite. The filtrate was washed with water (40 mL), then the aqueous phase was further extracted with EtOAc (2×40 mL). The combined organic fraction was washed with brine (40 mL), then passed over a Biotage 50 mL hydrophobic phase separator and concentrated in vacuo. The resulting crude orange solid (1.0 g) was purified by chromatography on silica gel, eluting with 0-15% methanol in EtOAc, followed by trituration with EtOAc, to afford the title compound (0.346 g, 46%) as an off-white powder. $\delta_H$ (500 MHz, DMSO-d$_6$) 8.91 (s, 1H), 8.73 (d, J 7.4 Hz, 1H), 8.29 (dt, J 8.1, 1.6 Hz, 1H), 8.22 (d, J 8.1 Hz, 1H), 7.54 (d, J 11.4 Hz, 1H), 7.16 (d, J 8.2 Hz, 1H), 7.08-6.97 (m, 2H), 5.65 (d, J 16.6 Hz, 1H), 5.54 (d, J 16.5 Hz, 1H), 4.93 (q, J 6.7 Hz, 1H), 4.54 (s, 1H), 3.23 (d, J 1.0 Hz, 3H), 2.31 (s, 3H), 1.49 (d, J 6.7 Hz, 3H). LCMS m/z 498, RT 1.25 minutes.

Examples 149 to 238

The following compounds were prepared from the specified starting materials using methods analogous to one or more of the foregoing procedures. Examples 149-152, 157, 158, 164, 165, 167, 168, 189-192, 194, 195, 197, 198, 203-206, 208 and 209 were prepared by chiral resolution.

| Ex. | Name | Starting Material | LCMS RT | LCMS m/z |
|---|---|---|---|---|
| 149 | (2S)-8-Fluoro-4-[(7-fluoro-6-{6-[imino(methyl)oxo-$\lambda^6$-sulfanyl]pyridin-3-yl}-2-methylimidazo[1,2-a]pyridin-3-yl)methyl]-2-methyl-3,4-dihydro-2H-1,4-benzoxazin-3-one Isomer 1 | Ex. 148 | 1.27 | 498 |
| 150 | (2S)-8-Fluoro-4-[(7-fluoro-6-{6-[imino(methyl)oxo-$\lambda^6$-sulfanyl]pyridin-3-yl}-2-methylimidazo[1,2-a]pyridin-3-yl)methyl]-2-methyl-3,4-dihydro-2H-1,4-benzoxazin-3-one Isomer 2 | Ex. 148 | 1.27 | 498 |
| 151 | (2R)-8-Fluoro-4-[(7-fluoro-6-{6-[imino(methyl)oxo-$\lambda^6$-sulfanyl]pyridin-3-yl}-2-methylimidazo[1,2-a]-pyridin-3-yl)methyl]-2-methyl-3,4-dihydro-2H-1,4-benzoxazin-3-one Isomer 1 | Ex. 144 | 1.24 | 498 |

| Ex. | Name | Starting Material | LCMS RT | LCMS m/z |
|---|---|---|---|---|
| 152 | (2R)-8-Fluoro-4-[(7-fluoro-6-{6-[imino(methyl)oxo-λ⁶-sulfanyl]pyridin-3-yl}-2-methylimidazo[1,2-a]pyridin-3-yl)methyl]-2-methyl-3,4-dihydro-2H-1,4-benzoxazin-3-one Isomer 2 | Ex. 144 | 1.24 | 498 |
| 153 | 8-Fluoro-4-[(7-fluoro-6-{6-[imino(methyl)oxo-λ⁶-sulfanyl]pyridin-3-yl}-2-methylimidazo[1,2-a]pyridin-3-yl)methyl]-3,4-dihydro-2H-1,4-benzoxazin-3-one | Int. 164 and Int. 173 | 1.19 | 484 |
| 154 | 8-Fluoro-4-[(7-fluoro-6-{6-[imino(methyl)oxo-λ⁶-sulfanyl]-4-methylpyridin-3-yl}-2-methylimidazo[1,2-a]pyridin-3-yl)methyl]-3,4-dihydro-2H-1,4-benzoxazin-3-one | Int. 164 and Int. 177 | 1.23 | 498 |
| 155 | (2S)-8-Fluoro-4-[(7-fluoro-6-{6-[imino(methyl)oxo-λ⁶-sulfanyl]-4-methylpyridin-3-yl}-2-methylimidazo[1,2-a]pyridin-3-yl)methyl]-2-methyl-3,4-dihydro-2H-1,4-benzoxazin-3-one | Int. 143 and Int. 177 | 1.28 | 512 |
| 156 | (2R)-8-Fluoro-4-[(7-fluoro-2-methyl-6-{6-[methyl(methylimino)oxo-λ⁶-sulfanyl]pyridin-3-yl}imidazo[1,2-a]pyridin-3-yl)methyl]-2-methyl-3,4-dihydro-2H-1,4-benzoxazin-3-one | Ex. 144 | 1.31 | 512 |
| 157 | 8-Fluoro-4-[(7-fluoro-6-{6-[imino(methyl)oxo-λ⁶-sulfanyl]pyridin-3-yl}-2-methylimidazo[1,2-a]pyridin-3-yl)methyl]-3,4-dihydro-2H-1,4-benzoxazin-3-one Isomer 1 | Ex. 153 | 1.19 | 484 |
| 158 | 8-Fluoro-4-[(7-fluoro-6-{6-[imino(methyl)oxo-λ⁶-sulfanyl]pyridin-3-yl}-2-methylimidazo[1,2-a]pyridin-3-yl)methyl]-3,4-dihydro-2H-1,4-benzoxazin-3-one Isomer 2 | Ex. 153 | 1.19 | 484 |
| 159 | (2R)-8-Fluoro-4-[(7-fluoro-6-{6-[imino(methyl)oxo-λ⁶-sulfanyl]-4-methylpyridin-3-yl}-2-methylimidazo[1,2-a]pyridin-3-yl)methyl]-2-methyl-3,4-dihydro-2H-1,4-benzoxazin-3-one | Int. 35 and Int. 177 | 1.28 | 512 |
| 160 | 8-Fluoro-4-[(7-fluoro-6-{4-[imino(oxo)(trifluoromethyl)-λ⁶-sulfanyl]phenyl}-2-methylimidazo[1,2-a]pyridin-3-yl)methyl]-3,4-dihydro-2H-1,4-benzoxazin-3-one, hydrochloric acid salt | Int. 164 and Int. 180 | 1.49 | 537 |
| 161 | (2S)-4-[(6-{6-[Ethyl(imino)oxo-λ⁶-sulfanyl]pyridin-3-yl}-7-fluoro-2-methylimidazo[1,2-a]pyridin-3-yl)methyl]-8-fluoro-2-methyl-3,4-dihydro-2H-1,4-benzoxazin-3-one | Int. 143 and Int. 183 | 1.29 | 512 |
| 162 | (2R)-4-[(6-{6-[Ethyl(imino)oxo-λ⁶-sulfanyl]pyridin-3-yl}-7-fluoro-2-methylimidazo[1,2-a]pyridin-3-yl)methyl]-8-fluoro-2-methyl-3,4-dihydro-2H-1,4-benzoxazin-3-one | Int. 35 and Int. 183 | 1.29 | 512 |
| 163 | (2R)-8-Chloro-4-[(7-fluoro-6-{6-[imino(methyl)oxo-λ⁶-sulfanyl]pyridin-3-yl}-2-methylimidazo[1,2-a]pyridin-3-yl)methyl]-2-methyl-3,4-dihydro-2H-1,4-benzoxazin-3-one | Int. 165 and Int. 173 | 1.29 | 514 |
| 164 | (2R)-8-Fluoro-4-[(7-fluoro-6-{6-[imino(methyl)oxo-λ⁶-sulfanyl]-4-methylpyridin-3-yl}-2-methylimidazo[1,2-a]pyridin-3-yl)methyl]-2-methyl-3,4-dihydro-2H-1,4-benzoxazin-3-one, maleic acid salt, Isomer 1 | Ex. 159 | 1.28 | 512 |
| 165 | (2R)-8-Fluoro-4-[(7-fluoro-6-{6-[imino(methyl)oxo-λ⁶-sulfanyl]-4-methylpyridin-3-yl}-2-methylimidazo[1,2-a]pyridin-3-yl)methyl]-2-methyl-3,4-dihydro-2H-1,4-benzoxazin-3-one, maleic acid salt, Isomer 2 | Ex. 159 | 1.30 | 512 |
| 166 | (2R)-8-Fluoro-4-[(7-fluoro-6-{4-[imino(oxo)(trifluoromethyl)-λ⁶-sulfanyl]phenyl}-2-methylimidazo[1,2-a]pyridin-3-yl)methyl]-2-methyl-3,4-dihydro-2H-1,4-benzoxazin-3-one, maleic acid salt | Int. 35 and Int. 181 | 1.54 | 551 |
| 167 | (2R)-4-[(6-{6-[Ethyl(imino)oxo-λ⁶-sulfanyl]pyridin-3-yl}-7-fluoro-2-methylimidazo[1,2-a]pyridin-3-yl)methyl]-8-fluoro-2-methyl-3,4-dihydro-2H-1,4-benzoxazin-3-one, maleic acid salt, Isomer 1 | Ex. 162 | 1.29 | 512 |
| 168 | (2R)-4-[(6-{6-[Ethyl(imino)oxo-λ⁶-sulfanyl]pyridin-3-yl}-7-fluoro-2-methylimidazo[1,2-a]pyridin-3-yl)methyl]-8-fluoro-2-methyl-3,4-dihydro-2H-1,4-benzoxazin-3-one, maleic acid salt, Isomer 2 | Ex. 162 | 1.29 | 512 |
| 169 | (2R)-8-Fluoro-4-[(7-fluoro-6-{6-[imino(methyl)oxo-λ⁶-sulfanyl]-2-methylpyridin-3-yl}-2-methylimidazo[1,2-a]pyridin-3-yl)methyl]-2-methyl-3,4-dihydro-2H-1,4-benzoxazin-3-one, maleic acid salt | Int. 35 and Int. 185 | 1.28 | 512 |
| 170 | (2R)-8-Fluoro-4-[(6-{6-[imino(methyl)oxo-λ⁶-sulfanyl]pyridin-3-yl}-2-methylimidazo[1,2-a]pyridin-3-yl)methyl]-2-methyl-3,4-dihydro-2H-1,4-benzoxazin-3-one, maleic acid salt | Int. 29 and Int. 173 | 1.23 | 480 |

-continued

| Ex. | Name | Starting Material | LCMS RT | LCMS m/z |
|---|---|---|---|---|
| 171 | 5-Fluoro-1-[(7-fluoro-6-{6-[imino(methyl)oxo-λ⁶-sulfanyl]pyridin-3-yl}-2-methylimidazo[1,2-a]pyridin-3-yl)methyl]-3-methyl-1,2,3,4-tetrahydroquinolin-2-one Isomer 1 | Int. 173 and Int. 190 | 1.28 | 496 |
| 172 | 5-Fluoro-1-[(7-fluoro-6-{6-[imino(methyl)oxo-λ⁶-sulfanyl]pyridin-3-yl}-2-methylimidazo[1,2-a]pyridin-3-yl)methyl]-3-methyl-1,2,3,4-tetrahydroquinolin-2-one Isomer 2 | Int. 173 and Int. 190 | 1.28 | 496 |
| 173 | (2S)-8-Fluoro-4-[(7-fluoro-2-methyl-6-{2-[(1s,3r)-1,3-dihydroxy-3-methylcyclobutyl]pyrimidin-5-yl}-imidazo[1,2-a]pyridin-3-yl)methyl]-2-methyl-3,4-dihydro-2H-1,4-benzoxazin-3-one Isomer 1 | Int. 143 and Int. 198 | 1.30 | 522 |
| 174 | (2S)-8-Fluoro-4-[(7-fluoro-2-methyl-6-{2-[(1s,3r)-1,3-dihydroxy-3-methylcyclobutyl]pyrimidin-5-yl}-imidazo[1,2-a]pyridin-3-yl)methyl]-2-methyl-3,4-dihydro-2H-1,4-benzoxazin-3-one Isomer 2 | Int. 143 and Int. 198 | 1.27 | 522 |
| 175 | (2S)-8-Fluoro-4-[(7-fluoro-2-methyl-6-{2-[(1s,3s)-1,3-dihydroxycyclobutyl]pyrimidin-5-yl}imidazo[1,2-a]-pyridin-3-yl)methyl]-2-methyl-3,4-dihydro-2H-1,4-benzoxazin-3-one | Int. 143 and Int. 200 | 1.26 | 508 |
| 176 | 8-Fluoro-4-[(7-fluoro-2-methyl-6-{2-[(1r,3s)-1,3-dihydroxy-3-methylcyclobutyl]pyrimidin-5-yl}-imidazo[1,2-a]pyridin-3-yl)methyl]-3,4-dihydro-2H-1,4-benzoxazin-3-one | Int. 164 and Int. 207 | 1.24 | 508 |
| 177 | (2R)-8-Fluoro-4-[(7-fluoro-2-methyl-6-{2-[(1r,3s)-1,3-dihydroxy-3-methylcyclobutyl]pyrimidin-5-yl}-imidazo[1,2-a]pyridin-3-yl)methyl]-2-methyl-3,4-dihydro-2H-1,4-benzoxazin-3-one | Int. 35 and Int. 201 | 1.24 | 522 |
| 178 | (2R)-6,8-Difluoro-2-methyl-4-[(2-methyl-6-{2-[(1r,3s)-1,3-dihydroxy-3-methylcyclobutyl]pyrimidin-5-yl}imidazo[1,2-a]pyrazin-3-yl)methyl]-3,4-dihydro-2H-1,4-benzoxazin-3-one | Int. 64 and Int. 201 | 1.37 | 523 |
| 179 | (2S)-8-Fluoro-4-[(7-fluoro-2-methyl-6-{2-[(1r,3s)-3-amino-1-hydroxycyclobutyl]pyrimidin-5-yl}imidazo-[1,2-a]pyridin-3-yl)methyl]-2-methyl-3,4-dihydro-2H-1,4-benzoxazin-3-one | Int. 143 and Int. 204 | 1.20 | 507 |
| 180 | 8-Fluoro-4-[(7-fluoro-2-methyl-6-{6-[(1r,3s)-1,3-dihydroxy-3-methylcyclobutyl]pyridin-3-yl}imidazo-[1,2-a]pyridin-3-yl)methyl]-3,4-dihydro-2H-1,4-benzoxazin-3-one | Int. 164 and Int. 210 | 1.26 | 507 |
| 181 | (2R)-8-Fluoro-4-[(7-fluoro-2-methyl-6-{6-[(1r,3s)-1,3-dihydroxy-3-methylcyclobutyl]pyridin-3-yl}imidazo-[1,2-a]pyridin-3-yl)methyl]-2-methyl-3,4-dihydro-2H-1,4-benzoxazin-3-one | Int. 35 and Int. 210 | 1.29 | 521 |
| 182 | 8-Fluoro-4-[(7-fluoro-2-methyl-6-{2-[(1r,3s)-3-ethyl-1,3-dihydroxycyclobutyl]pyrimidin-5-yl}imidazo[1,2-a]pyridin-3-yl)methyl]-3,4-dihydro-2H-1,4-benzoxazin-3-one | Int. 164 and Int. 212 | 1.27 | 522 |
| 183 | (2R)-4-{[6-(6-{[Dimethyl(oxo)-λ⁶-sulfanylidene]-amino}pyridin-3-yl)-7-fluoro-2-methylimidazo[1,2-a]-pyridin-3-yl]methyl}-8-fluoro-2-methyl-3,4-dihydro-2H-1,4-benzoxazin-3-one | Int. 35 and Int. 214 | 1.30 | 512 |
| 184 | (2R)-4-[(6-{6-[Ethyl(imino)oxo-λ⁶-sulfanyl]pyridin-3-yl}-2-methylimidazo[1,2-a]pyrazin-3-yl)methyl]-8-fluoro-2-methyl-3,4-dihydro-2H-1,4-benzoxazin-3-one | Int. 66 and Int. 183 | 1.25 | 495 |
| 185 | (2R)-8-Fluoro-2-methyl-4-[(2-methyl-6-{2-[(1r,3s)-3-ethyl-1,3-dihydroxycyclobutyl]pyrimidin-5-yl}-imidazo[1,2-a]pyrazin-3-yl)methyl]-3,4-dihydro-2H-1,4-benzoxazin-3-one | Int. 66 and Int. 212 | 1.29 | 519 |
| 186 | (2R)-6-Bromo-8-chloro-4-({7-fluoro-6-[2-(2-hydroxy-propan-2-yl)pyrimidin-5-yl]-2-methylimidazo[1,2-a]-pyridin-3-yl}methyl)-2-methyl-3,4-dihydro-2H-1,4-benzoxazin-3-one | Int. 107 and Int. 216 | 1.55 | 574 |
| 187 | 8-Fluoro-4-[(7-fluoro-6-{6-[imino(methyl)oxo-λ⁶-sulfanyl]pyridin-3-yl}-2-methylimidazo[1,2-a]pyridin-3-yl)methyl]-2,2-dimethyl-3,4-dihydro-2H-1,4-benzoxazin-3-one | Int. 58 and Int. 175 | 1.28 | 512 |
| 188 | (2R)-8-Fluoro-4-[(6-{6-[imino(methyl)oxo-λ⁶-sulfanyl]-2-methylpyridin-3-yl}-2-methylimidazo[1,2-a]pyridin-3-yl)methyl]-2-methyl-3,4-dihydro-2H-1,4-benzoxazin-3-one | Int. 29 and Int. 217 | 1.24 | 494 |
| 189 | (2R)-8-Fluoro-4-[(7-fluoro-6-{6-[imino(methyl)oxo-λ⁶-sulfanyl]-2-methylpyridin-3-yl}-2-methylimidazo-[1,2-a]pyridin-3-yl)methyl]-2-methyl-3,4-dihydro-2H-1,4-benzoxazin-3-one Isomer 1 | Ex. 169 | 1.26 | 512 |

-continued

| Ex. | Name | Starting Material | LCMS RT | LCMS m/z |
|---|---|---|---|---|
| 190 | (2R)-8-Fluoro-4-[(7-fluoro-6-{6-[imino(methyl)oxo-λ⁶-sulfanyl]-2-methylpyridin-3-yl}-2-methylimidazo-[1,2-a]pyridin-3-yl)methyl]-2-methyl-3,4-dihydro-2H-1,4-benzoxazin-3-one Isomer 2 | Ex. 169 | 1.24 | 512 |
| 191 | (2R)-8-Chloro-4-[(7-fluoro-6-{6-[imino(methyl)oxo-λ⁶-sulfanyl]pyridin-3-yl}-2-methylimidazo[1,2-a]-pyridin-3-yl)methyl]-2-methyl-3,4-dihydro-2H-1,4-benzoxazin-3-one Isomer 1 | Ex. 163 | 1.29 | 514 |
| 192 | (2R)-8-Chloro-4-[(7-fluoro-6-{6-[imino(methyl)oxo-λ⁶-sulfanyl]pyridin-3-yl}-2-methylimidazo[1,2-a]-pyridin-3-yl)methyl]-2-methyl-3,4-dihydro-2H-1,4-benzoxazin-3-one Isomer 2 | Ex. 163 | 1.29 | 514 |
| 193 | (2R)-8-Fluoro-2-methyl-4-[(2-methyl-6-{2-[(1r,3s)-1,3-dihydroxy-3-methylcyclobutyl]pyrimidin-5-yl}-imidazo[1,2-a]pyrazin-3-yl)methyl]-3,4-dihydro-2H-1,4-benzoxazin-3-one | Int. 66 and Int. 201 | 1.24 | 505 |
| 194 | 8-Fluoro-4-[(7-fluoro-6-{6-[imino(methyl)oxo-λ⁶-sulfanyl]pyridin-3-yl}-2-methylimidazo[1,2-a]pyridin-3-yl)methyl]-2,2-dimethyl-3,4-dihydro-2H-1,4-benzoxazin-3-one Isomer 1 | Ex. 187 | 1.29 | 512 |
| 195 | 8-Fluoro-4-[(7-fluoro-6-{6-[imino(methyl)oxo-λ⁶-sulfanyl]pyridin-3-yl}-2-methylimidazo[1,2-a]pyridin-3-yl)methyl]-2,2-dimethyl-3,4-dihydro-2H-1,4-benzoxazin-3-one Isomer 2 | Ex. 187 | 1.29 | 512 |
| 196 | (2R)-4-[(6-{6-[Cyclopropyl(imino)oxo-λ⁶-sulfanyl]-pyridin-3-yl}-7-fluoro-2-methylimidazo[1,2-a]pyridin-3-yl)methyl]-8-fluoro-2-methyl-3,4-dihydro-2H-1,4-benzoxazin-3-one | Int. 35 and Int. 221 | 1.29 | 524 |
| 197 | (2R)-8-Fluoro-4-[(6-{6-[imino(methyl)oxo-λ⁶-sulfanyl]-2-methylpyridin-3-yl}-2-methylimidazo[1,2-a]pyridin-3-yl)methyl]-2-methyl-3,4-dihydro-2H-1,4-benzoxazin-3-one Isomer 1 | Ex. 188 | 1.23 | 494 |
| 198 | (2R)-8-Fluoro-4-[(6-{6-[imino(methyl)oxo-λ⁶-sulfanyl]-2-methylpyridin-3-yl}-2-methylimidazo[1,2-a]pyridin-3-yl)methyl]-2-methyl-3,4-dihydro-2H-1,4-benzoxazin-3-one Isomer 2 | Ex. 188 | 1.23 | 494 |
| 199 | (2R)-8-Chloro-2-methyl-4-[(2-methyl-6-{2-[(1r,3s)-1,3-dihydroxy-3-methylcyclobutyl]pyrimidin-5-yl}-imidazo[1,2-a]pyrazin-3-yl)methyl]-3,4-dihydro-2H-1,4-benzoxazin-3-one | Int. 134 and Int. 201 | 1.31 | 521 |
| 200 | (2R)-8-Chloro-4-[(7-fluoro-2-methyl-6-{2-[(1r,3s)-1,3-dihydroxy-3-methylcyclobutyl]pyrimidin-5-yl}-imidazo[1,2-a]pyridin-3-yl)methyl]-2-methyl-3,4-dihydro-2H-1,4-benzoxazin-3-one | Int. 165 and Int. 201 | 1.29 | 524 |
| 201 | 8-Chloro-4-[(2-methyl-6-{2-[(1r,3s)-1,3-dihydroxy-3-methylcyclobutyl]pyrimidin-5-yl}imidazo[1,2-a]-pyrazin-3-yl)methyl]-3,4-dihydro-2H-1,4-benzoxazin-3-one | Int. 201 and Int. 257 | 1.25 | 507 |
| 202 | 8-Chloro-4-[(7-fluoro-2-methyl-6-{2-[(1r,3s)-1,3-dihydroxy-3-methylcyclobutyl]pyrimidin-5-yl}-imidazo[1,2-a]pyridin-3-yl)methyl]-3,4-dihydro-2H-1,4-benzoxazin-3-one | Int. 201 and Int. 258 | 1.27 | 524 |
| 203 | (2R)-4-[(6-{6-[Cyclopropyl(imino)oxo-λ⁶-sulfanyl]-pyridin-3-yl}-7-fluoro-2-methylimidazo[1,2-a]pyridin-3-yl)methyl]-8-fluoro-2-methyl-3,4-dihydro-2H-1,4-benzoxazin-3-one Isomer 1 | Ex. 196 | 1.3 | 524 |
| 204 | (2R)-4-[(6-{6-[Cyclopropyl(imino)oxo-λ⁶-sulfanyl]-pyridin-3-yl}-7-fluoro-2-methylimidazo[1,2-a]pyridin-3-yl)methyl]-8-fluoro-2-methyl-3,4-dihydro-2H-1,4-benzoxazin-3-one Isomer 2 | Ex. 196 | 1.33 | 538 |
| 205 | (2R)-8-Fluoro-2-methyl-4-[(2-methyl-6-{2-[(1s,3r)-1-amino-3-hydroxy-3-methylcyclobutyl]pyrimidin-5-yl}-imidazo[1,2-a]pyrazin-3-yl)methyl]-3,4-dihydro-2H-1,4-benzoxazin-3-one Isomer 1 | Int. 66 and Int. 229 | 1.22 | 504 |
| 206 | (2R)-8-Fluoro-2-methyl-4-[(2-methyl-6-{2-[(1s,3r)-1-amino-3-hydroxy-3-methylcyclobutyl]pyrimidin-5-yl}-imidazo[1,2-a]pyrazin-3-yl)methyl]-3,4-dihydro-2H-1,4-benzoxazin-3-one Isomer 2 | Int. 66 and Int. 229 | 1.23 | 504 |
| 207 | 8-Fluoro-4-({7-fluoro-6-[2-(2-hydroxypropan-2-yl)-pyrimidin-5-yl]-2-methylimidazo[1,2-a]pyridin-3-yl}-methyl)-2-methyl-3-oxo-N-(propan-2-yl)-3,4-dihydro-2H-1,4-benzoxazine-6-carboxamide | Ex. 131 | 1.35 | 565 |
| 208 | (2S)-8-Fluoro-4-({7-fluoro-6-[2-(2-hydroxypropan-2-yl)pyrimidin-5-yl]-2-methylimidazo[1,2-a]pyridin-3-yl}methyl)-2-methyl-3-oxo-N-(propan-2-yl)-3,4-dihydro-2H-1,4-benzoxazine-6-carboxamide | Ex. 131 | 2.12 | 565 |

| Ex. | Name | Starting Material | LCMS RT | LCMS m/z |
|---|---|---|---|---|
| 209 | (2R)-8-Fluoro-4-({7-fluoro-6-[2-(2-hydroxypropan-2-yl)pyrimidin-5-yl]-2-methylimidazo[1,2-a]pyridin-3-yl}methyl)-2-methyl-3-oxo-N-(propan-2-yl)-3,4-dihydro-2H-1,4-benzoxazine-6-carboxamide | Ex. 131 | 2.12 | 565 |
| 210 | 8-Fluoro-4-({7-fluoro-6-[2-(2-hydroxypropan-2-yl)-pyrimidin-5-yl]-2-methylimidazo[1,2-a]pyridin-3-yl}-methyl)-N-(1-hydroxy-2-methylpropan-2-yl)-2-methyl-3-oxo-3,4-dihydro-2H-1,4-benzoxazine-6-carboxamide | Ex. 131 | 1.30 | 595 |
| 211 | 8-Fluoro-4-({7-fluoro-6-[2-(2-hydroxypropan-2-yl)-pyrimidin-5-yl]-2-methylimidazo[1,2-a]pyridin-3-yl}-methyl)-N-(1-hydroxypropan-2-yl)-2-methyl-3-oxo-3,4-dihydro-2H-1,4-benzoxazine-6-carboxamide | Ex. 131 | 1.24 | 581 |
| 212 | N-Ethyl-8-fluoro-4-({7-fluoro-6-[2-(1-hydroxy-1-methylethyl)pyrimidin-5-yl]-2-methylimidazo[1,2-a]-pyridin-3-yl}methyl)-2-methyl-3-oxo-1,4-benzoxazine-6-carboxamide | Ex. 131 | 1.3 | 551 |
| 213 | tert-Butyl 4-[8-fluoro-4-({7-fluoro-6-[2-(1-hydroxy-1-methylethyl)pyrimidin-5-yl]-2-methylimidazo[1,2-a]-pyridin-3-yl}methyl)-2-methyl-3-oxo-1,4-benzoxazine-6-carbonyl]piperazine-1-carboxylate | Ex. 131 | 1.47 | 692 |
| 214 | 8-Fluoro-4-({7-fluoro-6-[2-(1-hydroxy-1-methylethyl)-pyrimidin-5-yl]-2-methylimidazo[1,2-a]pyridin-3-yl}-methyl)-2-methyl-6-(piperazine-1-carbonyl)-1,4-benzoxazin-3-one | Ex. 213 | 1.45 | 592 |
| 215 | 8-Fluoro-4-({7-fluoro-6-[2-(2-hydroxypropan-2-yl)-pyrimidin-5-yl]-2-methylimidazo[1,2-a]pyridin-3-yl}-methyl)-6-[(3-hydroxypyrrolidin-1-yl)carbonyl]-2-methyl-2H-1,4-benzoxazin-3(4H)-one | Ex. 131 | 1.23 | 593 |
| 216 | 8-Fluoro-4-({7-fluoro-6-[2-(2-hydroxypropan-2-yl)-pyrimidin-5-yl]-2-methylimidazo[1,2-a]pyridin-3-yl}-methyl)-N,N,2-trimethyl-3-oxo-3,4-dihydro-2H-1,4-benzoxazine-6-carboxamide | Ex. 131 | 1.30 | 551 |
| 217 | N-Cyclopropyl-8-fluoro-4-({7-fluoro-6-[2-(2-hydroxy-propan-2-yl)pyrimidin-5-yl]-2-methylimidazo[1,2-a]-pyridin-3-yl}methyl)-2-methyl-3-oxo-3,4-dihydro-2H-1,4-benzoxazine-6-carboxamide | Ex. 131 | 1.33 | 563 |
| 218 | 8-Fluoro-4-({7-fluoro-6-[2-(2-hydroxypropan-2-yl)-pyrimidin-5-yl]-2-methylimidazo[1,2-a]pyridin-3-yl}-methyl)-N-(2-hydroxyethyl)-2-methyl-3-oxo-3,4-dihydro-2H-1,4-benzoxazine-6-carboxamide | Ex. 131 | 1.22 | 567 |
| 219 | 8-Fluoro-4-({7-fluoro-6-[2-(1-hydroxy-1-methylethyl)-pyrimidin-5-yl]-2-methylimidazo[1,2-a]pyridin-3-yl}-methyl)-N-(2-methoxyethyl)-2-methyl-3-oxo-1,4-benzoxazine-6-carboxamide | Ex. 131 | 1.30 | 581 |
| 220 | 8-Fluoro-4-({7-fluoro-6-[2-(1-hydroxy-1-methylethyl)-pyrimidin-5-yl]-2-methylimidazo[1,2-a]pyridin-3-yl}-methyl)-2-methyl-N-(oxazol-4-ylmethyl)-3-oxo-1,4-benzoxazine-6-carboxamide | Ex. 131 | 1.27 | 604 |
| 221 | 8-Fluoro-4-({7-fluoro-6-[2-(1-hydroxy-1-methylethyl)-pyrimidin-5-yl]-2-methylimidazo[1,2-a]pyridin-3-yl}-methyl)-2-methyl-6-[3-(methylsulfonyl)azetidine-1-carbonyl]-1,4-benzoxazin-3-one | Ex. 131 | 1.27 | 641 |
| 222 | 8-Fluoro-4-({7-fluoro-6-[2-(1-hydroxy-1-methylethyl)-pyrimidin-5-yl]-2-methylimidazo[1,2-a]pyridin-3-yl}-methyl)-2-methyl-6-(3-oxopiperazine-1-carbonyl)-1,4-benzoxazin-3-one | Ex. 131 | 1.19 | 606 |
| 223 | 8-Fluoro-4-({7-fluoro-6-[2-(1-hydroxy-1-methylethyl)-pyrimidin-5-yl]-2-methylimidazo[1,2-a]pyridin-3-yl}-methyl)-2-methyl-3-oxo-1,4-benzoxazine-6-carboxamide | Ex. 131 | 1.24 | 523 |
| 224 | (2R)-8-Fluoro-2-methyl-4-({2-methyl-6-[2-(2-methyl-5-oxo-1,4-diazepan-1-yl)pyrimidin-5-yl]imidazo[1,2-a]pyrazin-3-yl}methyl)-1,4-benzoxazin-3-one | Int. 66 and Int. 232 | 1.31 | 531 |
| 225 | (2R)-8-Fluoro-2-methyl-4-({2-methyl-6-[2-(7-methyl-5-oxo-1,4-diazepan-1-yl)pyrimidin-5-yl]imidazo[1,2-a]pyrazin-3-yl}methyl)-1,4-benzoxazin-3-one | Int. 66 and Int. 233 | 1.31 | 531 |
| 226 | (2R)-8-Fluoro-4-[(7-fluoro-2-methyl-6-{2-[(1R,5S)-6-oxa-3-azabicyclo[3.1.1]heptan-3-yl]pyrimidin-5-yl}-imidazo[1,2-a]pyridin-3-yl)methyl]-2-methyl-1,4-benzoxazin-3-one | Int. 35 and Int. 158 | 1.40 | 519 |
| 227 | (2R)-6-Bromo-8-fluoro-4-({7-fluoro-6-[2-(1-hydroxy-1-methylethyl)pyrimidin-5-yl]-2-methylimidazo[1,2-a]pyridin-3-yl}methyl)-2-methyl-1,4-benzoxazin-3-one | Int. 234 | 1.50 | 560 |
| 228 | 4-[(6-Bromo-7-fluoro-2-methylimidazo[1,2-a]pyridin-3-yl)methyl]-8-chloro-N-isopropyl-2-methyl-3-oxo-1,4-benzoxazine-6-carboxamide | Int. 34 and Int. 231 | 1.50 | 525 |

-continued

| Ex. | Name | Starting Material | LCMS RT | LCMS m/z |
|---|---|---|---|---|
| 229 | (2R)-8-Chloro-4-({7-fluoro-6-[2-(1-hydroxy-1-methyl-ethyl)pyrimidin-5-yl]-2-methylimidazo[1,2-a]pyridin-3-yl}methyl)-N-isopropyl-2-methyl-3-oxo-1,4-benzoxazine-6-carboxamide | Ex. 228 | 1.39 | 581 |
| 230 | (2R)-8-Chloro-4-[(7-fluoro-6-{2-[3-hydroxy-3-(trifluoromethyl)azetidin-1-yl]pyrimidin-5-yl}-2-methylimidazo[1,2-a]pyridin-3-yl)methyl]-N-isopropyl-2-methyl-3-oxo-1,4-benzoxazine-6-carboxamide | Ex. 228 and Int. 148 | 1.43 | 662 |
| 231 | (2R)-8-Chloro-4-({7-fluoro-2-methyl-6-[4-(methyl-sulfonyl)phenyl]imidazo[1,2-a]pyridin-3-yl}methyl)-N-isopropyl-2-methyl-3-oxo-1,4-benzoxazine-6-carboxamide | Ex. 228 | 1.43 | 599 |
| 232 | 8-Chloro-4-({7-fluoro-2-methyl-6-[2-(3-oxopiperazin-1-yl)pyrimidin-5-yl]imidazo[1,2-a]pyridin-3-yl}-methyl)-N-isopropyl-2-methyl-3-oxo-1,4-benzoxazine-6-carboxamide | Ex. 228 and Int. 147 | 1.29 | 621 |
| 233 | (2R)-8-Fluoro-4-({7-fluoro-6-[2-(1-hydroxy-1-methyl-ethyl)pyrimidin-5-yl]-2-methylimidazo[1,2-a]pyridin-3-yl}methyl)-6-(3-hydroxyoxetan-3-yl)-2-methyl-1,4-benzoxazin-3-one | Int. 107 and Int. 238 | 1.26 | 552 |
| 234 | 8-Fluoro-4-({7-fluoro-6-[2-(1-hydroxy-1-methylethyl)-pyrimidin-5-yl]-2-methylimidazo[1,2-a]pyridin-3-yl}-methyl)-N-isopropyl-3-oxo-1,4-benzoxazine-6-carboxamide | Int. 240 | 1.28 | 551 |
| 235 | 4-({7-Fluoro-6-[2-(1-hydroxy-1-methylethyl)-pyrimidin-5-yl]-2-methylimidazo[1,2-a]pyridin-3-yl}-methyl)-N-isopropyl-2-methyl-3-oxopyrido[3,2-b]-[1,4]oxazine-6-carboxamide | Int. 107 and Int. 241 | 1.32 | 548 |
| 236 | (2R)-8-Fluoro-4-({7-fluoro-6-[2-(1-hydroxy-1-methyl-ethyl)pyrimidin-5-yl]-2-methylimidazo[1,2-a]pyridin-3-yl}methyl)-6-(3-methoxyoxetan-3-yl)-2-methyl-1,4-benzoxazin-3-one | Int. 242 | 1.33 | 566 |
| 237 | (2S)-8-Fluoro-4-({7-fluoro-6-[2-(1-hydroxy-1-methyl-ethyl)pyrimidin-5-yl]-2-methylimidazo[1,2-a]pyridin-3-yl}methyl)-6-(1-hydroxy-1-methylethyl)-2-methyl-1,4-benzoxazin-3-one | Int. 237 | 1.35 | 538 |
| 238 | (2R)-8-Fluoro-4-({7-fluoro-6-[2-(1-hydroxy-1-methyl-ethyl)pyrimidin-5-yl]-2-methylimidazo[1,2-a]pyridin-3-yl}methyl)-2-methyl-6-(methylsulfanyl)-1,4-benzoxazin-3-one | Int. 107 and Int. 230 | 1.48 | 527 |

Example 239

(2R)-8-Fluoro-4-({7-fluoro-6-[2-(1-hydroxy-1-methylethyl)pyrimidin-5-yl]-2-methyl-imidazo[1,2-a]pyridin-3-yl}methyl)-2-methyl-6-(methylsulfinyl)-1,4-benzoxazin-3-one Example 238 (0.10 g, 0.190 mmol) was dissolved in DCM (5 mL) and cooled to 0° C. with an ice bath. 3-Chloroperoxybenzoic acid (0.057 g, 0.2473 mmol) was added, then the mixture was allowed to warm to room temperature and stirred for 2 h. The reaction mixture was concentrated in vacuo. The crude material was purified by column chromatography on silica gel, using EtOAc/hexanes (50-100% EtOAc) then MeOH/EtOAc (0-20%), followed by freeze-drying (acetonitrile/water), to give the title compound (0.040 g, 39%), 1:1 mixture of diastereoisomers, as a white solid.

Diastereoisomer 1: $\delta_H$ (300 MHz, DMSO-$d_6$) 9.06 (d, 2H, J 1.4 Hz), 8.81 (d, 1H, J 7.3 Hz), 7.54 (d, 1H, J 11.2 Hz), 7.44 (s, 1H), 7.37 (m, 1H), 5.74 (d, 1H, J 16.5 Hz), 5.62 (d, 1H, J 16.5 Hz), 5.18 (s, 1H), 5.07 (dd, 1H, J 10.7, 6.7 Hz), 2.64 (s, 3H), 2.34 (s, 3H), 1.56 (s, 6H), 1.55 (d, 3H, J 5.2 Hz). LCMS MH$^+$ m/z 542.7.

Diastereoisomer 2: $\delta_H$ (300 MHz, DMSO-$d_6$) 9.05 (d, 2H, J 1.4 Hz), 8.79 (d, 1H, J 7.3 Hz), 7.54 (d, 1H, J 11.2 Hz), 7.44 (s, 1H), 7.35 (m, 1H), 5.68 (d, 1H, J 16.5 Hz), 5.58 (d, 1H, J 16.5 Hz), 5.18 (s, 1H), 5.04 (dd, 1H, J 10.7, 6.7 Hz), 2.60 (s, 3H), 2.34 (s, 3H), 1.56 (s, 6H), 1.55 (d, 3H, J 5.2 Hz). LCMS MH$^+$ m/z 542.7.

Example 240

(2R)-8-Fluoro-4-({7-fluoro-6-[2-(1-hydroxy-1-methylethyl)pyrimidin-5-yl]-2-methyl-imidazo[1,2-a]pyridin-3-yl}methyl)-2-methyl-6-(methylsulfonyl)-1,4-benzoxazin-3-one Prepared by the method described in Example 239 to give the title compound (0.065 g, 61%) as a white solid. $\delta_H$ (300 MHz, DMSO-$d_6$) 9.04 (d, 2H, J 1.5 Hz), 8.79 (d, 1H, J 7.3 Hz), 7.59 (m, 3H), 5.74 (d, 1H, J 16.6 Hz), 5.64 (d, 1H, J 16.6 Hz), 5.18 (s, 1H), 5.13 (dd, 1H, J 13.4, 6.7 Hz), 3.13 (s, 3H), 2.38 (s, 3H), 1.56 (s, 6H), 1.55 (d, 3H, J 5.2 Hz). LCMS MH$^+$ m/z 558.6.

Examples 241 to 256

The following compounds were prepared from the specified starting materials using methods analogous to one or more of the foregoing procedures. Examples 242, 243, 245 and 246 were prepared by chiral resolution.

| Ex. | Name | Starting Material | LCMS RT | LCMS m/z |
|---|---|---|---|---|
| 241 | 1-({7-Fluoro-6-[2-(2-hydroxypropan-2-yl)pyrimidin-5-yl]-2-methylimidazo[1,2-a]pyridin-3-yl}methyl)-3-methyl-3,4-dihydroquinolin-2(1H)-one | Int. 245 | 1.40 | 460 |
| 242 | 1-({7-Fluoro-6-[2-(2-hydroxypropan-2-yl)pyrimidin-5-yl]-2-methylimidazo[1,2-a]pyridin-3-yl}methyl)-3-methyl-3,4-dihydroquinolin-2(1H)-one Isomer 1 | Ex. 241 | | 461 |
| 243 | 1-({7-Fluoro-6-[2-(2-hydroxypropan-2-yl)pyrimidin-5-yl]-2-methylimidazo[1,2-a]pyridin-3-yl}methyl)-3-methyl-3,4-dihydroquinolin-2(1H)-one Isomer 2 | Ex. 241 | | 461 |
| 244 | 5-Fluoro-1-({7-fluoro-6-[2-(2-hydroxypropan-2-yl)-pyrimidin-5-yl]-2-methylimidazo[1,2-a]pyridin-3-yl}-methyl)-3-methyl-3,4-dihydroquinolin-2(1H)-one | Int. 189 | 1.43 | 479 |
| 245 | 5-Fluoro-1-({7-fluoro-6-[2-(2-hydroxypropan-2-yl)-pyrimidin-5-yl]-2-methylimidazo[1,2-a]pyridin-3-yl}-methyl)-3-methyl-3,4-dihydroquinolin-2(1H)-one Isomer 1 | Ex. 244 | 1.42 | 479 |
| 246 | 5-Fluoro-1-({7-fluoro-6-[2-(2-hydroxypropan-2-yl)-pyrimidin-5-yl]-2-methylimidazo[1,2-a]pyridin-3-yl}-methyl)-3-methyl-3,4-dihydroquinolin-2(1H)-one Isomer 2 | Ex. 244 | 1.42 | 479 |
| 247 | (8-anti)-3-(5-{7-Fluoro-3-[(5-fluoro-3-methyl-2-oxo-3,4-dihydroquinolin-1(2H)-yl)methyl]-2-methyl-imidazo[1,2-a]pyridin-6-yl}pyrimidin-2-yl)-3-azabicyclo[3.2.1]octane-8-carboxylic acid | Int. 189 and Int. 246 | 1.23 | 573 |
| 248 | (2R)-8-Fluoro-4-({6-[2-(2-hydroxypropan-2-yl)-4-methylpyrimidin-5-yl]-2-methylimidazo[1,2-a]-pyrazin-3-yl}methyl)-2-methyl-2H-1,4-benzoxazin-3(4H)-one | Int. 66 and Int. 253 | 1.34 | 478 |
| 249 | (2S)-8-Fluoro-4-({7-fluoro-2-methyl-6-[2-(3-oxo-piperazin-1-yl)pyrimidin-5-yl]imidazo[1,2-a]pyridin-3-yl}methyl)-2-methyl-2H-1,4-benzoxazin-3(4H)-one | Int. 143 and Int. 147 | 1.46 | 520.8 |
| 250 | (2S)-8-Fluoro-4-({7-fluoro-6-[6-(4-hydroxytetrahydro-2H-pyran-4-yl)pyridin-3-yl]-2-methylimidazo[1,2-a]-pyridin-3-yl}methyl)-2-methyl-2H-1,4-benzoxazin-3(4H)-one | Int. 143 and Int. 249 | 1.37 | 521.8 |
| 251 | (2R)-8-Fluoro-4-({6-[6-(4-hydroxytetrahydro-2H-pyran-4-yl)pyridin-3-yl]-2-methylimidazo[1,2-a]-pyrazin-3-yl}methyl)-2-methyl-2H-1,4-benzoxazin-3(4H)-one | Int. 66 and Int. 249 | 1.32 | 504.8 |
| 252 | 4-[(6-Bromo-7-fluoro-2-methylimidazo[1,2-a]pyridin-3-yl)methyl]-2H-1,4-benzothiazin-3(4H)-one | Int. 34 | 1.42 | 408.6 |
| 253 | 4-[(6-Bromo-7-fluoro-2-methylimidazo[1,2-a]pyridin-3-yl)methyl]-2H-1,4-benzothiazin-3(4H)-one 1-oxide | Ex. 252 | 1.12 | 422.6 |
| 254 | 4-({7-Fluoro-6-[2-(2-hydroxypropan-2-yl)pyrimidin-5-yl]-2-methylimidazo[1,2-a]pyridin-3-yl}methyl)-2H-1,4-benzothiazin-3(4H)-one 1-oxide | Ex. 255 | 1.12 | 480.6 |
| 255 | 4-({7-Fluoro-6-[2-(2-hydroxypropan-2-yl)pyrimidin-5-yl]-2-methylimidazo[1,2-a]pyridin-3-yl}methyl)-2H-1,4-benzothiazin-3(4H)-one | Ex. 252 | 1.30 | 464.8 |
| 256 | N-[(2R)-8-Fluoro-4-({7-fluoro-6-[2-(2-hydroxypropan-2-yl)pyrimidin-5-yl]-2-methylimidazo[1,2-a]pyridin-3-yl}methyl)-2-methyl-3-oxo-3,4-dihydro-2H-1,4-benzoxazin-6-yl]-2-methylpropanamide | Int. 256 | 1.38 | 565.3 |

The invention claimed is:

1. A compound represented by formula (IIB-A), (IIB-B) or (IIB-C), or an N-oxide thereof, or a pharmaceutically acceptable salt or solvate thereof:

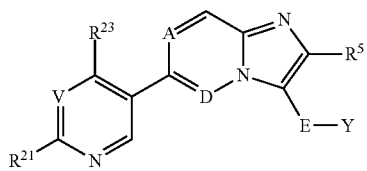

(IIB-A)

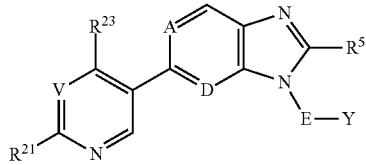

(IIB-B)

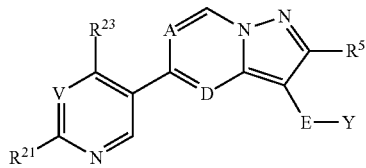

(IIB-C)

wherein

V represents C—R$^{22}$ or N;

R$^{21}$ represents hydroxy(C$_{1-6}$)alkyl, C$_{1-6}$ alkylsulphonyl, (C$_{1-6}$)alkyl-sulphoximinyl or [(C$_{1-6}$)alkyl][N—(C$_{1-6}$) alkyl]sulphoximinyl; or R$^{21}$ represents (C$_{3-7}$)-cycloalkyl, (C$_{3-7}$)heterocycloalkyl, (C$_{4-9}$)heterobicycloalkyl or (C$_{4-9}$)spiroheterocycloalkyl, any of which groups may be optionally substituted by one, two or three substituents independently selected from halogen, C$_{1-6}$ alkyl, trifluoromethyl, hydroxy, oxo, amino, carboxy and C$_{2-6}$ alkoxycarbonyl, R$^{22}$ represents hydrogen, halogen or C$_{1-6}$ alkyl;

R$^{23}$ represents hydrogen, C$_{1-6}$ alkyl, trifluoromethyl or C$_{1-6}$ alkoxy;

A represents C—R$^{2}$ or N;

D represents C—R$^{4}$ or N;

E represents —CH$_2$— or —CH(CH$_3$)—;

Y represents a group of formula (Ya-1), (Ya-2), (Ya-3), (Yb-1), (Yb-2), (Yb-3), (Yb-4), (Yb-5), (Yb-6), (Yb-7), (Yc-1) or (Yd-1):

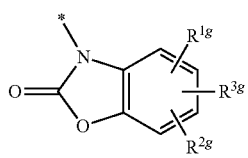

(Ya-1)

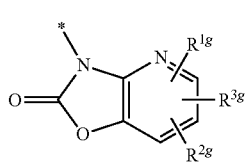

(Ya-2)

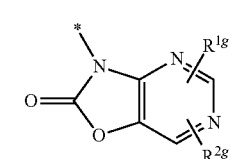

(Ya-3)

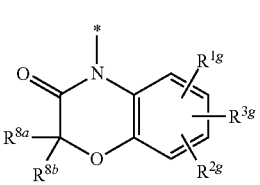

(Yb-1)

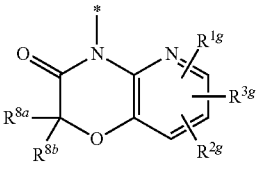

(Yb-2)

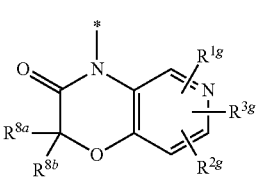

(Yb-3)

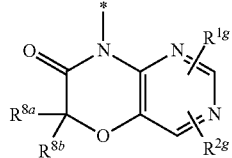

(Yb-4)

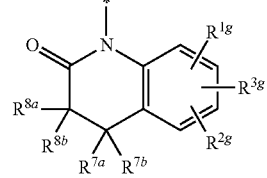

(Yb-5)

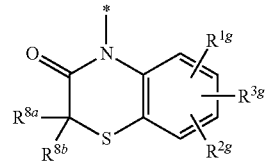

(Yb-6)

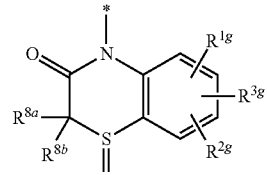

(Yb-7)

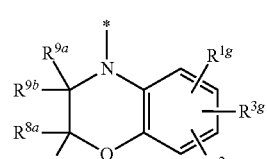

(Yc-1)

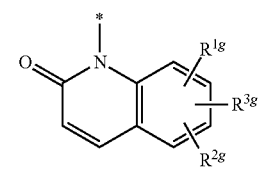

(Yd-1)

wherein the asterisk (*) represents the point of attachment to the remainder of the molecule;

R$^{1g}$ represents hydrogen, halogen, cyano, C$_{1-6}$ alkyl, fluoromethyl, difluoromethyl, trifluoromethyl, hydroxy, hydroxy(C$_{1-6}$)alkyl, C$_{1-6}$ alkoxy, difluoromethoxy, trifluoro-methoxy, pentafluorothio, C$_{1-6}$ alkylthio, C$_{1-6}$ alkylsulphinyl, C$_{1-6}$ alkylsulphonyl, amino, amino(C$_{1-6}$)alkyl, C$_{1-6}$ alkylamino, di(C$_{1-6}$)alkylamino, formyl, C$_{2-6}$ alkylcarbonyl, carboxy, C$_{2-6}$ alkoxycarbonyl, aminocarbonyl, C$_{1-6}$ alkylaminocarbonyl, di(C$_{1-6}$)alkyl-aminocarbonyl, hydroxy(C$_{1-6}$)alkylaminocarbonyl, (C$_{1-6}$)alkoxy(C$_{1-6}$)alkylaminocarbonyl, (C$_{3-7}$)cycloalkylaminocarbonyl, heteroaryl(C$_{1-6}$)alkylaminocarbonyl, aminosulphonyl, C$_{1-6}$ alkylaminosulphonyl, di(C$_{1-6}$)alkylaminosulphonyl, (C$_{1-6}$)alkylsulphoximinyl, [(C$_{1-6}$)alkyl][N—(C$_{1-6}$) alkyl]sulphoximinyl, hydroxy(C$_{3-7}$)heterocycloalkyl, (C$_{1-6}$)alkoxy-(C$_{3-7}$)heterocycloalkyl, (C$_{3-7}$)heterocycloalkylcarbonyl, hydroxy(C$_{3-7}$)heterocycloalkyl-carbonyl, oxo(C$_{3-7}$)heterocycloalkylcarbonyl, (C$_{1-6}$)alkyl-sulphonyl(C$_{3-7}$)heterocycloalkyl-carbonyl or (C$_{2-6}$)alkoxycarbonyl(C$_{3-7}$)heterocycloalkylcarbonyl;

R$^{2g}$ and R$^{3g}$ independently represent hydrogen or halogen;

R$^2$ represents hydrogen or halogen;

R$^4$ represents hydrogen;

R$^5$ represents C$_{1-6}$ alkyl, optionally substituted by halogen, hydroxy or C$_{1-6}$ alkoxy;

R$^{7a}$ and R$^{7b}$ independently represent hydrogen or C$_{1-6}$ alkyl;

R$^{8a}$ and R$^{8b}$ independently represent hydrogen, halogen or C$_{1-6}$ alkyl; or R$^{8a}$ and R$^{8b}$, when taken together with the carbon atom to which they are both attached, represent cyclopropyl; and R$^{9a}$ and R$^{9b}$ independently represent hydrogen or C$_{1-6}$ alkyl.

2. The compound as claimed in claim 1 wherein R$^{21}$ represents hydroxy(C$_{1-6}$)alkyl.

3. The compound as claimed in claim 2 represented by formula (IIC-A), (IID-A), (IIE-A), (IIF-A), (IIG-A), (IIH-A), (IIJ-A), (IIK-A), (IIL-A), (IIC-B), (IID-B), (IIE-B), (IIF-B), (IIG-B), (IIH-B), (IIJ-B), (IIK-B), (IIL-B), (IIC-C), (IID-C), (IIE-C), (IIF-C), (IIG-C), (IIH-C), (IIJ-C), (IIK-C) or (IIL-C), or an N-oxide thereof, or a pharmaceutically acceptable salt or solvate thereof:

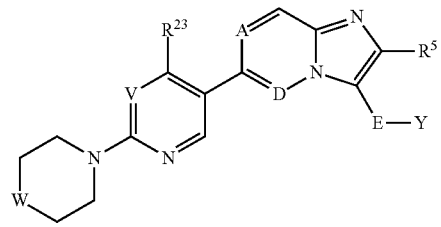
(IIC-A)

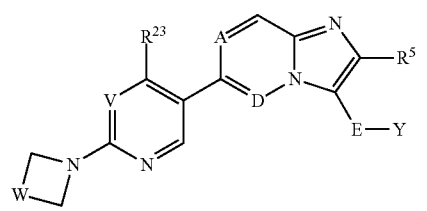
(IID-A)

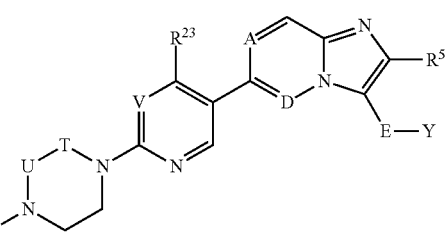
(IIE-A)

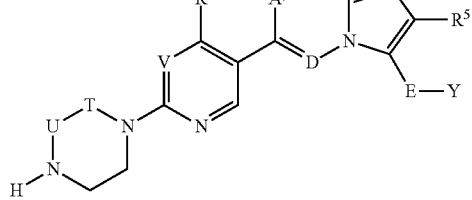
(IIF-A)

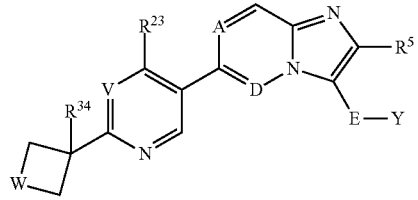
(IIG-A)

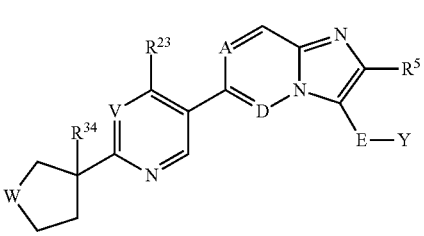
(IIH-A)

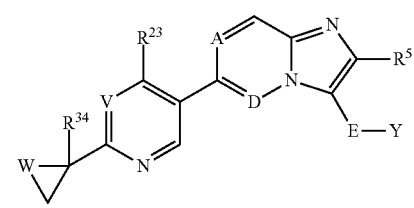
(IIJ-A)

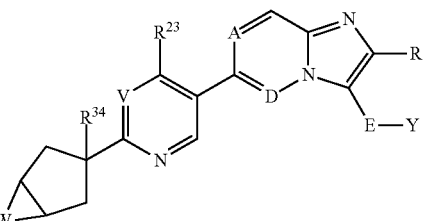
(IIK-A)

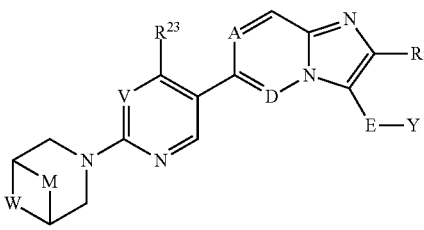
(IIL-A)

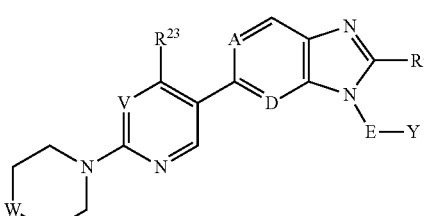
(IIC-B)

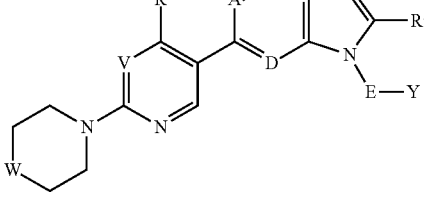
(IID-B)

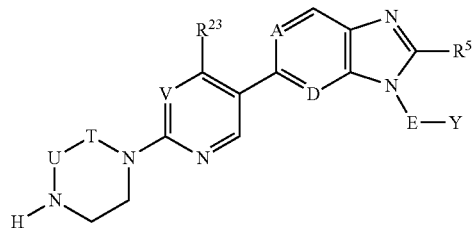 (IIE-B)
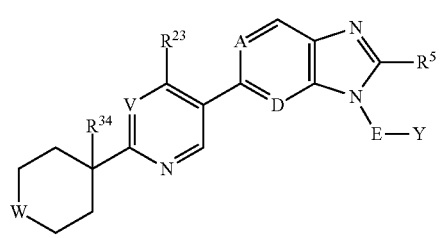 (IIF-B)
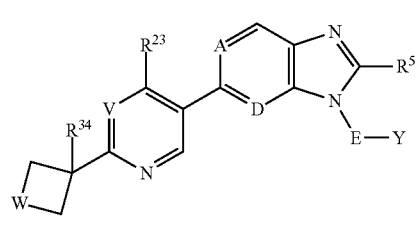 (IIG-B)
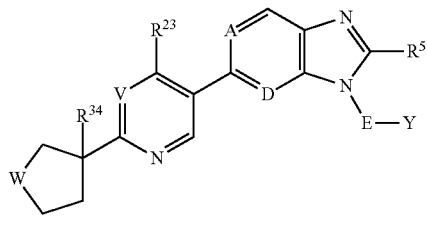 (IIH-B)
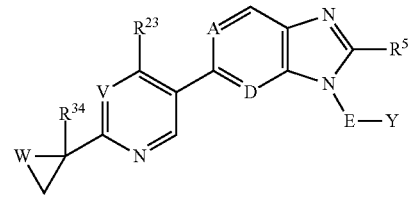 (IIJ-B)
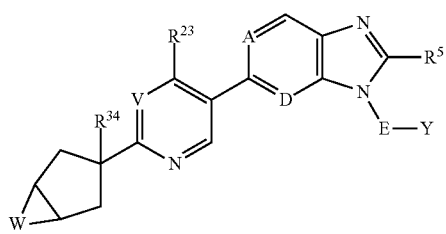 (IIK-B)
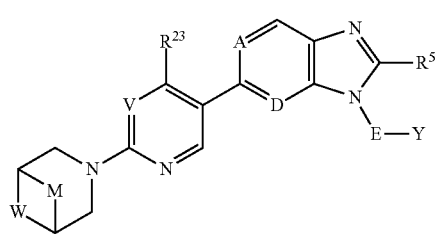 (IIL-B)
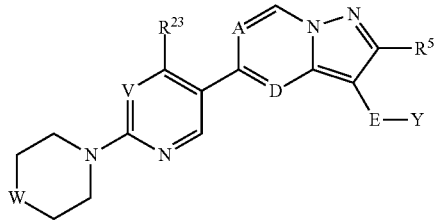 (IIC-C)
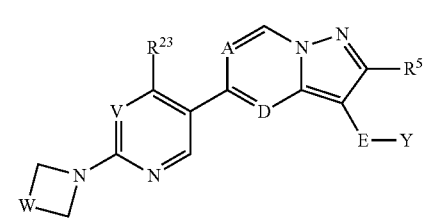 (IID-C)
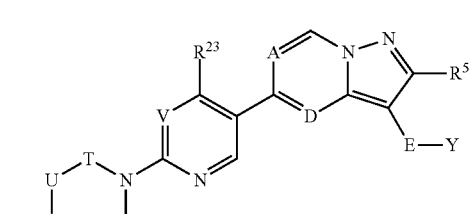 (IIE-C)
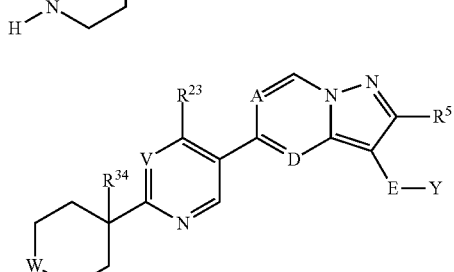 (IIF-C)
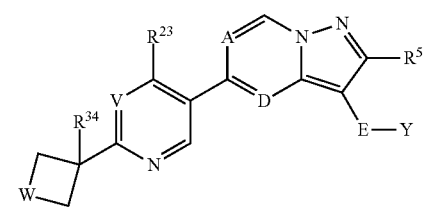 (IIG-C)
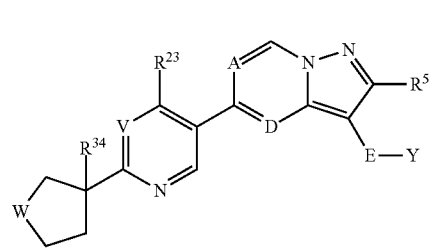 (IIH-C)
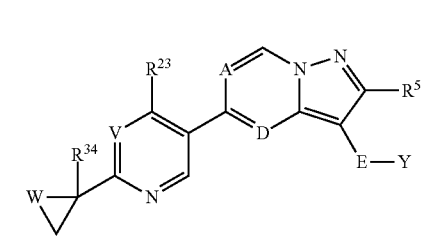 (IIJ-C)

(IIK-C)

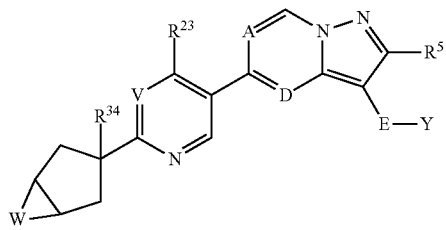

(IIL-C)

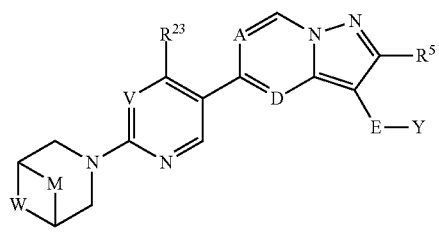

wherein

T represents —CH$_2$— or —CH$_2$CH$_2$—;

U represents C(O) or S(O)$_2$;

W represents O, N(R$^{31}$) or C(R$^{32}$)(R$^{33}$);

-M- represents —CH$_2$— or —CH$_2$CH$_2$—;

R$^{31}$ represents hydrogen, C$_{1-6}$ alkyl or C$_{2-6}$ alkylcarbonyl;

R$^{32}$ represents hydrogen, halogen, hydroxy, C$_{2-6}$ alkylcarbonyl or carboxy;

R$^{33}$ represents hydrogen, halogen, C$_{1-6}$ alkyl, trifluoromethyl or amino;

R$^{34}$ represents hydrogen, halogen, hydroxy or amino;

A represents C—R$^2$ or N;

D represents C—R$^4$ or N;

E represents —CH$_2$— or —CH(CH$_3$)—;

Y represents a group of formula (Ya-1), (Ya-2), (Ya-3), (Yb-1), (Yb-2), (Yb-3), (Yb-4), (Yb-5), (Yb-6), (Yb-7), (Yc-1) or (Yd-1):

(Ya-1)

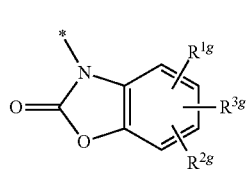

(Ya-2)

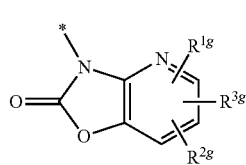

(Ya-3)

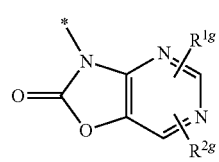

(Yb-1)

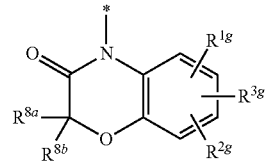

(Yb-2)

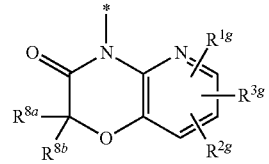

(Yb-3)

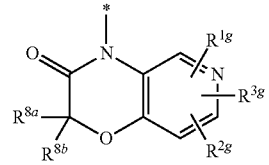

(Yb-4)

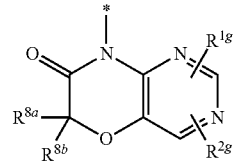

(Yb-5)

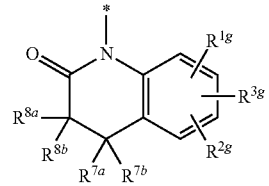

(Yb-6)

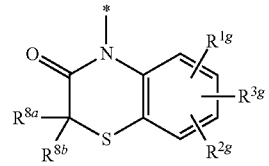

(Yb-7)

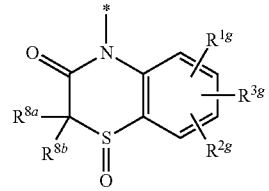

(Yc-1)

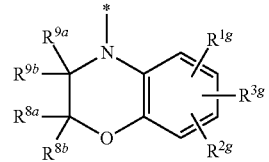

-continued

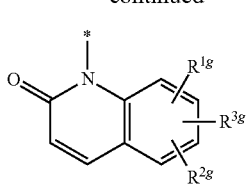

(Yd-1)

wherein
the asterisk (*) represents the point of attachment to the remainder of the molecule;
$R^{1g}$ represents hydrogen, halogen, cyano, $C_{1-6}$ alkyl, fluoromethyl, difluoromethyl, trifluoromethyl, hydroxy, hydroxy($C_{1-6}$)alkyl, $C_{1-6}$ alkoxy, difluoromethoxy, trifluoro-methoxy, pentafluorothio, $C_{1-6}$ alkylthio, $C_{1-6}$ alkylsulphinyl, $C_{1-6}$ alkylsulphonyl, amino, amino($C_{1-6}$)alkyl, $C_{1-6}$ alkylamino, di($C_{1-6}$)alkylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkyl-aminocarbonyl, hydroxy($C_{1-6}$)alkylaminocarbonyl, ($C_{1-6}$)alkoxy($C_{1-6}$)alkylaminocarbonyl, ($C_{3-7}$)cycloalkylaminocarbonyl, heteroaryl($C_{1-6}$)alkylaminocarbonyl, aminosulphonyl, $C_{1-6}$ alkylaminosulphonyl, di($C_{1-6}$)alkylaminosulphonyl, ($C_{1-6}$)alkylsulphoximinyl, [($C_{1-6}$alkyl][N—$C_{1-6}$(alkyl ]sulphoximinyl, hydroxy($C_{3-7}$)heterocycloalkyl, ($C_{1-6}$) alkoxy-($C_{3-7}$)heterocycloalkyl, ($C_{3-7}$) heterocycloalkylcarbonyl, hydroxy($C_{3-7}$) heterocycloalkyl-carbonyl, oxo($C_{3-7}$)heterocycloalkylcarbonyl, ($C_{1-6}$)alkylsulphonyl($C_3$)heterocycloalkylcarbonyl or ($C_{2-6}$)alkoxycarbonyl($C_{3-7}$)heterocycloalkylcarbonyl;
$R^{2g}$ and $R^{3g}$ independently represent hydrogen or halogen;
$R^2$ represents hydrogen or halogen;
$R^4$ represents hydrogen;
$R^5$ represents $C_{1-6}$ alkyl, optionally substituted by halogen, hydroxy or $C_{1-6}$ alkoxy;
$R^{7a}$ and $R^{7b}$ independently represent hydrogen or $C_{1-6}$ alkyl;
$R^{8a}$ and $R^{8b}$ independently represent hydrogen, halogen or $C_{1-6}$ alkyl; or
$R^{8a}$ and $R^{8b}$, when taken together with the carbon atom to which they are both attached, represent cyclopropyl; and
$R^{9a}$ and $R^{9b}$ independently represent hydrogen or $C_{1-6}$ alkyl.

4. The compound as claimed in claim 3 wherein $R^{34}$ represents hydrogen, fluoro, hydroxy or amino.

5. A compound which is
4-{6-(6-Methanesulfonylpyridin-3-yl)-2-methylimidazo[1,2-a]pyridin-3-yl]methyl}-2H,3H,4H-pyrido[3,2-b][1,4]oxazin-3-one;
8-Fluoro-4-({6-[2-(2-hydroxypropan-2-yl)pyrimidin-5-yl]-2-methylimidazo[1,2-a]-pyridin-3-yl}methyl)-3,4-dihydro-2H-1,4-benzoxazin-3-one;
7-Fluoro-3-({6-[2-(2-hydroxypropan-2-yl)pyrimidin-5-yl]-2-methylimidazo[1,2-a]-pyridin-3-yl}methyl)-2,3-dihydro-1,3-benzoxazol-2-one;
3-({6-[2-(2-Hydroxypropan-2-yl)pyrimidin-5-yl]-2-methylimidazo[1,2-a]pyridin-3-yl}methyl)-2H,3H-[1,3]oxazolo[4,5-d]pyrimidin-2-one;
8-Fluoro-4-{[6-(6-methanesulfonylpyridin-3-yl)-2-methylimidazo[1,2-a]pyridin-3-yl]-methyl}-3,4-dihydro-2H-1,4-benzoxazin-3-one;
tert-Butyl 4-(5-{3-[(8-Fluoro-3-oxo-3,4-dihydro-2H-1,4-benzoxazin-4-yl)methyl]-2-methylimidazo[1,2-a]pyridin-6-yl}pyrimidin-2-yl)piperazine-1-carboxylate;
8-Fluoro-4-({2-methyl-6-[2-(morpholin-4-yl)pyrimidin-5-yl]imidazo[1,2-a]pyridin-3-yl}methyl)-3,4-dihydro-2H-1,4-benzoxazin-3-one;
8-Fluoro-4-({2-methyl-6-[2-(piperazin-1-yl)pyrimidin-5-yl]imidazo[1,2-a]pyridin-3-yl}-methyl)-3,4-dihydro-2H-1,4-benzoxazin-3-one hydrochloride;
(2R)-8-Fluoro-4-({6-[2-(2-hydroxypropan-2-yl)pyrimidin-5-yl]-2-methylimidazo[1,2-a]-pyridin-3-yl}methyl)-2-methyl-3,4-dihydro-2H-1,4-benzoxazin-3-one;
Ethyl 1-(5-{3-[(8-Fluoro-3-oxo-3,4-dihydro-2H-1,4-benzoxazin-4-yl)methyl]-2-methyl-imidazo[1,2-a]pyridin-6-yl}pyrimidin-2-yl)-4-methylpiperidine-4-carboxylate;
8-Fluoro-4-({6-[6-(2-hydroxypropan-2-yl)pyridin-3-yl]-2-methylimidazo[1,2-a]pyridin-3-yl}methyl)-3,4-dihydro-2H-1,4-benzoxazin-3-one;
8-Fluoro-4-({2-methyl-6-[2-(3-oxopiperazin-1-yl)pyrimidin-5-yl]imidazo[1,2-a]pyridin-3-yl}methyl)-3,4-dihydro-2H-1,4-benzoxazin-3-one;
1-(5-{3-[(8-Fluoro-3-oxo-3,4-dihydro-2H-1,4-benzoxazin-4-yl)methyl]-2-methylimidazo-[1,2-a]pyridin-6-yl}pyrimidin-2-yl)-4-methylpiperidine-4-carboxylic acid;
(2R)-8-Fluoro-2-methyl-4-({2-methyl-6-[2-(3-oxopiperazin-1-yl)pyrimidin-5-yl]imidazo-[1,2-a]pyridin-3-yl}methyl)-3,4-dihydro-2H-1,4-benzoxazin-3-one;
8-Fluoro-4-({2-methyl-6-[6-(piperazin-1-yl)pyridin-3-yl]imidazo[1,2-a]pyridin-3-yl}-methyl)-3,4-dihydro-2H-1,4-benzoxazin-3-one;
Methyl (1S,5R)-3-(5-{3-[(8-fluoro-3-oxo-3,4-dihydro-2H-1,4-benzoxazin-4-yl)methyl]-2-methylimidazo[1,2-a]pyridin-6-yl}pyrimidin-2-yl)-3-azabicyclo[3.2.1]octane-8-carboxylate;
(1r,4r)-4-(5-{3-[(8-Fluoro-3-oxo-1,4-benzoxazin-4-yl)methyl]-2-methylimidazo[1,2-a]-pyridin-6-yl}pyrimidin-2-yl)cyclohexanecarboxylic acid;
(2R)-8-Fluoro-4-({7-fluoro-6-[2-(2-hydroxypropan-2-yl)pyrimidin-5-yl]-2-methyl-imidazo[1,2-a]pyridin-3-yl}methyl)-2-methyl-3,4-dihydro-2H-1,4-benzoxazin-3-one;
(2R)-6,8-Fluoro-4-({7-fluoro-6-[2-(2-hydroxypropan-2-yl)pyrimidin-5-yl]-2-methylimidazo[1,2-a]pyridin-3-yl}methyl)-2-methyl-3,4-dihydro-2H-1,4-benzoxazin-3-one;
4-(5-{3-[(8-Fluoro-2-methyl-3-oxo-3,4-dihydro-2H-1,4-benzoxazin-4-yl)methyl]-2-methylimidazo[1,2-a]pyridin-6-yl}pyrimidin-2-yl)cyclohexane-1-carboxylic acid;
(2R)-6,8-Difluoro-4-({7-fluoro-6-[2-(3-hydroxyoxetan-3-yl)pyrimidin-5-yl]-2-methyl-imidazo[1,2-a]pyridin-3-yl}methyl)-2-methyl-3,4-dihydro-2H-1,4-benzoxazin-3-one;
(2R)-8-Fluoro-4-({7-fluoro-2-methyl-6-[2-(3-oxopiperazin-1-yl)pyrimidin-5-yl]imidazo-[1,2-a]pyridin-3-yl}methyl)-2-methyl-3,4-dihydro-2H-1,4-benzoxazin-3-one;
(2R)-8-Fluoro-4-({7-fluoro-6-[2-(3-hydroxyoxetan-3-yl)pyrimidin-5-yl]-2-methyl-imidazo[1,2-a]pyridin-3-yl}methyl)-2-methyl-3,4-dihydro-2H-1,4-benzoxazin-3-one;
(2R)-6,8-Difluoro-4-({7-fluoro-6-[2-(3-hydroxyazetidin-3-yl)pyrimidin-5-yl]-2-methyl-imidazo[1,2-a]pyridin-3-yl}methyl)-2-methyl-3,4-dihydro-2H-1,4-benzoxazin-3-one;

(2R)-6,8-Difluoro-4-({7-fluoro-6-[2-(4-hydroxytetrahydropyran-4-yl)pyrimidin-5-yl]-2-methylimidazo[1,2-a]pyridin-3-yl}methyl)-2-methyl-1,4-benzoxazin-3-one;

(2R)-8-Fluoro-4-({7-fluoro-6-[2-(1-hydroxycyclobutyl)pyrimidin-5-yl]-2-methylimidazo-[1,2-a]pyridin-3-yl}methyl)-2-methyl-3,4-dihydro-2H-1,4-benzoxazin-3-one;

(2R)-8-Fluoro-4-(1-{7-fluoro-6-[2-(2-hydroxypropan-2-yl)pyrimidin-5-yl]-2-methyl-imidazo[1,2-a]pyridin-3-yl}ethyl)-2-methyl-3,4-dihydro-2H-1,4-benzoxazin-3-one;

8-Fluoro-4-({7-fluoro-6-[2-(2-hydroxypropan-2-yl)pyrimidin-5-yl]-2-methylimidazo[1,2-a]pyridin-3-yl}methyl)-2,2-dimethyl-3,4-dihydro-2H-1,4-benzoxazin-3-one;

(2R)-8-Fluoro-4-({7-fluoro-6-[2-(3-hydroxy-1-methylazetidin-3-yl)pyrimidin-5-yl]-2-methylimidazo[1,2-a]pyridin-3-yl}methyl)-2-methyl-3,4-dihydro-2H-1,4-benzoxazin-3-one formic acid salt;

(7R)-5-({6-[2-(2-Hydroxypropan-2-yl)pyrimidin-5-yl]-2-methylimidazo[1,2-a]pyrazin-3-yl}methyl)-7-methyl-5H,6H,7H-pyrimido[4,5-b][1,4]oxazin-6-one;

(2R)-6,8-Difluoro-4-({6-[2-(2-hydroxypropan-2-yl)pyrimidin-5-yl]-2-methylimidazo[1,2-a]pyrazin-3-yl}methyl)-2-methyl-3,4-dihydro-2H-1,4-benzoxazin-3-one;

(2R)-8-Fluoro-4-({6-[2-(3-hydroxyoxetan-3-yl)pyrimidin-5-yl]-2-methylimidazo[1,2-a]-pyrazin-3-yl}methyl)-2-methyl-3,4-dihydro-2H-1,4-benzoxazin-3-one;

8-Fluoro-4-({6-[2-(2-hydroxypropan-2-yl)pyrimidin-5-yl]-2-methylimidazo[1,2-a]pyrazin-3-yl}methyl)-2,2-dimethyl-3,4-dihydro-2H-1,4-benzoxazin-3-one;

(2R)-8-Fluoro-4-({6-[2-(4-hydroxytetrahydropyran-4-yl)pyrimidin-5-yl]-2-methyl-imidazo[1,2-a]pyrazin-3-yl}methyl)-2-methyl-1,4-benzoxazin-3-one;

(2R)-4-({6-[2-(1,1-Difluoroethyl)pyrimidin-5-yl]-2-methylimidazo[1,2-a]pyrazin-3-yl}methyl)-8-fluoro-2-methyl-3,4-dihydro-2H-1,4-benzoxazin-3-one;

(2R)-6,8-Difluoro-4-({7-fluoro-2-methyl-6-[2-(3-oxopiperazin-1-yl)pyrimidin-5-yl]-imidazo[1,2-a]pyridin-3-yl}methyl)-2-methyl-3,4-dihydro-2H-1,4-benzoxazin-3-one;

4-({6-[2-(2-Hydroxypropan-2-yl)pyrimidin-5-yl]-2-methylimidazo[1,2-a]pyrazin-3-yl}-methyl)-2H,3H,4H-pyrido[4,3-b][1,4]oxazin-3-one;

4-({7-Fluoro-6-[2-(2-hydroxypropan-2-yl)pyrimidin-5-yl]-2-methylimidazo[1,2-a]-pyridin-3-yl}methyl)-2H,3H,4H-pyrido[3,2-b][1,4]oxazin-3-one;

4-({6-[2-(2-Hydroxypropan-2-yl)pyrimidin-5-yl]-2-methylimidazo[1,2-a]pyrazin-3-yl}-methyl)-2H,3H,4H-pyrido[3,2-b][1,4]oxazin-3-one;

6,8-Difluoro-4-[(7-fluoro-6-{2-[3-hydroxy-3-(trifluoromethyl)azetidin-1-yl]pyrimidin-5-yl}-2-methylimidazo[1,2-a]pyridin-3-yl)methyl]-3,4-dihydro-2H-1,4-benzoxazin-3-one;

(2R)-6,8-Difluoro-2-methyl-4-({2-methyl-6-[2-(5-oxo-1,4-diazepan-1-yl)pyrimidin-5-yl]-imidazo[1,2-a]pyrazin-3-yl}methyl)-3,4-dihydro-2H-1,4-benzoxazin-3-one;

(2R)-4-{[6-(2-{3,7-Dioxa-9-azabicyclo[3.3.1]nonan-9-yl}pyrimidin-5-yl)-7-fluoro-2-methylimidazo[1,2-a]pyridin-3-yl]methyl}-8-fluoro-2-methyl-3,4-dihydro-2H-1,4-benzoxazin-3-one;

6,8-Difluoro-4-[(7-fluoro-6-{2-[3-hydroxy-3-(trifluoromethyl)azetidin-1-yl]pyrimidin-5-yl}-2-methylimidazo[1,2-a]pyridin-3-yl)methyl]-2,2-dimethyl-3,4-dihydro-2H-1,4-benzoxazin-3-one;

(2R)-6,8-Difluoro-4-[(6-{2-[3-hydroxy-3-(trifluoromethyl)azetidin-1-yl]pyrimidin-5-yl}-2-methylimidazo[1,2-a]pyrazin-3-yl)methyl]-2-methyl-3,4-dihydro-2H-1,4-benzoxazin-3-one;

(2S)-6,8-Difluoro-4-[(6-{2-[3-hydroxy-3-(trifluoromethyl)azetidin-1-yl]pyrimidin-5-yl}-2-methylimidazo[1,2-a]pyrazin-3-yl)methyl]-2-methyl-3,4-dihydro-2H-1,4-benzoxazin-3-one;

(2R)-6,8-Difluoro-4-({7-fluoro-6-[2-(3-fluorooxetan-3-yl)pyrimidin-5-yl]-2-methyl-imidazo[1,2-a]pyridin-3-yl}methyl)-2-methyl-3,4-dihydro-2H-1,4-benzoxazin-3-one;

6,8-Difluoro-4-({6-[2-(2-hydroxypropan-2-yl)pyrimidin-5-yl]-2-methylimidazo[1,2-a]-pyrazin-3-yl}methyl)-3,4-dihydro-2H-1,4-benzoxazin-3-one;

(2R)-6,8-Difluoro-2-methyl-4-({2-methyl-6-[2-(3-oxopiperazin-1-yl)pyrimidin-5-yl]-imidazo[1,2-a]pyrazin-3-yl}methyl)-3,4-dihydro-2H-1,4-benzoxazin-3-one;

6,8-Difluoro-4-({6-[2-(3-hydroxy-3-methylazetidin-1-yl)pyrimidin-5-yl]-2-methyl-imidazo[1,2-a]pyrazin-3-yl}methyl)-2,2-dimethyl-3,4-dihydro-2H-1,4-benzoxazin-3-one;

(2R)-6,8-Difluoro-4-({6-[2-(3-fluorooxetan-3-yl)pyrimidin-5-yl]-2-methylimidazo[1,2-a]-pyrazin-3-yl}methyl)-2-methyl-3,4-dihydro-2H-1,4-benzoxazin-3-one;

(2S)-6,8-Difluoro-4-({7-fluoro-6-[2-(3-hydroxy-3-methylazetidin-1-yl)pyrimidin-5-yl]-2-methylimidazo[1,2-a]pyridin-3-yl}methyl)-2-methyl-3,4-dihydro-2H-1,4-benzoxazin-3-one;

(2R)-6,8-Difluoro-4-[(7-fluoro-6-{2-[3-hydroxy-3-(trifluoromethyl)azetidin-1-yl]-pyrimidin-5-yl}-2-methyl-imidazo[1,2-a]pyridin-3-yl)methyl]-2-methyl-3,4-dihydro-2H-1,4-benzoxazin-3-one;

7-Fluoro-3-({7-fluoro-6-[2-(3-hydroxy-3-methylazetidin-1-yl)pyrimidin-5-yl]-2-methyl-imidazo[1,2-a]pyridin-3-yl}methyl)-2,3-dihydro-1,3-benzoxazol-2-one formate;

(2R)-6,8-Difluoro-2-methyl-4-({2-methyl-6-[2-(morpholin-4-yl)pyrimidin-5-yl]imidazo-[1,2-a]pyrazin-3-yl}methyl)-3,4-dihydro-2H-1,4-benzoxazin-3-one;

(2R)-6,8-Difluoro-4-({6-[2-(3-hydroxy-3-methylazetidin-1-yl)pyrimidin-5-yl]-2-methyl-imidazo[1,2-a]pyrazin-3-yl}methyl)-2-methyl-3,4-dihydro-2H-1,4-benzoxazin-3-one;

6,8-Difluoro-4-({7-fluoro-6-[2-(3-hydroxy-3-methylazetidin-1-yl)pyrimidin-5-yl]-2-methylimidazo[1,2-a]pyridin-3-yl}methyl)-2,2-dimethyl-3,4-dihydro-2H-1,4-benzoxazin-3-one;

(2R)-8-Fluoro-4-({7-fluoro-6-[2-(3-hydroxy-3-methylazetidin-1-yl)pyrimidin-5-yl]-2-methylimidazo[1,2-a]pyridin-3-yl}methyl)-2-methyl-3,4-dihydro-2H-1,4-benzoxazin-3-one;

6,8-Difluoro-4-({7-fluoro-6-[2-(3-hydroxy-3-methylazetidin-1-yl)pyrimidin-5-yl]-2-methylimidazo[1,2-a]pyridin-3-yl}methyl)-3,4-dihydro-2H-1,4-benzoxazin-3-one;

2,2,6,8-Tetrafluoro-4-({7-fluoro-6-[2-(2-hydroxypropan-2-yl)pyrimidin-5-yl]-2-methyl-imidazo[1,2-a]pyridin-3-yl}methyl)-3,4-dihydro-2H-1,4-benzoxazin-3-one;

(2S)-6,8-Difluoro-4-({6-[2-(2-hydroxypropan-2-yl)pyrimidin-5-yl]-2-methylimidazo[1,2-a]pyrazin-3-yl}methyl)-2-methyl-3,4-dihydro-2H-1,4-benzoxazin-3-one;

2,2,6,8-Tetrafluoro-4-({7-fluoro-6-[2-(3-hydroxy-3-methylazetidin-1-yl)pyrimidin-5-yl]-2-methylimidazo[1,2-a]pyridin-3-yl}methyl)-3,4-dihydro-2H-1,4-benzoxazin-3-one;

(2S)-6,8-Difluoro-4-[(7-fluoro-6-{2-[3-hydroxy-3-(trifluoromethyl)azetidin-1-yl]-pyrimidin-5-yl}-2-methylimidazo[1,2-a]pyridin-3-yl)methyl]-2-methyl-3,4-dihydro-2H-1,4-benzoxazin-3-one;

(2R)-6,8-Difluoro-4-({7-fluoro-2-methyl-6-[2-(morpholin-4-yl)pyrimidin-5-yl]imidazo-[1,2-a]pyridin-3-yl}methyl)-2-methyl-3,4-dihydro-2H-1,4-benzoxazin-3-one;

6,8-Difluoro-4-[(6-{2-[3-hydroxy-3-(trifluoromethyl)azetidin-1-yl]pyrimidin-5-yl}-2-methylimidazo[1,2-a]pyrazin-3-yl)methyl]-2,2-dimethyl-3,4-dihydro-2H-1,4-benzoxazin-3-one;

7-Fluoro-3-({7-fluoro-6-[2-(2-hydroxypropan-2-yl)pyrimidin-5-yl]-2-methylimidazo[1,2-a]pyridin-3-yl}methyl)-2,3-dihydro-1,3-benzoxazol-2-one;

(2R)-6,8-Difluoro-4-({7-fluoro-2-methyl-6-[2-(3-oxopiperazin-1-yl)pyrimidin-5-yl]-imidazo[1,2-a]pyridin-3-yl}methyl)-2-methyl-3,4-dihydro-2H-1,4-benzoxazin-3-one;

2,2,6,8-Tetrafluoro-4-[(7-fluoro-6-{2-[3-hydroxy-3-(trifluoromethyl)azetidin-1-yl]-pyrimidin-5-yl}-2-methylimidazo[1,2-a]pyridin-3-yl)methyl]-3,4-dihydro-2H-1,4-benzoxazin-3-one;

(2R)-4-({6-[2-(2-Hydroxypropan-2-yl)pyrimidin-5-yl]-2-methylimidazo[1,2-a]pyrazin-3-yl}methyl)-2-methyl-2H,3H,4H-pyrido[3,2-b][1,4]oxazin-3-one;

4-({7-Fluoro-6-[2-(2-hydroxypropan-2-yl)pyrimidin-5-yl]-2-methylimidazo[1,2-a]-pyridin-3-yl}methyl)-2H,3H,4H-pyrido[4,3-b][1,4]oxazin-3-one;

(2R)-6,8-Difluoro-4-({7-fluoro-6-[2-(3-hydroxy-3-methylazetidin-1-yl)pyrimidin-5-yl]-2-methylimidazo[1,2-a]pyridin-3-yl}methyl)-2-methyl-3,4-dihydro-2H-1,4-benzoxazin-3-one;

(2R)-8-Fluoro-4-[(7-fluoro-6-{2-[3-hydroxy-3-(trifluoromethyl)azetidin-1-yl]pyrimidin-5-yl}-2-methylimidazo[1,2-a]pyridin-3-yl)methyl]-2-methyl-3,4-dihydro-2H-1,4-benzoxazin-3-one;

6,8-Difluoro-4-({7-fluoro-6-[2-(2-hydroxypropan-2-yl)pyrimidin-5-yl]-2-methylimidazo-[1,2-a]pyridin-3-yl}methyl)-2,2-dimethyl-3,4-dihydro-2H-1,4-benzoxazin-3-one;

(2R)-4-({6-[2-(3,7-Dioxa-9-azabicyclo[3.3.1]nonan-9-yl)pyrimidin-5-yl]-2-methyl-imidazo[1,2-a]pyrazin-3-yl}methyl)-6,8-difluoro-2-methyl-3,4-dihydro-2H-1,4-benzoxazin-3-one;

(2R)-6,8-Difluoro-4-({7-fluoro-2-methyl-6-[2-(5-oxo-1,4-diazepan-1-yl)pyrimidin-5-yl]-imidazo[1,2-a]pyridin-3-yl}methyl)-2-methyl-3,4-dihydro-2H-1,4-benzoxazin-3-one;

(2R)-8-Fluoro-4-({7-fluoro-6-[2-(1-hydroxycyclopropyl)pyrimidin-5-yl]-2-methyl-imidazo[1,2-a]pyridin-3-yl}methyl)-2-methyl-3,4-dihydro-2H-1,4-benzoxazin-3-one;

4-({6-[2-(3,3-Difluoro-1-hydroxycyclobutyl)pyrimidin-5-yl]-2-methylimidazo[1,2-a]-pyrazin-3-yl}methyl)-6,8-difluoro-2,2-dimethyl-3,4-dihydro-2H-1,4-benzoxazin-3-one;

(2R)-4-({7-Fluoro-6-[2-(2-hydroxypropan-2-yl)pyrimidin-5-yl]-2-methylimidazo[1,2-a]-pyridin-3-yl}methyl)-2-methyl-2H,3H,4H-pyrido[3,2-b][1,4]oxazin-3-one;

4-({7-Fluoro-6-[2-(1-hydroxy-1-methylethyl)pyrimidin-5-yl]-2-methylimidazo[1,2-a]-pyridin-3-yl}methyl)spiro[1,4-benzoxazine-2,1'-cyclopropane]-3-one;

Methyl (2R)-8-fluoro-4-({7-fluoro-6-[2-(1-hydroxy-1-methylethyl)pyrimidin-5-yl]-2-methylimidazo[1,2-a]pyridin-3-yl}methyl)-2-methyl-3-oxo-1,4-benzoxazine-6-carboxylate;

(2R)-7,8-Difluoro-4-({7-fluoro-6-[2-(1-hydroxy-1-methylethyl)pyrimidin-5-yl]-2-methyl-imidazo[1,2a-]pyridin-3-yl}methyl)-2-methyl-1,4-benzoxazin-3-one;

8-Fluoro-4-({7-fluoro-6-[2-(1-hydroxy-1-methylethyl)pyrimidin-5-yl]-2-methylimidazo-[1,2a-]pyridin-3-yl}methyl)spiro[1,4-benzoxazine-2,1'-cyclopropane]-3-one;

-8-Fluoro-4-({7-fluoro-6-[2-(3-hydroxy-3-methylazetidin-1-yl)pyrimidin-5-yl]-2-methyl-imidazo[1,2a-]pyridin-3-yl}methyl)spiro[1,4-benzoxazine-2,1'-cyclopropane]-3-one;

8-Fluoro-4-[(7-fluoro-6-{2-[3-hydroxy-3-(trifluoromethyl)azetidin-1-yl]pyrimidin-5-yl}-2-methylimidazo[1,2-a]pyridin-3-yl)methyl]spiro[1,4-benzoxazine-2,1'-cyclopropane]-3-one;

(2R)-5,6,8-Trifluoro-4-[(6-{2-[3-hydroxy-3-(trifluoromethyl)azetidin-1-yl]pyrimidin-5-yl}-2-methylimidazo[1,2-a]pyrazin-3-yl)methyl]-2-methyl-1,4-benzoxazin-3-one;

2-(5-{7-Fluoro-3-[(8-fluoro-3-methyl-2,3-dihydro-1,4-benzoxazin-4-yl)methyl]-2-methylimidazo[1,2a-]pyridin-6-yl}pyrimidin-2-yl)propan-2-ol;

(2R)-8-Chloro-6-fluoro-4-({6-[2-(3-hydroxy-3-methylazetidin-1-yl)pyrimidin-5-yl]-2-methylimidazo[1,2a-]pyrazin-3-yl}methyl)-2-methyl-1,4-benzoxazin-3-one;

(2R)-8-Chloro-4-({6-[2-(3-hydroxy-3-methylazetidin-1-yl)pyrimidin-5-yl]-2-methyl-imidazo[1,2-a]pyrazin-3-yl}methyl)-2-methyl-1,4-benzoxazin-3-one;

(2S)-8-Fluoro-4-({6-[2-(1-hydroxy-1-methylethyl)pyrimidin-5-yl]-2-methylimidazo[1,2-a]pyrazin-3-yl}methyl)-2-methyl-1,4-benzoxazin-3-one;

(2S)-8-Fluoro-4-[(7-fluoro-6-{2-[3-hydroxy-3-(trifluoromethyl)azetidin-1-yl]pyrimidin-5-yl}-2-methylimidazo[1,2-a]pyridin-3-yl)methyl]-2-methyl-1,4-benzoxazin-3-one;

(2S)-8-Fluoro-4-({7-fluoro-6-[2-(3-hydroxy-3-methylazetidin-1-yl)pyrimidin-5-yl]-2-methylimidazo[1,2a-]pyridin-3-yl}methyl)-2-methyl-1,4-benzoxazin-3-one;

(2R)-4-({7-Fluoro-6-[2-(1-hydroxy-1-methylethyl)pyrimidin-5-yl]-2-methylimidazo[1,2a-]pyridin-3-yl}methyl)-2-methyl-8-(trifluoromethyl)pyrido[3,2-b][1,4]oxazin-3-one;

(2R)-4-({6-[2-(1-Hydroxy-1-methylethyl)pyrimidin-5-yl]-2-methylimidazo[1,2a-]-pyrazin-3-yl}methyl)-2-methyl-8-(trifluoromethyl)pyrido[3,2-b][1,4]oxazin-3-one;

(2R)-8-Fluoro-4-({6-[2-(1-hydroxy-1-methylethyl)pyrimidin-5-yl]-2-methylimidazo[1,2-a]pyrazin-3-yl}methyl)-2-methyl-1,4-benzoxazin-3-one;

(2R)-8-Fluoro-4-({7-fluoro-6-[2-(1-hydroxy-1-methylethyl)pyrimidin-5-yl]-2-methyl-imidazo[1,2a-]pyridin-3-yl}methyl)-2-methyl-3-oxo-1,4-benzoxazine-6-carbonitrile;

(2S)-8-Fluoro-4-({7-fluoro-6-[6-(1-hydroxy-1-methylethyl)pyridin-3-yl]-2-methyl-imidazo[1,2a-]pyridin-3-yl}methyl)-2-methyl-1,4-benzoxazin-3-one;

(2R)-8-Fluoro-4-({6-[2-(1-hydroxycyclobutyl)pyrimidin-5-yl]-2-methylimidazo[1,2-a]-pyrazin-3-yl}methyl)-2-methyl-1,4-benzoxazin-3-one;

(2R)-8-Fluoro-4-[(6-{2-[3-hydroxy-3-(trifluoromethyl)azetidin-1-yl]pyrimidin-5-yl}-2-methylimidazo[1,2-a]pyrazin-3-yl)methyl]-2-methyl-1,4-benzoxazin-3-one;
(2R)-8-Fluoro-2-methyl-4-({2-methyl-6-[2-(morpholin-4-yl)pyrimidin-5-yl]imidazo[1,2a-]pyrazin-3-yl}methyl)-1,4-benzoxazin-3-one;
(2R)-8-Fluoro-4-({6-[2-(3-hydroxy-3-methylazetidin-1-yl)pyrimidin-5-yl]-2-methyl-imidazo[1,2-a]pyrazin-3-yl}methyl)-2-methyl-1,4-benzoxazin-3-one;
(2R)-8-Fluoro-4-({6-[6-(1-hydroxy-1-methylethyl)pyridin-3-yl]-2-methylimidazo[1,2a-]-pyrazin-3-yl}methyl)-2-methyl-1,4-benzoxazin-3-one;
(2R)-8-Fluoro-2-methyl-4-({2-methyl-6-[2-(6-oxa-3-azabicyclo[3.1.1]heptan-3-yl)-pyrimidin-5-yl]imidazo[1,2a-]pyrazin-3-yl}methyl)-1,4-benzoxazin-3-one;
8-Fluoro-4-[(6-{2-[3-hydroxy-3-(trifluoromethyl)azetidin-1-yl]pyrimidin-5-yl}-2-methyl-imidazo[1,2a]pyrazin-3-yl)methyl]-1,4-benzoxazin-3-one;
(2R)-6-Bromo-8-fluoro-4-({6-[2- (1-hydroxy-1-methylethyl)pyrimidin-5-yl]-2-methyl-imidazo[1,2a-]pyrazin-3-yl}methyl)-2-methyl-1,4-benzoxazin-3-one;
(2R)-8-Fluoro-2-methyl-4-{[2-methyl-6-(6-methylsulfonylpyridin-3-yl)imidazo[1,2-a]-pyrazin-3-yl]methyl}-1,4-benzoxazin-3-one;
(2R)-4-({6-[2-(6,6-Dioxo-λ⁶-thia-2-azaspiro[3.3]heptan-2-yl)pyrimidin-5-yl]-2-methyl-imidazo[1,2a]pyrazin-3-yl}methyl)-8-fluoro-2-methyl-1,4-benzoxazin-3-one;
(2R)-8-Fluoro-2-methyl-4-({2-methyl-6-[2-(3-oxa-6-azaspiro[3.3]heptan-6-yl)pyrimidin-5-yl]imidazo[1,2a-]pyrazin-3-yl}methyl)-1,4-benzoxazin-3-one;
(2R)-7,8-Difluoro-4-[(6-{2-[3-hydroxy-3-(trifluoromethyl)azetidin-1-yl]pyrimidin-5-yl}-2-methylimidazo[1,2a-]pyrazin-3-yl)methyl]-2-methyl-1,4-benzoxazin-3-one;
4-({6-[2-(1-Hydroxy-1-methylethyl)pyrimidin-5-yl]-2-methylimidazo[1,2a-]pyrazin-3-yl}methyl)spiro[1,4-benzoxazine-2,1'-cyclopropane]-3-one;
8-Fluoro-4-({6-[2-(1-hydroxy-1-methylethyl)pyrimidin-5-yl]-2-methylimidazo[1,2-a]-pyrazin-3-yl}methyl)spiro[1,4-benzoxazine-2,1'-cyclopropane]-3-one;
(2R)-8-Fluoro-2-methyl-4-({2-methyl-6-[2-(3-oxopiperazin-1-yl)pyrimidin-5-yl]imidazo-[1,2a-]pyrazin-3-yl}methyl)-1,4-benzoxazin-3-one;
(2R)-4-({6-[2-(3,3-Difluoroazetidin-1-yl)pyrimidin-5-yl]-2-methylimidazo[1,2-a]pyrazin-3-yl}methyl)-8-fluoro-2-methyl-1,4-benzoxazin-3-one;
(2R)-8-Fluoro-4-({7-fluoro-2-(hydroxymethyl)-6-[2-(1-hydroxy-1-methylethyl)-pyrimidin-5-yl]imidazo[1,2a-]pyrazin-3-yl}methyl)-2-methyl-1,4-benzoxazin-3-one;
(2R)-8-Fluoro-4-({6-[2-(1-hydroxy-1-methylethyl)pyrimidin-5-yl]-2-methylimidazo[1,2-b]pyridazin-3-yl}methyl)-2-methyl-1,4-benzoxazin-3-one;
(2R)-8-Fluoro-2-methyl-4-({2-methyl-6-[2-(5-oxo-1,4-diazepan-1-yl)pyrimidin-5-yl]-imidazo[1,2-a]pyrazin-3-yl}methyl)-1,4-benzoxazin-3-one;
(2R)-8-Fluoro-4-({7-fluoro-6-[2-(1-hydroxy-1-methylethyl)pyrimidin-5-yl]-2-methyl-imidazo[1,2a-]pyridin-3-yl}methyl)-2-methyl-3-oxo-1,4-benzoxazine-6-carboxylic acid;
(2R)-8-Fluoro-4-({7-fluoro-6-[2-(1-hydroxy-1-methylethyl)pyrimidin-5-yl]-2-methyl-imidazo[1,2a-]pyridin-3-yl}methyl)-N,2-dimethyl-3-oxo-1,4-benzoxazine-6-carboxamide;
(2S)-6,8-Difluoro-4-({7-fluoro-6-[2-(2-hydroxypropan-2-yl)pyrimidin-5-yl]-2-methyl-imidazo[1,2a-]pyridin-3-yl}methyl)-2-methyl-3,4-dihydro-2H-1,4-benzoxazin-3-one;
(2S)-8-Fluoro-4-({7-fluoro-6-[2-(2-hydroxypropan-2-yl)pyrimidin-5-yl]-2-methyl-imidazo[1,2a-]pyridin-3-yl}methyl)-2-methyl-3,4-dihydro-2H-1,4-benzoxazin-3-one;
(2R)-8-Fluoro-4-({7-fluoro-6-[2-(1-hydroxy-1-methylethyl)pyrimidin-5-yl]-2-methyl-imidazo[1,2a-]pyridin-3-yl}methyl)-6-(1-hydroxy-1-methylethyl)-2-methyl-1,4-benzoxazin-3-one;
8-Fluoro-4-({6-[6-(methanesulfonyl)pyridin-3-yl]-2-methylimidazo[1,2a-]pyridin-3-yl}-methyl)-3,4-dihydro-2H-1,4-benzoxazin-3-one;
(2R)-8-Fluoro-4-[(7-fluoro-6-{6-[imino(methyl)oxo-λ⁶-sulfanyl]pyridin-3-yl}-2-methylimidazo[1,2-a]-pyridin-3-yl)methyl]-2-methyl-3,4-dihydro-2H-1,4-benzoxazin-3-one;
(2S)-8-Fluoro-4-[(7-fluoro-6-{6-[imino(methyl)oxo-λ⁶-sulfanyl]pyridin-3-yl}-2-methyl-imidazo[1,2a-]pyridin-3-yl)methyl]-2-methyl-3,4-dihydro-2H-1,4-benzoxazin-3-one;
8-Fluoro-4-[(7-fluoro-6-{6-[imino(methyl)oxo-λ⁶-sulfanyl]pyridin-3-yl}-2-methylimidazo[1,2-a]pyridin-3-yl)methyl]-3,4-dihydro-2H-1,4-benzoxazin-3-one;
8-Fluoro-4-[(7-fluoro-6-{6-[imino(methyl)oxo-λ⁶-sulfanyl]-4-methylpyridin-3-yl}-2-methylimidazo[1,2a-]pyridin-3-yl)methyl]-3,4-dihydro-2H-1,4-benzoxazin-3-one;
(2S)-8-Fluoro-4-[(7-fluoro-6-{6-[imino(methyl)oxo-λ⁶-sulfanyl]-4-methylpyridin-3-yl}-2-methylimidazo[1,2a-]pyridin-3-yl)methyl]-2-methyl-3,4-dihydro-2H-1,4-benzoxazin-3-one;
(2R)-8-Fluoro-4-[(7-fluoro-2-methyl-6-{6-[methyl(methylimino)oxo-λ⁶-sulfanyl]pyridin-3-yl}imidazo-[1,2-a]pyridin-3-yl)methyl]-2-methyl-3,4-dihydro-2H-1,4-benzoxazin-3-one;
(2R)-8-Fluoro-4-[(7-fluoro-6-{6-[imino(methyl)oxo-λ⁶-sulfanyl]-4-methylpyridin-3-yl}-2-methylimidazo-[1,2a-]pyridin-3-yl)methyl]-2-methyl-3,4-dihydro-2H-1,4-benzoxazin-3-one;
(2S)-4-[(6-{6-[Ethyl(imino)oxo-λ⁶-sulfanyl]pyridin-3-yl}-7-fluoro-2-methylimidazo[1,2a-]pyridin-3-yl)-methyl]-8-fluoro-2-methyl-3,4-dihydro-2H-1,4-benzoxazin-3-one;
(2R)-4-[(6-{6-[Ethyl(imino)oxo-λ⁶-sulfanyl]pyridin-3-yl}-7-fluoro-2-methylimidazo[1,2a-]pyridin-3-yl)-methyl]-8-fluoro-2-methyl-3,4-dihydro-2H-1,4-benzoxazin-3-one;
(2R)-8-Chloro-4-[(7-fluoro-6-{6-[imino(methyl)oxo-λ⁶-sulfanyl]pyridin-3-yl}-2-methylimidazo[1,2-a]-pyridin-3-yl)methyl]-2-methyl-3,4-dihydro-2H-1,4-benzoxazin-3-one;
(2R)-8-Fluoro-4-[(7-fluoro-6-{6-[imino(methyl)oxo-λ⁶-sulfanyl]-4-methylpyridin-3-yl}-2-methylimidazo-[1,2-a]pyridin-3-yl)methyl]-2-methyl-3,4-dihydro-2H-1,4-benzoxazin-3-one, maleic acid salt;
(2R)-4-[(6-{6-[Ethyl(imino)oxo-λ⁶-sulfanyl]pyridin-3-yl}-7-fluoro-2-methylimidazo[1,2-a]pyridin-3-yl)-methyl]-8-fluoro-2-methyl-3,4-dihydro-2H-1,4-benzoxazin-3-one, maleic acid salt;
(2R)-8-Fluoro-4-[(6-{6-[imino(methyl)oxo-λ⁶-sulfanyl]pyridin-3-yl}-2-methylimidazo[1,2-a]pyridin-3-yl)methyl]-2-methyl-3,4-dihydro-2H-1,4-benzoxazin-3-one, maleic acid salt;

5-Fluoro-1-[(7-fluoro-6-{6-[imino(methyl)oxo-λ⁶-sulfa-nyl]pyridin-3-yl}-2-methylimidazo[1,2-a]pyridin-3-yl)methyl]-3-methyl-1,2,3,4-tetrahydroquinolin-2-one;

(2S)-8-Fluoro-4-[(7-fluoro-2-methyl-6-{2-[(1s,3r)-1,3-dihydroxy-3-methylcyclobutyl]pyrimidin-5-yl}-imidazo[1,2-a]pyridin-3-yl)methyl]-2-methyl-3,4-dihydro-2H-1,4-benzoxazin-3-one;

(2S)-8-Fluoro-4-[(7-fluoro-2-methyl-6-{2-[(1s,3s)-1,3-dihydroxycyclobutyl]pyrimidin-5-yl}imidazo[1,2-a]pyridin-3-yl)methyl]-2-methyl-3,4-dihydro-2H-1,4-benzoxazin-3-one;

8-Fluoro-4-[(7-fluoro-2-methyl-6-{2-[(1r,3s)-1,3-dihydroxy-3-methylcyclobutyl]pyrimidin-5-yl}-imidazo[1,2-a]pyridin-3-yl)methyl]-3,4-dihydro-2H-1,4-benzoxazin-3-one;

(2R)-8-Fluoro-4-[(7-fluoro-2-methyl-6-{2-[(1r,3s)-1,3-dihydroxy-3-methylcyclobutyl]pyrimidin-5-yl}-imidazo[1,2-a]pyridin-3-yl)methyl]-2-methyl-3,4-dihydro-2H-1,4-benzoxazin-3-one;

(2R)-6,8-Difluoro-2-methyl-4-[(2-methyl-6-{2-[(1r,3s)-1,3-dihydroxy-3-methylcyclobutyl]pyrimidin-5-yl}imidazo[1,2-a]pyrazin-3-yl)methyl]-3,4-dihydro-2H-1,4-benzoxazin-3-one;

(2S)-8-Fluoro-4-[(7-fluoro-2-methyl-6-{2-[(1s,3s)-3-amino-1-hydroxycyclobutyl]pyrimidin-5-yl}imidazo-[1,2-a]pyridin-3-yl)methyl]-2-methyl-3,4-dihydro-2H-1,4-benzoxazin-3-one;

8-Fluoro-4-[(7-fluoro-2-methyl-6-{6-[(1r,3s)-1,3-dihydroxy-3-methylcyclobutyl]pyridin-3-yl}imidazo-[1,2-a]pyridin-3-yl)methyl]-3,4-dihydro-2H-1,4-benzoxazin-3-one;

(2R)-8-Fluoro-4-[(7-fluoro-2-methyl-6-{6-[(1r,3s)-1,3-dihydroxy-3-methylcyclobutyl]pyridin-3-yl}imidazo-[1,2-a]pyridin-3-yl)methyl]-2-methyl-3,4-dihydro-2H-1,4-benzoxazin-3-one;

8-Fluoro-4-[(7-fluoro-2-methyl-6-{2-[(1r,3s)-3-ethyl-1,3-dihydroxycyclobutyl]pyrimidin-5-yl}imidazo[1,2-a]pyridin-3-yl)methyl]-3,4-dihydro-2H-1,4-benzoxazin-3-one;

(2R)-4-{[6-(6-{[Dimethyl(oxo)-λ⁶-sulfanylidene]-amino}pyridin-3-yl)-7-fluoro-2-methylimidazo[1,2a-]pyridin-3-yl]methyl}-8-fluoro-2-methyl-3,4-dihydro-2H-1,4-benzoxazin-3-one;

(2R)-4-[(6-{6-[Ethyl(imino)oxo-λ⁶-sulfanyl]pyridin-3-yl}-2-methylimidazo[1,2-a]pyrazin-3-yl)methyl]-8-fluoro-2-methyl-3,4-dihydro-2H-1,4-benzoxazin-3-one;

(2R)-8-Fluoro-2-methyl-4-[(2-methyl-6-{2-[(1r,3s)-3-ethyl-1,3-dihydroxycyclobutyl]pyrimidin-5-yl}-imidazo[1,2-a]pyrazin-3-yl)methyl]-3,4-dihydro-2H-1,4-benzoxazin-3-one;

(2R)-6-Bromo-8-chloro-4-({7-fluoro-6-[2-(2-hydroxypropan-2-yl)pyrimidin-5-yl]-2-methylimidazo[1,2a-]pyridin-3-yl}methyl)-2-methyl-3,4-dihydro-2H-1,4-benzoxazin-3-one;

8-Fluoro-4-[(7-fluoro-6-{6-[imino(methyl)oxo-λ⁶-sulfa-nyl]pyridin-3-yl}-2-methylimidazo[1,2-a]pyridin-3-yl)methyl]-2,2-dimethyl-3,4-dihydro-2H-1,4-benzoxazin-3-one;

(2R)-8-Fluoro-2-methyl-4-[(2-methyl-6-{2-[(1r,3s)-1,3-dihydroxy-3-methylcyclobutyl]pyrimidin-5-yl}-imidazo[1,2-a]pyrazin-3-yl)methyl]-3,4-dihydro-2H-1,4-benzoxazin-3-one;

(2R)-4-[(6-{6-[Cyclopropyl(imino)oxo-λ⁶-sulfanyl]-pyridin-3-yl}-7-fluoro-2-methylimidazo[1,2a-]pyridin-3-yl)methyl]-8-fluoro-2-methyl-3,4-dihydro-2H-1,4-benzoxazin-3-one; (2R)-8-Chloro-2-methyl-4-[(2-methyl-6-{2-[(1r,3s)-1,3-dihydroxy-3-methylcyclobutyl]pyrimidin-5-yl}-imidazo[1,2-a]pyrazin-3-yl)methyl]-3,4-dihydro-2H-1,4-benzoxazin-3-one;

(2R)-8-Chloro-4-[(7-fluoro-2-methyl-6-{2-[(1r,3s)-1,3-dihydroxy-3-methylcyclobutyl]pyrimidin-5-yl}-imidazo[1,2-a]pyridin-3-yl)methyl]-2-methyl-3,4-dihydro-2H-1,4-benzoxazin-3-one;

8-Chloro-4-[(2-methyl-6-{2-[(1r,3s)-1,3-dihydroxy-3-methylcyclobutyl]pyrimidin-5-yl}imidazo[1,2a-]-pyrazin-3-yl)methyl]-3,4-dihydro-2H-1,4-benzoxazin-3-one;

8-Chloro-4-[(7-fluoro-2-methyl-6-{2-[(1r,3s)-1,3-dihydroxy-3-methylcyclobutyl]pyrimidin-5-yl}-imidazo[1,2a-]pyridin-3-yl)methyl]-3,4-dihydro-2H-1,4-benzoxazin-3-one;

(2R)-8-Fluoro-2-methyl-4-[(2-methyl-6-{2-[(1s,3r)-1-amino-3-hydroxy-3-methylcyclobutyl]pyrimidin-5-yl}-imidazo[1,2-a]pyrazin-3-yl)methyl]-3,4-dihydro-2H-1,4-benzoxazin-3-one;

8-Fluoro-4-({7-fluoro-6-[2-(2-hydroxypropan-2-yl)-pyrimidin-5-yl]-2-methylimidazo[1,2a-]pyridin-3-yl}-methyl)-2-methyl-3-oxo-N-(propan-2-yl)-3,4-dihydro-2H-1,4-benzoxazine-6-carboxamide;

(2S)-8-Fluoro-4-({7-fluoro-6-[2-(2-hydroxypropan-2-yl)pyrimidin-5-yl]-2-methylimidazo[1,2a-]pyridin-3-yl}methyl)-2-methyl-3-oxo-N-(propan-2-yl)-3,4-dihydro-2H-1,4-benzoxazine-6-carboxamide;

(2R)-8-Fluoro-4-({7-fluoro-6-[2-(2-hydroxypropan-2-yl)pyrimidin-5-yl]-2-methylimidazo[1,2a-]pyridin-3-yl}methyl)-2-methyl-3-oxo-N-(propan-2-yl)-3,4-dihydro-2H-1,4-benzoxazine-6-carboxamide;

8-Fluoro-4-({7-fluoro-6-[2-(2-hydroxypropan-2-yl)-pyrimidin-5-yl]-2-methylimidazo[1,2a-]pyridin-3-yl}-methyl)-N-(1-hydroxy-2-methylpropan-2-yl)-2-methyl-3-oxo-3,4-dihydro-2H-1,4-benzoxazine-6-carboxamide;

8-Fluoro-4-({7-fluoro-6-[2-(2-hydroxypropan-2-yl)-pyrimidin-5-yl]-2-methylimidazo[1,2a-]pyridin-3-yl}-methyl)-N-(1-hydroxypropan-2-yl)-2-methyl-3-oxo-3,4-dihydro-2H-1,4-benzoxazine-6-carboxamide;

N-Ethyl-8-fluoro-4-({7-fluoro-6-[2-(1-hydroxy-1-methyl-ethyl)pyrimidin-5-yl]-2-methylimidazo[1,2a-]-pyridin-3-yl}methyl)-2-methyl-3-oxo-1,4-benzoxazine-6-carboxamide;

tert-Butyl 4-[8-fluoro-4-({7-fluoro-6-[2-(1-hydroxy-1-methylethyl)pyrimidin-5-yl]-2-methylimidazo[1,2a-]-pyridin-3-yl}methyl)-2-methyl-3-oxo-1,4-benzoxazine-6-carbonyl]piperazine-1-carboxylate;

8-Fluoro-4-({7-fluoro-6-[2-(1-hydroxy-1-methylethyl)-pyrimidin-5-yl]-2-methylimidazo[1,2-a]pyridin-3-yl}-methyl)-2-methyl-6-(piperazine-1-carbonyl)-1,4-benzoxazin-3-one;

8-Fluoro-4-({7-fluoro-6-[2-(2-hydroxypropan-2-yl)-pyrimidin-5-yl]-2-methylimidazo[1,2-a]pyridin-3-yl}-methyl)-6-[(3-hydroxypyrrolidin-1-yl)carbonyl]-2-methyl-2H-1,4-benzoxazin-3(4H)-one;

8-Fluoro-4-({7-fluoro-6-[2-(2-hydroxypropan-2-yl)-pyrimidin-5-yl]-2-methylimidazo[1,2a-]pyridin-3-yl}-methyl)-N,N,2-trimethyl-3-oxo-3,4-dihydro-2H-1,4-benzoxazine-6-carboxamide;

N-Cyclopropyl-8-fluoro-4-({7-fluoro-6-[2-(2-hydroxy-propan-2-yl)pyrimidin-5-yl]-2-methylimidazo[1,2a-]-pyridin-3-yl}methyl)-2-methyl-3-oxo-3,4-dihydro-2H-1,4-benzoxazine-6-carboxamide;

8-Fluoro-4-({7-fluoro-6-[2-(2-hydroxypropan-2-yl)-pyrimidin-5-yl]-2-methylimidazo[1,2a-]pyridin-3-yl}- methyl)-N-(2-hydroxyethyl)-2-methyl-3-oxo-3,4-di-
hydro-2H-1,4-benzoxazine-6-carboxamide;
8-Fluoro-4-({7-fluoro-6-[2-(1-hydroxy-1-methylethyl)-
pyrimidin-5-yl]-2-methylimidazo[1,2a-]pyridin-3-yl}-
methyl)-N-(2-methoxyethyl)-2-methyl-3-oxo-1,4-ben-
zoxazine-6-carboxamide;
8-Fluoro-4-({7-fluoro-6-[2-(1-hydroxy-1-methylethyl)-
pyrimidin-5-yl]-2-methylimidazo[1,2-a]pyridin-3-yl}-
methyl)-2-methyl-N-(oxazol-4-ylmethyl)-3-oxo-1,4-
benzoxazine-6-carboxamide;
8-Fluoro-4-({7-fluoro-6-[2-(1-hydroxy-1-methylethyl)-
pyrimidin-5-yl]-2-methylimidazo[1,2-a]pyridin-3-yl}-
methyl)-2-methyl-6-[3-(methylsulfonyl)azetidine-1-
carbonyl]-1,4-benzoxazin-3-one;
8-Fluoro-4-({7-fluoro-6-[2-(1-hydroxy-1-methylethyl)-
pyrimidin-5-yl]-2-methylimidazo[1,2-a]pyridin-3-yl}-
methyl)-2-methyl-6-(3-oxopiperazine-1-carbonyl)-1,4-
benzoxazin-3-one;
8-Fluoro-4-({7-fluoro-6-[2-(1-hydroxy-1-methylethyl)-
pyrimidin-5-yl]-2-methylimidazo[1,2a-]pyridin-3-yl}-
methyl)-2-methyl-3-oxo-1,4-benzoxazine-6-carbox-
amide;
(2R)-8-Fluoro-2-methyl-4-({2-methyl-6-[2-(2-methyl-5-
oxo-1,4-diazepan-1-yl)pyrimidin-5-yl]imidazo[1,2a-]
pyrazin-3-yl}methyl)-1,4-benzoxazin-3-one;
(2R)-8-Fluoro-2-methyl-4-({2-methyl-6-[2-(7-methyl-5-
oxo-1,4-diazepan-1-yl)pyrimidin-5-yl]imidazo[1,2a-]
pyrazin-3-yl}methyl)-1,4-benzoxazin-3-one;
(2R)-8-Fluoro-4-[(7-fluoro-2-methyl-6-{2-[(1R,5S)-6-
oxa-3-azabicyclo[3.1.1]heptan-3-yl]pyrimidin-5-yl}-
imidazo[1,2-a]pyridin-3-yl)methyl]-2-methyl-1,4-ben-
zoxazin-3-one;
(2R)-6-Bromo-8-fluoro-4-({7-fluoro-6-[2-(1-hydroxy-1-
methylethyl)pyrimidin-5-yl]-2-methylimidazo[1,2a-]
pyridin-3-yl}methyl)-2-methyl-1,4-benzoxazin-3-one;
(2R)-8-Chloro-4-({7-fluoro-6-[2-(1-hydroxy-1-methyl-
ethyl)pyrimidin-5-yl]-2-methylimidazo[1,2a-]pyridin-
3-yl}methyl)-N-isopropyl-2-methyl-3-oxo-1,4-benzo-
xazine-6-carboxamide;
(2R)-8-Chloro-4-[(7-fluoro-6-{2-[3-hydroxy-3-(trifluo-
romethyl)azetidin-1-yl]pyrimidin-5-yl}-2-methylimi-
dazo[1,2-a]pyridin-3-yl)methyl]-N-isopropyl-2-
methyl-3-oxo-1,4-benzoxazine-6-carboxamide;
8-Chloro-4-({7-fluoro-2-methyl-6-[2-(3-oxopiperazin-1-
yl)pyrimidin-5-yl]imidazo[1,2a-]pyridin-3-yl}-
methyl)-N-isopropyl-2-methyl-3-oxo-1,4-benzox-
azine-6-carboxamide;
(2R)-8-Fluoro-4-({7-fluoro-6-[2-(1-hydroxy-1-methyl-
ethyl)pyrimidin-5-yl]-2-methylimidazo[1,2a-]pyridin-
3-yl}methyl)-6-(3-hydroxyoxetan-3-yl)-2-methyl-1,4-
benzoxazin-3-one;
8-Fluoro-4-({7-fluoro-6-[2-(1-hydroxy-1-methylethyl)-
pyrimidin-5-yl]-2-methylimidazo[1,2a]pyridin-3-yl}-
methyl)-N-isopropyl-3-oxo-1,4-benzoxazine-6-car-
boxamide;
4-({7-Fluoro-6-[2-(1-hydroxy-1-methylethyl)-pyrimidin-
5-yl]-2-methylimidazo[1,2a]pyridin-3-yl}-methyl)-N-
isopropyl-2-methyl-3-oxopyrido[3,2-b]-[1,4]oxazine-
6-carboxamide;
(2R)-8-Fluoro-4-({7-fluoro-6-[2-(1-hydroxy-1-methyl-
ethyl)pyrimidin-5-yl]-2-methylimidazo[1,2-a]pyridin-
3-yl}methyl)-6-(3-methoxyoxetan-3-yl)-2-methyl-1,4-
benzoxazin-3-one;
(2S)-8-Fluoro-4-({7-fluoro-6-[2-(1-hydroxy-1-methyl-
ethyl)pyrimidin-5-yl]-2-methylimidazo[1,2-a]pyridin-
3-yl}methyl)-6-(1-hydroxy-1-methylethyl)-2-methyl-
1,4-benzoxazin-3-one;
(2R)-8-Fluoro-4-({7-fluoro-6-[2-(1-hydroxy-1-methyl-
ethyl)pyrimidin-5-yl]-2-methylimidazo[1,2-a]pyridin-
3-yl}methyl)-2-methyl-6-(methyl sulfanyl)-1,4-benzo-
xazin-3-one;
(2R)-8-Fluoro-4-({7-fluoro-6-[2-(1-hydroxy-1-methyl-
ethyl)pyrimidin-5-yl]-2-methyl-imidazo[1,2-a]pyridin-
3-yl}methyl)-2-methyl-6-(methyl sulfinyl)-1,4-benzo-
xazin-3-one;
(2R)-8-Fluoro-4-({7-fluoro-6-[2-(1-hydroxy-1-methyl-
ethyl)pyrimidin-5-yl]-2-methyl-imidazo[1,2-a]pyridin-
3-yl}methyl)-2-methyl-6-(methyl sulfonyl)-1,4-benzo-
xazin-3-one;
1-({7-Fluoro-6-[2-(2-hydroxypropan-2-yl)pyrimidin-5-
yl]-2-methylimidazo[1,2-a]pyridin-3-yl}methyl)-3-
methyl-3,4-dihydroquinolin-2(1H)-one;
5-Fluoro-1-({7-fluoro-6-[2-(2-hydroxypropan-2-yl)-py-
rimidin-5-yl]-2-methylimidazo[1,2-a]pyridin-3-yl}-
methyl)-3-methyl-3,4-dihydroquinolin-2(1H)-one;
(8-anti)-3-(5-{7-Fluoro-3-[(5-fluoro-3-methyl-2-oxo-3,4-
dihydroquinolin-1 (2H)-yl)methyl]-2-methyl-imidazo
[1,2-a]pyridin-6-yl}pyrimidin-2-yl)-3-azabicyclo
[3.2.1]octane-8-carboxylic acid;
(2R)-8-Fluoro-4-({6-[2-(2-hydroxypropan-2-yl)-4-meth-
ylpyrimidin-5-yl]-2-methylimidazo[1,2-a]-pyrazin-3-
yl}methyl)-2-methyl-2H-1,4-benzoxazin-3 (4H)-one;
(2S)-8-Fluoro-4-({7-fluoro-2-methyl-6-[2-(3-oxo-piper-
azin-1-yl)pyrimidin-5-yl]imidazo[1,2-a]pyridin-3-
yl}methyl)-2-methyl-2H-1,4-benzoxazin-3(4H)-one;
(2S)-8-Fluoro-4-({7-fluoro-6-[6-(4-hydroxytetrahydro-
2H-pyran-4-yl)pyridin-3-yl]-2-methylimidazo[1,2-a]-
pyridin-3-yl}methyl)-2-methyl-2H-1,4-benzoxazin-3
(4H)-one;
(2R)-8-Fluoro-4-({6-[6-(4-hydroxytetrahydro-2H-pyran-
4-yl)pyridin-3-yl]-2-methylimidazo[1,2-a]-pyrazin-3-
yl}methyl)-2-methyl-2H-1,4-benzoxazin-3 (4H)-one;
4-({7-Fluoro-6-[2-(2-hydroxypropan-2-yl)pyrimidin-5-
yl]-2-methylimidazo[1,2-a],pyridin-3-yl}methyl)-2H-
1,4-b enzothiazin-3 (4H)-one 1-oxide;
4-({7-Fluoro-6-[2-(2-hydroxypropan-2-yl)pyrimidin-5-
yl]-2-methylimidazo[1,2-a]pyridin-3-yl}methyl)-2H-
1,4-b enzothiazin-3 (4H)-one; or
N-[(2R)-8-Fluoro-4-({7-fluoro-6-[2-(2-hydroxypropan-
2-yl)pyrimidin-5-yl]-2-methylimidazo[1,2a-]pyridin-
3-yl}methyl)-2-methyl-3-oxo-3,4-dihydro-2H-1,4-
benzoxazin-6-yl]-2-methylpropanamide.

6. A pharmaceutical composition comprising a compound of formula (IIB-A), (IIB-B) or (IIB-C) as defined in claim 1 or an N-oxide thereof, or a pharmaceutically acceptable salt or solvate thereof, in association with a pharmaceutically acceptable carrier.

7. A method for the treatment of rheumatoid arthritis, Crohn's disease, pain or a nociceptive disorder, a cardiovascular disorder, a metabolic disorder, an ocular disorder, or an oncological disorder, which comprises administering to a patient in need of such treatment an effective amount of a compound of formula (IIB-A), (IIB-B) or (IIB-C) as defined in claim 3 or an N-oxide thereof, or a pharmaceutically acceptable salt or solvate thereof.

* * * * *